US008062340B2

(12) United States Patent
Berrevoets et al.

(10) Patent No.: US 8,062,340 B2
(45) Date of Patent: Nov. 22, 2011

(54) SPINAL ROD ANCHOR DEVICE AND METHOD

(75) Inventors: Gregory A. Berrevoets, Skandia, MI (US); Jeffrey L. Trudeau, Marquete, MI (US); Jeffrey Hoffman, Marquette, MI (US)

(73) Assignee: Pioneer Surgical Technology, Inc., Marquette, MI (US)

( * ) Notice: Subject to any disclaimer, the term of this patent is extended or adjusted under 35 U.S.C. 154(b) by 688 days.

(21) Appl. No.: 11/839,843

(22) Filed: Aug. 16, 2007

(65) Prior Publication Data
US 2008/0045955 A1    Feb. 21, 2008

Related U.S. Application Data

(60) Provisional application No. 60/825,366, filed on Sep. 12, 2006, provisional application No. 60/822,603, filed on Aug. 16, 2006.

(51) Int. Cl.
*A61B 17/70* (2006.01)
(52) U.S. Cl. ........................................ 606/270; 606/272
(58) Field of Classification Search .......... 606/246–279; A61B 17/70
See application file for complete search history.

(56) References Cited

U.S. PATENT DOCUMENTS

| | | |
|---|---|---|
| 4,887,596 A | 12/1989 | Sherman |
| 4,946,458 A | 8/1990 | Harms et al. |
| 4,950,269 A | 8/1990 | Gaines, Jr. |
| 5,207,678 A | 5/1993 | Harms et al. |
| 5,257,993 A | 11/1993 | Asher et al. |
| 5,261,913 A | 11/1993 | Marnay |
| 5,346,493 A | 9/1994 | Stahurski et al. |
| 5,385,583 A | 1/1995 | Cotrel |
| 5,443,467 A | 8/1995 | Biedermann et al. |
| 5,466,237 A | 11/1995 | Byrd, III et al. |
| 5,474,555 A | 12/1995 | Puno et al. |
| 5,496,321 A | 3/1996 | Puno et al. |
| 5,520,689 A | 5/1996 | Schlapfer et al. |
| 5,545,167 A | 8/1996 | Lin |
| 5,562,663 A | 10/1996 | Wisnewski et al. |
| 5,593,407 A | 1/1997 | Reis |

(Continued)

FOREIGN PATENT DOCUMENTS

EP    0 947 174 A2    10/1999
(Continued)

OTHER PUBLICATIONS

Order dated Oct. 13, 2005, Case No. 2:05-CV-41, Western District of Michigan Northern Division.

(Continued)

*Primary Examiner* — Eduardo C Robert
*Assistant Examiner* — Steven Cotroneo
(74) *Attorney, Agent, or Firm* — Fitch, Even, Tabin & Flannery

(57) ABSTRACT

A spinal fixation system is provided that includes a coupling member and a locking device that is operable to fix an elongate member in the coupling member. There is also provided insertion instruments configured to install and remove various components of the spinal fixation system. In one form, the coupling member includes opposing side wall portions having a resilient portion on at least one of the side wall portions that cooperates with the locking device for being inserted into the coupling member via resilient flexing of the resilient portion. The coupling member and locking device also preferably include cooperating structure therebetween to define a plurality of distinct positions of the locking device in the coupling member.

17 Claims, 99 Drawing Sheets

U.S. PATENT DOCUMENTS

| | | | |
|---|---|---|---|
| 5,667,508 | A | 9/1997 | Errico et al. |
| 5,683,390 | A | 11/1997 | Metz-Stavenhagen et al. |
| 5,683,392 | A | 11/1997 | Richelsoph et al. |
| 5,690,630 | A | 11/1997 | Errico et al. |
| 5,728,098 | A | 3/1998 | Sherman et al. |
| 5,782,833 | A | 7/1998 | Haider |
| 5,797,911 | A | 8/1998 | Sherman et al. |
| 5,863,293 | A | 1/1999 | Richelsoph |
| 5,879,350 | A | 3/1999 | Sherman et al. |
| 5,885,286 | A | 3/1999 | Sherman et al. |
| 5,997,539 | A | 12/1999 | Errico et al. |
| 6,010,503 | A | 1/2000 | Richelsoph et al. |
| 6,063,090 | A | 5/2000 | Schlapfer |
| 6,077,262 | A | 6/2000 | Schlapfer et al. |
| 6,090,111 | A | 7/2000 | Nichols |
| 6,110,172 | A | 8/2000 | Jackson |
| 6,280,442 | B1 | 8/2001 | Barker et al. |
| 6,302,888 | B1 | 10/2001 | Mellinger et al. |
| 6,355,040 | B1 | 3/2002 | Richelsoph et al. |
| 6,379,356 | B1 | 4/2002 | Jackson |
| 6,402,752 | B2 | 6/2002 | Schaffler-Wachter et al. |
| 6,478,797 | B1 | 11/2002 | Paul |
| 6,485,491 | B1 | 11/2002 | Farris et al. |
| 6,485,492 | B1 | 11/2002 | Halm et al. |
| 6,485,494 | B1 | 11/2002 | Haider |
| 6,488,681 | B2 | 12/2002 | Martin et al. |
| 6,488,682 | B2 | 12/2002 | Kikuchi et al. |
| 6,554,834 | B1 | 4/2003 | Crozet et al. |
| 6,565,565 | B1 | 5/2003 | Yuan et al. |
| 6,652,526 | B1 | 11/2003 | Arafiles |
| 6,660,004 | B2 | 12/2003 | Barker et al. |
| 6,695,843 | B2 | 2/2004 | Biedermann et al. |
| 6,755,829 | B1 | 6/2004 | Bono |
| 6,837,889 | B2 | 1/2005 | Shluzas |
| 6,858,030 | B2 | 2/2005 | Martin et al. |
| 6,866,664 | B2 * | 3/2005 | Schär et al. .......... 606/252 |
| 6,869,433 | B2 | 3/2005 | Glascott |
| 6,905,500 | B2 | 6/2005 | Jeon et al. |
| 6,918,911 | B2 | 7/2005 | Biedermann et al. |
| 7,066,937 | B2 | 6/2006 | Shluzas |
| 7,081,117 | B2 | 7/2006 | Bono |
| 7,087,057 | B2 | 8/2006 | Konieczynski |
| 7,090,674 | B2 | 8/2006 | Doubler et al. |
| 7,125,426 | B2 | 10/2006 | Moumene |
| 7,128,743 | B2 | 10/2006 | Metz-Stavenhagen |
| 7,144,396 | B2 | 12/2006 | Shluzas |
| 2002/0010467 | A1 | 1/2002 | Cooper et al. |
| 2002/0026193 | A1 | 2/2002 | Barker |
| 2002/0082602 | A1 | 6/2002 | Biedermann et al. |
| 2002/0111626 | A1 | 8/2002 | Ralph |
| 2002/0116001 | A1 | 8/2002 | Schafer et al. |
| 2002/0120272 | A1 * | 8/2002 | Yuan et al. .......... 606/61 |
| 2002/0133154 | A1 | 9/2002 | Saint Martin |
| 2002/0151900 | A1 | 10/2002 | Glascott |
| 2003/0004511 | A1 | 1/2003 | Ferree |
| 2003/0004512 | A1 | 1/2003 | Farris et al. |
| 2003/0093081 | A1 | 5/2003 | Hawkes |
| 2003/0100896 | A1 | 5/2003 | Biedermann et al. |
| 2003/0125741 | A1 | 7/2003 | Biedermann et al. |
| 2003/0125742 | A1 | 7/2003 | Yuan et al. |
| 2003/0187433 | A1 | 10/2003 | Lin |
| 2004/0097933 | A1 | 5/2004 | Lourdel et al. |
| 2004/0176766 | A1 | 9/2004 | Shluzas |
| 2004/0236330 | A1 | 11/2004 | Purcell et al. |
| 2004/0249380 | A1 | 12/2004 | Glascott |
| 2004/0260283 | A1 * | 12/2004 | Wu et al. .......... 606/61 |
| 2005/0049589 | A1 | 3/2005 | Jackson |
| 2005/0096659 | A1 | 5/2005 | Freudiger |
| 2005/0119658 | A1 | 6/2005 | Ralph et al. |
| 2005/0187548 | A1 | 8/2005 | Butler et al. |
| 2005/0228385 | A1 * | 10/2005 | Iott et al. .......... 606/61 |
| 2005/0240180 | A1 | 10/2005 | Vienney et al. |
| 2005/0261687 | A1 | 11/2005 | Garamszegi et al. |
| 2005/0277924 | A1 | 12/2005 | Roychowdhury |
| 2005/0288671 | A1 | 12/2005 | Yuan et al. |
| 2006/0025767 | A1 | 2/2006 | Khalili |
| 2006/0036244 | A1 | 2/2006 | Spitler et al. |
| 2006/0084996 | A1 | 4/2006 | Metz-Stavenhagen |
| 2006/0089643 | A1 * | 4/2006 | Mujwid .......... 606/61 |
| 2006/0129149 | A1 | 6/2006 | Iott et al. |
| 2006/0161152 | A1 | 7/2006 | Ensign et al. |
| 2006/0161153 | A1 | 7/2006 | Hawkes et al. |
| 2006/0173456 | A1 | 8/2006 | Hawkes et al. |
| 2006/0235393 | A1 | 10/2006 | Bono et al. |
| 2006/0241599 | A1 | 10/2006 | Konieczynski |
| 2006/0247636 | A1 | 11/2006 | Yuan et al. |
| 2006/0264933 | A1 | 11/2006 | Baker et al. |
| 2006/0276789 | A1 | 12/2006 | Jackson |
| 2006/0276791 | A1 | 12/2006 | Shluzas |
| 2006/0293665 | A1 | 12/2006 | Shluzas |
| 2006/0293666 | A1 | 12/2006 | Matthis et al. |
| 2007/0055241 | A1 | 3/2007 | Matthis et al. |

FOREIGN PATENT DOCUMENTS

| | | |
|---|---|---|
| WO | 02 054966 | 7/2002 |
| WO | 2004 047657 A2 | 6/2004 |
| WO | 2006 119271 A2 | 11/2006 |

OTHER PUBLICATIONS

Opinion dated Oct. 13, 2005, Case No. 2:05-CV-41, Western District of Michigan Northern Division.
Declaration of Richard V. Baratta, dated Jun. 1, 2005.
Pioneer's Opposition to Defendants' Motion for Summary Judgment that the '565 Patent is not Invalid, dated Jun. 1, 2005.
Pioneer's Opposition to Defendants' Motion for Summary Judgment of Infringement, dated Jun. 1, 2005.
Appeal Brief dated Feb. 21, 2006, Case No. 2:05-CV-014, Western District of Michigan Northern Division.
Brief for Plaintiff dated Apr. 3, 2006, Case No. 2:05-CV-041, Western District of Michigan Northern Division.
Reply Appeal Brief dated Apr. 17, 2006, Case No. 2:05-CV-041, Western District of Michigan Northern Division.
Judgment, United States Court of Appeals for the Federal Circuit, dated Aug. 11, 2006, Case No. 06-1142 (2:05-CV-41, W.D. Mich.).
USPTO Non-Final Office action dated Feb. 9, 2005 U.S. Appl. No. 10/358,530.
Response to Non-Final Office action dated Jul. 8, 2005 U.S. Appl. No. 10/358,530.
USPTO Final Office action dated Oct. 31, 2005 U.S. Appl. No. 10/358,530.
USPTO Interview Summary dated Dec. 6, 2005 U.S. Appl. No. 10/358,530.
Response to Final Office action dated May 1, 2006 U.S. Appl. No. 10/358,530.
Notice of Allowance dated May 15, 2006 U.S. Appl. No. 10/358,530.

* cited by examiner

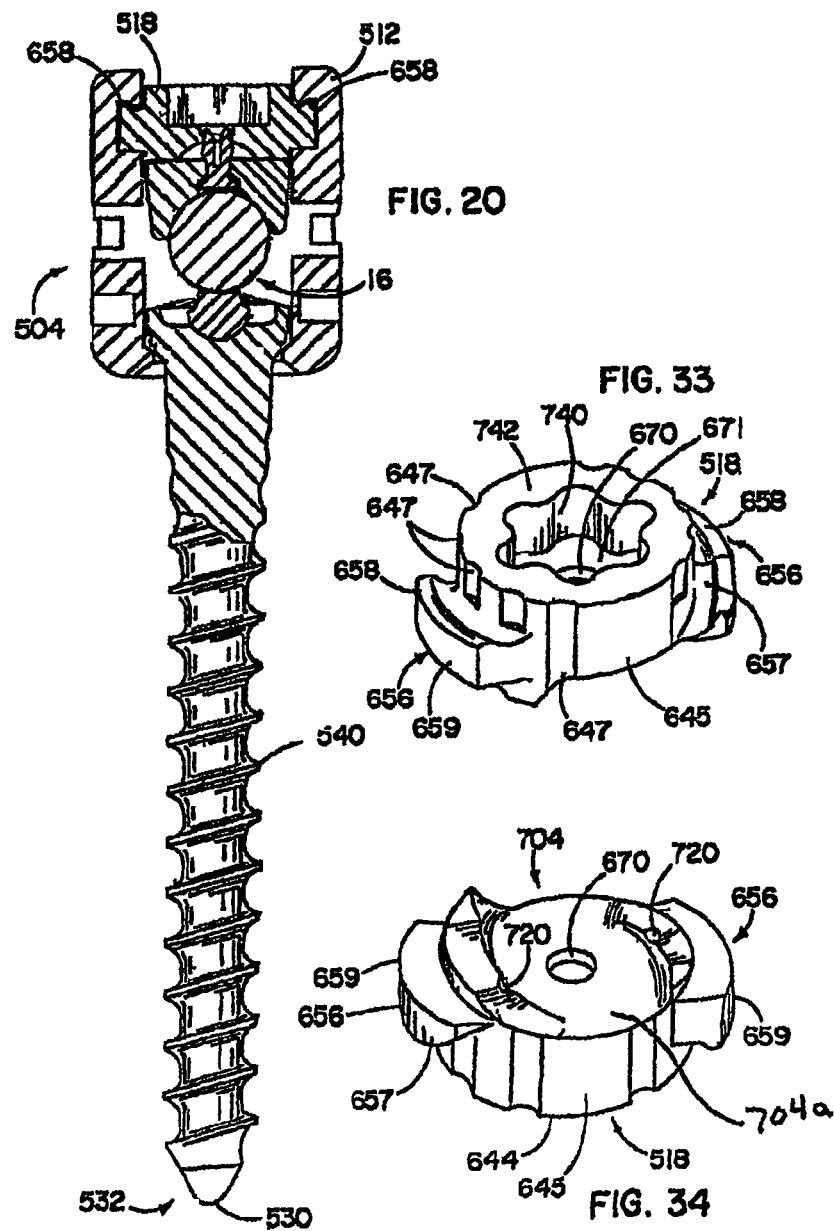

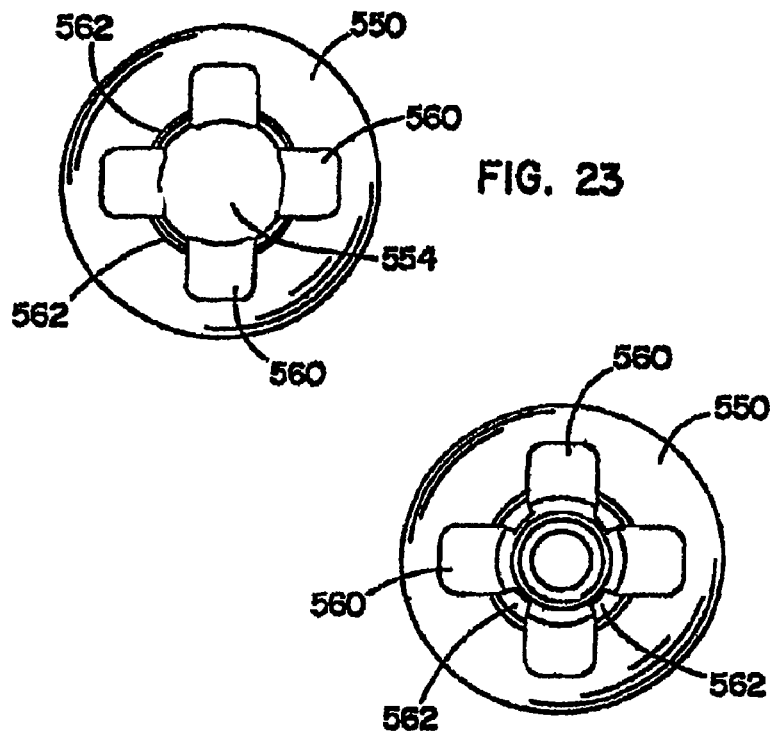
FIG. 23
FIG. 26
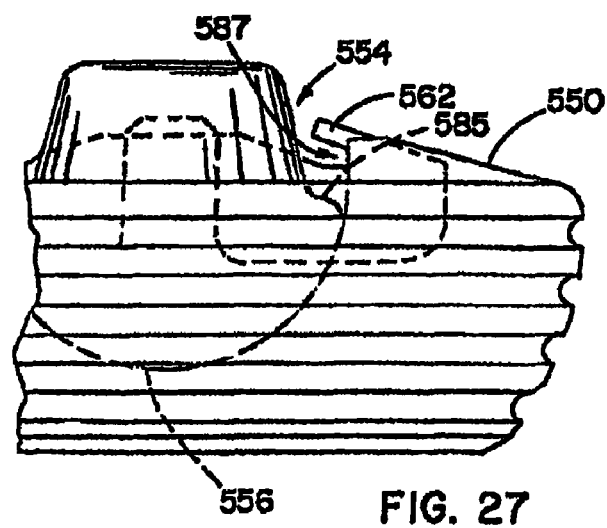
FIG. 27

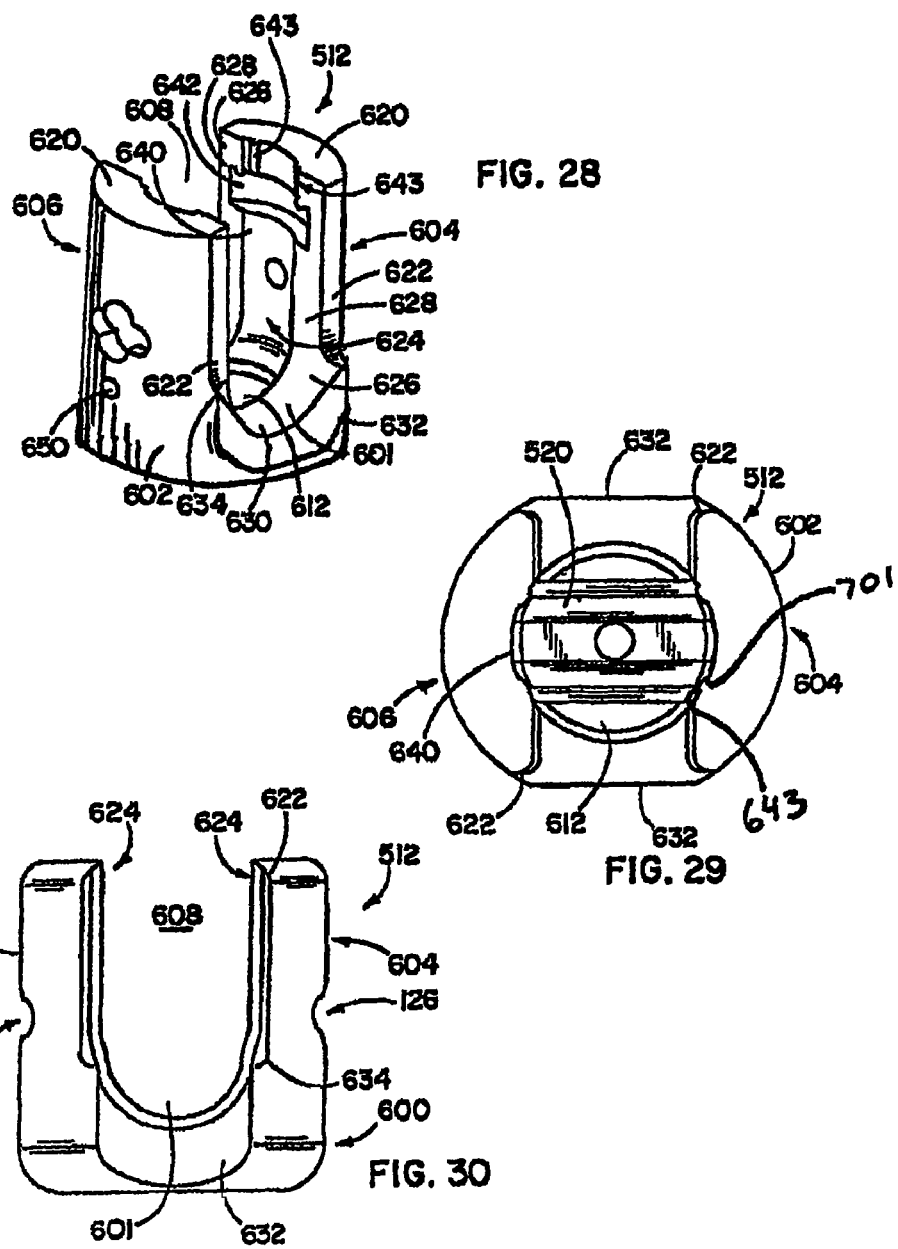

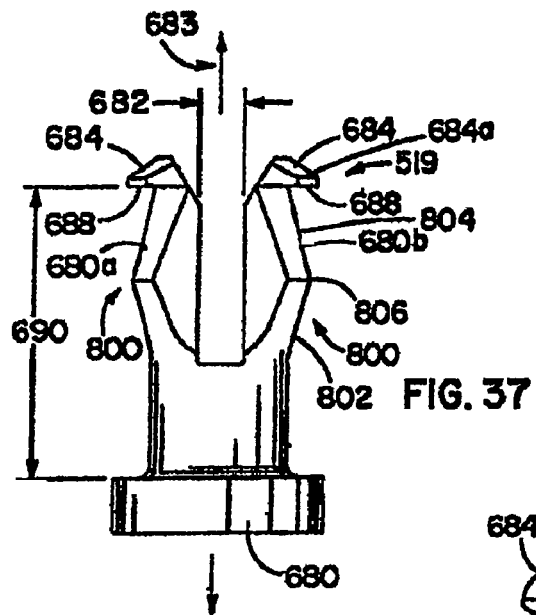
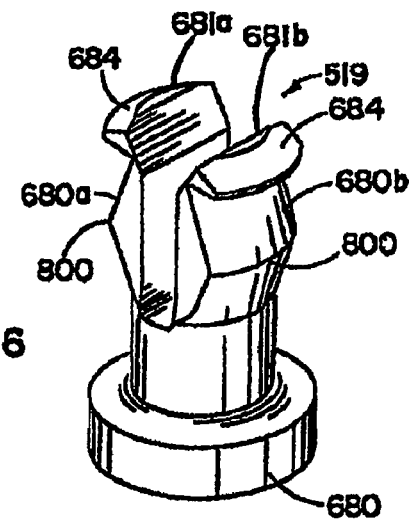
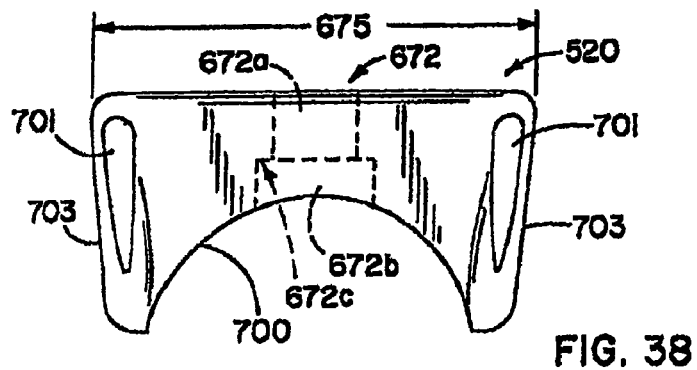

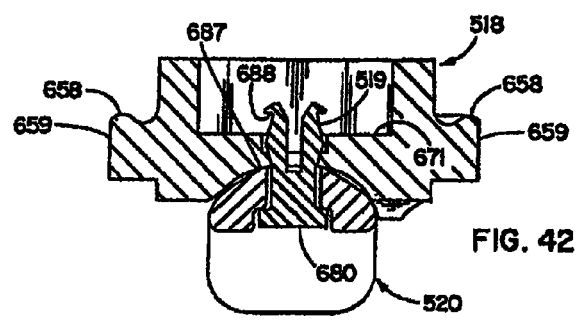
FIG. 42
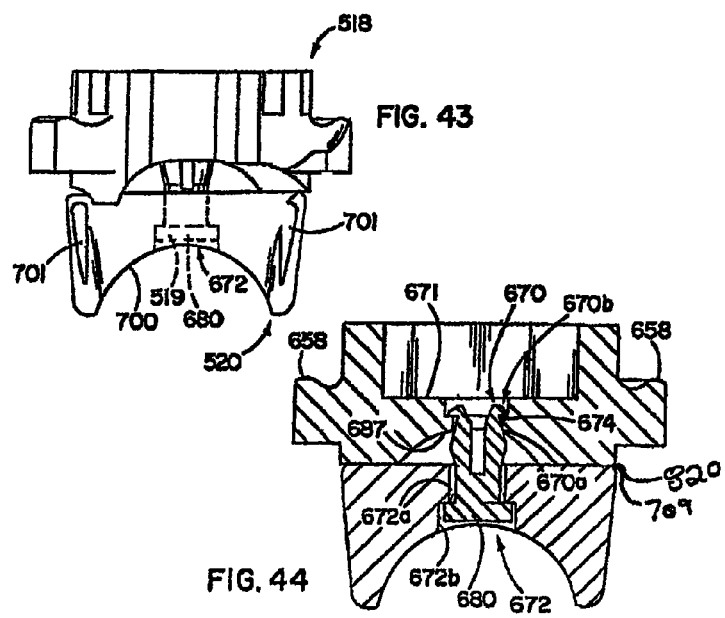
FIG. 43
FIG. 44

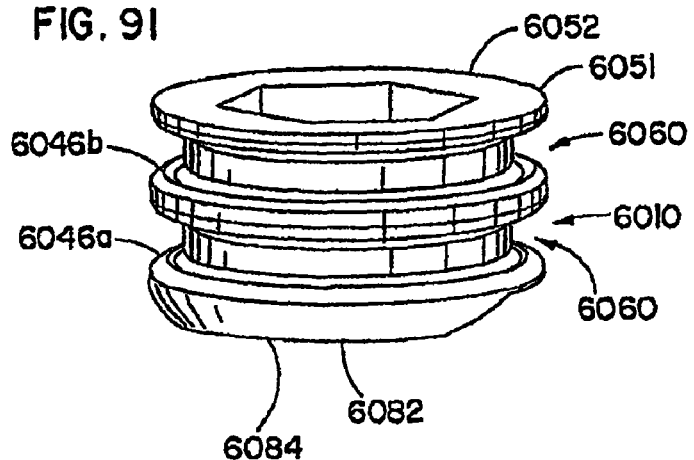
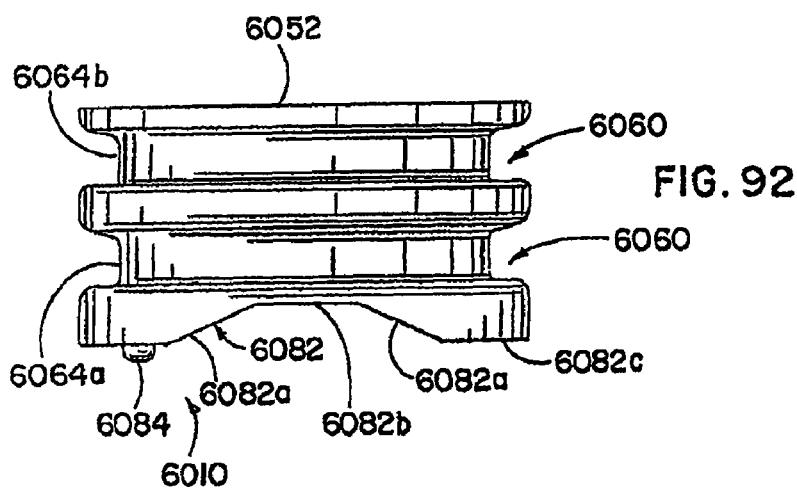
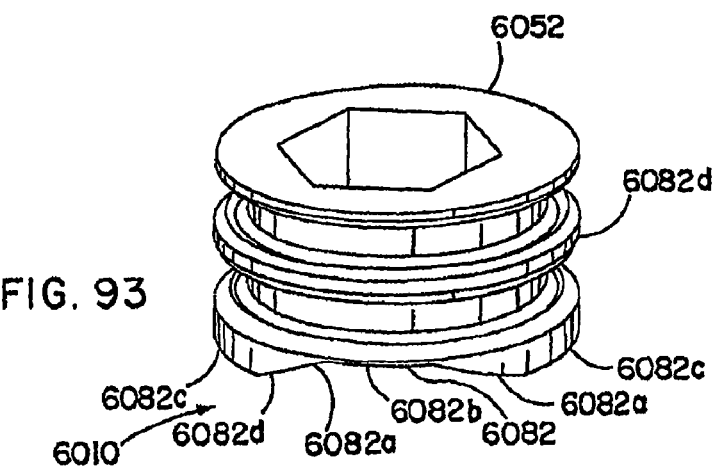

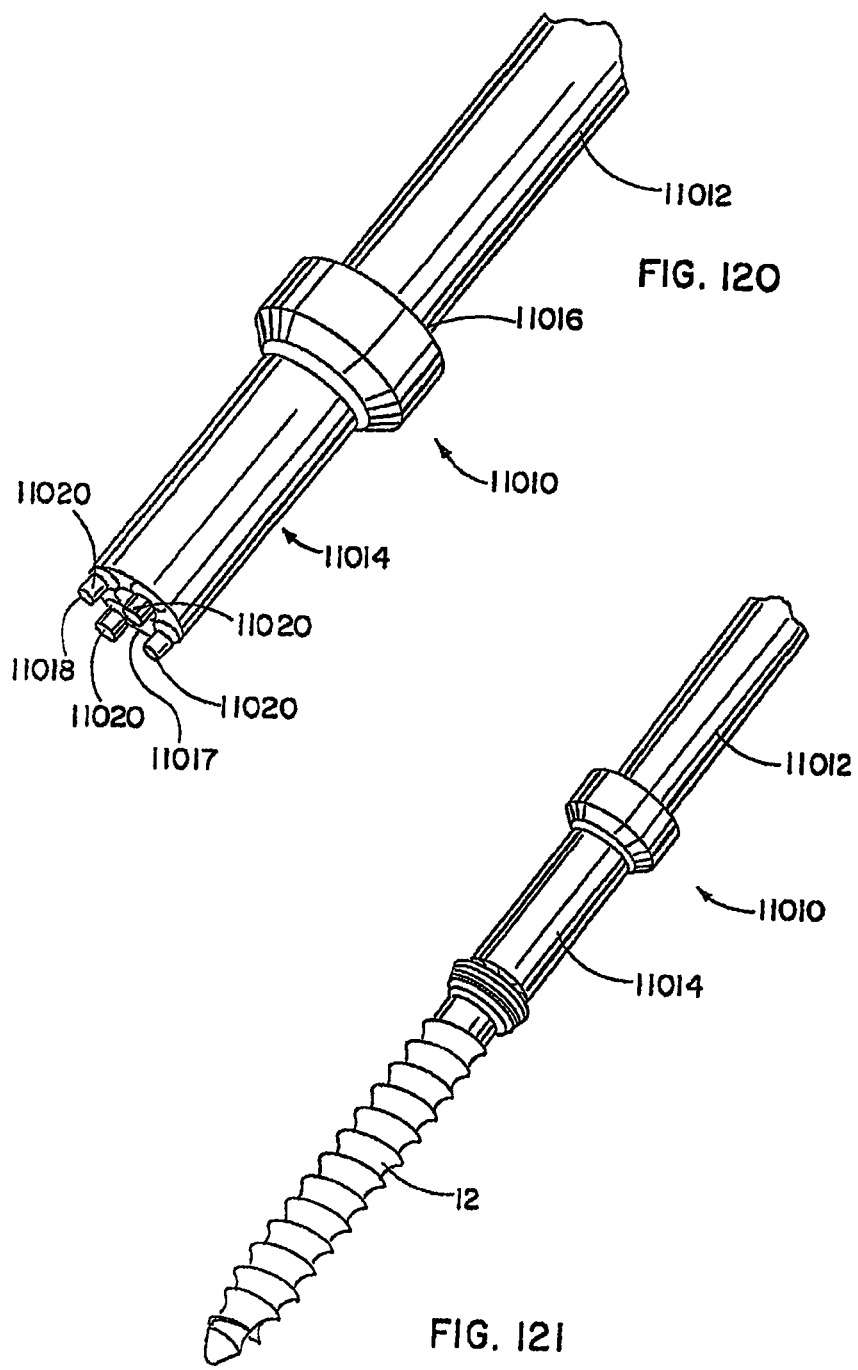

SPINAL ROD ANCHOR DEVICE AND METHOD

CROSS REFERENCE TO RELATED APPLICATIONS

This application claims benefit of U.S. Provisional Application No. 60/822,603, filed Aug. 16, 2006, and Provisional Application No. 60/825,366, filed Sep. 12, 2006, both of which are also hereby incorporated herein by reference in their entirety.

FIELD OF THE INVENTION

The invention relates to spinal fixation systems and, more particularly, to spinal fixation systems having non-threaded locking devices and instruments for insertion thereof.

BACKGROUND OF THE INVENTION

Spinal rods for immobilizing vertebral bones of the spinal column are typically anchored to the vertebrae via anchor members such as bone screws or hooks. The rods are connected to the anchor members by generally yoke-shaped coupling members that can be integral with the anchor member. Alternatively, the coupling members may be a separate component from the anchor member to form the coupling device for use in polyaxial pedicle screw systems for spinal rod fixation. Generally, these prior systems employ a compression or lock member that is advanced toward the spinal rod for securing it relative to the anchor member, and in polyaxial systems for securing the anchor member relative to the coupling member.

For this purpose, the compression member and coupling device typically have a threading engagement therebetween such that the compression member is threaded down into its locked position in or about the yoke-shaped coupler. In this regard, wedge cam surfaces provided on radial flanges of the compression member and in radial recesses in the upstanding walls of the coupling yoke member have also been employed to advance the compression member for pushing the spinal rod down into fixed position relative to the screw anchor member, see U.S. Pat. No. 6,565,565, to Yuan, et al. The problem with the threaded or cam wedge systems of spinal rod locking is that to allow the compression member to advance relative to the coupler, the size or profile of the coupler as well as the compression member may be increased. In other words, to have threads or cam surfaces formed on the coupler requires that the walls be provided with a sufficient axial extent for the advancement of the threaded or cammed compression member therealong.

In polyaxial spinal fixation systems, the use of inserts between the head of the anchor member and the spinal rod has been proposed, see U.S. Pat. No. 5,733,286 to Errico, et al. The large hemispherical insert of Errico, et al. is engaged on a concave recess formed in a screw head received in the coupler allowing the coupler to adjust relative to the polyaxial pedicle screw for receipt of the spinal rod in its desired position. However, the entire Errico, et al. system has an undesirably large profile as it employs a threaded set screw for clamping on the spinal rod, and the hemispherical insert extends well beyond the top of the screw head into the coupler channel through which the spinal rod is received.

With prior threaded systems, it is often difficult for the surgeon to reposition or adjust the spinal rod relative to the fixation system during the surgical procedure after the compression member is inserted into the cap. Once the compression member is initially threaded into the coupling member, any space between the spinal rod and the compression member for final positioning of the rod prior to locking is randomly achieved. For example, the surgeon can randomly thread the compression member a few turns to provide a re-positioning gap between the compression member and rod or completely thread the compression member into a locking position and then back-off the threading to form this re-positioning gap. As a result, the current threaded systems for immobilizing vertebral bones with spinal rods typically require the surgeon to spend more time and guess work for achieving a gap between the compression member and rod for any final positioning of the rod prior to locking. If the re-positioning gap is not large enough, the spinal rod may bind during repositioning, thereby requiring even additional time and adjustment of the compression member to form a larger gap. All this random threading and guesswork by the surgeon requires additional time in the operating room for performing the surgical procedure on the patient.

SUMMARY OF THE INVENTION

In accordance with one aspect of the present invention, a low-profile spinal fixation system is provided. In one aspect, a cam lock member of a coupling device is fixed against translation as it is turned so that a cam surface of the lock member causes an elongate member that extends generally along the spinal column, e.g. spinal rod, to be forced or pushed downward. As the cam lock member does not translate along the coupling device, the size of the coupling device can be kept to a minimum. Further, the low profile of the present system may allow for minimally invasive surgical procedures to be employed therewith such as with the components thereof being cannulated for use with a guide wire.

In another aspect, a polyaxial spinal fixation system is provided having a coupling member including an internal seat surface and a central bore sized to allow the anchor member to extend through the bore in several different orientations. The anchor member includes a head having an upper recess in which a low profile insert is provided. In a preferred form, the insert has an upper surface that is substantially flat. Other alternatives for the insert including the upper surface thereof are that the insert may or may not deform when compressed, the insert upper surface may have radially oriented concave paths or valleys so that the insert rotates to the closest path to meet with the spinal rod, or the insert may have a cup or peripheral ridge that deforms when compressed by the spinal rod to form a path without deforming the spinal rod. The upper surface is fit in the head recess with the insert sized so that the upper surface projects only slightly beyond the proximal end of the anchor member to keep the profile of the insert to a minimum. In one form, the insert upper surface is sized from the interface with the head recess at the bottom of the insert so that even with the anchor member pivoted to its maximum extent relative to the coupling member, the insert upper surface still projects slightly beyond the upper end of the anchor member head, e.g. by approximately 0.010 inch.

In a preferred form, the insert has an enlarged lower portion having a lower arcuate surface thereon for bearing against the concave recess surface of the anchor member head, and a central projection that extends upwardly from the lower portion and includes the flat upper surface thereon. The anchor member head preferably includes a retainer such as in the form of staked portions that allow the insert to self-adjust as the angle of the coupling member is adjusted with the flat surface projecting above the anchor member head for engaging the spinal rod.

In another preferred form, the cam member cooperates with a saddle or clamping member disposed between the cam member and the spinal rod. Upon turning of the cam member to lock the spinal rod, the cam member does not move axially along the coupling member but instead cams against the saddle member driving it axially toward the spinal rod until the spinal rod is secured between the clamping member and the insert. The cam member preferably is secured in assembly to the clamping member with a connector in the form of a dual-pronged spring clip so that the cam member stays assembled with the clamping member during a surgical procedure.

In another preferred form, a spinal fixation system for securing a spinal rod is provided that allows insertion of a lock device or compression assembly to a plurality of predetermined lock positions within a coupling member. The system includes a bone anchor and a coupling device for securing the spinal rod relative to the bone anchor. The coupling device preferably includes a yoke member sized and configured to receive the lock device. The lock device may include multiple components or may be a one-piece or unitary member. This form of the spinal fixation system is advantageous because it permits greater flexibility in adjusting and/or aligning the spinal rod during insertion thereof while keeping the lock device in a releasably held condition in the yoke. With the plurality of lock positions, the spinal fixation system provides ease of adjustment and alignment of a spinal rod particularly where severe spinal curvatures are involved, such as a spinal rod used with scoliosis or kyphosis (three dimensional curvature). In this regard, the spinal fixation system employs a top loading or axial insertion of the lock device into the yoke along its axis to a selected one of a plurality of predetermined axial lock positions. Depending on the specific lock position selected, different predetermined spacing between the lock device and the spinal rod is possible for various amounts or types of shifting, positioning, or aligning of the spinal rod in the yoke prior to the final locking of the rod In one form, there are at least two distinct axially spaced lock positions that are achieved by linearly advancing the lock device without requiring rotation thereof. Preferably, these are lock positions of the lock device that are sequentially reached prior to the final lock position at which the lock device is operable to fix the spinal rod in the yoke member. These preliminary lock positions are preferably achieved exclusively by shifting the lock device in translation along the yoke axis. In this regard, in contrast to prior threaded locking devices, the present system avoids the need to rotate the locking device while still being able to shift the lock device to be releasably held by the yoke member at least two distinct axial position thereof. For this purpose, the lock device is axially inserted into the yoke member via a top loading of the lock device through an upper opening of the yoke member. It is anticipated that the above system will be of particular advantage in minimally invasive surgical systems that employ tubular members through which devices such as the spinal fixation device or system described above may be advanced to the application site. In particular, the lock device can be readily advanced axially through a tubular member holding the yoke member at its distal end to achieve the preliminary lock positions.

In one aspect, the spinal fixation system includes at least three different predetermined lock positions. In a first lock position, the locking device forms a first gap with an inserted spinal rod of a predetermined size to allow movement of the rod both along the yoke axis and also transverse to the yoke axis. This first gap permits ease of shifting a spinal rod with extreme curvatures. In a second lock position, the lock device forms a second, smaller gap with the spinal rod of predetermined size that primarily allows movement of the spinal rod transverse to the yoke axis or along the axis of the rod itself. This second gap permits final adjustments of the rod position prior to final locking of the spinal rod into a fixed position relative to the yoke. In a third lock position, the lock device locks the spinal rod relative to the yoke. Preferably, the first and second lock positions are achieved through a top loading of the lock device along the yoke axis into the yoke. The third lock position is preferably achieved through both a rotational and axial movement of the lock device such as by components of a cap assembly including an upper cap lock member that is rotated while a lower saddle member is shifted axially.

In another aspect, the insertion of the lock device into the coupling device is preferably achieved via flexible or resilient portions of a side wall of the yoke. Alternatively, the resilient portions could be provided on the lock device, or on both the lock device and coupling device. In the preferred form, the yoke side wall includes a resilient portion, and preferably facing resilient portions of wall portions at opposite sides of the yoke, that resiliently or elastically flex in order to permit the receipt of the lock device into an internal space between the wall portions along the yoke axis. The resilient portion is of sufficient resiliency to allow sufficient flexure thereof in a direction transverse to the insertion direction of the lock device during insertion thereof while the wall portions are also sufficiently stiff to retain the lock device in the various locked positions relative to the yoke despite the forces generated between the lock device and the yoke wall portions, particularly with the lock device in the above-described third-lock position.

The lock device and yoke member include cooperating portions preferably in the form of ramp surfaces on both the lock device and the yoke member. As the lock device is advanced axially into the yoke member, a first set of lower ramp surfaces engage corresponding ramp surfaces of the yoke resilient wall portions shifting the wall portions outwardly away from the yoke axis in order to initially receive at least a portion of the lock device in the yoke internal space. As the cap is inserted further along the axis during this initial insertion stage of the lock device, yoke flanges are received in upwardly opening seats or depressions of the lock device adjacent and above the lower ramp surfaces with an audible "click" or other indication as the bottom of the yoke flanges clear the upper edge of the lock device extending about the depressions and the resilient portions resiliently shift back toward their original, undeflected position. The audible indication provides the surgeon feedback that the lock device is in the first locked position in the yoke. The snap-fit receipt of the yoke flanges in the lock device seat keeps the lock device from backing out of the yoke member unless the yoke resilient portions are moved apart such as with a tool.

In this first position, a relatively large gap is formed between the lock device, and specifically the lower saddle member thereof, and the spinal rod. The shifting or snapping back of the resilient portions such that the yoke flanges are received in the depressions also provides the surgeon with tactile feedback along with the audible indication that the lock device is at its first locked position. This large gap has a predetermined axial size such that shifting of the spinal rod both along the yoke axis and transverse to the yoke axis is permitted. The large gap is advantageous because it allows the surgeon to make relatively large adjustments to the position of the spinal rod such as may be necessary to accommodate spines with extensive curvature thereto especially with scoliosis and kyphosis of the spine while the lock device is securely held in fixed axial position relative to the yoke member particularly against axially shifting away from the rod.

Once the surgeon has positioned the spinal rod near its final orientation and position an axial force directed toward the rod is applied to which causes the lock device to advance in the yoke internal space from the first lock position along the yoke axis to a second lock position. During this intermediate insertion stage, a second set of upper ramp surfaces of the lock device push against the ramp surfaces of the resilient portions to shift the resilient portions away from the axis. Similar to the first lock position, a snap-fit of the yoke flanges in an upwardly opening seat adjacent and above the lower ramp surfaces of the lock device is provided. The surgeon again is provided with feedback such as via an audible or tactile indication that the lock device has been properly received in the second lock position. In this position, the yoke flanges keep the lock device from backing out of the yoke space without bending of the resilient wall portions of the yoke member.

When the surgeon is satisfied with the final positioning of the spinal rod after inserting the locking device into the second lock position, the surgeon can lock or fix the spinal rod relative to the yoke via the provision of a third lock position. This locked position is achieved by rotation of the lock device or a portion thereof to axially translate another portion of the lock device into a locked engagement with the spinal rod in order to fix the rod relative to the yoke. Accordingly, in this final insertion stage of the lock device, only a portion thereof is advanced further axially in the yoke member while the rotated actuator portion does not shift axially relative to the yoke member.

BRIEF DESCRIPTION OF THE DRAWINGS

FIG. 20 is a side elevation view partially in section of the system of FIG. 19 in a locked position showing a spinal rod secured between the clamping and insert members;

FIG. 23 is a plan view of the bone screw head showing a recess for the insert;

FIG. 26 is a plan view of the insert retained in the screw head recess;

FIG. 27 is an enlarged cross-sectional view of the screw head and the insert showing one of the staked head portions that retain the insert in the head recess;

FIG. 28 is a perspective view of the coupling member of FIG. 19 including a pair of integral spaced side wall portions;

FIG. 29 is a plan view of the coupling member showing a bottom throughbore through which the bone screw extends, and a saddle located therewithin;

FIG. 30 is a side view of the coupling member showing the spacing between the side walls;

FIG. 33 is a perspective view of the cam lock member of FIG. 19;

FIG. 34 is a bottom perspective view of the cam lock member showing a programmed cam surface at the bottom thereof;

FIG. 36 is a perspective view of the spring clip connector of FIG. 19 showing a pair of resilient prongs;

FIG. 37 is a side elevation view of the connector showing the spacing of the prongs and the flanged free ends thereof;

FIG. 38 is a side view of the clamping member of FIG. 19;

FIG. 42 is a cross-sectional view similar to FIG. 41 showing the spring clip connector with the flanged ends of the clip prongs spaced from the cap member;

FIG. 43 is a side elevation view of the cam lock member and the clamping member in a locked position relative to the spinal rod;

FIG. 44 is a cross-sectional view similar to FIG. 43 showing the clamping member shifted down along with the spring clip connector with the cap member axially fixed and rotated to its locked position;

FIG. 91 is a perspective view of an alternative lock device in the form of a one-piece lock member;

FIG. 92 is an elevational view of the lock device of FIG. 91 showing seating surfaces and lower cam surfaces;

FIG. 93 is a perspective view of the alternative cap assembly showing the lower cam surfaces;

FIG. 120 is a perspective view of a driver tip positioned on the distal end of an elongate shaft of the instrument of FIG. 119;

FIG. 121 is a perspective view of the driver tip of FIG. 120 shown coupled to an exemplary anchor member;

FIG. 129 is a perspective view of the collar of FIG. 125 showing a pair of annular seating grooves on a sidewall thereof;

FIG. 130 is a perspective view of the collar of FIG. 125 showing a ramped cam surfaces on a lower surfaced thereof and a central passage configured to receive the cylindrical body member of the lock member;

FIG. 131 is an elevational view of another form of the spinal fixation system in accordance with the present invention showing a yoke coupling member, spinal rod, and a lock member in the maximum clearance cap-lock position;

FIG. 132 is an elevational view of the spinal fixation system of FIG. 131 showing the lock member in the minimum clearance cap-lock position;

FIG. 133 is an elevational view of the spinal fixation system of FIG. 131 showing the lock member in the rod lock cap-lock position;

FIG. 134 is a perspective view of the lock member of FIG. 131 showing curved cam surfaces on a lower surface thereof;

FIG. 135 is an elevational view of the lock member of FIG. 134 showing a curved portion of the lower surface thereof and annular seating grooves on a side wall thereof;

FIG. 136 is a perspective view of the lock member of FIG. 131 showing curved cam surfaces on the lower surface thereof;

FIG. 137 is an elevational view of the lock member of FIG. 134 showing a curved portion of the lower surface thereof and annular seating grooves on a side wall thereof;

FIG. 138 is an elevational view of another form of the spinal fixation system in accordance with the present invention showing a yoke coupling member, spinal rod, and a lock member in the maximum clearance cap-lock position;

FIG. 139 is an elevational view of the spinal fixation system of FIG. 138 showing the lock member in the minimum clearance cap-lock position;

FIG. 140 is an elevational view of the spinal fixation system of FIG. 138 showing the lock member in the rod lock cap-lock position;

Figure 138:
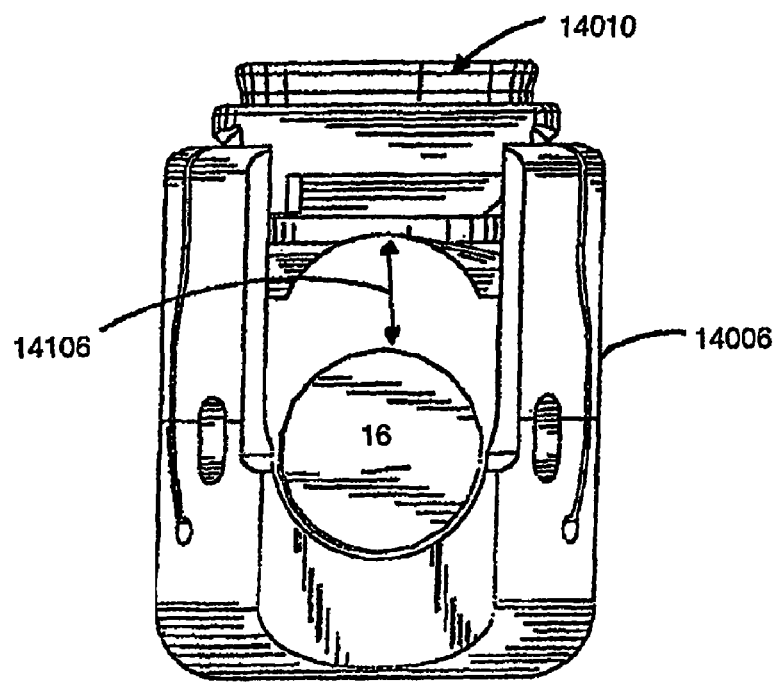
Figure 141:
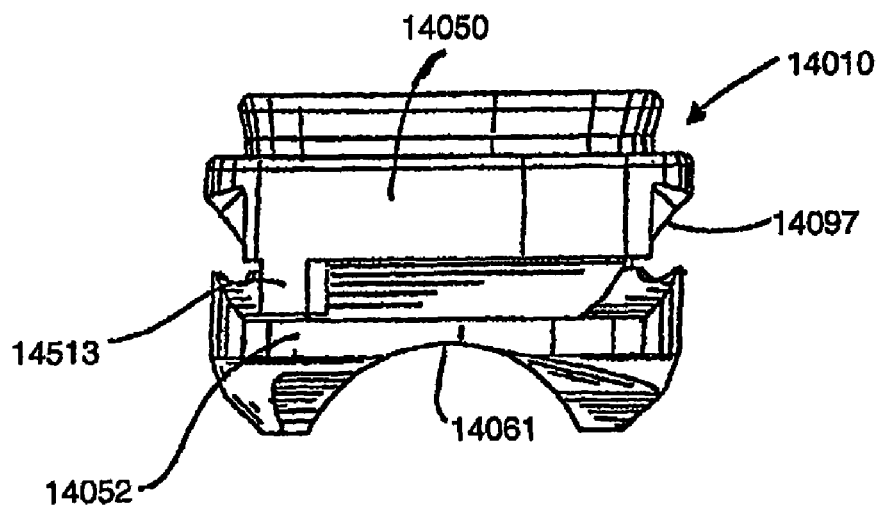
Figure 143:
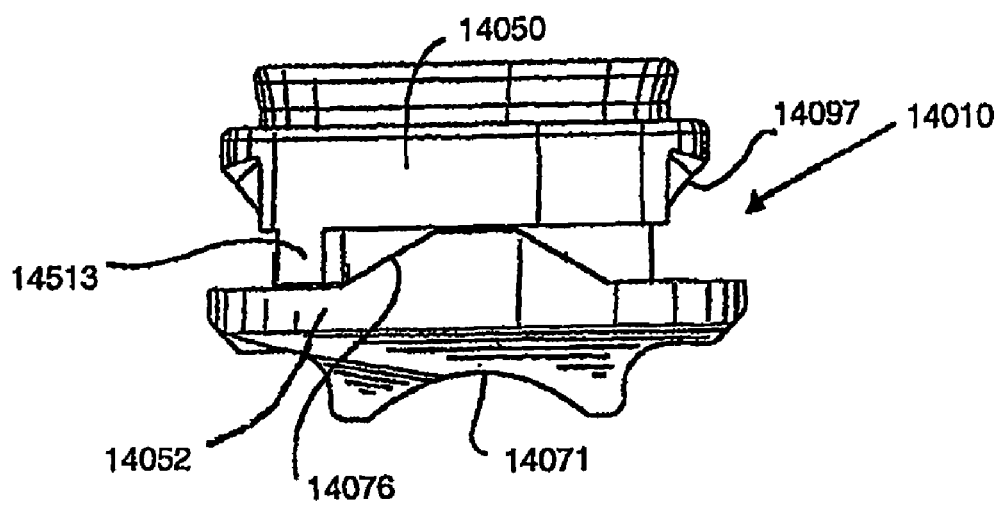
Figure 142:
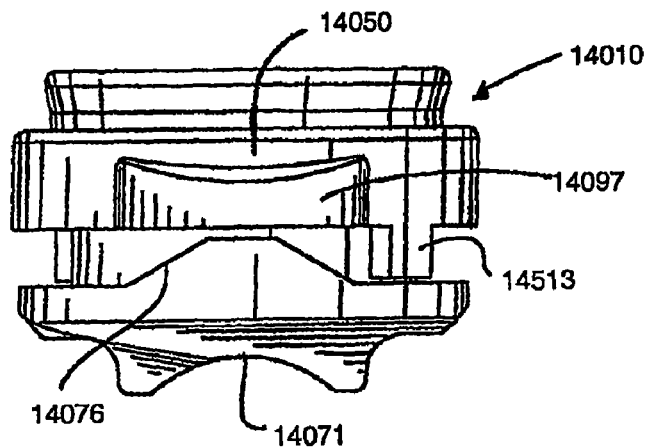
Figure 144:
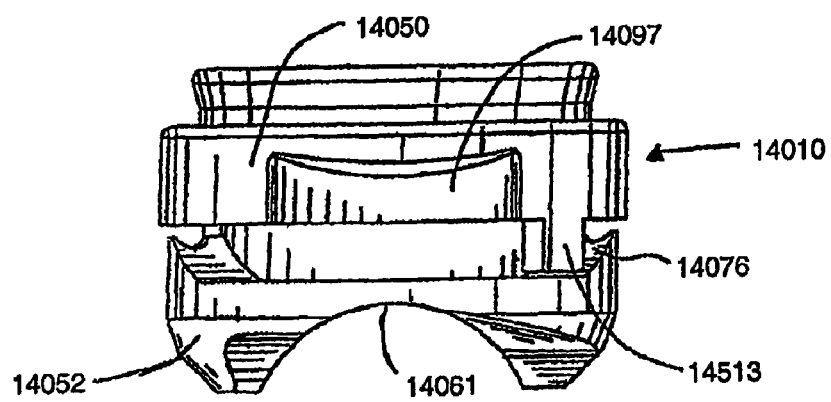
Figure 145:
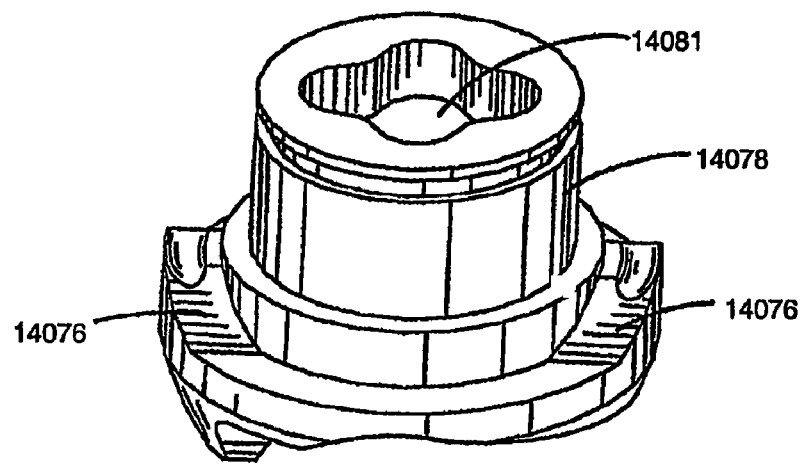
Figure 146:
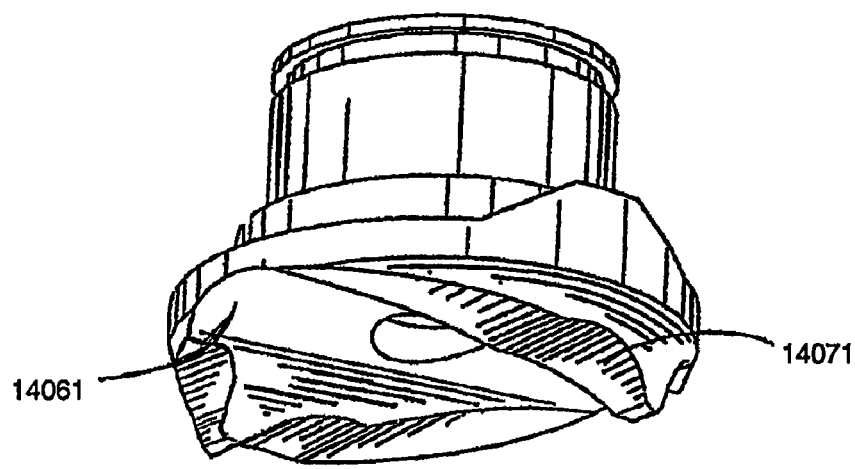
Figure 147:
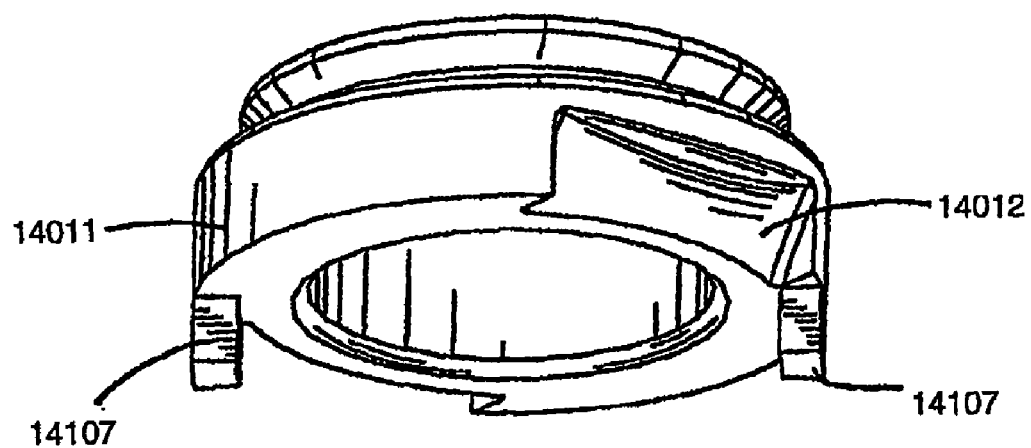
Figure 148:
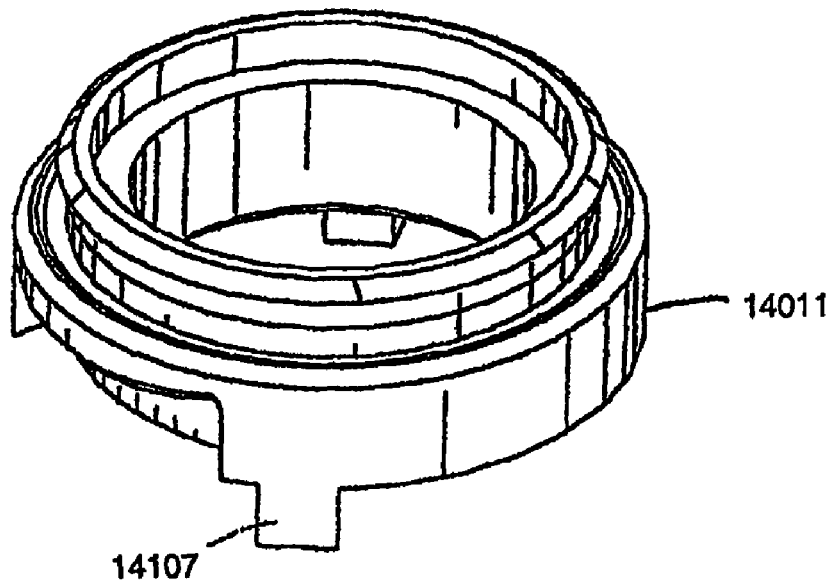
Figure 149:
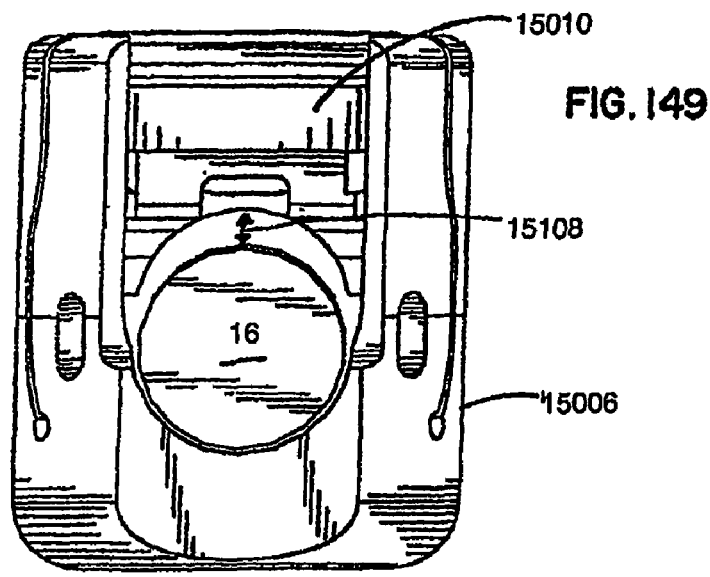
Figure 150:
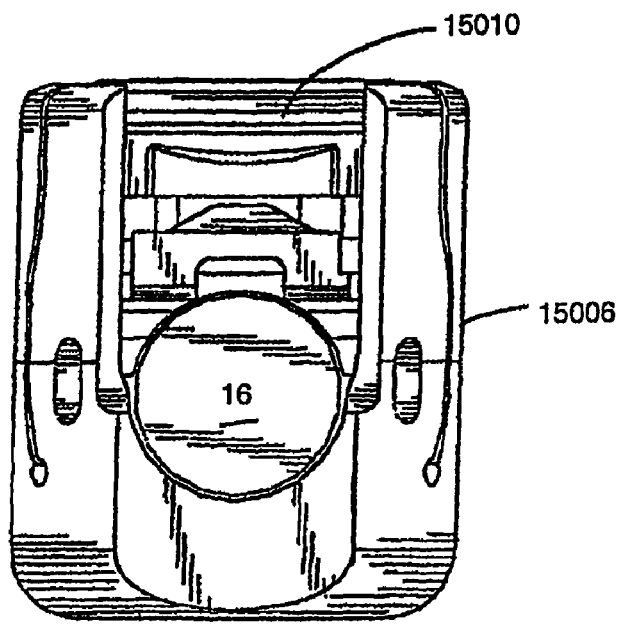
Figure 151:
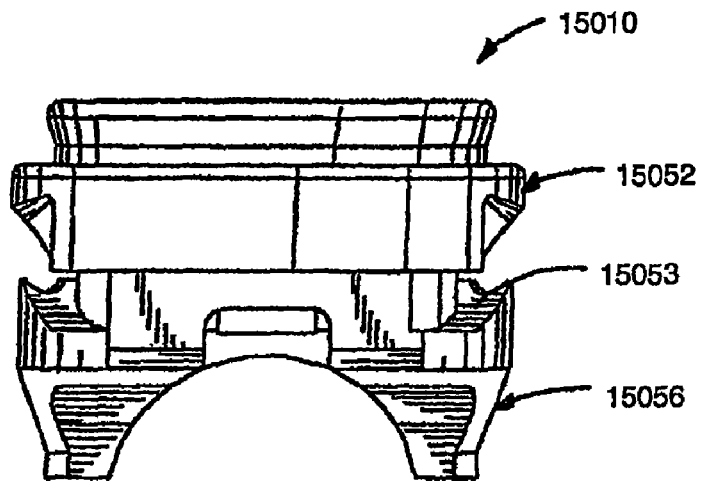
Figure 152:
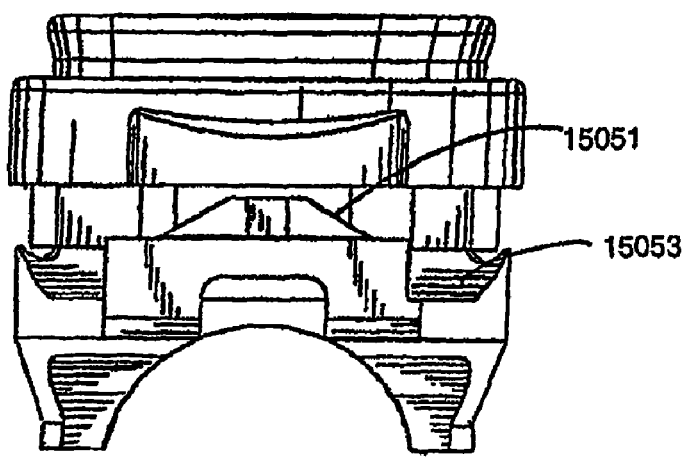
Figure 153:
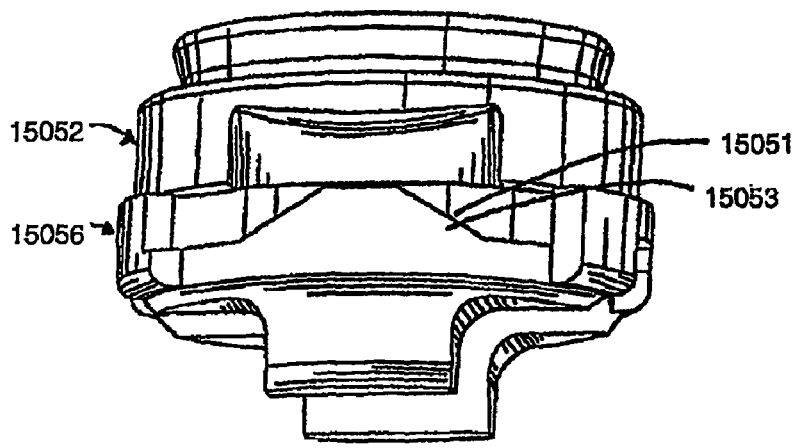
Figure 154:
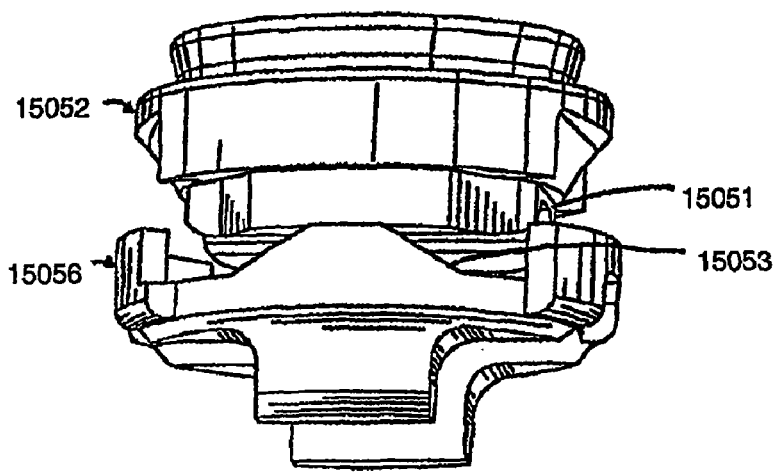
Figure 155:
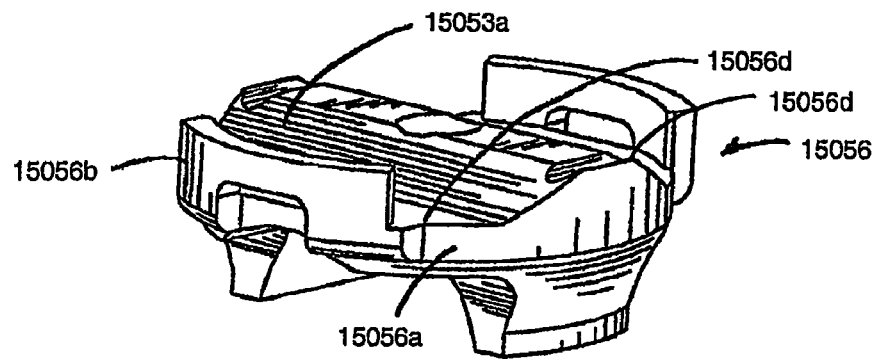
Figure 156:
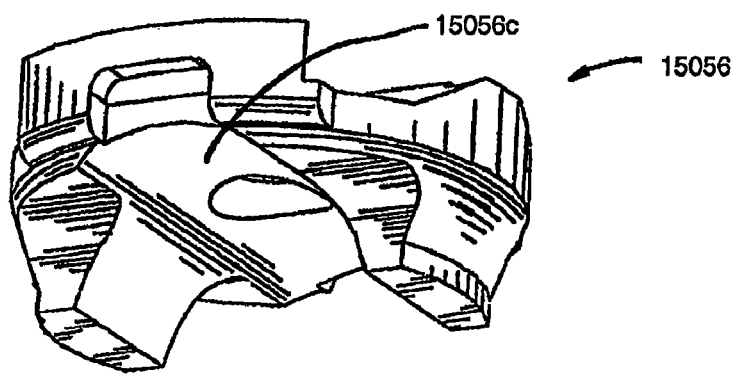
Figure 157:
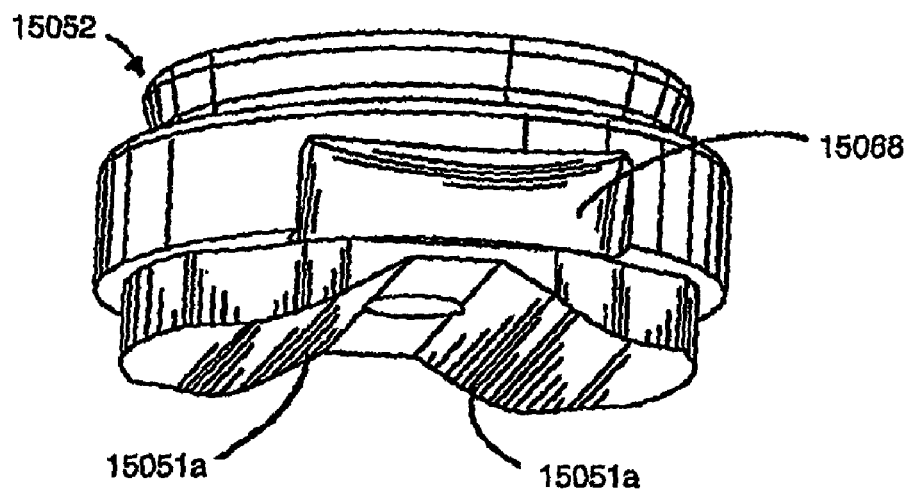
Figure 158:
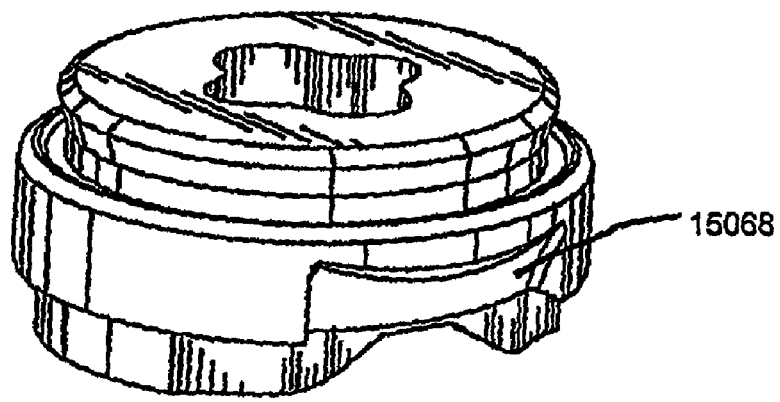

FIG. 141 is an elevational view of the lock device of FIG. 138 showing respective engaging surfaces of a collar and a lock member in mating relation such that the collar and lock member are in an unlocked configuration;

FIG. 142 is another elevational view of the collar and lock member of FIG. 141 showing the respective engaging surfaces positioning the collar and lock member in the unlocked configuration;

FIG. 143 is an elevational view of the collar and lock member of FIG. 141 showing the respective engaging surfaces rotated relative to each other to shift the collar and the lock member into an locked configuration;

FIG. 144 is another elevational view of the collar and lock member of FIG. 143 showing the respective engaging surfaces rotated relative to each other to shift the collar and lock member into an locked configuration;

FIG. 145 is a perspective view of the lock member of FIG. 138 showing a base member having ramped surfaces on an upper surface thereof and a main cylindrical body having a lobed recess thereof;

FIG. 146 is a perspective view of the lock member of FIG. 138 showing a lower surface of the base member including curved cam surfaces thereof;

FIG. 147 is a perspective view of the collar of FIG. 188 showing inclined ramp surfaces on an annular sidewall thereof and depending lock arms;

FIG. 148 is a perspective view of the collar of FIG. 138 showing an annular seating surface thereof;

FIG. 149 is an elevational view of another form of the spinal fixation system in accordance with the present invention showing a yoke coupling member, spinal rod, and a lock device in the minimum clearance cap-lock position;

FIG. 150 is an elevational view of the spinal fixation system of FIG. 149 showing the lock device in the rod-lock position;

FIG. 151 is an elevational view of the lock device of FIG. 149 showing respective engaging surfaces of a lock member and a saddle member in mating relation to position the lock member and saddle member in an axially compact configuration;

FIG. 152 is an elevational view of the lock member and saddle member of FIG. 149 showing the respective engaging surfaces rotated relative to each other to shift the lock member and the saddle member into an axially extended configuration;

FIG. 153 is another elevational view of the lock device of FIG. 149 showing respective engaging surfaces of the lock member and the saddle member in mating relation to position the collar and lock member in an axially compact configuration;

FIG. 154 is another elevational view of the lock member and saddle member of FIG. 149 showing the respective engaging surfaces rotated relative to each other to shift the lock member and the saddle member into an axially extended configuration;

FIG. 155 is a perspective view of the saddle member of FIG. 149 showing a disk-shaped base member and extensions extending upwardly from outer edges thereof; seating surfaces on the extensions; and ramp surfaces on an upper surface thereof;

FIG. 156 is a perspective view of the saddle member of FIG. 149 showing a saddle surface on a lower surface of the base member thereof;

FIG. 157 is a perspective view of the lock device of FIG. 149 showing an annular body having upwardly inclined ramp surfaces on a lower surface thereof; and FIG. 158 is a perspective view of the lock device of FIG. 149 showing an annular seating surface on a side wall thereof.

DETAILED DESCRIPTION OF THE PREFERRED EMBODIMENTS

Figure 1:
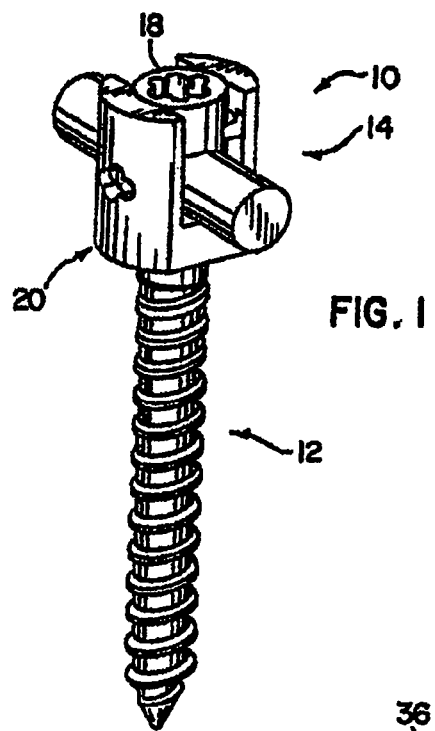
FIG. 1 is a perspective view of the spinal fixation system in accordance with one form of the present invention showing a bone screw and a coupling device including a coupling member and a cam lock member for securing a spinal rod relative to the bone screw.
Figure 2:
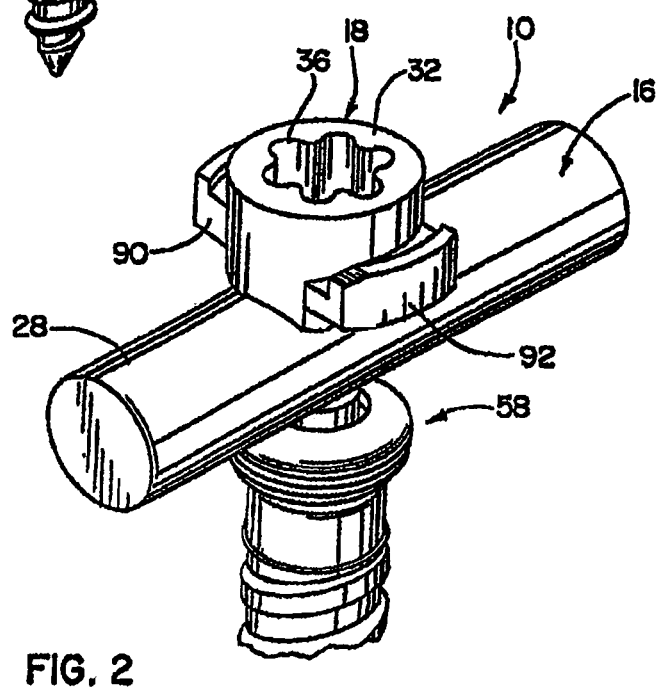
FIG. 2 is an enlarged perspective view of the spinal fixation system of FIG. 1 with the coupling member removed to better illustrate the cam lock member and to show the configuration of the head of the bone screw.
Figure 4:
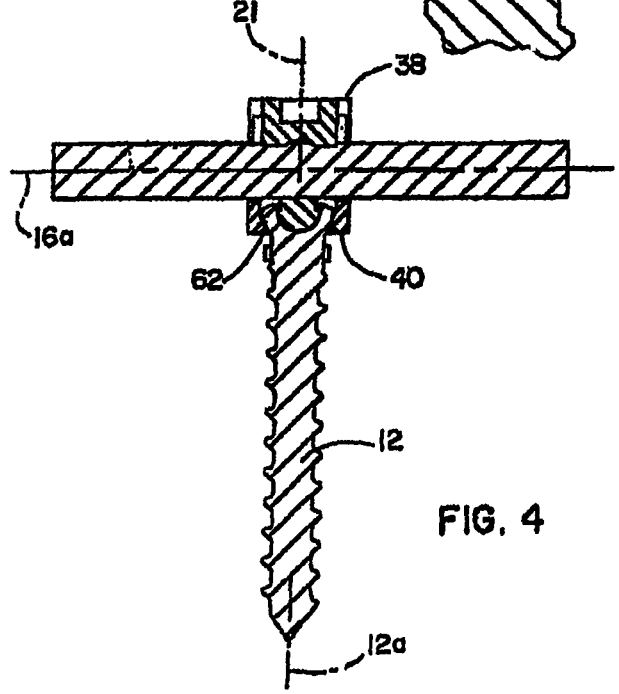
FIG. 4 is a cross-sectional view similar to FIG. 3 showing the relative sizes of the various components of the spinal fixation system.

In FIGS. 1 and 2, a low profile spinal fixation system 10 in accordance with one form of the present invention is depicted. As shown, the spinal fixation system 10 includes a bone anchor member in the form of a bone screw 12 and a coupling device generally designated 14. The coupling device 14 is operable to secure an elongate member in the form of spinal rod 16 in place relative to the bone screw 12. The coupling device 14 includes a compression or cam lock member 18 and a coupling member 20, which cooperate to secure the spinal rod 16 relative to the bone screw 12 anchored in a vertebral bone with the rod 16 generally extending axially along the spinal column. The coupling device 14 and specifically the cam lock member 18 and coupling member 20 are provided with a compact configuration. In particular, the cam lock member 18 and coupling member 20 are provided with a very low profile in a direction indicated by axis line 21 extending transverse and specifically orthogonally to the axis 16a of the spinal rod 16 fixed relative to the bone screw 12 by the coupling device 14, as best seen in FIG. 4.

More specifically, the low profile of the coupling device 14 is obtained by having the cam lock member 18 be effective to lock the spinal rod 16 without the need to advance the cam lock member 18 along the coupling member 20. In this regard, the coupling member 20 can be provided with a body 22 having side openings 24 and 26 through which the spinal rod 16 passes with the body 22 free of any threading or cam surfaces that cooperate with the cam lock member 18 for locking of the spinal rod 16 relative to the bone screw 12. Instead, the cam lock member 18 is fixed against translation relative to the coupling member 20, and preferably cooperates with the outer curved surface 28 of the rod 16 itself to secure it in position relative to the screw 12 in the system 10.

Figure 8:
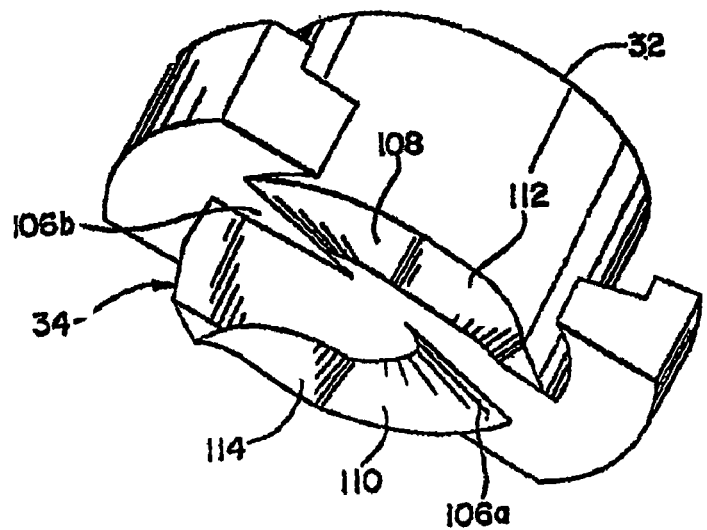
Figure 9:
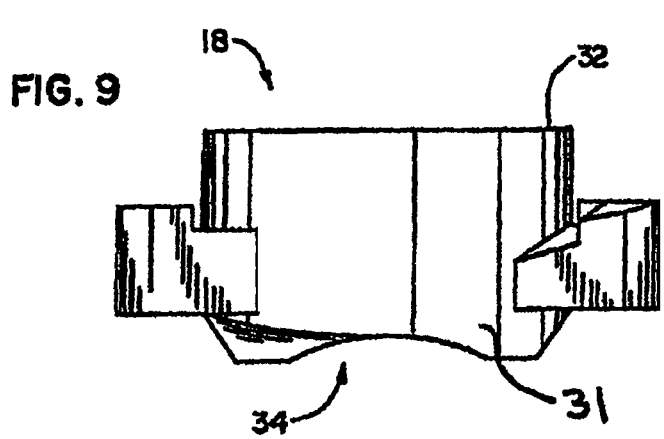
Figure 10:
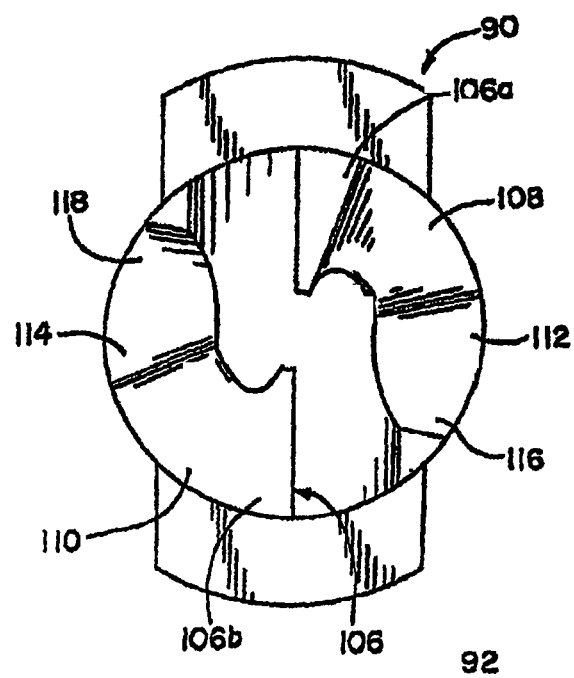

For this purpose, the cam lock member 18 has a generally annularly configured body 30 having a very short axial extent along turning axis 21 thereof via annular side surface 31 extending between its top and bottom surfaces 32 and 34. The top surface 32 is provided with driving surface portions 36 which cooperate to form a predetermined configuration for the receipt of a similarly configured drive tool for turning the cap member 18 between unlocked and locked positions thereof. The bottom surface 34 is programmed or contoured to provide a camming action on the curved surface 28 of the rod 16 when the cam lock member 18 is turned, as best seen in FIGS. 8 and 10 and as will be described more fully hereinafter.

Figure 16:
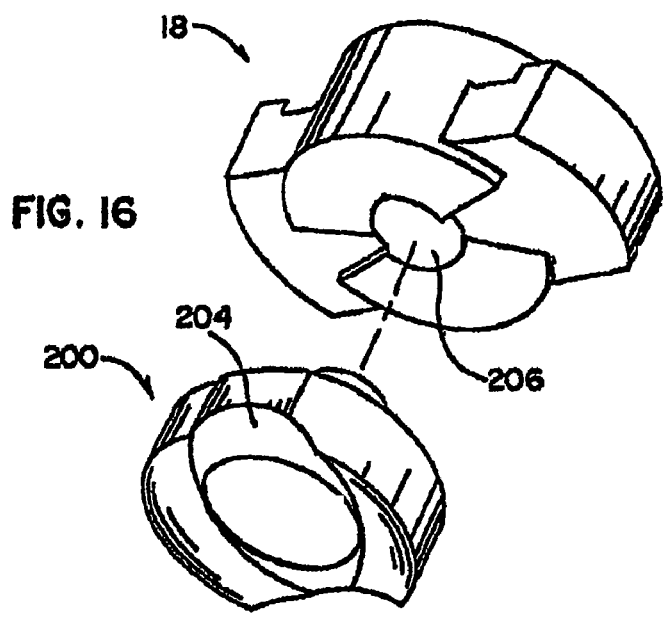
FIGS. 16-18 are various views of alternative camming system employing both a cam lock member and a saddle member.
Figure 17:
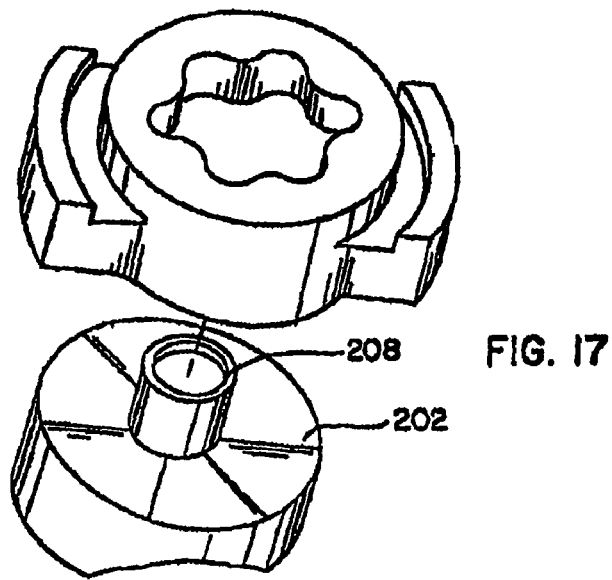
Figure 18:
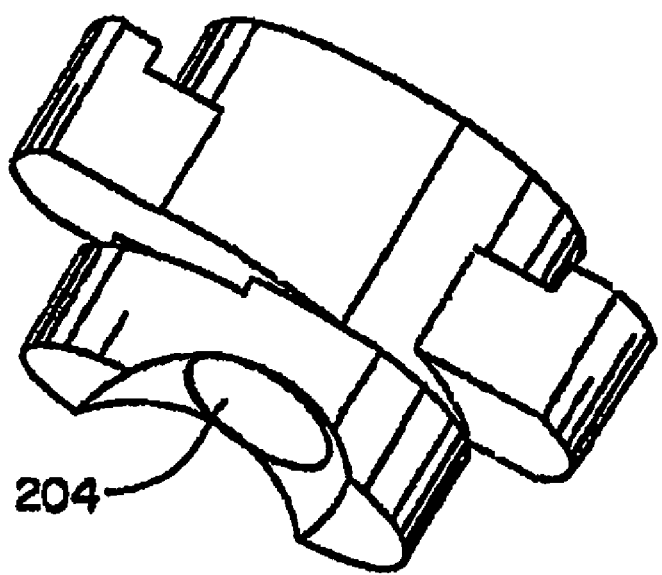

Although less preferred in terms of maintaining a low profile for the spinal fixation system 10 herein, an intermediate clamping member in the form of saddle member 200 can be provided between the lock member 18 and spinal rod 16, as shown in FIGS. 16-18. The saddle member 200 has an upper cam surface 202 configured for cooperation with lock member cam surface 34 when the lock member 18 is turned to its locked position so that the saddle member 200 shifts downwardly along axis 21 for clamping against the rod 16. The saddle member is provided with a curved bottom surface 204 which substantially matches the curvature of rod surface 28 so that the saddle member 200 engages and pushes against the rod 16 without camming thereagainst. The cam lock member 18 can include a center opening 206 which receives a central post 208 projecting upward from the saddle member 200 to keep the cam lock member 18 and saddle member 200 oriented properly with respect to each other.

Figure 11:
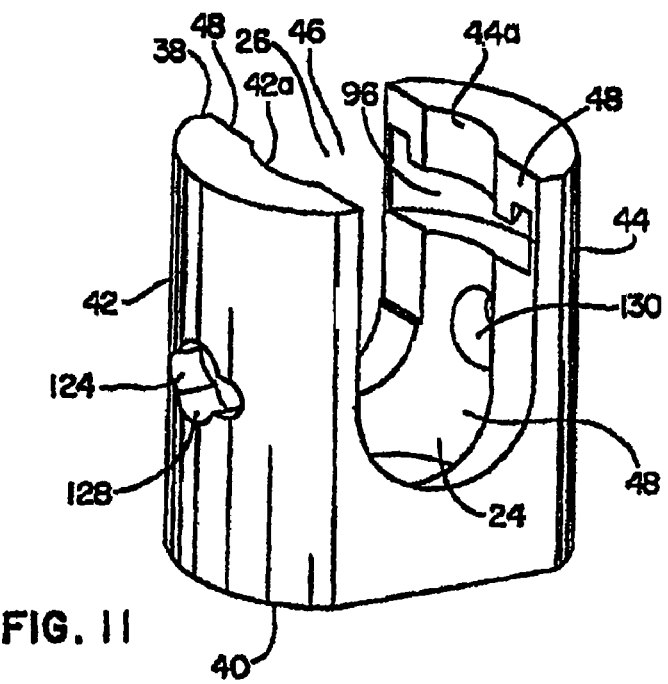
FIGS. 11-13 are various views of the yoke-shaped coupling member.
Figure 12:
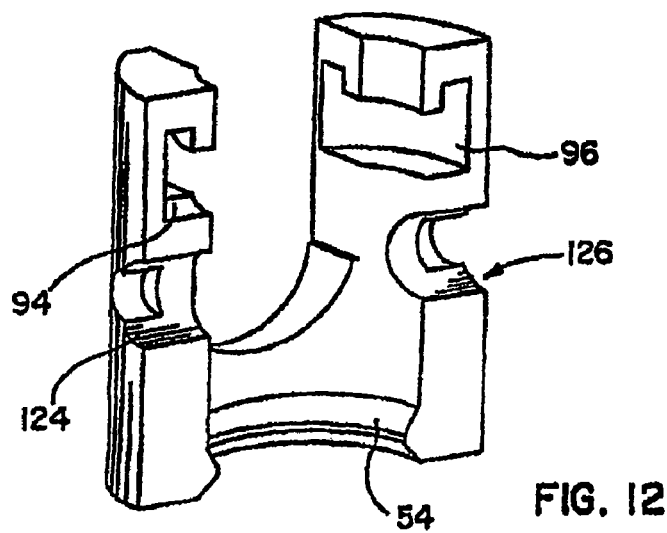
Figure 13:
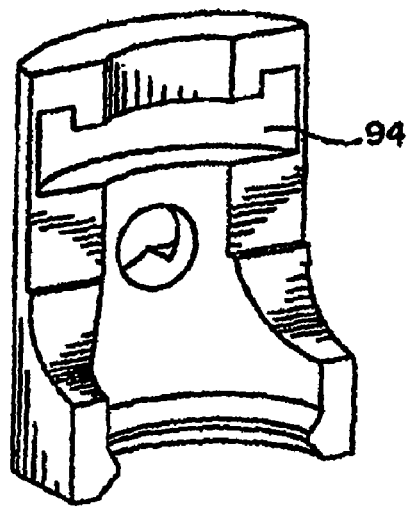
Figure 14:
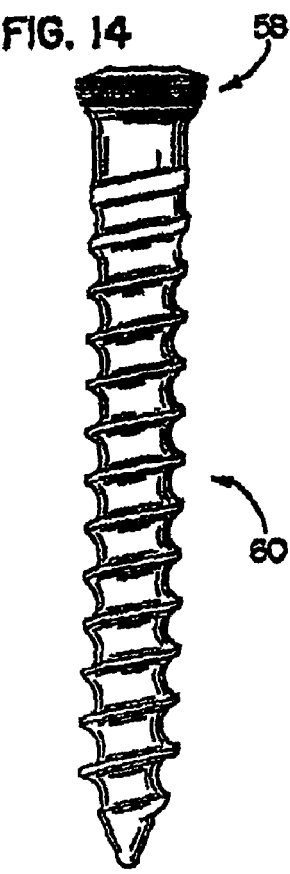
FIGS. 14 and 15 are elevational and sectional views, respectively, of the bone screw anchor member.

Similar to the cam lock member 18, the coupling member 20 also has a relatively small axial extent between top and bottom surfaces 38 and 40 thereof. As best seen in FIG. 11, the body 22 of the coupling member generally has a U-shaped or yoke configuration including opposing upstanding walls 42 and 44 spaced from each other by the rod openings 24 and 26 which can have an elongate configuration and be open to the top 38 of the coupling member body 22. Since the cam lock member 18 need not be advanced down along the walls 42 and 44 in the direction 21, the size in this direction can be minimized. By way of example and not limitation, the length or distance that the walls 42 and 44 extend between the top 38 and bottom 40 of the coupling member body 22 can be approximately 13.47 millimeters. The cam lock member 18 has a profile along axis 21 between the top 32 and the lowest most point of the contoured bottom cam surface 34 of approximately 5.08 millimeters.

Figure 7:
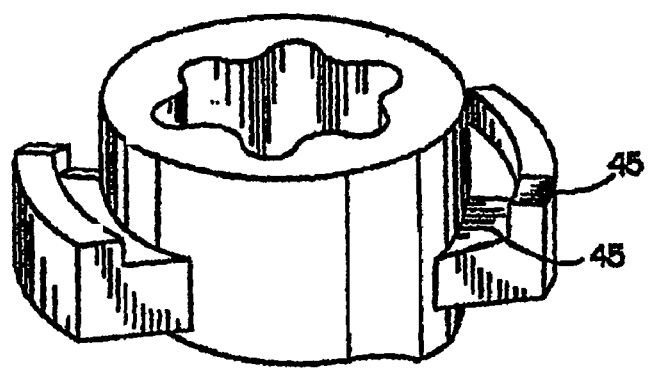
FIGS. 7-10 are various views of the cam lock member.

As shown, the annular body 30 of cam lock member 18 is sized to fit in internal space 46 of the coupling member 20 between the arcuate walls 42 and 44 thereof. The walls 42 and 44 are free of threading or cam surfaces that cooperate with the cam lock member 18 for shifting it to a locked position. More particularly, the inner surface 48 of the coupling member 20 including arcuate surface portions 42a and 44a on the respective coupling member walls 42 and 44 are sized to closely receive the outer surface 31 of the cam lock member annular body 30 therebetween. These surface portions 42a and 44a are each free of threading or cam surfaces and thus only serve as guide surfaces for the cam lock member body 30 as it is turned about axis 21. Since the walls 42 and 44 do not need to be threaded or provided with recessed cam surfaces or the like, the size of the coupling device 14 can be kept to a minimum in the widthwise direction along the axis 16a of the spinal rod 16 as well. By way of example and not limitation, the diametrical width of the coupling device along spinal rod axis 16a can be approximately 10.03 millimeters. As can be seen in FIG. 7, guides 45 may be provided. The guides 45 are provided to initially pilot the cam lock member 18 into engagement with the walls 42 and 44.

Figure 3:
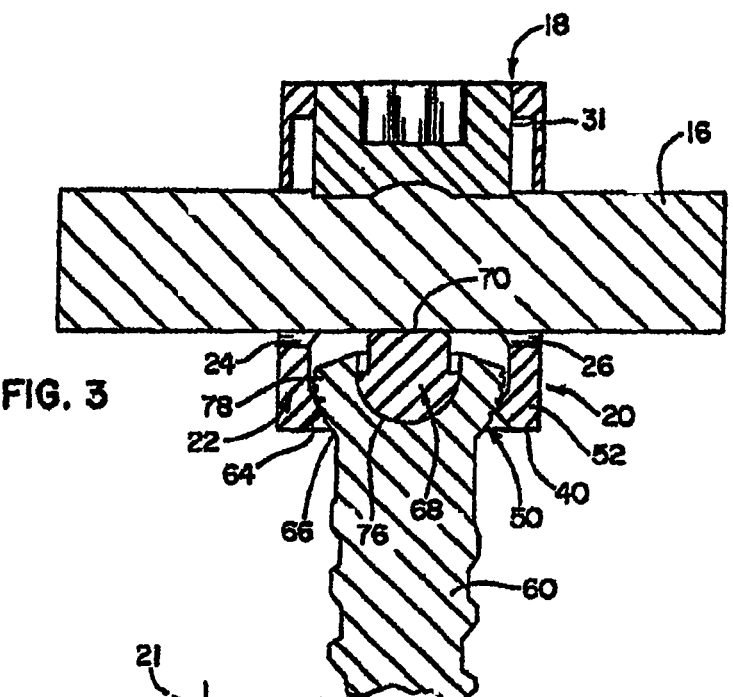
FIG. 3 is a cross-sectional view of the spinal fixation system showing a recess formed in the screw head in which a low profile anvil insert is received for clamping of the spinal rod thereagainst.

Referring next to FIGS. 3 and 4, the illustrated spinal fixation system 10 has a polyaxial bone screw 12 whose orientation can be changed such that its longitudinal axis 12a extends transverse to the axis 21 of the coupling device 14 or is substantially aligned therewith. To this end, the coupling device 18, and specifically the coupling member 20 thereof is provided with a bottom throughbore 50 that extends through bottom wall 52 of the coupling member 20. The bottom wall 52 includes an inner surface portion 54 that tapers or curves inwardly from the surface portions 42a and 44a toward the center axis 21. The diameter across the inner surface portion 54 at its lowermost end 56 is sized to be smaller than an enlarged head 58 of the bone anchor screw 12. In addition, the diameter at 56 is sufficiently large to allow the threaded shank 60 depending from the screw head 58 to be advanced therethrough. In this manner, the inner surface portion 54 serves as a seating surface for the screw head 58. As an alternative, the diameter 56 is threaded with a thread oversized relative to the shank 60, thereby allowing the screw shank 60 to be loosely threaded through. In this instance, the diameter 56 is sized as to hold the shank 60 from passing easily through so that the screw 12 and coupling member 20 may be handled by a surgeon as a single component during the operation. In addition, the oversized threads allow the screw to be polyaxial in its orientation. As a further alternative, the screw 12 may be passed through the diameter 56, and a c-ring or radial spring may be attached to the screw 12 immediately adjacent to the coupling member 20, thereby holding the two together and allowing the surgeon to utilize them as a single component during the operation.

The throughbore 50 extends centrally through the inner surface portion 54 and includes an enlarged diameter lower portion 62 formed by tapered or curved surface portion 64 on the bottom wall 52 of the coupling member 20. The tapered surface portion 64 extends from the smallest diameter of the bore 50 at 56 tapering outwardly relative to the center axis 21 of the coupling member 20 to the bottom surface 40 thereof. The enlarged bore portion 62 allows the screw 12 to swivel or pivot to a variety of different orientations thereof relative to the coupling device 14. For example, in the illustrated form, the enlarged bore portion 62 allows the screw shank to pivot by 20 degrees on either side of the coupling device axis 21. As the screw 12 is pivoted, the outer arcuate surface 66 of the screw head 58 rides or shifts on the tapered seat surface 54 in the coupling member 20. Once the orientation of the coupling device 14 relative to the bone screw 12 fastened into a vertebral bone is determined with the spinal rod 16 extending through the coupling member 20 and up along the spinal column, the cam lock member 18 is then turned to its locked position. In the locked position, the cam lock member 18 anchors the rod 16 to the spinal column so it is fixed relative to the bone screw 12 fastened into a vertebral bone with the bone screw head 58 clamped against the seat 54 therefor in the coupling member 20 thereby fixing coupling device 14 against shifting relative to the bone screw 12. The outer screw head surface 66 can be configured with concentric friction enhancing ridges or helical threads 67 to enhance the locking action between the screw head 58 and the seat 54.

Continuing reference to FIGS. 3 and 4, it can be seen that in the preferred and illustrated polyaxial spinal fixation system 10, the spinal rod 16 is pushed downwardly for being clamped against a small anvil insert 68. It should be noted that the previously described low profile coupling device 14 could be employed in spinal fixation systems that are not polyaxial and/or which do not employ an insert as described hereinafter.

Similarly, the present insert 68 could be advantageously employed in systems that employ threads or cams in the coupling members thereof.

The insert 68 has an upper anvil surface 70 that engages against the underside of the spinal rod surface 28 to maintain enhanced contact therewith over the curved surfaces of bone screw heads used in prior systems. The insert 68 has an upper surface 70 that may be substantially flat, may have radially oriented concave paths or valleys so that the insert 68 rotates to the closest path to meet with the spinal rod surface 28, or may have a cup or peripheral ridge that deforms when compressed by the spinal rod 12 to form a path without deforming the spinal rod. Accordingly, the insert 68 provides at least a line of contact with the curved rod surface 28, whereas prior systems engaging spinal rods with their curved fastener heads have a point contact with the spinal rod when clamped thereagainst which can more easily damage the rod 16.

Figure 5:
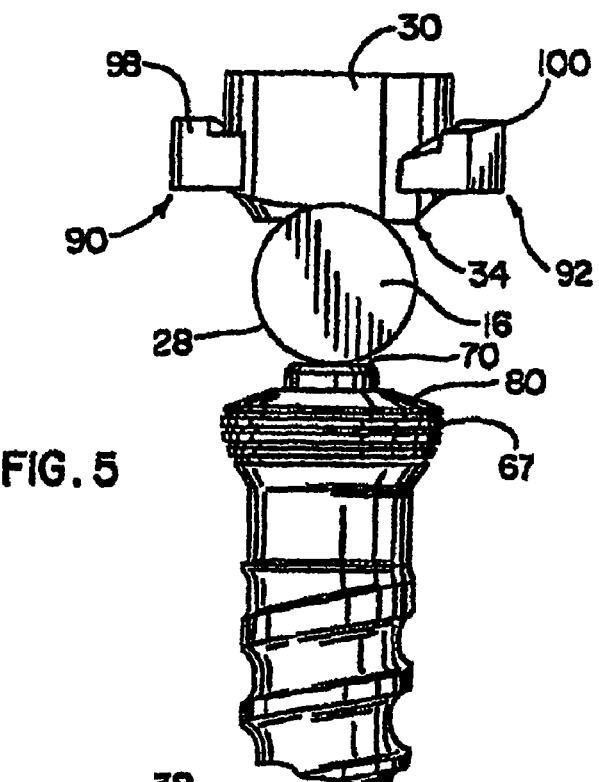
FIG. 5 is an elevational view similar to FIG. 2 with the coupling member removed to show the radial flanges on the cam lock member and a bottom cam surface thereof.

The present insert 68 is also provided with a very low profile to minimize the space it takes up in the coupling member 20. More particularly, the bone screw anchor 12 has an upper concave recess 72 formed in the screw head 58 thereof to form a cup-shaped wall 73 of the screw head 58 having an upwardly opening cavity 74 in which insert 68 is received. The insert 68 has an arcuate bottom surface 76 having a curvature similar to that of the concave surface 72 so that it can shift or slide thereon as the polyaxial screw 12 is moved to various orientations thereof relative to the coupling device 14. The insert 68 is sized such that the distance between the lowermost point of the bottom surface 76 and the top flat surface 70 is slightly larger than the depth of the cavity 74. In this manner, the flat surface 70 projects only slightly above the proximal end 78 of the screw 12 at the top surface 80 of the screw head wall 73 extending about the cavity 74, as can be best seen in FIG. 5. Accordingly, the insert 68 only nominally increases the height of the screw head 58 in the internal space 46 of the coupling member 20 allowing the coupling device 14 to maintain its low profile character, as previously described. By way of example, the distance between the bottom 40 of the coupling member 20 and the spinal rod axis 16a with the rod 16 clamped against the insert 68 can be approximately 6.34 millimeters. It is preferred that the insert 68 has a greater elastic deformation than the coupling member 20 or the spinal rod 16 so that it has a greater spring-like property. Accordingly, the material of the insert 68 preferably has a lower Young's Modulus than the coupling member 20 and spinal rod, thereby reducing the criticality of the dimensional tolerances. Alternatively, a material, such as cobalt chrome, may be used for the insert 68 that is harder than the rod to increase the clamping force therebetween.

In the preferred and illustrated form, the small, low profile insert 68 has an enlarged lower portion 82 including the arcuate bottom surface 76 thereon with an upper portion 84 projecting centrally upward from the enlarged lower portion 82 and having the top surface 70 thereon. Accordingly, the top surface 70 is narrower in the directions orthogonal to the axis 21 than the bottom surface 76 so that a shoulder surface 86 is formed between the insert portions 82 and 84. The above-described structure for the low profile insert 68 provides it with an inverted mushroom-like configuration with the enlarged head portion 82 riding on the concave recess surface 72 in the screw head 58.

To keep the insert 68 in the cavity 74 formed in the screw head 58, a retainer such as in the form of staked portions 88 of the screw head wall 73 are provided. These staked portions 88 extend radially inward at the proximal end 78 of the screw 12 so as to be in interference with the shoulder surface 86 on the insert 68 for keeping it retained in the cavity 74, and in a substantially upright position while providing for a small amount of rotation therein as shown in FIGS. 3-6. It should be noted that the term rotation is meant to include any pivoting of the insert within the screw head 58. As can be seen, the insert 68 is not fixed with respect to the coupling member 20, instead being retained in the screw head with the staked portions 88. This allows the insert 68 to have a slight mobility, or play, and allows the insert 68 to shift independently of the screw 12 and the rod surface 28. Accordingly, the insert 68 may follow the rod surface 28 and seat itself between the rod surface 28 and the screw head 58 for a self-aligning capability.

Figure 6:
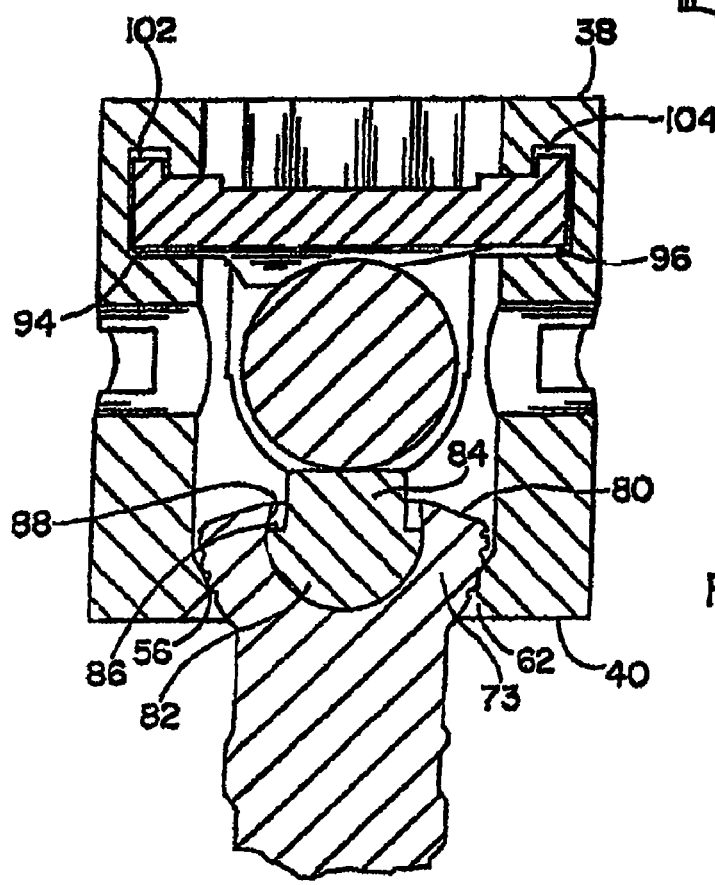
FIG. 6 is a cross-sectional view of the spinal fixation system showing the recesses formed in the coupling member configured to receive the radial flanges on the cam lock member.

As previously mentioned, the cam lock member 18 does not translate along the coupling member 20 when it is turned to its locked position. In order to keep the cam lock member 18 fixed against movement in the direction along axis 21, it is provided with radial flanges 90 and 92 extending radially outwardly from the annular body 30 at diametrically opposite positions thereon. The flanges 90 and 92 are received in correspondingly configured recesses 94 and 96 formed in the coupling member walls 42 and 44, as can be seen in FIG. 6. The recesses 94 and 96 have an arcuate configuration extending about axis 21 as do the radial flanges 90 and 92 for fitting therein and allowing turning of the cam lock member 18 between unlocked and locked positions thereof. The flanges 90 and 92 are received in the recesses 94 and 96 when the cam lock member 18 is turned toward its locked position. With the cam surface 34 camming on the rod surface 28, the flanges 90 and 92 in the closely conforming recesses 94 and 96 prevent the cam lock member 18 from shifting upwardly away from the spinal rod 16 and instead forces the spinal rod 16 down into clamping engagement with the insert 68 which, in turn, causes the screw head 58 and specifically outer head surface 66 to be clamped against the seat surface 54 in the coupling member 20 thus fixing the coupling device 14 relative to the bone screw 12 and anchoring the spinal rod 16 to the spinal column.

The downwardly directed clamping forces exerted by the cam lock member 18 between the screw head 58 and the bottom wall 52 of the coupling member 20 and in particular between the respective engaging surfaces 66 and 54 thereof can cause the coupling member walls 42 and 44 to spread apart. Accordingly, the flanges 90 and 92 are also provided with distal portions 98 and 100, respectively, that extend along axis 21. In this instance, the distal portions 98 and 100 are shown as being upturned from the distal ends of the radial flanges 90 and 92 although they could likewise be configured so that they extend downwardly in the direction along axis 21. The recesses 94 and 96 also include portions 102 and 104, respectively, that extend in an upward direction along the axis 21 in the coupler member walls 42 and 44 for receiving the upturned distal portions 98 and 100 on the respective radial flanges 90 and 92. With the flange portions 98 and 100 received in the recess portions 102 and 104, any spreading action of the walls 42 and 44 during the locking operation with turning of the cam lock member 18 is resisted.

As previously mentioned, the cam lock member has a contoured bottom cam surface 34 that cams on the curved cam surface 28 of the spinal rod 16. The cam surface 34 is best seen in FIGS. 8 and 10. In the illustrated and preferred form, the cam surface 34 is contoured to provide three distinct regions defined in relation to their action on the spinal rod 16. A first concave region 106 is provided to substantially mate with the rod surface 28 in the unlocked position. Concave surface region 106 extends across the bottom 34 of the cam lock member body 30 and can be aligned with the radial flanges 90 and 92. Accordingly, the radial flanges 90 and 92 will be disposed slightly above the bottom 34 of the cam lock member body 30 to accommodate the spinal rod curved surface 28 extending therebelow with the cam lock member 18 in the unlocked position thereof. In this position, the flanges 90 and 92 are not received or fully received in the recesses 94 and 96 therefor.

Diametrically opposite sections 106a and 106b of the concave surface region 106 are provided so that rotation of the cam lock member 18 in the unlocked position does not cause a camming action to occur with only a slight initial turning action thereof. With the spinal rod surface 106 aligned with the surface portions 106a and 106b, the spinal rod 16 is still loosely received under the cam lock member 18 and is not cammed thereby. Beneficially, the spinal rod 16 is captured under the cam lock member 18 so as to provide the surgeon with greater freedom of manipulation before finally locking the cam lock member 18. With continued turning of the cam lock member 18, the camming action begins at ramp regions 108 and 110 that are diametrically opposite to each other on the cap bottom surface 34 and project downwardly from the adjacent surface sections 106a, 106b along direction 21. The ramp regions 108 and 110 are configured so that the rod 16 is progressively pushed downward in the direction 21 as the cam lock member 18 is turned about the turning axis 21 toward the locked position. Accordingly, in the unlocked position these ramp surface regions 108 and 110 on the bottom cam surface 34 extend down along either side of the spinal rod 16 so as to advantageously take up the space on either side thereof thus serving to keep the space occupied by the cam lock member 18 in the coupling member 20 to a minimum for providing the overall coupling device 14 with a low profile.

Continued turning of the cam lock member 18 toward the locked position causes the rod surface 28 to be engaged against diametrically opposite generally flat surface regions 112 and 114 adjacent to the ramp surface regions 108 and 110, respectively. In an alternative form, the surface regions 112 and 114 may be a valley shape providing a depression such that the rod 12 is received into the depression. The surface regions 112 and 114 are not inclined relative to the axis 21 like the preceding ramp surfaces 108 and 110 and are the lowest point of engagement of the cam surface 34 with the rod surface 28. With the cam lock member 18 turned so that the rod surface 28 is only engaged by the surface regions 112 and 114, the cam lock member 18 is in its fully locked position with the cam lock member flanges 90 and 92 fully received in the corresponding yoke wall recesses 94 and 96 therefor, as shown in FIGS. 1 and 6. Continued turning of the cam lock member in the same direction after the fully locked position has been reached is prevented by abutment surface regions 116 and 118 adjacent to the surface regions 112 and 114, respectively. These abutment surfaces 116 and 118 extend further downwardly in direction 21 from the surface regions 112 and 114.

Accordingly, the illustrated and preferred programmed cam surface 34 provides several stages for the camming and locking action on the spinal rod 16. As shown, the cam lock member 18 can be rotated by approximately 20 degrees from the unlocked position before the rod surface 28 reaches the ramp surfaces 108 and 110. At this point, the rod 16 is cammed downwardly and the cam lock member can be turned for another 60 degrees before the rod surface 28 reaches the flat locking surfaces 112 and 114. The cam lock member 18 can then be turned by another 20 degrees before the rod surface 28 abuts against the stop surfaces 116 and 118 and the cam lock member 18 is in its fully locked position. Thus, there is approximately 100 degrees of rotation of the cam lock member 18 that is required from the fully unlocked position to the fully locked position with 20 degrees of play provided before the camming action begins and the camming of the rod 16 occurring over the final 80 degrees of rotation to the fully locked position.

Turning to more of the details, as previously mentioned, the cap cam lock member 18 includes drive surface portion 36 recessed in the top surface 32. As best seen in FIG. 2, the drive surface portion 36 can be formed with a plurality of lobes extending radially outward from the center axis 21 for receiving a similarly lobed drive tool. The lobe drive surface portions 36 provide an increased area for surface contact and torque transmission between the drive tool and the cam lock member 18.

Figure 15:
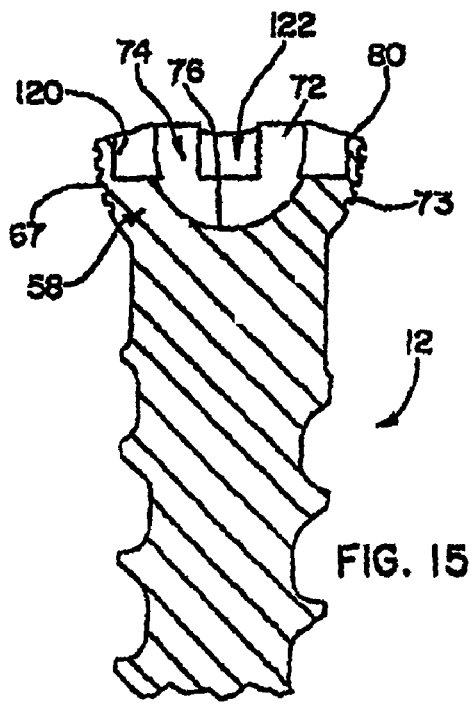

For the bone screw 12, the screw head 58 is provided with peripheral driving surfaces 120 and recessed notches 122 formed in the proximal end 78 of the screw head and recessed or notched into the top surface 80 thereof, as can be seen in FIG. 15. In this manner, a driving tool having peripheral prongs for fitting in the notches 122 can be utilized while the anvil insert 68 is in the screw head cavity 74 and slightly projecting out therefrom, as previously described.

Referring to FIGS. 1 and 11-13, it can be seen that the yoke coupler walls 42 and 44 are provided with a key slot 124 and 126, respectively, with the slots 124 and 126 having enlarged central throughbore 128 and 130 extending through the walls 42 and 44. The slots enable the coupling device 14 to be held as by arms on a device used to insert the spinal rod 16 into the coupling member 20, e.g. a rod persuader. The arms can have engaging ends that locate in the slots 124 and 126 and extend into the through bores 128 and 130.

Figure 19:
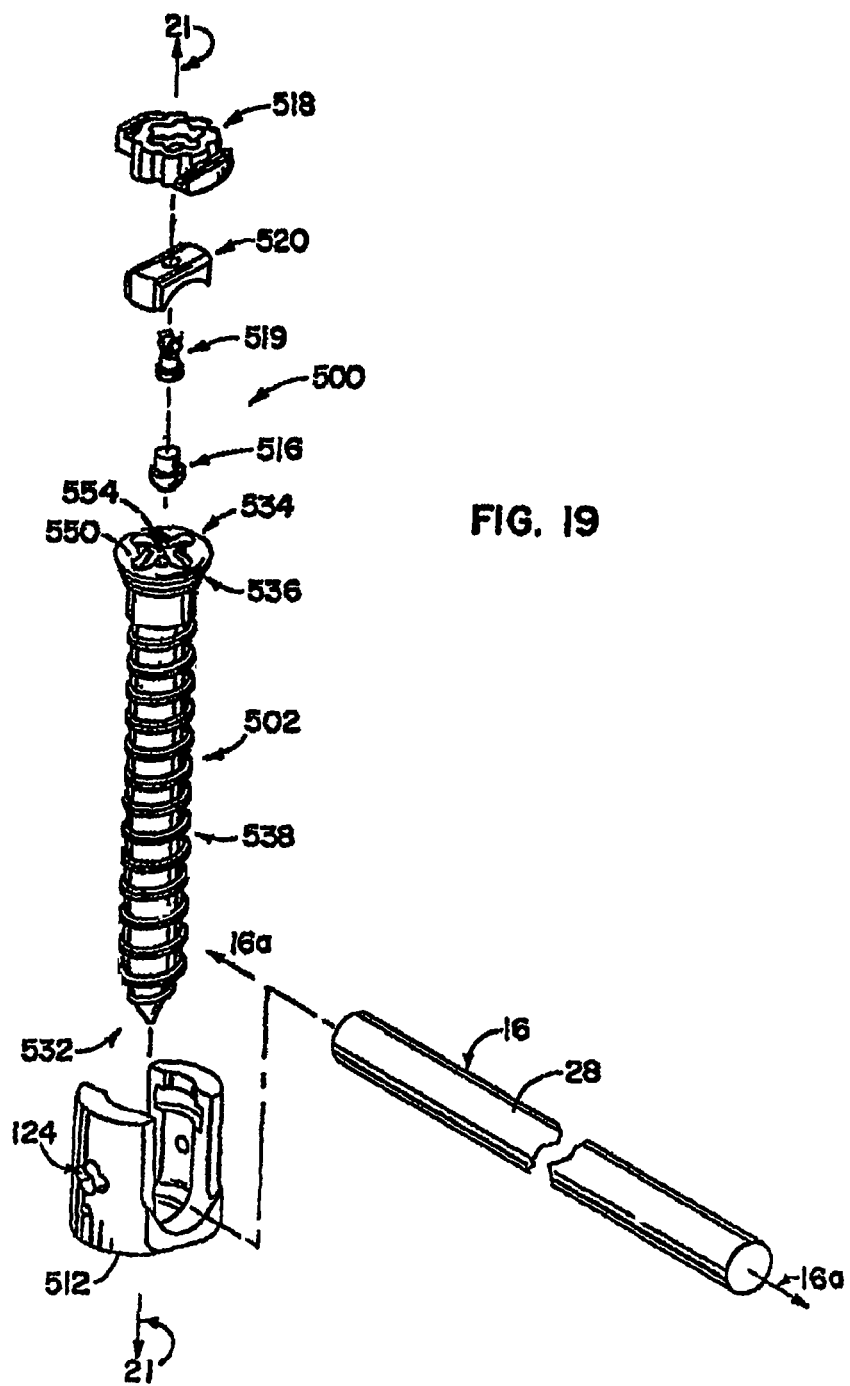
FIG. 19 is an exploded perspective view of another form of the spinal fixation system in accordance with the present invention showing a bone screw and a coupling device including a coupling member, a cam lock member, a spring clip connector member, a clamping member, and an insert for securing a spinal rod relative to the bone screw.
Figure 25:
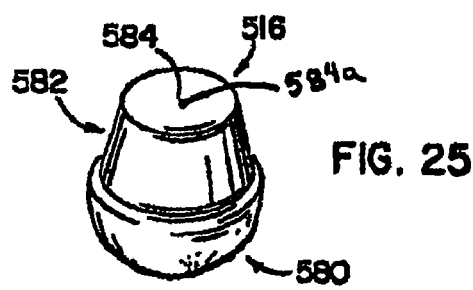
FIG. 25 is a perspective view of the insert showing a flat upper anvil surface thereof.

Referring now to FIGS. 19-44, a low profile spinal fixation system 500 for securing a spinal rod 16 in accordance with another form of the present invention is depicted. As can be seen in FIGS. 19 and 20, the system 500 includes a bone anchor member such as screw 502 and a coupling device 504 for securing the spinal rod 16 relative to the bone screw 502. The coupling device includes a coupling member in the form of a unitary yoke 512, an insert in the form of anvil 516, a cam lock member in the form of cap 518, a connector member in the form of a spring clip 519, and a clamping member in the form of a saddle 520. The fixation system 500 is similar to the embodiment of FIGS. 1-18 in that the cap 518 and yoke 512 are provided with a very low profile in the direction indicated by yoke axis line 21 extending transverse and specifically orthogonally to the axis 16a of the spinal rod 16 fixed relative to the bone screw 502 by the coupling device 504, as best seen in FIG. 20.

The screw 502 is directed through the yoke 512 and attaches the yoke 512 to a bone or bone fragment. The screw 502 has a head 536 with a recess 554, and the recess 554 receives the anvil 516. The spinal rod 16 is received within an internal space or channel 601 in the yoke 512 and is seated on top of the anvil 516. The screw 502 is preferably a polyaxial screw, and the anvil 516 is permitted to move within the head 536 of the screw 502. Accordingly, prior to the system 500 being secured, the screw 502 may move relative to the yoke 512 so that the yoke 512 and screw 502 may be selectively positioned to assume different orientations relative to each other so that their respective axes 21 and 544 are not necessarily aligned with each other, and the anvil 516 may move and pivot or rotate relative to the screw 502 so that the anvil 516 may be properly positioned by orienting itself with the outer surface 28 of the rod 16 similar to the previously described anvil 68.

The rod 16 is secured or locked within the yoke 512 with the cap 518 and saddle 520. As will be discussed below, rotation of the cap 518 has the dual function of securing the cap 518 within recesses 642 in the yoke 512 and of forcing the saddle 520 against the rod 16 to lock the rod 16 between the saddle 520 and the anvil 516. The saddle 520 and cap 518 are secured together in assembly by a distinct connector in the form of the dual-pronged, spring clip 519.

Figure 22:
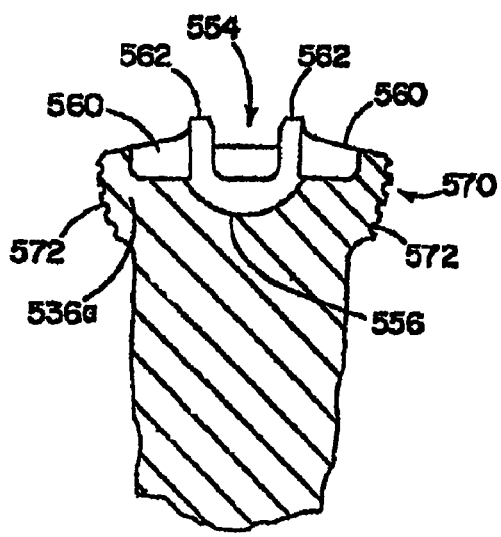
FIG. 22 is an enlarged cross-sectional view of a head of the bone screw of FIG. 21.
Figure 21:
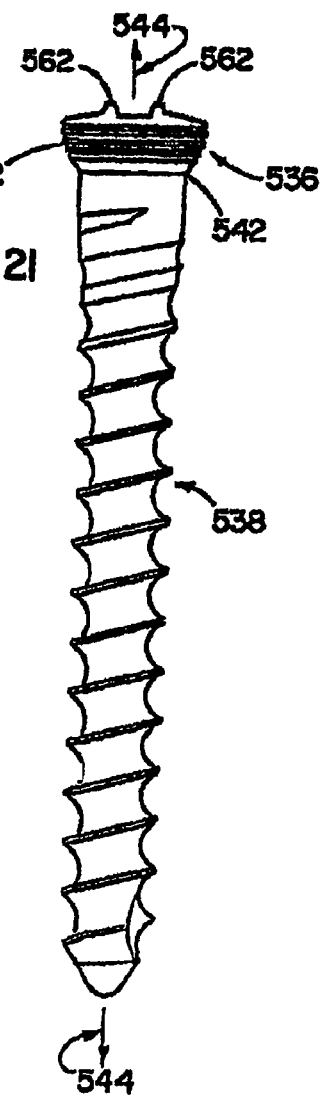
FIG. 21 is a side elevation view of the bone screw of FIG. 19.

In FIGS. 21-22, the bone screw 502 is depicted. The bone screw 502 includes a tip 530 at a distal end 532, a proximal end 534 including a screw head 536, a shank 538 including external threads 540 for driving and securing the screw into a bone or bone fragment, and a neck 542 where the head 536 and the shank 538 meet. The screw 502 is driven by rotation around its central longitudinal axis 544. The tip 530 of the screw may be provided with a variety of configurations such as a self-tapping structure or self-drilling structure, as is known. As discussed, the screw 502 is preferably polyaxial, and the head 536 is diametrically larger than the shank 538 at the neck 542. The polyaxial features of the screw 502 allow the screw 502 to be secured to a bone in a desired orientation for proper fixation to the bone while allowing the yoke 512 to be oriented relative to the screw 502 in an orientation desired for seating a rod 16 therein.

The head 536 of the screw has an arcuate or slightly ramped top surface 550 which meets a peripheral outer surface 552 of the screw head 536. The peripheral outer surface 552 of the screw head 536 has a generally arcuate or spherical profile 570. The profile 570 is interrupted with a series of concentric ridges or circular grooves 572 cut therein. As discussed above, the screw 502 is polyaxial so that its orientation relative to the yoke 512 can be precisely positioned. When the coupling device 504 is secured to the screw 502, the grooves 572 grip or cut into the interior of the yoke 512 to immobilize the screw 502 in the desired position against the yoke 512. By way of example, the grooves 572 can be approximately 0.012 inches in width to provide sufficient gripping strength or purchase in the yoke 512.

The top surface 550 includes an upwardly opening recess 554 formed therein for receiving the anvil 516. As can be seen in FIGS. 24-27, the recess 554 has an arcuate or, preferably, spherical bottommost surface portion 556 sized and configured to allow the small anvil 516 to shift when seated in the recess 554. To this end, the anvil 516 has a bottom surface 558 supported on and slidable against the bottommost surface portion 556. Furthermore, the recess 554 has two pair of diametrically opposed notches 560, each pair perpendicularly oriented from the other pair, for receiving similarly configured prongs of a driver without interfering with the anvil 516 therein. The top surface 550 includes a retainer or staked portion in the form of short tabs 562 located at the opening to the recess 554 and between each notch 560. Prior to disposing the anvil 516 in the recess 554, the tabs 562 rise upwardly from the top surface 550 in the axial direction so that the tabs 562 do not hinder insertion of the anvil 516. Once the anvil 516 is located in the recess 554, the tabs 562 are deflected over to extend radially into interference with the anvil 516 while still allowing the anvil 516 to move within the recess 554 but be captured therein by the tabs 562. After assembly, heat or other treatment may be utilized to relieve residual stresses within the bent tabs 562.

The anvil 516 has a bottom portion 580 with a generally arcuate or spherical bottom surface 558 which rests against the bottommost portion 556 of the seat 554. Accordingly, the anvil 516 may pivot or rotate within the recess seat 554. The anvil 516 further includes a seat portion 582 extending centrally upward from the anvil bottom portion 580 to a top surface 584 with a transverse shoulder surface 585 between the anvil portions 580 and 582. As seen best in FIG. 27, with the anvil 516 seated upright in the recess 554 there is a gap spacing 587 between the bent tabs 562 and the anvil transverse surface 585. This gap spacing 587, along with the narrower width of the anvil upper portion 582 extending generally upwardly in the recess 554, allows for the anvil 516 to toggle or pivot in the recess 554 with the anvil surface 558 sliding on the recess surface 556 until the surface 585 abuts against one or more of the tabs 562.

The seat portion 582 is preferably frusto-conical so that compression stresses thereon are distributed through to the bottom portion 580 while minimizing the possibility of damage to the outer edge 584a of the top surface 584. Like the previously described anvil 68, the anvil bottom portion 580 is enlarged relative to the upper portion 582 so that top surface 584 may move within the recess 554 and in the space 587 between the anvil shoulder surface 585 and the tabs 562.

When the rod 16 is inserted within the yoke 512, the side surface 28 of the rod 16 is advanced into contact with the anvil 516. If the bone screw 502 is deflected or secured so that its central axis 544 is not coincident or aligned with the yoke central axis, the anvil 516 is initially deflected or tilted in a similar deflection. As the rod 16 is secured and forced against the anvil 516, the anvil 516 pivotable in the recess 554 will shift to require the minimize distance between the rod 16 and the bottom surface portion 556 of the recess 554. As the anvil top surface 584 is flat while the bottom surface 558 is spherical, the shortest distance from the top surface 584 to the bottom surface 558 is through the geometric center 584a to the center 590a of the bottom surface 584.

As discussed herein, in order to have a low profile, it is preferred to minimize the height of the anvil 516 while remaining above the top surface 550 of the screw head 536. The anvil top surface 584 is sized so that, when deflected due to the deflection of the bone screw 502, at least a portion of the top surface 584 is contacted by rod 16 being advanced towards the anvil 516 in the yoke 512. Accordingly, the anvil 516 is self-righting as the rod 16 contacting the anvil top surface 584 forces the anvil 516 to shift to align tangentially its minimum height, as discussed above, with the surface 28 of the rod 16.

Figure 24:
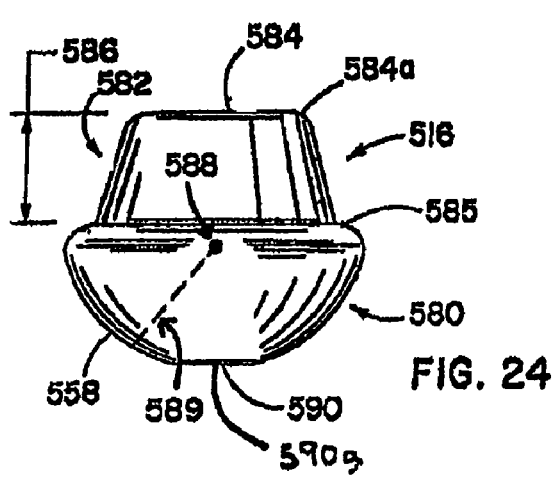
FIG. 24 is a side elevation view of the insert of FIG. 19 showing an enlarged arcuate lower portion and a narrower upper portion projecting upward from the lower portion.

The polyaxial screw 502 is inserted through the yoke 512 and secured to a bone, and the rod 16 rests against the top surface 584 of the anvil 516. As the orientation of the screw 502 relative to the yoke 516 may pivot, the anvil 516 may pivot within the recess 554 so that the top surface 584 remains tangential to the generally cylindrical outer surface 28 of the rod 16. Generally, the anvil 516 and screw head 536, and specifically the recess 554 thereof are sized relative to each other so that the anvil top surface 584 always extends slightly beyond the top of the cup-shaped head wall 536a at the head upper surface 550 even with the screw 502 pivoted to its maximum extent relative to the yoke 512, e.g. twenty degrees from axis 21. More specifically, as previously mentioned, the anvil bottom portion 580 can have its bottom surface 558 curved to have a generally spherical configuration with a radius 589, as shown in FIG. 24. As the bottom surface 558 pivots in the arcuate recess surface 556, the radius 589 extends from the general center of rotation 588 of the anvil 516. The anvil 516 is fashioned from a generally spherical component to have the shoulder surface 585 and the seat portion 582. Accordingly, the height distance 586 from the center of rotation 588 to the anvil seat surface 584 is at least slightly less than the length of the radius 589. By way of example, the height distance 586 can be approximately 0.043 inches and the radius 589 can be approximately 0.0625 inches so that the distance 586 is approximately 0.0195 inches less than the radius. If the height 586 of the anvil top surface 584 is increased significantly, the width of the anvil top surface 584 must be increased, which would limit the polyaxial motion of the screw 502 as the anvil 516 would come into contact with the tabs 562 with a smaller degree of deflection. If the height 586 of the anvil top surface 584 is decreased significantly, the rod 16 would not be able to contact anvil top surface 584 without contacting the screw head 536 first, an event that becomes more acute at greater deflection angles.

Thus, the configuration of the anvil 516 and the recess 554 including the tabs 562 extending therein allows the anvil 516 to pivot to follow the position of the rod 16 and to promote self-righting of the anvil 516. In addition, the size of the anvil 516 between surfaces 584 and 558 including the height 586 is selected so that the top surface 584 is lower than a top surface of a completely spherical screw head would be to keep the profile of the anvil assembly including the screw head 536 and anvil 516 in the yoke 512 to a minimum. That is, if the screw head 536 were spherical, the height of the top of the screw head 536 would be higher than the top surface 584 of the anvil 516, which would increase the overall height of the system 500. When the coupling device 504 is in its locked condition, the top surface 584 of the anvil 516 may slightly deform, thereby forming a depression which is tightly engaged with and conforming to the outer surface 28 of the rod. By deforming, the anvil 516 and rod 16 form a substantially flush mating surface contact, as opposed to a line contact. The bottom surface 558 of the anvil 516 includes a small flat 590 which assists in minimizing friction between the anvil bottom surface 558 and the seat 554.

As has been stated, the screw 502 is inserted through the yoke 512. As can be seen in FIGS. 28-32, the yoke 512 has an enlarged base portion 600 and a shape with a generally cylindrical outer surface 602 formed by a pair of opposed side wall portions 604, 606 extending from the enlarged base 600 and defining a channel 601 for receiving a rod 16 therebetween. The channel 601 may have a liner made of, for instance, a polymer such as PEEK, for promoting low-friction contact between the rod 16 and the channel 601. A recess 608 including the channel 601 is formed between the walls 604, 606 with vertical axis 21, and the recess 608 includes a throughbore 612 in the bottom or base 600 of the yoke 512 through which the screw 502 is inserted. The throughbore 612 may be constructed as the throughbore 50 of the coupling member 20, discussed above, and may include a polymer liner, such as PEEK, for promoting low-friction polyaxial movement of the screw 502 therein.

In similar fashion to that depicted in FIGS. 1 and 11-13, the outer surfaces 602 of the yoke walls 604, 606 are provided with a key slot 124 and 126, respectively, with the slots 124 and 126 having enlarged central throughbore 128 and 130 extending through the walls 604, 606. The slots enable the coupling device 512 to be held as by arms on a device used to insert the spinal rod 16 into the yoke 512, e.g. a rod persuader. The arms can have engaging ends that locate in the slots 124 and 126 and extend into the through bores 128 and 130.

The outer surface 602 of the yoke 512 also includes blind apertures or holes 650. As can be seen best in FIG. 32, the blind hole 650 does not extend into the interior recess 608, instead terminating at a thin wall portion 652 of the yoke 512. Once the screw 502 and its secured anvil 516 have been inserted through the throughbore 612, the thin wall portion 652 adjacent each blind hole 650 is deformed into the recess 608 so that the screw 502 and anvil 516 subassembly cannot be pulled back out of the yoke 512 and thus stays in assembly therewith. With the screw 502 retained in the yoke 512, the surgeon need only handle the screw 502, yoke 512, and anvil 516 as a single item or assembly.

Figure 31:
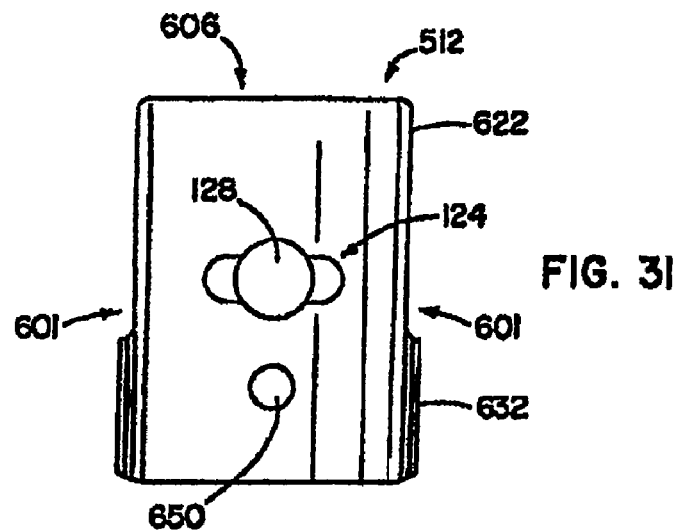
FIG. 31 is a side view of the coupling member rotated ninety degrees from the FIG. 30 view showing an enlarged width lower portion of one of the side walls at the base of the coupling member.
Figure 32:
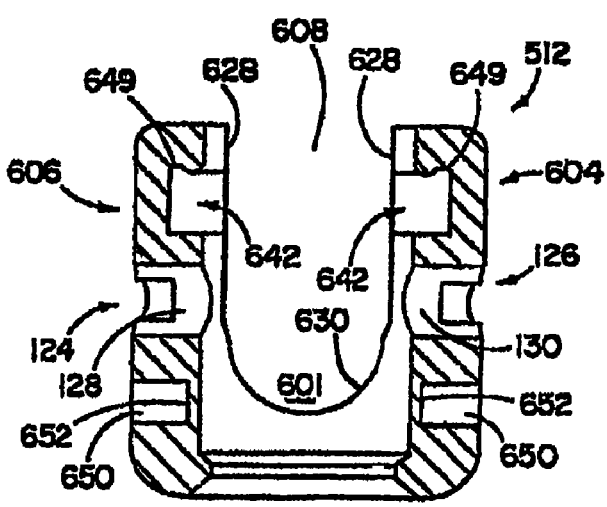
FIG. 32 is a cross-sectional view of the coupling member showing blind apertures toward the lower ends of the side walls.

In the preferred illustrated form, the yoke 512 has a high strength unitary construction as described below. Each integral side wall portion 604, 606 has a top surface 620, end surfaces 622, and inner surfaces 624. The inner surface 624 of each wall 604, 606 is generally a mirror of the surface on the opposed wall. The walls 604, 606 cooperate with each other to form two U-shaped interior surfaces 626, each with a pair of leg portions 628 that are vertically opposed in a region from the top surface 620 extending downward. Each pair of leg portions 628 meets a generally semi-circular portion 630 interconnecting the leg portions 628. To the outside of the surfaces 626, the cylindrical outer surface 602 of the yoke 512 is truncated to form the end surfaces 622 of the walls 604, 606, and is truncated to form end surfaces 632 on the base 600. The truncation of the ends of the yoke 512 reduces the overall size of the yoke 512 in a widthwise direction transverse to the axial direction 21. Referring to FIGS. 28 and 31, as the base 600 has a greater dimension between its end surfaces 632 than the walls 604, 606 have between their end surfaces 622, there is a shoulder 634 formed between the end surfaces 632 and the end surfaces 622. The enlargement of the base portion 600 at the lower end portions of the walls 604 and 606 provides increased strength to the yoke 512 in the area of highest stress concentration where the rod 16 is clamped down on the curved surface portions 630 of the yoke 512 toward the bottom end thereof. The cut-away of the yoke 512 along the side wall portions 604 and 606 extending up from the base portion 600 keeps the width of the yoke 512 for a majority of its axial length to a minimum, as previously described.

The inner surfaces 624 of the walls 604, 606 each include a surface 640 having a generally cylindrical configuration extending between the U-shaped interior surfaces 626. The cylindrical surfaces 640 and interior surfaces 626 define interior recesses 642 extending circumferentially in the sides with a constant cross-section. Guides 643 in the form of small projections or nubs are located on the interior surface 626, as depicted in FIG. 28, above the recesses 642. When the saddle 520 is inserted into the yoke 512, as seen in FIG. 29, the guides 643 assist in proper positioning of the saddle therein, as will be discussed below. In addition, the guides 643 serve as detents to provide distinct rotary positions for the cap 518 as it is turned. Similar to the cam lock member 18 described above, the cap 518 has a generally cylindrical body portion 644 with an outer surface 645 including a number of recesses arranged thereon in the form of generally vertical, arcuate indentations 647 circumferentially spaced about the outer surface 645. The indentations 647 cooperate with the detents 643 to provide a tactile indication to a surgeon as to how far the cap 518 has been turned in the yoke 512 as the nub detents 643 snap into and out from the indentations 647. For instance, with the cap 518 in its locked position, the detents 643 and indentations 647 can be spaced so that a predetermined number of clicks are generated when the cap 518 is turned to its completely locked position, e.g. one-hundred degrees from the unlocked position.

The recesses 642 extend generally horizontally for receiving the cap 518 and, more specifically, a pair of radial flanges 656 of the cap 518 that fit into the correspondingly configured recesses 642 of the yoke 512 in a manner similar to previously described flanges 90 and 92 and corresponding recesses 94 and 96. The radial flanges 656 and recesses 642 keep the cap 518 from shifting axially along the yoke 512 as it is turned so that the camming action generated between the cap 518 and saddle 520 only causes axial shifting of the saddle 520 toward and against the spinal rod 16. Each of the flanges 656 includes a flat ramp lead-in surface 657 that assists in guiding the flanges 656 as they are turned from the slots formed between the side wall portions 604 and 606 with the cap 518 in its unlocked position to shift the flanges 656 to be inserted in their respective recesses 642. No camming action, however, occurs between the surfaces of the recesses 642 and the flanges 656 that shifts the lower surface 700 of the saddle 520 relative to the cap 518. As explained below, the camming action is solely generated between the bottom surface 704 of the cap 518 and the top surface 702 of the saddle 520.

The radial flanges 656 also include upturned portions 658 at their distal ends 659, and the recesses 642 also include corresponding portions 649 that extend in an upward, axial direction in the respective yoke walls 604, 606 for receiving the upturned flange portions 658 therein. With the flange portions 658 received in the corresponding recess portions 649, any spreading action of the yoke walls 604, 606 during the locking operation with the turning of the cap 518 is resisted.

As depicted in FIGS. 41-44, the cap 518 and the saddle 520 each define central openings 670, 672, respectively, through which the clip 519 extends. The cap opening 670 is segmented between a lower portion 670a and an upper portion 670b that steps open to a diameter larger than that of the lower portion 670a. An annular shoulder seating surface 674 is at the transition between the lower portion 670a and the upper portion 670b of the cap opening 670. The upper portion 670b also opens to a recessed bottom surface 671 in the drive socket of the cap member 518.

Referring to FIGS. 36 and 37, the clip 519 includes an annular base portion 680 and two resilient prongs or stems 680a, 680b projecting upward therefrom along clip axis 683 and spaced by an axially extending gap 682 therebetween. Each stem 680a, 680b terminates at their free ends with flanges 681a and 681b including an upwardly facing cam surface 684 that can be ramped or inclined relative to the clip axis 683, or have a curvature thereto. The cam surfaces 684 aid in insertion of the clip 519 through the openings 670 and 672, and a corresponding lower stop surface 688 is provided at the prong flanged ends 681a and 681b extending normal to clip axis 683 that substantially prevents unintentional removal of the clip 519 back through the openings 670, 672.

The central opening 672 of the saddle 520 also includes an upper portion 672a and a lower portion 672b. The lower portion 672b opens to a concave bottom 700 of the saddle 520 and has a larger diameter than the upper portion 672a so that there is an annular shoulder surface 672a extending therebetween. The enlarged lower portion 672b is sized such that the base portion 680 of the clip 519 is fit and held therein in interference with the surface 672c. Preferably, the diameter of the opening lower portion 672b is kept to a minimum to increase the surface contact area of the saddle surface 700 on the rod 16. The opening upper portion 672a can be sized to have a similar diameter as that of the smaller lower portion 670a of the cap opening 670.

To assemble the cap member 518 and saddle member 520 together, initially the spring clip member 519 is axially inserted in saddle opening 672 with prong free ends 681a and 681b first inserted in enlarged lower opening 672b. With continued axial insertion, the cam surfaces 684 engage and cam against shoulder surface 672c resiliently forcing the spring prongs 680a and 680b toward each other to take up the gap 682 therebetween. With the prongs 680a and 680b pushed together, the lateral outer edges 684a of the cam surfaces 684 are spaced by a distance slightly less than the diameter of the opening portions 670a and 672a. This allows the clip member 519 to continue to be inserted through the opening 672 including the smaller diameter opening upper portion 672a. Depending on the distance across the underformed prong upper edges 684a relative to the diameter of opening lower portion 672b, there may also be camming against the saddle surface 700 with some attendant prong deformation to enable the clip prongs 680a and 680b to fit into opening lower portion 672b. Once the prong ends 681a and 681b and specifically the prong surfaces 688 thereat clear the opening upper portion 672a, the clip prongs 680a and 680b return to their original undeformed state with surfaces 688 in conforming relation with upper surface 702 of the saddle 520 so that absent exerting a force to bring the prongs 680a and 680b together, the clip member 519 and saddle member 520 stay assembled together.

To complete the assembly process, the prong ends 681a and 681b are next axially inserted in the cap opening 670, and specifically smaller lower portion 670a thereof. Accordingly, the cam surfaces 684 cam against a lower surface 687 of the cap 518 about the central opening 670 therein which forces the resilient stems 680a, 680b together taking up the gap 682 therebetween to allow the clip prongs 680a and 680b to be inserted through the opening portion 670a. Once the clip cam surfaces 684 pass through the lower portion 670a of the cap opening 670, the stems 680a, 680b resiliently return back toward their non-flexed position. After the prong ends 681a and 681b exit the opening 670, the prongs 680a and 680b will return to their undeformed state, and the stop surfaces 688 will be facing the cap surface 671 and spaced therefrom so that there is play between the connected components, i.e. the cap 518, saddle 520, and clip 519, as shown in FIG. 42. Upon turning the cap 518 toward its locked position, the prong ends 681a and 681b re-enter the opening upper portion 670b as the saddle member 520 is driven toward the rod 16 shifting the spring clip member 519 axially therewith due to engagement of the surface 672c on the clip base 680 with the stop surfaces 688 brought into abutting engagement with the seating surface 674 to substantially prevent the clip 519 from being unintentionally pulled back through the openings 670, 672 as the cap is turned to its locked position.

Figure 41:
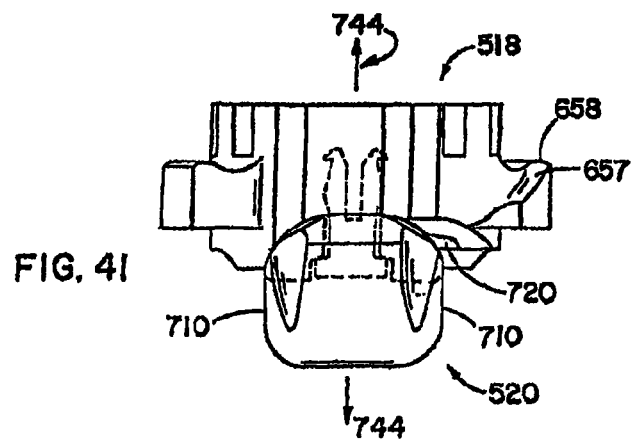
FIG. 41 is a side elevation view of the cam lock member, and the clamping member in a unlocked position relative to the spinal rod.

The stems 680a, 680b of the clip 519 further include an intermediate cam portion including a central, double-ramped cam surface 800. When initially prepared for implantation, the clip 519 holds the cap 518 and saddle 520 in a compact, assembled arrangement with the clip base 680 drawn into abutting engagement with the saddle opening shoulder surface 672c so that the saddle 520 is against or closely adjacent to the cap 518, as shown in FIGS. 41 and 42. In the compact arrangement, the double-ramped surface 800 is located within the cap opening 670 to hold cap 518 against the saddle 520. The stop surfaces 688 at the terminal ends 681a, 681b of the stems 680a, 680b allow the cap 518 to remain in assembly with the saddle 520 in the event the cap 518 and saddle 520 are removed from the yoke 512, such as when a surgeon removes the fixation system 500 from a patient's spine.

More particularly, the ramp cam surfaces 800 include a lower cam surface portion 802 and an upper cam surface portion 804 that meet at a laterally common outer edge 806. Referring to FIG. 37, it can be seen that the intermediate outer cam surface edge 806 is sized approximately the same as the distance across the distal upper prong edge at 684a. As shown, the cam surface 802 is inclined away from axis 683 as it extends upwardly to edge 806 while the cam surface 804 is inclined toward the axis 683 as it extends upwardly from the edge 806. Thus, during assembly, the upper cam surface 804 can assist in shifting of the prongs 680a and 680b toward each other so they can fit through cap and saddle openings 670 and 672. Similarly, when turning of the cap 518 to loosen the saddle 520 on the rod 16, the upper cam surface 804 allows the saddle 520 along with the clip member 519 to be drawn back axially upward.

With the cap 518 and saddle 520 assembled as shown in FIG. 42, the edges 806 will be disposed in saddle opening upper portion 670*b* so that the lower ramp surface 802 frictionally bears on the surfaces about the opening lower portion 670*a* to hold the saddle upper surface 702 up against or closely adjacent the cap bottom surface 704. In addition, the ramped or inclined orientation of the cam surface 802 allows the saddle 520 to be driven downwardly or away from the axially stationary turning cap member 518. Turning of the cap member 518 toward its locked position causes the cam surfaces 802 to cammingly bear against the surfaces about opening portion 670*a* urging the resilient prongs 680*a* and 680*b* toward each other to allow the prongs including the edges 806 thereof to fit through the opening portion 670*a*. However, the axial distance between the cam surface edges 806 and the stop surfaces 688 is larger than the axial extent of the lower opening portion 670*a* of the saddle so that once the edges 806 clear the bottom of the opening portion 670*a*, the prongs 680*a* and 680*b* will be able to resiliently return toward their undeformed configuration so that the stop surfaces 688 are in interference with the seating surface 674 in the opening 670. In addition, with the saddle member 520 shifted axially downward, the cam surface edges 806 will be exposed out from the openings 670 and 672, as shown in FIG. 44.

Figure 39:
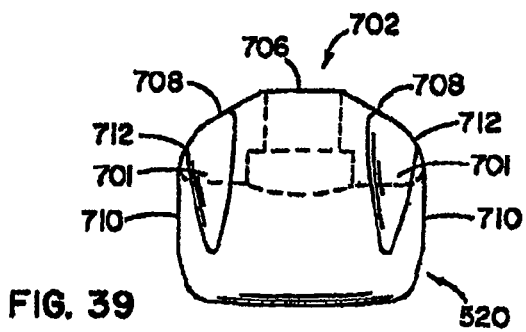
FIG. 39 is a side view of the clamping member rotated ninety degrees from the FIG. 38 view showing a pair of guide channels on one side wall portion thereof.
Figure 40:
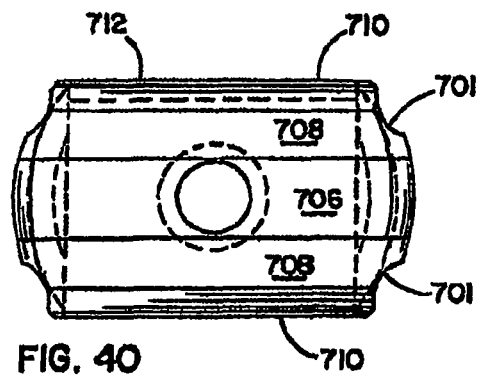
FIG. 40 is a plan view of the clamping member showing a through opening in the saddle member for the spring clip connector member.

As can be seen in FIGS. 38-40, the saddle 520 has grooves 701 along its sides 710. As mentioned above, when the saddle 520 is inserted into the yoke 512, as seen in FIG. 29, the grooves 701 receive the nub guides or detents 643 of the yoke 512, which direct the proper positioning and insertion of the saddle 520 within the yoke 512 with the saddle sides 710 guided along the interior of the yoke side wall portions 604 and 606. The saddle 520 further has tapered ends 703, as can be seen in FIG. 38, which assists in moving the saddle 520 into or out of the yoke 512.

In addition, the bottom surface 700 of the saddle 520 is concave to engage the rod 16 in a complementary fashion. The saddle 520 also includes a distinctly profiled upper or top surface 702 designed to cooperate with a distinctly profiled bottom surface 704 of the cap 518 to cammingly shift the bottom surface 700 of the saddle 520 into locking engagement with the rod 16. More specifically, the top surface 702 of the saddle 520 has a generally horizontal and substantially flat portion 706 extending lengthwise toward each yoke side wall portion 604 and 606 in a direction generally orthogonal to the direction of the axis 524 of the rod 16. In this regard, the saddle 520 presents an elongate cam surface 702 that is oriented ninety degrees from the elongate cam surface presented by the surface of the rod such as in the previously described system 10.

When the saddle 520 is deployed in the locked position with the cap 518, as see in FIG. 44, force between the cap and saddle 520 is generally transmitted through the bottom cam surface portions 820 generally positioned at lateral portions 709 of the saddle lengthwise top surface 706. The positioning of the saddle 520 transversely to a rod received in the bottom surface 700 thereof allows the saddle 520 to distribute locally the forces resolved through its lateral portions to a surface contact area in a local region of the rod 16. In contrast, were the saddle 520 oriented along the longitudinal axis 16*a* of the rod 16, or ninety degrees shifted from that depicted, the saddle 520 providing force through its lateral ends 709 would transmit the forces through a pair of local regions disposed along the top of the surface of the rod 16 mating therewith.

Such arrangement may cause fretting, or damage and wear, to the rod 16 which may lead to failure of the rod or shearing of rod and saddle fragments. Furthermore, such an arrangement may impart a stiffness to a length of the rod 16 that is undesirable for the performance of the system when the patient is permitted to move, which places stress on the system.

The top surface 702 also includes two substantially flat side cam surfaces 708 flanking and meeting the flat portion 706. Each of the cam surfaces 708 is inclined from the flat portion 706 down to lower sides 710 of the saddle 520. The edge 712 between the cam surfaces 708 to the lower sides 710 is slightly rounded to allow the cap 518 to cam easily against the edge 712. Accordingly, the faceted cam surface 702 extends about an axis that is generally normal to the rod axis 16*a*.

Although the top surface 702 could, alternatively, be arcuately sloped upward for receiving the bottom cam surface 704 of the cap 518, the flat portions 706 provide a preferable distribution of stress during camming action. More specifically, a round or arcuate cam surface requires a significant amount of work to be done by the camming engagement in the initial portion of the arcuate cam surface, and then that amount of work decreases as the cam engagement travels up to the top of the arcuate can surface. In contrast, generally flat surfaces, such as flat portions 706, provide that the work is a more distribution along the flat portion 706 as the mating cam surface 704 of the cap 518 is directed over the flat portions 706.

Upon rotation of the cap 518 relative to the saddle 520, the bottom surface 704 of the cap 518 cams against the top surface 702 of the saddle 520 so that the bottom surface 704 of the cap 518 engages the top surface 702 of the saddle 520, which shifts the saddle 520 axially away from the cap 518 and into a tight engagement with the spinal rod 16. In this regard, the cap 518 itself does not shift vertically along and within the yoke 512, instead only rotating around its central vertical axis, as the cap 518 is turned for locking of the spinal rod 16. As previously discussed, the length 690 of the clip 519 between the base portion 680 and the stop surfaces 688 are designed specifically to allow this shifting operation between the cap 518 and the saddle 520.

As depicted in FIG. 34, the bottom surface 704 of the cap 518 is a programmed cam surface in the same manner as the cam lock member 18 discussed above and depicted in FIGS. 8 and 10, albeit shifted ninety degrees therefrom on the cap 518 so that in the unlocked position of the cap 518, as shown in FIG. 34, the cap cam surface 704 generally extends about an axis normal to the rod axis 16*a*. This is because the cam surface 702 of the saddle 520 is rotated ninety degrees from that of the rod surface as previously mentioned so that the corresponding cam surface portions of the cap cam surface 704 are also shifted ninety degrees from their location on the previously described cam lock member 18, as can be seen best in FIG. 34. This also allows the cam surfaces 702 and 704 to seat in close fitting relation prior to turning of the cap 518 toward its locked position so that the cap 518 and saddle 520 have a low profile in the yoke 512 with side portions of the cap 518 extending down about the saddle 520, as can be seen in FIG. 20. Accordingly, turning the cap member 518 toward its locked position will generate a camming action on the faceted cam surface 702 of the saddle 520 in much the same manner as the cam member 18 does on the rod 16 as discussed earlier. In addition, the bottom surface 704 includes additional cutaway recesses 720, depicted in FIG. 41. The recesses 720 are located on an interior portion of ramp surfaces 108, 110 and serve to reduce wear and deformation of the ramp surfaces 108, 110 when rotated along the saddle cam surface 702. In contrast to the cam lock member 18 discussed above, the cap cam surface 704 includes a flat central portion 704a against which the top surface 706 rests when the saddle 520 and cap 518 are in the compact configuration of FIG. 42.

Figure 35:
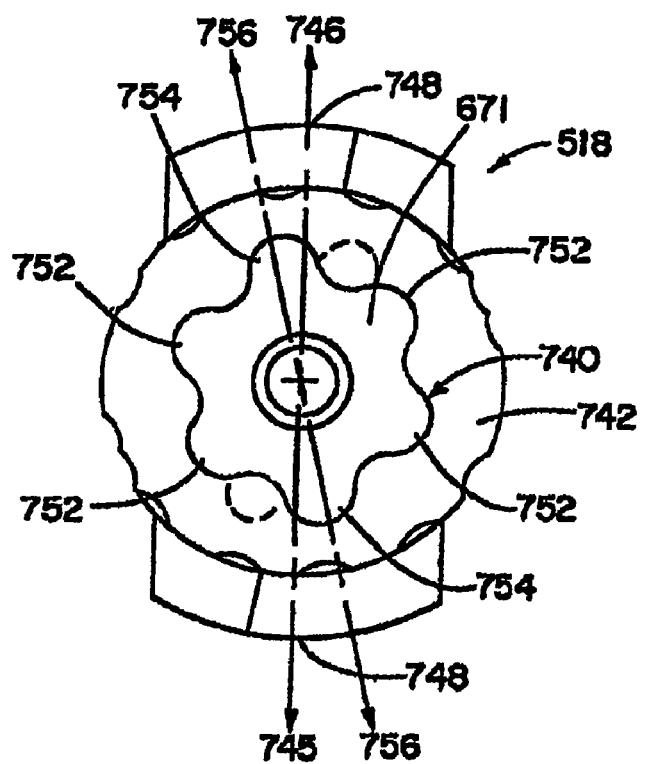
FIG. 35 is a plan view of the cam lock member showing a drive socket including asymmetric drive surfaces.

Referring now to FIG. 35, the cap 518 further includes a socket 740 for receiving a driver or a portion of a rod persuader. The cap 518 has a top surface 742, a central axis of rotation 744, and a central laterally extending axis 746. The central axis of rotation 744 and the central vertical axis 21 of the yoke 512 are generally aligned and coincident (see FIGS. 41 and 19). The lateral axis 746 is drawn along the midpoints 748 of each flange 656 intersecting the rotary axis 744 at the center of the socket 740. The socket 740 in the present form has a plurality of lobes 752 including a pair of lobes 754 which have a size larger than the other lobes 752 so that the lobes 752 are generally asymmetric about the socket 740. In addition, the larger lobes 754 are diametrically opposed and oriented along an axis 756 perpendicular to the axis of rotation 744 and angularly shifted from the central lateral axis 746, preferably by approximately 10 degrees. The geometry of the lobes 752 and 754 provides a driver or rod persuader received by the receptor 740 with only two distinct mating positions, and the offset axis 756 of the lobes 754 provides a surgeon an indication of the position of the cap 518 relative to the driver or rod persuader. It should be noted that the lobes 752, 754 could be arranged and located in a plurality of configurations and orientations provided the cap 518 and instrument have, preferably, only one relative orientation therebetween for mating. Although the preferred embodiment includes the lobes 752 and 754, other geometry may be employed. The lobes 752 and 754, however, enable greater torque to be used between the cap 518 and driver than other known geometries.

In other forms of the systems 10 and 500 described above, the bone anchor member may be provided as a number of variations. For instance, a fixed screw may be employed with the system, either as an integral component with the coupling member or as a component received in the coupling member, as has been described. In the same manner, a hook may be employed with the coupling members.

Figure 45:
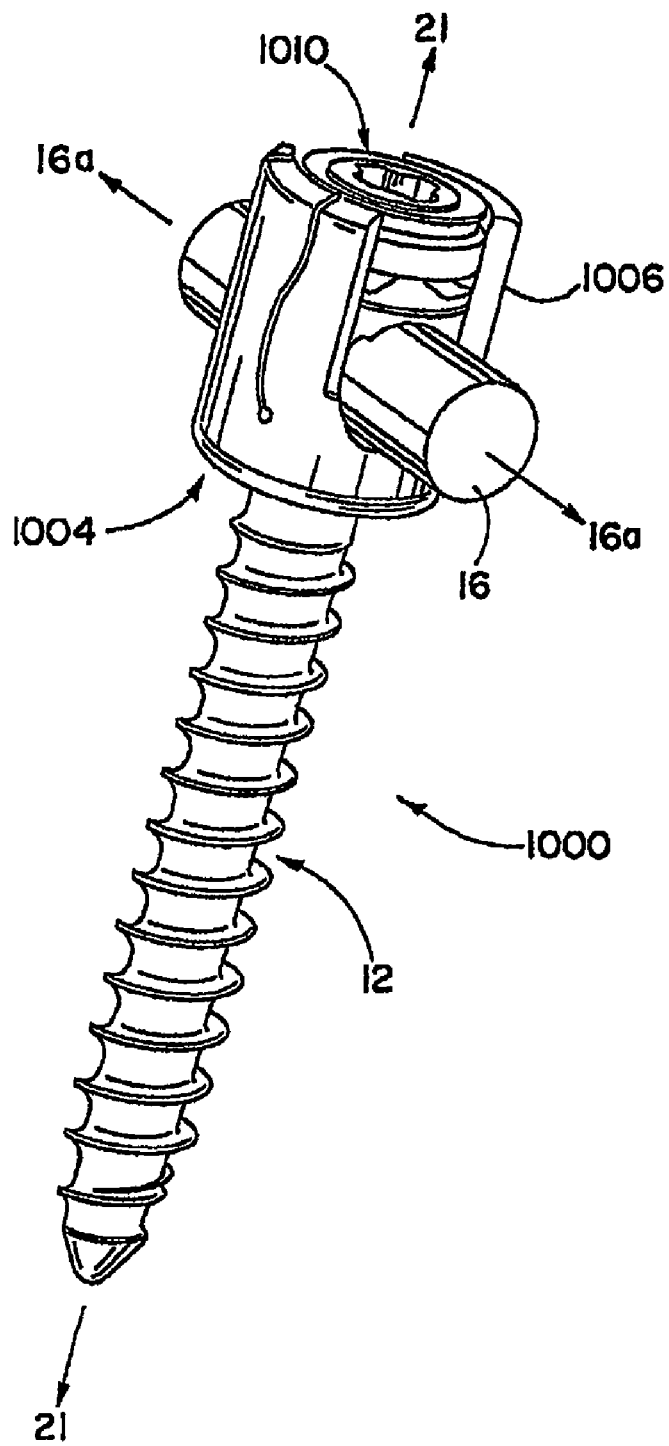
FIG. 45 is a perspective view of another form of the spinal fixation system in accordance with the present invention showing a bone screw and a coupling device including a yoke coupling member, and a lock device for securing a spinal rod relative to the bone screw.
Figure 46:
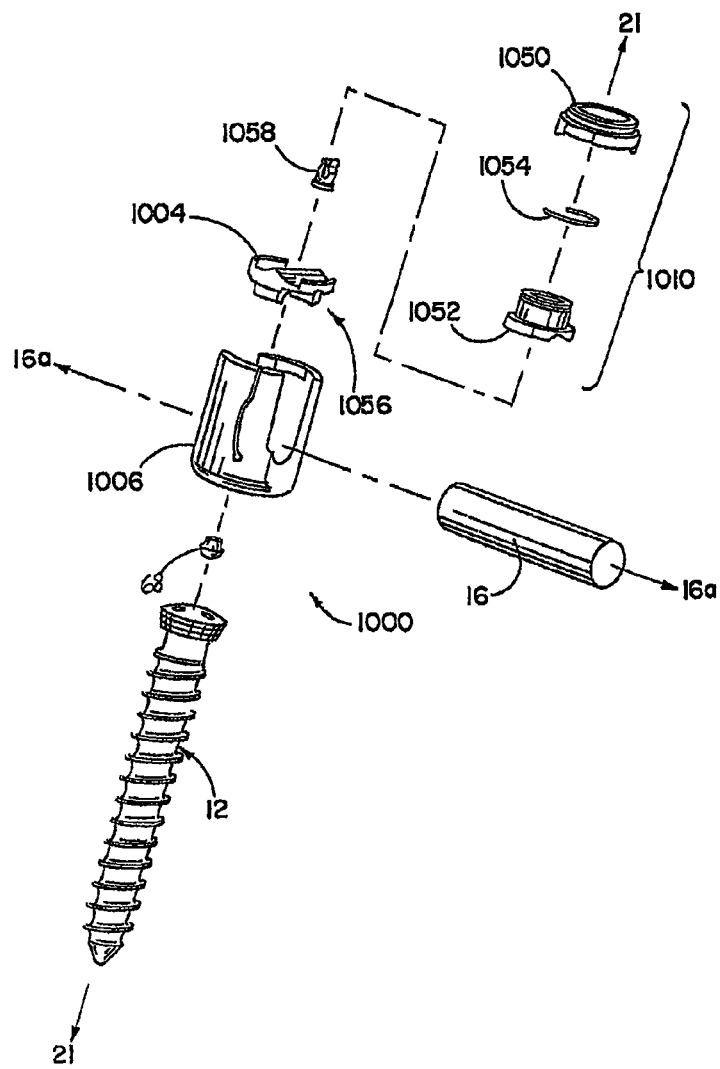
FIG. 46 is an exploded view of the spinal fixation system of FIG. 45 showing the lock device including a collar, a retainer, a lock member, a connecting member, and a saddle.

Referring now to FIGS. 45 to 69, a spinal fixation system 1000 for securing the previously described spinal rod 16 in accordance with another embodiment is depicted. As can be seen in FIGS. 45 and 46, the system 1000 includes a bone anchor member such as the above mentioned bone screw 12 and a coupling device 1004 for securing the spinal rod 16 relative to the bone screw 12. The coupling device 1004 includes a coupling member in the form of a yoke member 1006, an insert in the form of the previously described anvil 68, and a lock or compression device in the form of a cap assembly 1010.

The spinal fixation system 1000 is advantageous because it specifically contemplates and allows for greater flexibility in adjusting and/or aligning the spinal rod 16 during the application thereof while the lock device 1010 is in a predetermined axially fixed position relative to the yoke member 1006. The spinal fixation system 1000 specifically makes provision for easy adjustments and alignment of a spinal rod extending transversely through the yoke member, which, while advantageous in all uses thereof, is particularly advantageous in cases involving severe curvatures, such as a spinal rod used for a patient with scoliosis or kyphosis (three dimensional curvature). In this regard, the spinal fixation system 1000 involves a top loading or axial insertion of the cap assembly 1010 into the yoke member 1006 along the yoke axis 21 to a plurality of predetermined axial cap-lock positions. Depending on the specific cap-lock position selected, different spacing between the cap 1010 and spinal rod 16 is possible for various amounts of shifting, positioning, or aligning of the spinal rod 16 in the yoke 1006 prior to the final locking of the rod.

For instance, in a preferred embodiment, the spinal fixation system 1000 includes three different cap lock positions. In a first cap-lock position, the cap assembly 1010 forms a first relatively large gap 1106 (FIG. 65B) with an inserted spinal rod 16 with sufficient space to allow movement of the rod both along the yoke axis 21 and also along directions transverse to the yoke axis 21 such as along the rod axis 16a. This large gap 1106 permits ease of shifting a spinal rod with enhanced curvatures. In a second cap-lock position, the cap assembly 1010 forms a second, smaller gap 1108 (FIG. 66B) with the spinal rod 16 that primarily allows movement of the spinal rod along directions transverse to the yoke axis 21. This smaller gap 1108 permits final adjustments of the rod position prior to final locking of the spinal rod 16 into a fixed position relative to the yoke member 1006. In a third cap-lock position, the cap assembly 1010 locks the spinal rod 16 relative to the yoke 16 and bone screws 12. Preferably, the first and second cap-lock positions are reached by axial insertion of the cap assembly 1010 via a top loading thereof along the yoke axis 21 into the yoke member 1006, and the third cap-lock position is achieved through both rotational and axial movement of specific portions of the cap assembly 1010, as described more fully hereinafter.

In the spinal fixation system 1000, the bone screw 12, the anvil 68, and the spinal rod 16 as well as their relationship with the coupling device 1004 are preferably similar to that previously described with regard to the embodiments of FIGS. 1-44. As such, these features will not be described in any further detail with respect to the spinal fixation system 1000. The differences in the coupling device 1004, including variations in the yoke member 1006 and cap assembly 1010, will be described hereafter.

The yoke member 1006 is illustrated in FIGS. 47 to 50. The yoke member 1006 is a generally cylindrical structure having a disk-shaped base portion 1020 and an arcuate side wall 1022 that extends upwardly from outside edges of the base portion 1020. The side wall 1022 has a generally annular configuration that is split into two facing arcuate portions 1022a and 1022b with a pair of U-shaped upwardly opening slots 1026 between two pairs of facing, generally vertical edges 1026a, 1026b of the side wall portions 1022a and 1022b. The slots 1026 are sized to allow the spinal rod 16 to extend therethrough transversely relative to the yoke axis 21 similar to the previously described embodiments. The facing side wall portions 1022a and 1022b also define an internal space 1028 (FIG. 49) of the yoke member 1006 sized and configured to axially receive the cap assembly 1010 along the axis 21 in order to fix or lock the spinal rod 16 within the yoke member 1006. The yoke member 1006 has an upper opening 1029 leading to the internal space 1028.

The side wall 1022 includes at least one resilient portion 1030 that resiliently deflects or bends in order to permit axial receipt of the cap assembly 1010 into the yoke internal space 1028 along the axis 21. While a tool can be utilized to bend the wall resilient portions 1030 to provide sufficient clearance for axial insertion of the cap assembly 1010 to the various lock gap positions thereof, it is preferable from an ease of application standpoint to simply use the cap assembly 1010. The resilient portion 1030, in addition, is configured to provide sufficient strength in order to retain the cap assembly 1010 in the yoke member 1006.

Each resilient portion 1030 is configured to resiliently shift outwardly away from the axis 21 in response to engagement with the cap assembly 1010 as the cap assembly 1010 is shifted axially in order to receive the cap assembly 1010 in the yoke member 1006, and then resiliently shift back to substantially its original configuration to hold the cap assembly 1010 within the yoke member 1006 in one of the plurality of cap-lock positions. As will be further described below, the resilient portion 1030 and cap assembly 1010 include cooperating engagement portions that permit the yoke member 1006 to receive the cap assembly 1010 in one of a plurality of cap-lock positions along the axis 21 during its insertion into the yoke space 1028. Each cap-lock position locates the cap assembly 1010 or a portion thereof in a predetermined vertical or axial location along the axis 21 within the yoke space 1028. In certain of the lock positions, an audible "click" or other tactile indication may be generated that provides confirmation to the surgeon that the cap assembly 1010 has been properly received in the respective cap-lock position. The audible and/or tactile indication is advantageous because such signal lets a surgeon know that successful insertion of the cap assembly 1010 into the yoke member 1006 has occurred and that there is a known, predetermined gap between the cap assembly and spinal rod in the yoke space engaged on the insert.

Figure 47:
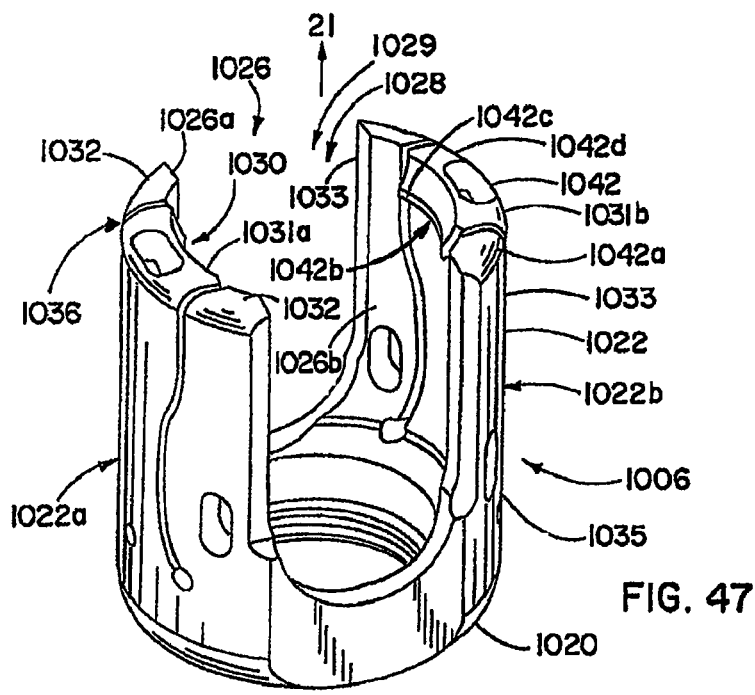
FIG. 47 is a perspective view of the coupling member of FIG. 46 showing slits in the yoke side wall portions to form resiliently flexible portions thereof.
Figure 48:
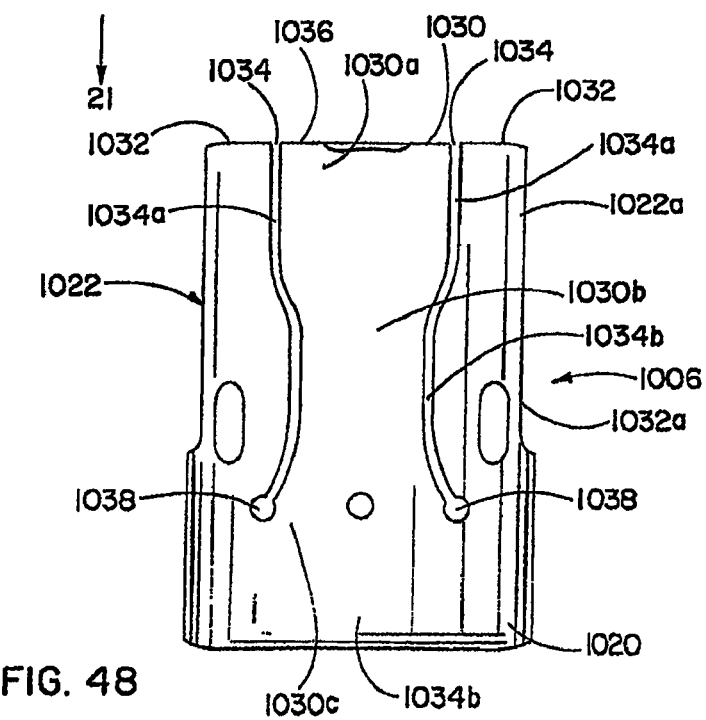
FIG. 48 is an elevational view of the yoke of FIG. 47 showing the configuration of the slits in the yoke side wall portions.
Figure 49:
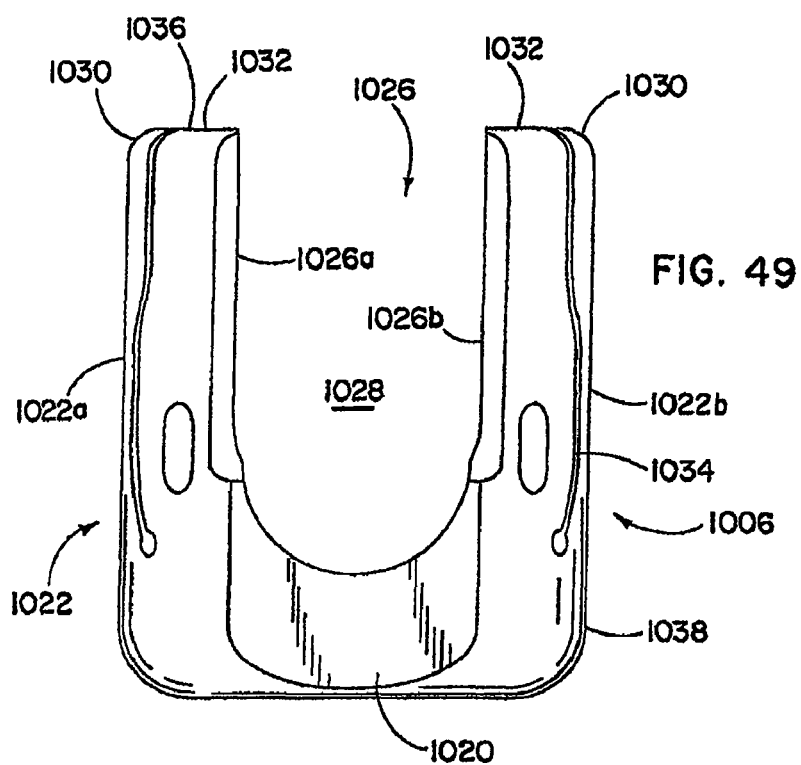
FIG. 49 is another elevational view of the yoke member of FIG. 47 showing slot openings between facing side wall portions.
Figure 50:
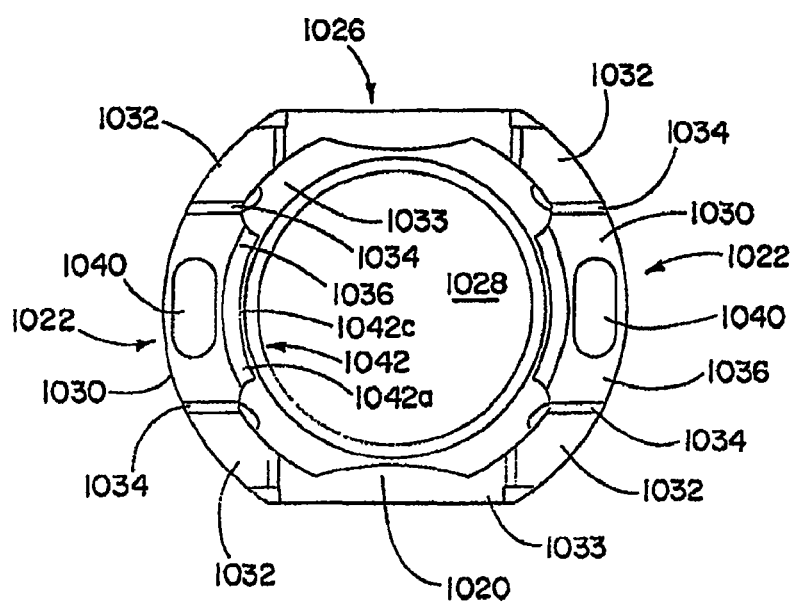
FIG. 50 is a top plan view of the yoke of FIG. 47 showing the flexible portions circumferentially extending between side wall guide or post portions.

The upstanding post portions 1032 of the side wall portions 1022*a* and 1022*b* are generally more rigid than the resilient portions 1030 and exhibit minimal bending or flexing thereof during insertion of the cap assembly 1010. As best shown in FIG. 48, the post portions 1032 are generally more rigid because of an increased width in the circumferential direction about the side wall portions along an axially intermediate portion 1032*a* of the post portions that provides resistance to bending or flexing. The posts 1032 serve as a guide to direct and align the cap assembly 1010 for proper orientation within the yoke member 1006. In this regard, as best illustrated in FIGS. 47 and 50, an inner surface 1033 of the posts 1032 includes an arcuate profile to guide the cap assembly 1010 into the receiving space 1028. That is, for example, the arcuate inner surface 1033 of the four posts 1032 substantially matches the annular or cylindrical profile or contour of the outer surface 1070*c* (FIG. 55) of a lower portion of the cap assembly 1010 as described more fully hereinafter. The four post portions 1032 are each generally spaced by 90 degrees from an adjacent post portion 1032 about the yoke side wall 1022 so that the cap assembly 1010 is securely retained in the yoke space 1028 when received therein. But for upper flanges 1042 of the resilient portions 1030 as described hereinafter, the resilient portions also include an arcuate inner surface 1035 having the same radius of curvature as that of the surfaces 1033 of the posts positions 1032.

Referring next to FIG. 48, the resilient portion 1030 is a substantially separated, elongate arm portion 1031*a* or 1031*b* in each of the side wall portions 1022*a* and 1022*b* formed by elongate slits 1034 that generally extend along the length of the side wall portions 1022*a* or 1022*b*. More specifically, each side wall portion 1022*a* and 1022*b* preferably includes an associated resilient arm portion 1031*a* and 1031*b*, respectively, between a pair of upstanding guide or post portions 1032. As will be described in more detail hereinafter, the resilient arm portions 1031*a* and 1031*b* are configured to enable resilient flexing of the arm during cap insertion as well as to provide enhanced strength to support the loading applied to the cap assembly 1010 received in the yoke. To this end, the slits 1034 extend along either side of the resilient portions 1030 so that they have a predetermined configuration allowing for their resilient bending during insertion of the cap assembly 1010 as well as providing the resilient portions 1030 sufficient strength to withstand forces generated between the cap assembly 1010 and yoke wall portions 1022*a* and 1022*b* so as to securely hold and retain the cap assembly 1010 in the various lock positions thereof.

Preferably, the resilient portion 1030 has a generally elongate, hour-glass shape so that various sections of the resilient portion have different levels of flexibility that optimize the manual insertion of the cap assembly 1010 along the yoke axis 21 and retention of the cap assembly 1010 within the yoke member 1006. That is, the hour-glass shape permits both resilient flexing of the resilient arm portions as well as enhanced strength in order to support any load or force on a received cap assembly 1010. Manifestly, other configurations for the resilient arm portions could also be employed for these purposes.

With the preferred hour-glass configuration, the arm portions 1031*a*, 1031*b* each include a circumferentially wider, upper holding portion 1030*a*, a circumferentially narrower, intermediate neck portion 1030*b*, and a circumferentially wider, lower base portion 1030*c*. The wider upper holding portion 1030*a* and lower base portion 1030*c* each have a radial thickness and width extending in the circumferential direction selected to provide sufficient strength and stiffness to the side wall 1022 at these portions in order to resist deformation or bending due to forces or loads applied to the received and locked cap assembly 1010 over the lifespan of the spinal fixation system 1000. The narrower intermediate portion 1030*b* has a radial thickness and circumferential width selected to permit elastic rather than plastic bending of the resilient portion 1030 during insertion of the cap assembly 1010 in order to minimize deformation of the yoke member 1006. In this regard, the narrow portion 1030*b* acts as a hinge section with the stiffer upper portion 1030*a* pivoting relative to the stiff lower portion 1030*c* thereabout during the various stages of cap insertion into the yoke member. By way of example and not limitation, the resilient portions 1030 can be approximately 1.3 mm in radial thickness except at the thicker upper flanges 1042 thereof, and the upper holding portion 1030*a* can be approximately 5.5 mm in circumferential width at its widest section, the intermediate neck portion 1030*b* can be approximately 3.9 mm in circumferential width at its narrowest section, and the lower base portion 1030*b* can be approximately 5.6 mm in circumferential width at its widest section; however, different sizes and configurations of the resilient portion 1030 can be employed.

As mentioned, the arm portion 1030 is formed from the slits 1034 generally extending along the length of the side wall 1022. The slits may be approximately 0.012 inch wide and extend from an upper edge 1036 of the side wall downwardly toward the base portion 1020 to form the hour-glass shape. In this regard, the slits 1034 each have an upper, linear section 1034*a* that extends axially and a lower, arcuate section 1034*b* with the opposite sections 1034*b* curved toward each other as best seen in FIG. 48. The slits 1034 terminate in enlarged openings 1038 corresponding to the widest section of the base portion 1030*c* thereacross. The enlarged openings 1038 that also minimize stress risers in the side wall 1022 as the resilient arm portion 1030 is flexing or bending. The openings 1038 may also serve as the starting point for EDM (electro-discharge machining) of the slits in the yoke side wall.

Referring to FIG. 50, the upper edge 1036 of the yoke arm portions 1030 each preferably includes recesses 1040 in the form of kidney shaped depressions. The recesses 1040 provide a slot for receipt or removal of a tool for bending the arm portions 1030 outwardly during insertion or removal of the cap assembly 1010. While the yoke member 1006 preferably includes the recesses 1040 to aid in the insertion or removal of the cap assembly 1010 via a cooperating tool that fits therein, the resilient portions 1030 also allow insertion and removal of the cap assembly 1010 without the use of such a tool through the action of the cap assembly 1010 against the yoke itself by inserting the cap assembly 1010 using a driver tool rather than with a persuader tool or other instrument to spread the yoke arms apart.

To hold the cap assembly 1010 in the cap-lock positions, the yoke member 1006 also includes securing structure in the form of a pair of lip flanges 1042 that each extend inwardly in the yoke inner space 1028 from the upper edge 1036 of the yoke resilient portions 1030. As best illustrated in FIGS. 47, 50, 65B, and 66B, the flanges 1042 have a wedge shape and each include a tapered upper surface 1042a that extends downwardly at an incline to the yoke axis into the inner space 1028 from the flex portion upper edge 1036 and also includes a lower surface 1042b that extends back towards an inner surface of the wall 1022 from an inner, lower edge 1042c of the flange.

The upper ramp surfaces 1042a of the flanges 1042 cooperate with the cap assembly 1010 upon engagement therewith for elastically bending the resilient portions 1030 laterally outward during insertion. The flanges 1042 permit the yoke member 1006 to receive the cap assembly 1010 in at least one of the plurality of cap-lock positions, and preferably both of the preferred preliminary cap lock positions at which the spinal rod can still be adjusted, and audibly indicate the receipt of the cap assembly 1010 in these positions. The profile of the flanges 1042 is also preferred because it resists, and preferably eliminates, splaying of the yoke member 1006; that is, the flanges 1042 cooperate with the cap assembly 1010 to resist outward spreading of the resilient portions 1030 after the yoke member 1006 has received the cap assembly 1010 in the locked positions therein, as is described more fully below in conjunction with FIGS. 63 and 64.

Referring now to FIGS. 51-64, the cap assembly 1010 is illustrated in more detail. In this form, the cap assembly 1010 is configured to facilitate top loading into the yoke member 1006 or insertion of the cap assembly 1010 along the yoke axis 21. The cap assembly 1010 also includes structure that cooperates with the yoke flanges 1042 so that the cap assembly 1010 may be received in a plurality axial cap-lock positions that permit various degrees of rod positioning prior to the final rod locking.

Preferably, the cap assembly 1010 includes an upper retainer in the form of a collar 1050, a cam lock member 1052 rotatably joined to the collar 1050, and a saddle member 1056 rotatably joined to the cam lock member 1052 and that locks the rod 16 within the yoke member 1006 in one of the cap-lock positions. The cam lock member 1052 is rotatably joined to the collar 1050 by a retainer 1054, such as a resilient C-clip. In this manner, the cam lock member 1052 is rotatable relative to the collar 1050 and remains fixed relative thereto when the rotary force applied between the collar and the cam lock member ceases. The saddle 1056 is rotatably joined to the cam lock member 1052 by a connector 1058, such as the previously described spring clip 519, so that the saddle 1056 can move axially along the axis 21 upon rotation of the cam lock member 1052 with the cap assembly in the second lock position therein in order to lock the spinal rod 16 within the yoke member 1006. This is the third and final cap-lock position of the cam lock member 1052.

Figure 51:
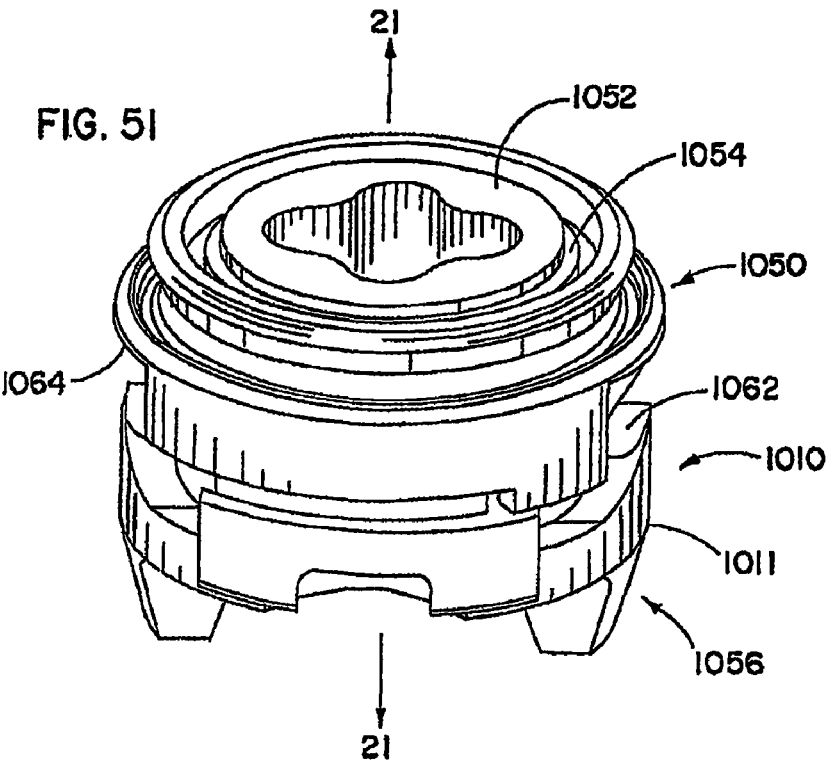
FIG. 51 is a perspective view showing the lock device in an axially compact configuration showing two sets of axially spaced ramp surfaces.
Figure 52:
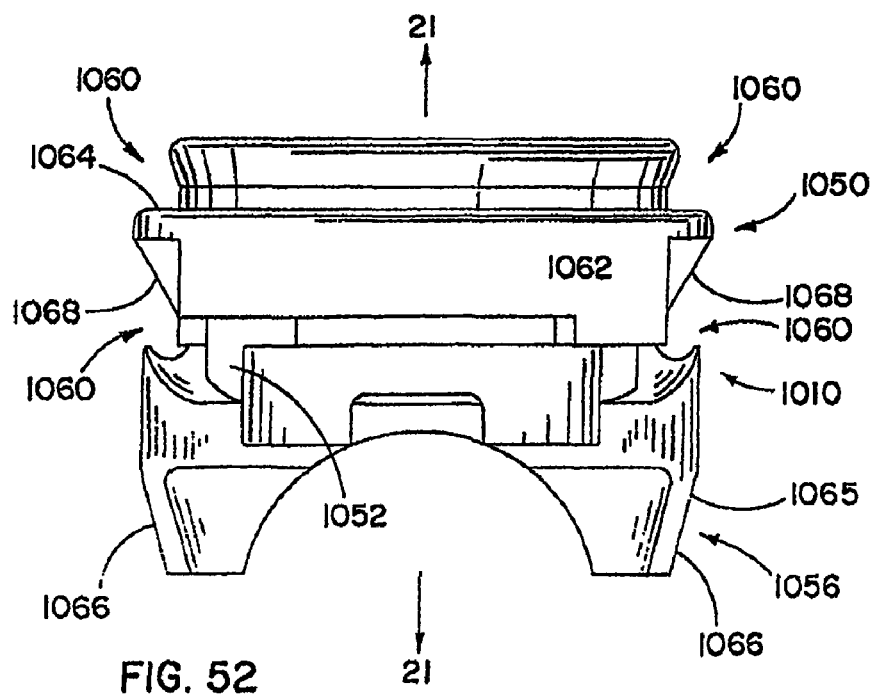
FIG. 52 is a side elevational view of the lock device of FIG. 51.
Figure 65A:
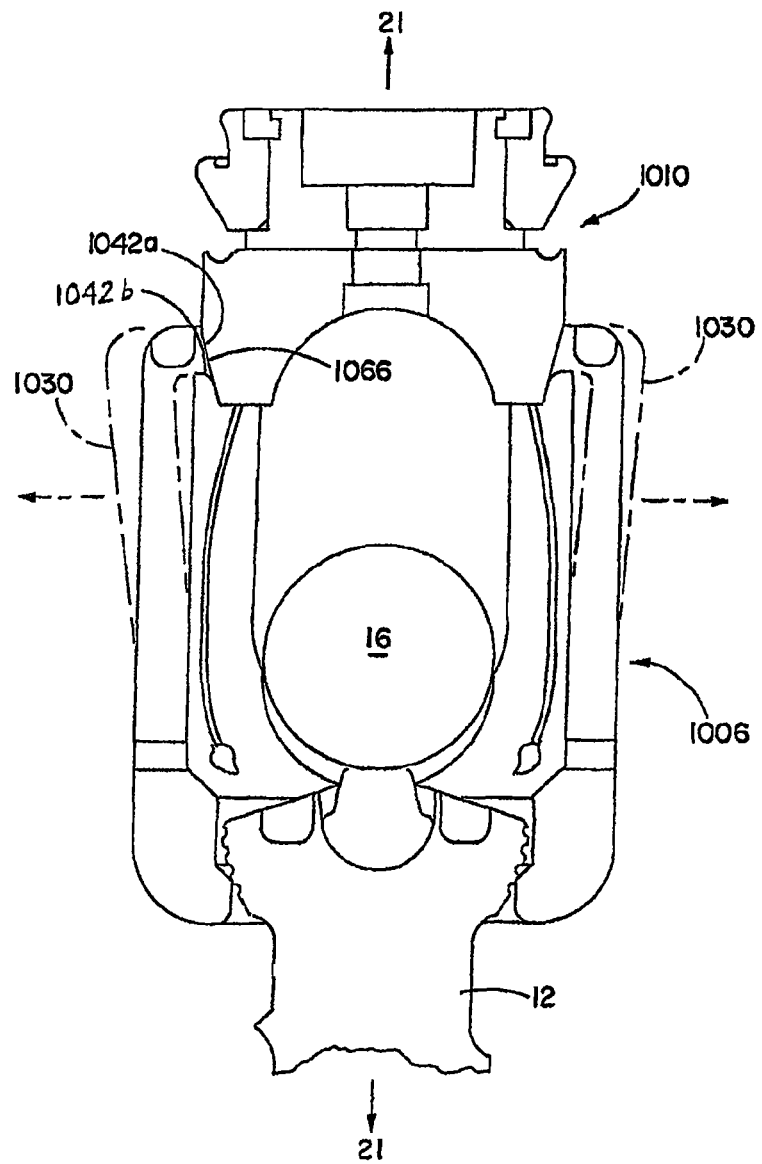
FIG. 65A is a cross-sectional view showing the lock device inserted into the coupling member with the axially lower set of ramp surfaces thereof pushing the resilient portions of the coupling member walls in an outward direction as shown in phantom lines.
Figure 66A:
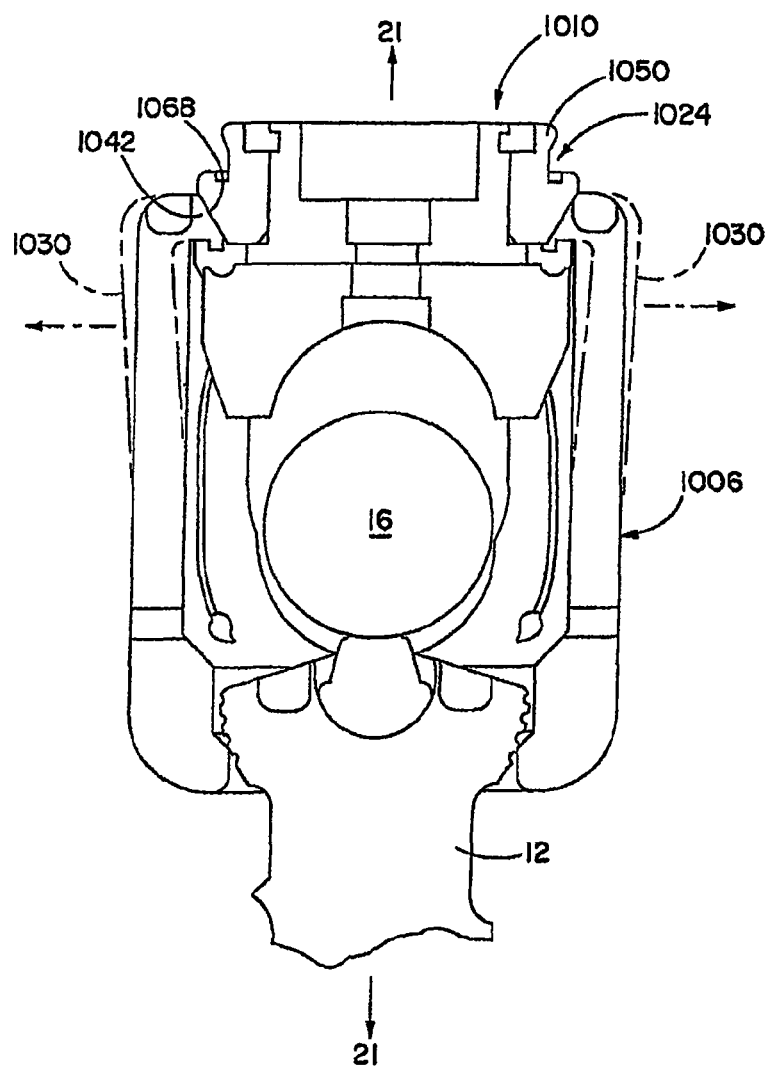
FIG. 66A is a cross-sectional view of the lock device inserted into the coupling member with an axially upper set of ramp surfaces thereof pushing the resilient portions of the coupling walls in an outward direction as shown in phantom lines.

For receipt in the multiple cap-lock positions, the cap assembly 1010 includes engagement or seating surfaces 1060 that cooperate with the yoke flanges 1042. Referring to FIG. 51, the saddle 1056 includes a first engagement surface in the form of upwardly opening recesses or depressions 1062 at an outer edge thereof that receives a depending end portion 1042c of the yoke flanges 1042 therein when the cap assembly 1010 is in the first cap-lock position. The collar 1050 also includes a second engagement surface in the form of an annular groove 1064 that receives the end portion 1042c of the yoke flanges 1042 therein when the cap assembly 1010 is inserted into the yoke member 1006 in the second cap-lock position. To permit the cap assembly 1010 to be inserted into the cap-lock positions in the yoke space 1028 along the axis 21, the cap assembly 1010 also includes ramp surfaces that push the yoke resilient portions 1030 outwardly away from the axis 21 during axial insertion thereof into the yoke internal space 1028. That is, for example, the saddle 1056 includes a set of inclined ramp surfaces 1066 (FIG. 52) on a lower portion 1065 thereof that pushes the resilient portions 1030 outwardly transverse to the axis 21 during initial insertion of the cap assembly 1010 for receipt of the cap assembly 1010 in the first cap-lock position (FIG. 65A). Likewise, the collar 1050 also includes a second set of inclined ramp surfaces 1068 (FIG. 52) that also pushes the resilient portions 1030 outwardly transverse to axis 21 as the cap assembly 1010 is pushed further into the yoke member 1006 along the axis 21 from the first cap-lock position to the second cap-lock position (FIG. 66A). To this end, the ramp surfaces 1066 and 1068 cooperate with the ramp surfaces 1042a of the yoke flanges to effect outward pushing of the yoke resilient portions 1031a and 1031b Referring to FIGS. 55-57, an example of the saddle 1056 is illustrated in more detail. The saddle 1056 includes a disk-shaped base member 1070 having an upper surface 1070a, a lower surface 1070b, and an outer or peripheral surface 1070c. The base member surface 1070c has a curvature that can conform to the inside diameter of the yoke side wall 1022, and the curvature and profile of the arcuate inner surfaces 1033 of the yoke guide posts 1032 and the inner surfaces 1035 of the resilient portions. Extending from opposite sides of the base surface 1070c are upward extensions 1072. The extensions 1072 are preferably in the form of arcuate walls that are configured for receipt in the yoke slots 1026 (see, e.g., FIG. 57) such that that the saddle 1056 preferably cannot rotate about the yoke axis 21 when received within the yoke member 1006, but only axially moves along the axis 21 in response to rotation of the cam lock member 1052. The arcuate wall extensions 1072 have an arcuate inner surface 1073 with a radius of curvature sized to be larger than that of a lower portion of the cam lock member 1052 so that it can readily be rotated relative to the saddle member 1056. In this manner, rotation of the cap lock assembly 1010, and specifically the cam lock member 1052 thereof, is guided by the saddle wall surfaces only, and thus the cam lock member 1052 does not interact with or engage the yoke member side wall for locking of the spinal rod in the yoke.

The saddle lower surface 1070b includes a surface portion 1074 (FIG. 56) that is configured to the shape of the spinal rod 16. When the cap assembly 1010 is in the third-cap lock position, the saddle surface portion 1074 pushes flush against the spinal rod 16 in order to fix or lock the rod within the yoke internal space 1028 similar to the previously described embodiments. The saddle 1056 also includes a central opening 1071 for receipt of the connecting member 1058 in order to join the saddle 1056 to the cam lock member 1052.

The saddle upper surface 1070a includes ramped portions 1076 that include inclined ramps 1076a and 1076b that extend upwardly and radially inwardly toward each other and an upper flat surface 1076c that extends between the inclined side ramps 1076a and 1076b. With the saddle received in the yoke member, the side incline surface portions 1076a and 1076b extend obliquely at an incline relative to the yoke axis 21, and the upper surface 1076c extends normal thereto. As will be further discussed below, the configuration of the ramped portions 1076 preferably conforms to a similar configuration of a lower, recessed surface 1082 of the cam lock member 1052 in order to permit the cap assembly 1010 to have a compact position when the saddle inclined surface portions 1076a and 1076b and upper surface portion 1076c are seated flush against the recessed surface 1082 created by the corresponding included upper surface portions 1082a, 1082b of the cam lock member 1082 (i.e., FIGS. 52 and 60) and an expanded position when the cam lock member is rotated relative to the saddle so that the respective engaging surfaces 1082, 1076 no longer sit flush with each other (i.e., FIGS. 53 and 61). Accordingly, the cap assembly 1010 shifts from one position to the other through rotation of the cam lock member 1052.

Figure 58:
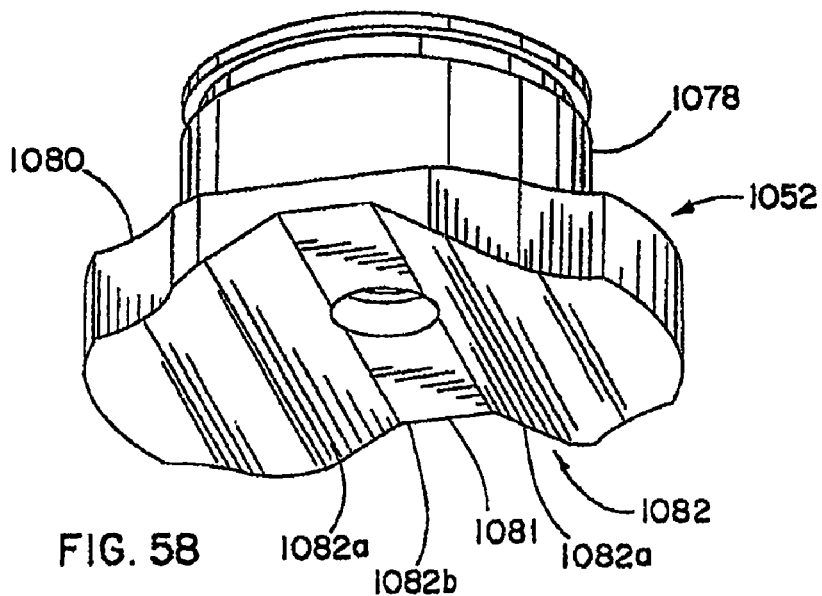
FIG. 58 is a perspective view of the cam lock member of FIG. 54 showing a lower profile thereof.
Figure 59:
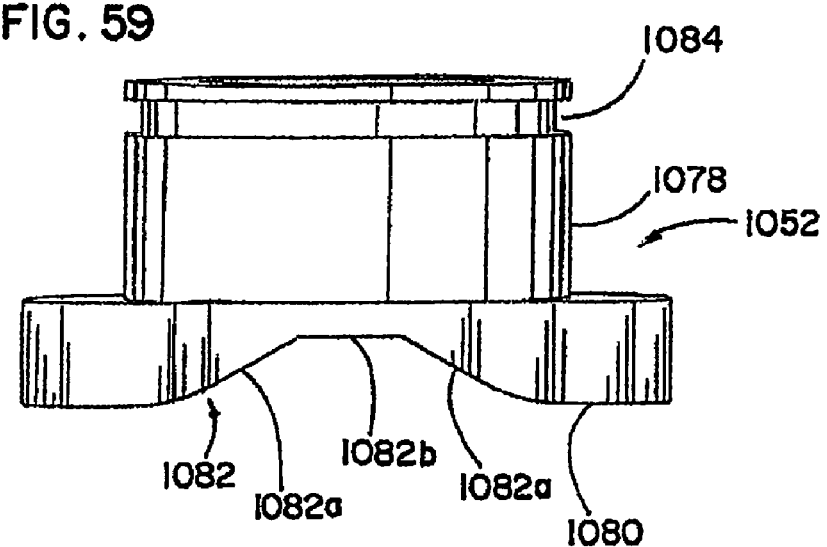
FIG. 59 is an elevational view of the cam lock member of FIG. 54 showing oppositely inclined lower, side surface portions and a central, flat surface portion extending therebetween.
Figure 60:
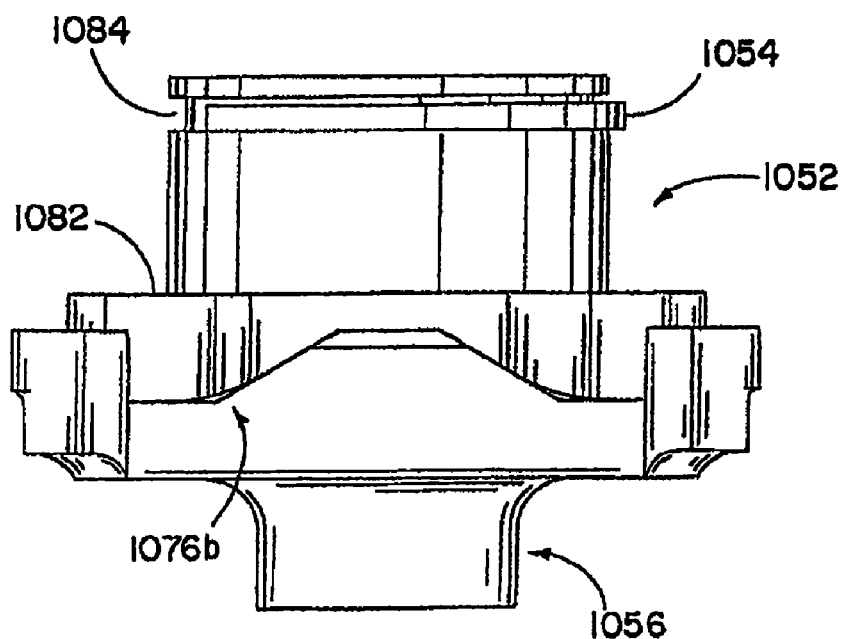
FIG. 60 is an elevational view of the cam lock member and saddle member showing the respective engaging surfaces thereof in mating relation in the compact configuration thereof.

Referring to FIGS. 58-60, one form of the cam lock member 1052 is illustrated in more detail. The cam lock member 1052 preferably includes an upper cylindrical body portion 1078 and a larger, lower base portion 1080. In order to be rotatably joined with the saddle 1056, the body 1078 includes a central opening 1081 extending therethrough that is sized to receive the connecting member 1058. As previously mentioned, a lower surface 1082 of the cam lock member 1052 has a configuration that preferably conforms to the configuration on the saddle upper surface 1070b. That is, the actuating member lower surface 1082 includes ramped or inclined surface portions 1082a that extend upwardly and radially inwardly toward each other and an upper surface portion 1082b that extends between the side inclined surface portions 1082a.

When the saddle 1056 is rotatably joined to the cam lock member 1052 by the connecting member 1058, the cap assembly 1010 can take on either a compact or an expanded configuration. More specifically, referring to FIGS. 52 and 60, the initial or compact configuration of the saddle 1056 and the cam lock member 1052 is illustrated where the upper surface 1076b of the saddle 1056 is seated flush against the lower, recessed surface 1082 of the cam lock member 1052. In this axially compact form, when the cap assembly 1010 has been inserted in the yoke member 1006 in either the first or second cap-lock positions, gaps between the lower surface 1070b of the saddle 1056 and the spinal rod are formed (e.g., FIGS. 65B and 66B). Assuming the spinal rod is engaged against the insert, these gaps are of a predetermined axial size with respect to a given diameter of the spinal rod, as discussed further hereinafter. The gaps and advantages thereof will be described in more detail below.

Figure 53:
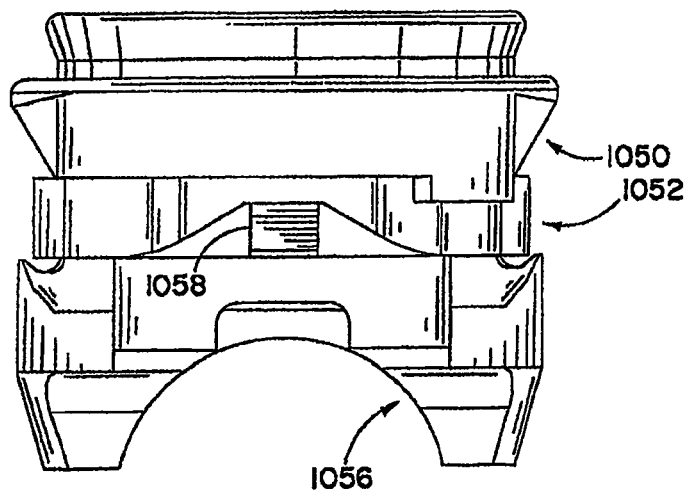
FIG. 53 is a side elevational view of the lock device in an extended configuration showing a connecting member extending between a cam lock member and a saddle member of the lock device.
Figure 54:
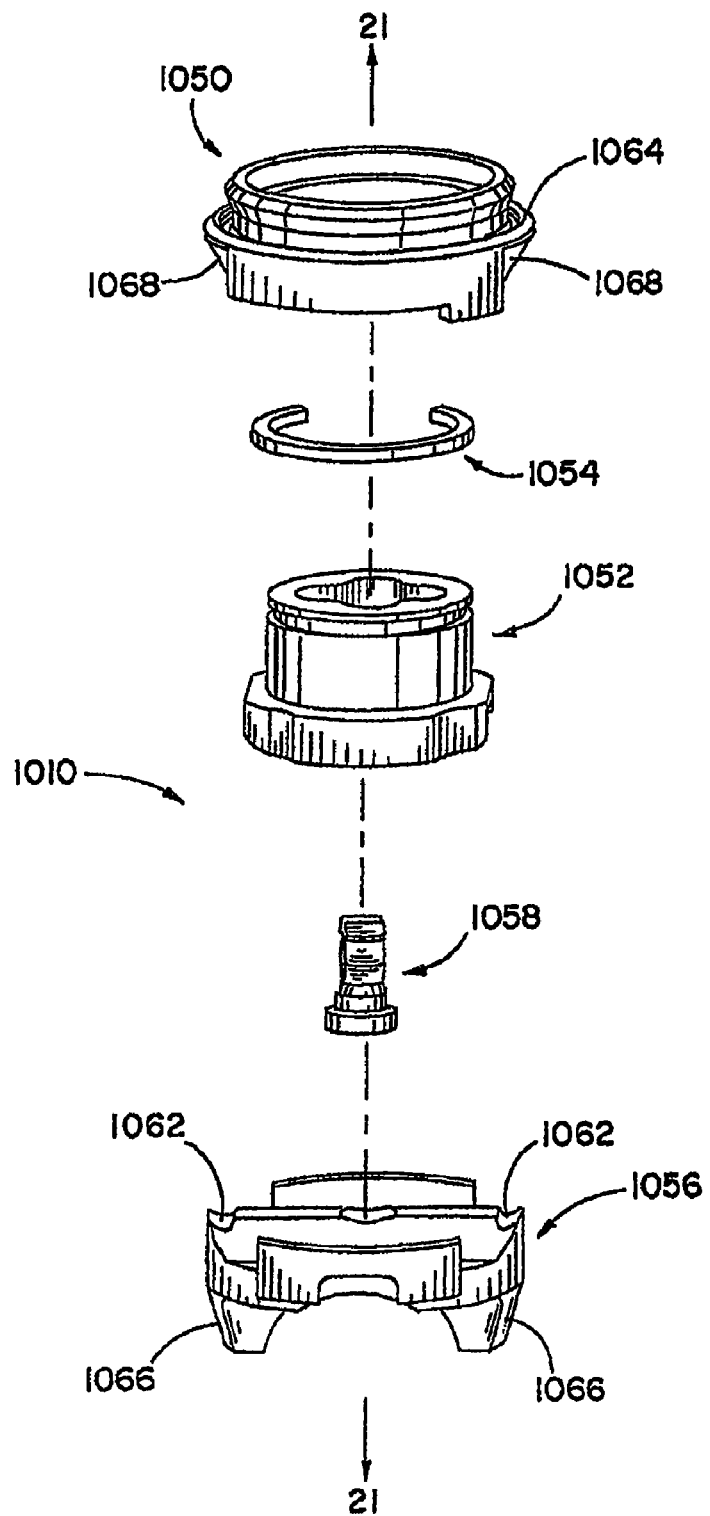
FIG. 54 is an exploded view of the lock device of FIG. 51 showing the collar, retainer, the cam lock member, the connecting member, and the saddle member.
Figure 55:
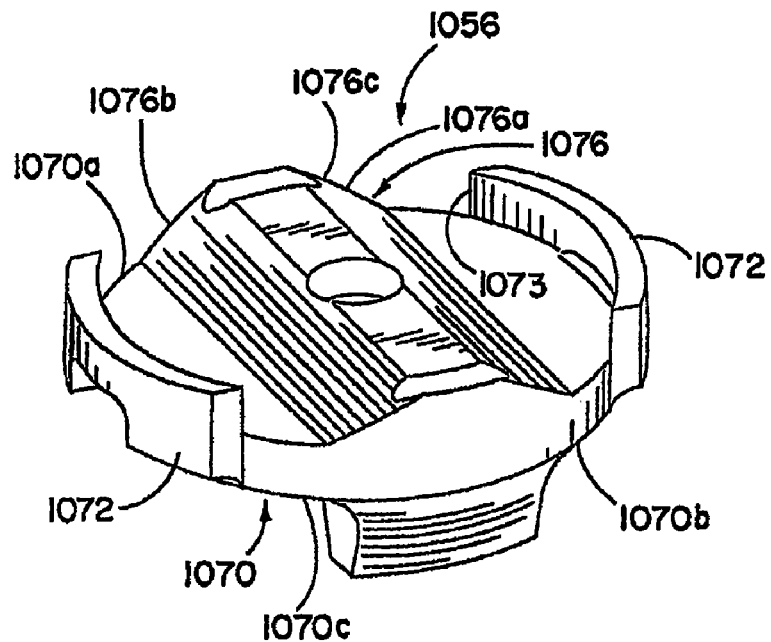
FIG. 55 is a perspective view of the saddle member showing an upper profile thereof.
Figure 61:
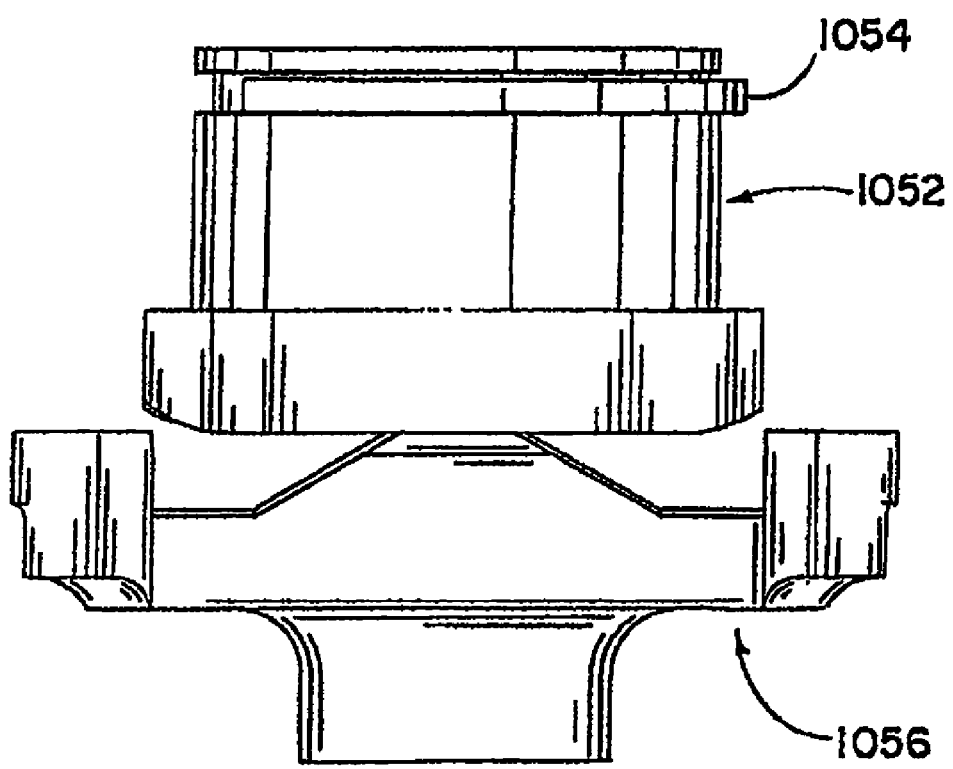
FIG. 61 is an elevational view of the cam lock member and saddle member showing the respective engaging surfaces rotated relative to each other to shift the members to the axially extended configuration thereof.

Referring to FIGS. 53 and 61, the second or expanded configuration of the saddle 1056 and the cam lock member 1052 is illustrated where rotation of the cam lock member by a predetermined angular amount, e.g., between approximately 80 to approximately 100 degrees, drivingly cams the saddle 1056 downwardly along the axis 21. That is, when received in the yoke member 1006, upon rotation of the cam lock member 1052 relative to the saddle 1056, the ramped or inclined surface portions 1082a of the cam lock member 1052 and the inclined surface portions 1076a, 1076b of the saddle 1056 cooperate to cam the saddle 1056 downwardly along the axis 21 to form the axially expanded configuration of the cap assembly 1010. In this expanded position, as will be further discussed below, the cap assembly 1010 is in the third cap-lock position and fixes or locks the spinal rod 16 relative to the yoke.

An annular groove 1084 sized to receive the retainer 1054 is formed toward the upper end of the cam lock member cylindrical body portion 1078. With the cylindrical body portion 1078 received in the collar 1050, the retainer cooperates with structure of the collar 1050 in order to rotatably join the actuating member thereto. As will be described below, the cylindrical body portion 1078 has a diameter sized to provide clearance with an inner diameter of the collar 150 such that it is rotatably received in the collar 1050.

Figure 62:
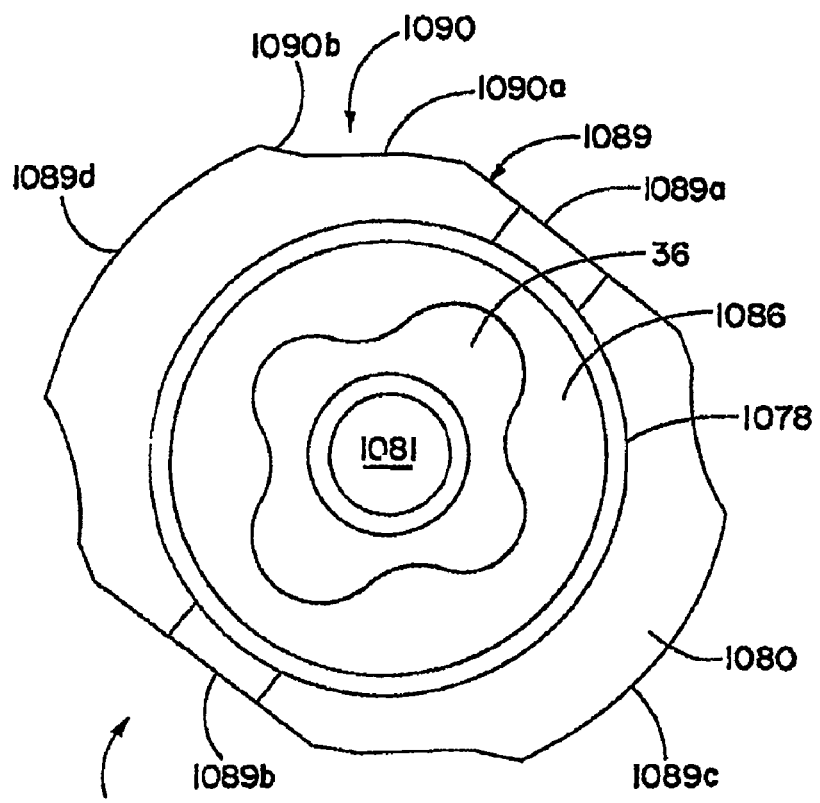
FIG. 62 is a top plan view of the cam lock member showing a drive recess thereof.

Similar to the previous embodiments, the cam lock member 1052 also includes the driving surface portion 36 in the form of a lobed recessed surface 1086 of the cylindrical body 1078 (FIG. 62). The lobed recessed surface 1086 receives the operative end of a similarly shaped tool in order to rotate the cam lock member once the cap assembly 1010 has been received in the second locking position. Once in this position, rotation of the cam lock member by a predetermined amount, e.g., between approximately 80 to approximately 100 degrees, drivingly cams the saddle 1056 from its position in the compact configuration of the cap assembly to an axially extended position in the expanded configuration of the cap assembly in order to lock the spinal rod 16 within the yoke member 1006.

Figure 68:
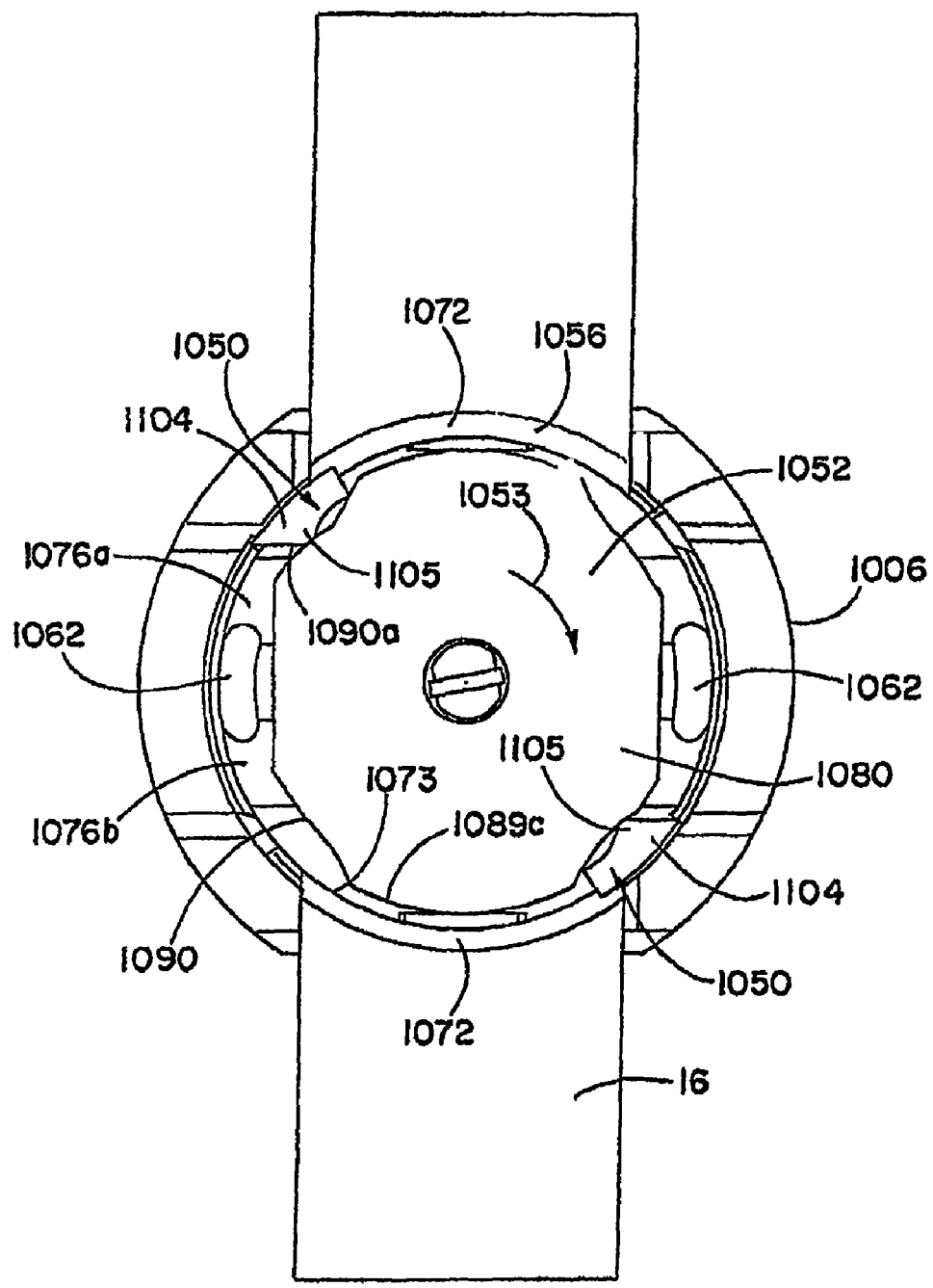
FIG. 68 is a cross-sectional view of the lock member in the second lock position showing the relationship between stop members on the collar and the edges of the actuating member.

As will be further described below, the base portion 1080 of the cam lock member 1052 includes a peripheral surface 1089 having opposite side flats 1089a and 1089b and opposite curved sides 1089c and 1089d with truncated corner portions 1090 therebetween that function as stops in combination with depending abutments or stops 1104 of the collar 1050 to limit rotation of the cam lock member 1052. The arcuate side portions 1089c and 1089d of the peripheral surface 1089 are spaced farther radially outward from the central axes 21 than the flat side portions 1089a and 1089b but still are in clearance relative to the arcuate inner surfaces 1073 of the saddle extension walls 1072, as can be seen in FIG. 68.

Figure 63:
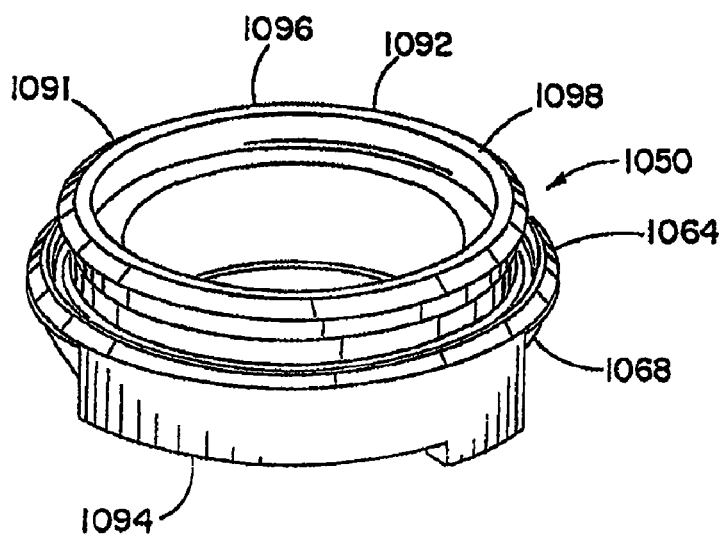
FIG. 63 is a perspective view of the collar of FIG. 54 showing an annular seating groove thereof.
Figure 64:
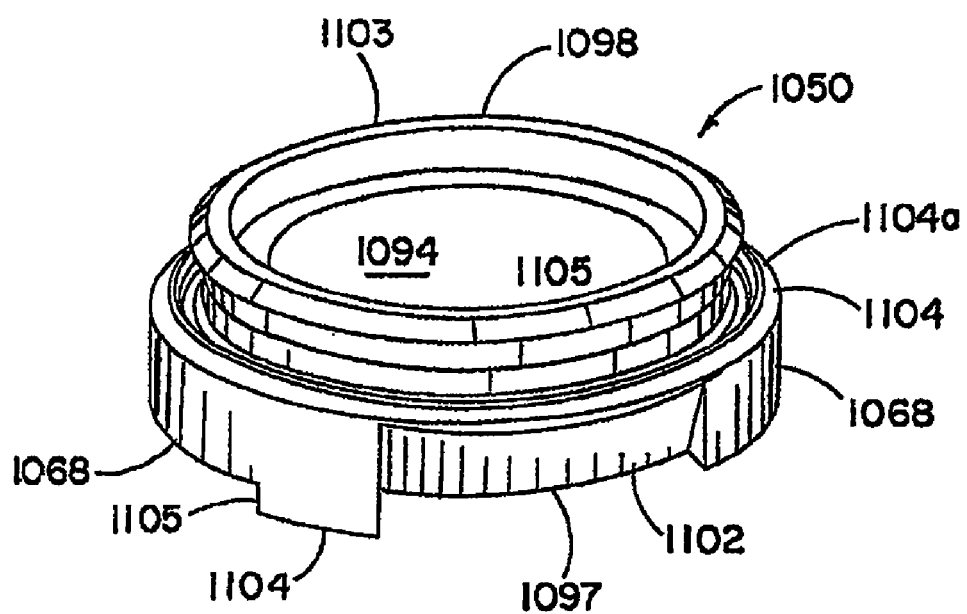
FIG. 64 is a perspective view of the collar of FIG. 54 showing depending stop portions and side ramp surfaces thereof.

Referring now to FIGS. 63 and 64, one form of the collar 1050 is illustrated. In this form, the collar 1050 includes an annular body portion 1092 defining a central through opening 1094 having an inner diameter sized to receive at least a portion of the lock member cylindrical body 1078 therein. Once the cam lock member 1052 is received in the opening 1094, the C-clip retainer 1054 may be inserted into the annular groove 1084 thereof and engage or abut a lower shoulder surface 1096 of the collar 1050 that extends radially into the central opening 1094 from collar inner surface 1091. The engagement of the retainer 1054 against the projecting surface 1096 rotatably retains the cam lock actuating member 1052 with the collar 1050 against removal of the cylindrical body 1078 out from the bottom of the collar opening 1094.

Figure 66B:
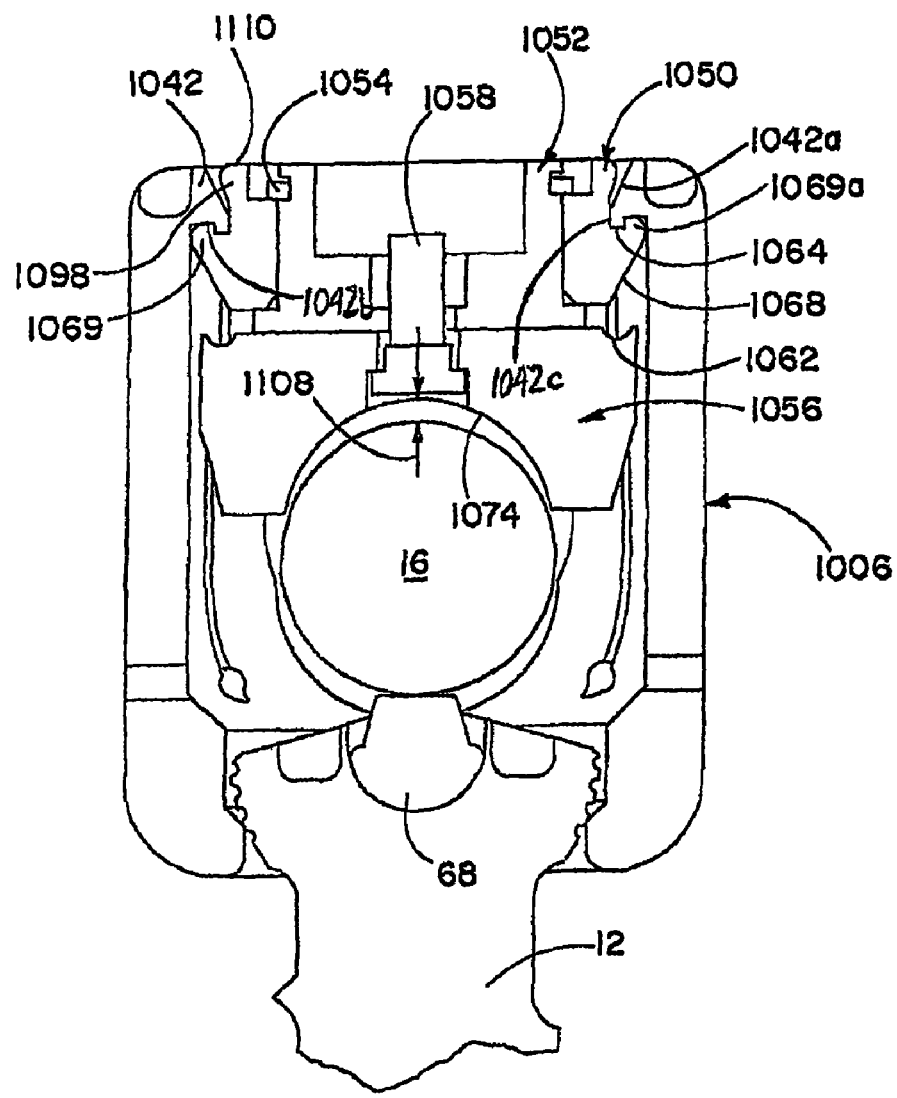
FIG. 66B is a cross-sectional view of the lock device in a second lock-position providing a small gap between the lock device and spinal rod.

The collar 1050 also includes the previously described second seating or engagement surface, preferably in the form of the annular groove 1064, extending around the collar 1050. The annular groove 1064 receives the resilient portion flanges 1042 when the cap assembly 1010 is inserted to the second cap-lock position. Extending upwardly from an inner edge of the groove 1064 is an upstanding annular rim 1098 that tapers radially outwardly partially over the annular groove 1064. The rim 1098 serves to hold the flanges 1042 within the groove 1064. As best shown in FIG. 66B, the ramp surfaces 1068 on the collar 1050 taper inwardly from an axially intermediate rim 1069 of the collar 1050 toward the central opening. The rim 1069 is adjacent the groove 1064 and axially below the upper rim 1098. The lower rim 1069 projects out radially further than the upper rim 1098 and includes an upstanding lip 1069a that is in a confronting relationship with the yoke flange lower edge 1042c. As a result, this confronting relationship between the rim 1069 and flange 1042 prevents the outward splaying of the yoke arms 1030.

Another set of ramp surfaces 1068 of the cap assembly 1010 are formed on opposite sides of the collar 1050. These surfaces taper inwardly along the outer surface of the collar 1050 toward the central opening 1094. The ramp surfaces 1068 engage the ramp surfaces of the yoke flanges 1042 to push the resilient portions 1030 outwardly away from the yoke axis 21 during axial insertion of the cap assembly 1010 from the first cap-lock position to the second cap-lock position (FIG. 66A).

Depending below a lower surface 1102 of the collar 1050 are spaced stops or abutments 1104 that cooperate with the truncated corner portions 1090 of the cam lock member 1052 to avoid over rotation thereof. As illustrated, the abutments 1104 include a depending post that projects downward from the collar lower surface 1102. The abutments 1104 are formed at an end of arcuate outer surface portions 1103 of the collar 1050 so that the stops are in diametrically opposing relation across the annular body portion 1097 of the collar. Referring to FIG. 64, it can be seen that the outer surface portions of the posts are flush with the arcuate surface portions 1103. Also, it can be seen that the ramp surfaces 1068 extend between the arcuate surface portions and are radially recessed therefrom.

Referring to FIGS. 65A-69, one exemplary mode of operation of the spinal fixation system 1000 will be described. As mentioned above, the spinal fixation system 1000 permits the cap assembly 1010 to be received within the yoke in a plurality of cap-locking positions. For example, the system 1000 includes at least one and preferably two adjustment or pre rod-lock positions that allow for shifting of the rod 16 within the yoke member 1006 while the cap assembly 1010 is securely held in position relative to the yoke member 1006, and a locked position that fixes the rod 16 in the yoke member 1006.

Figure 65B:
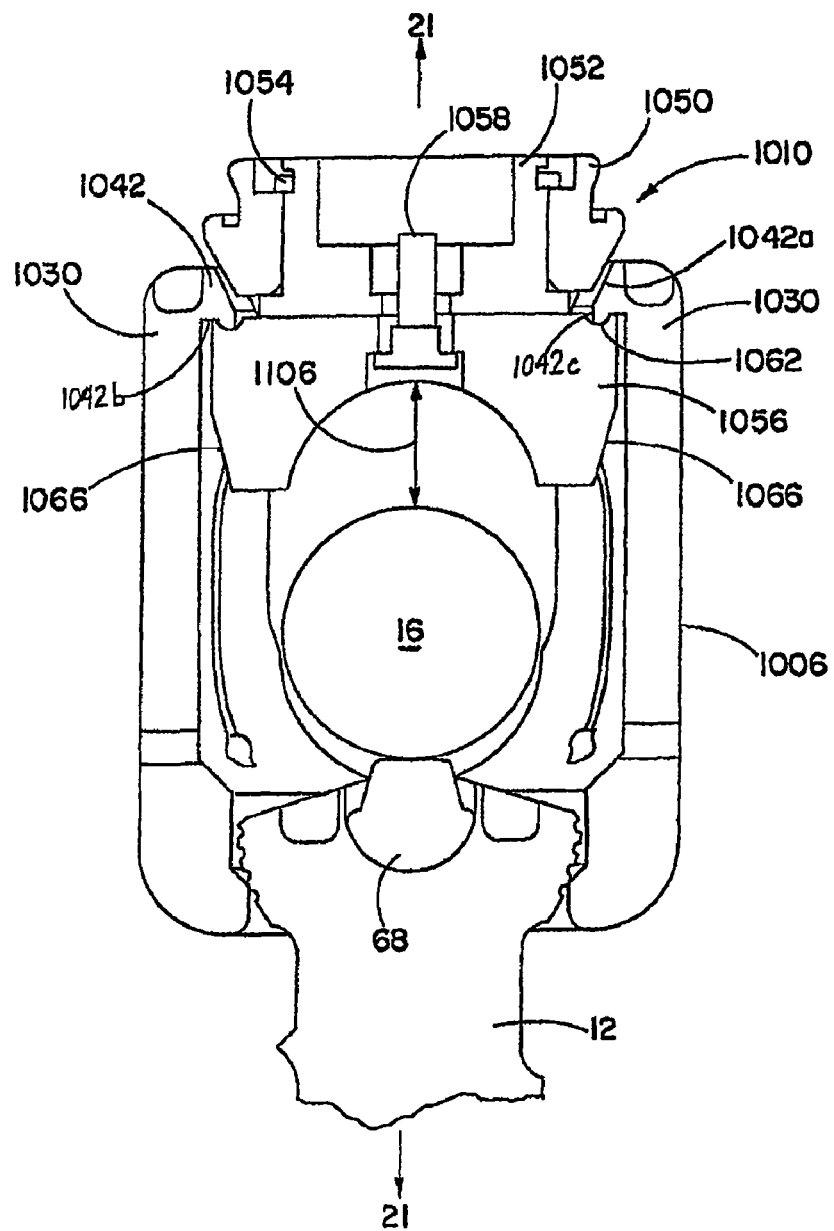
FIG. 65B is a cross-sectional view of the lock device in a first lock-position in the yoke providing a large gap between the lock device and spinal rod.

More specifically, FIG. 65B shows the cap assembly 1010 in a first cap-lock position or a maximum clearance position in the yoke member 1006 that provides a first or relatively large gap 1106 between the saddle 1056 and the spinal rod 16. In this position, there is a predetermined axial distance between the saddle lower surface 1082 and the rod surface 16*a* that is sufficiently large to permit shifting of the spinal rod both transverse to the yoke axis 21 and also along the yoke axis 21.

FIGS. 66B and 68 show the cap assembly 1010 in a second cap-lock position or a minimum clearance position in the yoke member 1006 that provides a second or relatively small gap 1108 between the saddle 1056 and the spinal rod 16. In this position, the predetermined axial distance between the surfaces 1082 and 16*a* is smaller to primarily permit shifting of the spinal rod 16 transverse to the yoke axis 21 and only minimal shifting along the yoke axis 21.

Figure 67:
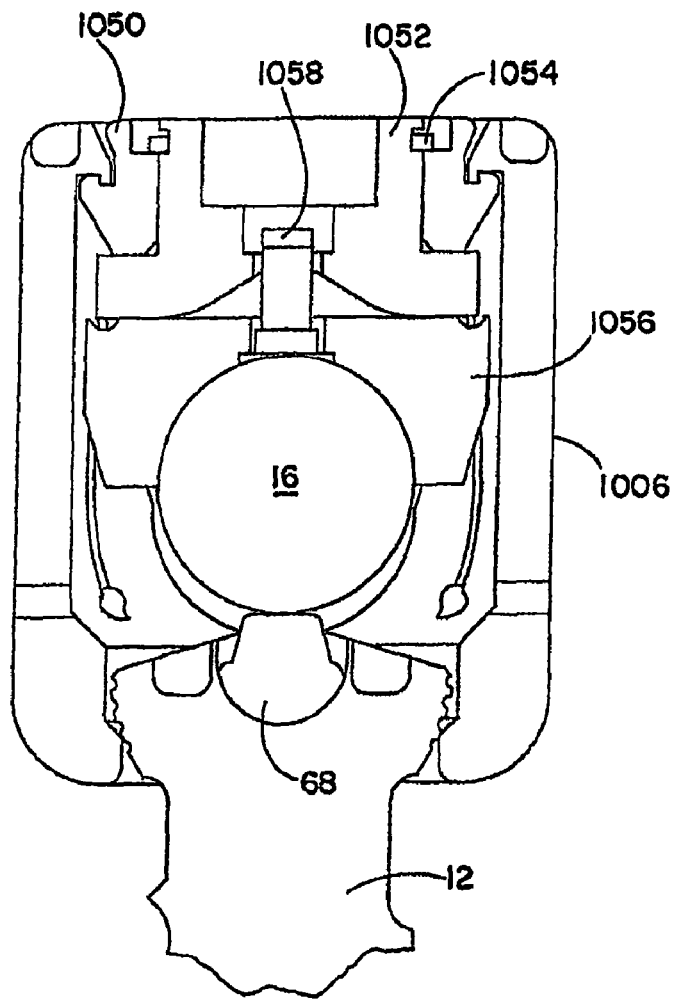
FIG. 67 is a cross-sectional view of the lock device in a third lock-position with the saddle member lower surface engaged flush against the spinal rod to fix the spinal rod relative to the bone screw.
Figure 69:
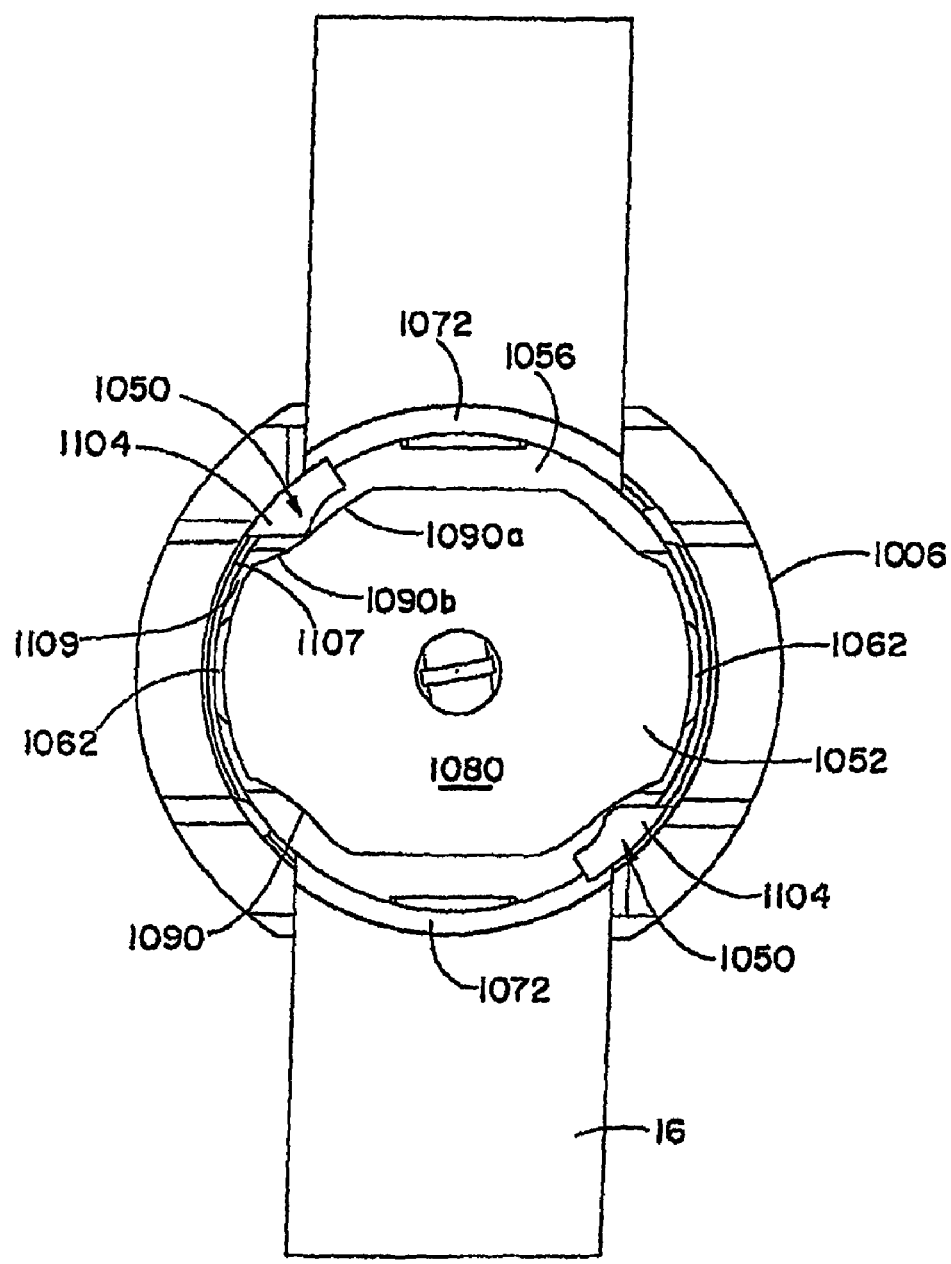
FIG. 69 is a cross-sectional view of the lock member in the third lock position showing the stop members on the collar and the edges of the actuating member hindering over rotation of the actuating member.
Figure 70:
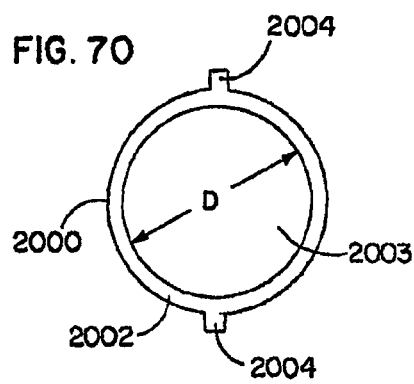
FIG. 70 is a plan view of a support device for use in the various coupling members described herein.
Figure 71:
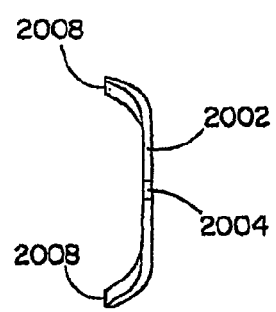
FIG. 71 is a side elevational view of the support device of FIG. 70.
Figure 72:
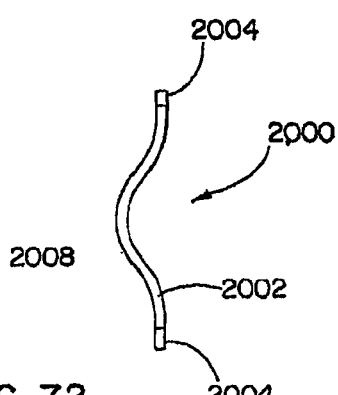
FIG. 72 is another side elevational view of the support device of FIG. 70.

FIGS. 67 and 69 show the cap assembly 1010 in a third cap-lock position or rod lock position in the yoke member 1006 in which the saddle 1056 bears tightly against the spinal rod 16 to lock or secure the spinal rod 16 relative to the yoke member 1006. Preferably, the cap assembly 1010 is inserted into the first two cap-lock positions without the use of an instrument to spread the yoke arms apart. However, such an insertion tool may also be used if desired.

Once the spinal rod 16 is positioned into the internal space 1028 and through the yoke slots 1026, the cap assembly 1010 may be inserted from over the top of the yoke member 1006 or along the yoke axis 21 into the internal space 1028 between the side wall portions 1022*a* and 1022*b*. As shown in FIG. 65A, the first lower set of ramp surfaces 1066 on the saddle 1056 engage the corresponding flange ramp surfaces 1042*a* to push the resilient portions 1030 outwardly away from the axis 21 for initial receipt of the cap assembly 1010 in the yoke internal space 1028 (the outward flexing of the resilient portions 1030 is shown in phantom lines). As the cap assembly 1010 is linearly inserted further along the axis 21, once the radially outer edge 1070*c* of the saddle 1056 clears the radially inner edge 1042*b* of the flanges 1042, the yoke flanges 1042 are received in the saddle seats or edge depressions 1062 with an audible "click" and also can provide the surgeon tactile feedback that the first cap-lock position has been reached as the flex portions resiliently bend or snap back substantially to their original undeflected position, as illustrated in FIG. 65B. The audible indication provides the surgeon feedback that the cap assembly has been properly seated in the first lock position relative to the yoke member. With the flanges rightly received in the saddle seats, the cap assembly cannot be backed out axially relative to the yoke member 1006 absent shifting of the yoke wall portions radially outwardly. Further, the tight frictional engagement between the flanges and seats keeps the cap assembly securely held relative to the yoke member against shifting axially farther into the yoke inner space 1028 until an axial force in this direction is applied to the cap assembly for such purpose.

In this first position, the first gap 1106 is of a relatively large size and formed between the saddle lower surface 1074 and the spinal rod 16. As previously discussed, the first gap 1106 has a predetermined axial size such that shifting of the spinal rod along the axis 21 and transverse to the axis 21 is permitted. For example, with a rod having a diameter approximately 6.35 mm, the large axial gap 1106 to the saddle member lower surface can be approximately 2.54 mm. The first gap 1106 is advantageous because it allows ease of alignment of the spinal rod 16 with extensive curvature thereto especially with scoliosis and kyphosis of the spine. It will be appreciated, however, that use of the system 1000 with rods having a different diameter may form a gap 1106 having a larger or smaller size. In addition, it may also be preferable to provide additional yoke members 1006 having different side wall heights for use with rods of different diameters such that the large axial gap 1106 remains relatively constant when rods of different diameters are used.

Once the surgeon has positioned the spinal rod 16 near its final orientation and position, the cap assembly 1010 is advanced further into the yoke internal space 1028 along the yoke axis 21 by application of an axially directed force in a direction toward the rod until the cap assembly 1010 reaches the second cap-lock position, as illustrated in FIG. 66B. As the cap assembly is axially advanced from the first to the second lock position, the second set of ramp surfaces 1068 on the collar 1050 function similar to the ramp surfaces 1066 on the saddle. That is, as illustrated in FIG. 66A, the ramp surfaces 1068 push against the corresponding ramp surfaces 1042*a* of the resilient portion flanges 1042 to bend the resilient portions 1030 away from the axis 21 until the radially outer edge 1070*c* of the saddle 1056 clears the radially inner edge 1042*b* of the flanges 1042 so that the seat or annular groove 1064 in the collar 1050 may receive the yoke flanges 1042 (the outward flexing of the resilient portions 1030 is shown in phantom lines). As with the receipt of the flanges 1042 in the saddle depressions 1062, the flanges 1042 snap into the annular groove 1064 to generate an audible "click" as well as tactile feedback that notifies the surgeon that the cap assembly 1010 has been properly received in the second cap-lock position. With the flanges tightly received in the collar seat 1064, the cap assembly 1010 is restricted against axial motion in the same manner as in the first lock position.

In this second position, the second, smaller gap 1108 is formed between the saddle lower surface 1074 and the spinal rod 16 that primarily permits shifting of the spinal rod 16 transverse to the yoke axis 21 with only minimal shifting along the yoke axis 21. In this manner, the surgeon can fine tune the positioning of the spinal rod 16 prior to final locking. By way of example, with the 6.35 mm diameter rod, the small axial gap 1108 to the saddle member lower surface can be approximately 0.60 mm. Similar to the discussion above regarding sizing of the large gap 1106, the small axial gap 1108 can vary with rods of different diameters or can remain constant by providing a yoke member 1006 having a different wall height. In this second position, it is also preferred that an upper edge 1110 of the collar upstanding rim 1098 be flush with the yoke upper edge 1036 so that there are no portions of the cap assembly 1010 that project axially beyond the upper end 1036 of the yoke member, as can be seen in FIG. 66B.

It should be appreciated that FIGS. 65A and 66A illustrate only exemplary resilient or elastic bending of the resilient portions 1030. More or less of the resilient portions 1030 may be resiliently bent outwardly in response to the action of the cap assembly 1010. Furthermore, the posts 1032 are preferably more rigid than the portions 1030; however, the posts 1032 may also resiliently or elastically bend outwardly in a similar fashion in response to the insertion of the cap in the yoke member 1006. Also, instead of having portions of the yoke side wall deflect, the portions of the cap assembly including the ramp surfaces could deflect radially inward during axial insertion, or both the cap assembly and the yoke side wall could include resilient portions for this purpose. Moreover, ramp surfaces need not be provided on both the cap assembly and yoke side wall and instead could be provided in only one or the other.

The saddle 1056 and cam lock member 1052 are in the compact configuration of FIG. 60 where the lower surface 1082 of the cam lock member 1052 and the upper surface 1076 of the saddle are in full mating or conforming relation with each other when the cap lock assembly 1010 is advanced to its first lock position and then from this position to its second lock position. This relationship is also shown in the cross-sectional view of FIG. 68 that further illustrates the relationship of the collar abutments 1104 and the truncated corner portions 1090 of the cam lock member 1052. In this configuration, the stop radial projections 1105 are tightly engaging the curved or outwardly bowed section 1090*a* of the corner surface portions 1090. In this position, the abutments 1104 and corners 1090 cooperate to frictionally retain the actuating member in this initial, mated configuration with the saddle 1056. As can be seen, turning of the cam lock member 1052 in the tightening or clockwise direction indicated by arrow 1053 necessitates that the radial projections 1105 traverse the curved sections 1090 to cam the depending abutments 1104 radially outwardly. There is some slight play or radial space between the outer curved surfaces 1104*a* of the abutments 1104 and the inner curved surfaces 1033 of the adjacent wall portions 1032 to allow the slight deflection of the abutments 1104. Accordingly, without such a turning force applied to the cam lock member 1052, the cam lock member 1052 and saddle 1056 will be retained in the described predetermined orientation relative to each other by the collar 1050, and particularly the abutments 1104 thereof. As the cap assembly 1010 is provided to the surgeon separate from the yoke member 1006, this initial interference of the abutments 1104 and the cam lock member truncated corner portions 1090 also allows the cap assembly 1010 to be provided in a predetermined configuration that is pre-oriented for proper installation in the yoke inner space 1028 so that curve side surfaces 1089*c* and 1089*d* of the cam lock member base 1080 are adjacent to the arcuate wall extensions 1072 of the saddle member 1056.

When the surgeon is satisfied with the final positioning of the spinal rod 16 after inserting the cap assembly 1010 into the second cap-lock position, the surgeon can lock or fix the spinal rod relative to the yoke member 1006 into the third cap-lock position illustrated in FIGS. 67 and 69. This locking is preferably accomplished by clockwise rotation of the cam lock member 1052 via a separate tool (not shown) engaging the lobed profile 36 on the top surface 1086 of the lock member.

As best illustrated in FIGS. 62, 68, 69, the corner portions 1090 of the cam lock member 1052 include a slightly curved section 1090*a* that has an outward curvature and a generally flat section 1090*b* that extends outwardly from an end of the curved portion. The abutments 1104 of the collar 1050 further include a radial projection 1105 that curves inwardly along the lower surface 1102 toward the central opening 1094. Upon rotation of the cam lock member 1052, the outwardly curved section 1090*a* of the lock member 1052 pushes the abutments 1104 radially outward. Due to the very slight outward curvature of the sections 1090*a*, only a small torque is needed to turn the cam lock member 1052 in order to move the stop projections 1105 over the sections 1090*a* as the cam lock member is rotated. Once the cam lock member 1052 has been sufficiently turned so that the flats 1089*a* and 1089*b* are in confronting relation with the abutment radial projections 1105, further turning of the cam lock member 1052 occurs substantially friction free relative to the abutments 1104 as the flats 1089*a*, 1089*b* are in clearance therewith.

With further rotation, the abutments 1104 will once again be in confronting relation to the truncated corner portions 1090 of the cam lock member, albeit those corner portions 1090 are adjacent to the corner portions 1090 with which the abutments 1104 were in initial engagement. The corner portions 1090 are configured so that after a predetermined amount of rotation from the initial position of the cam lock member, e.g., 100 degrees, and further rotation of the cam lock member 1052 is limited by the stop radial projections 1105 engaging or abutting an adjacent corner portion 1090. Specifically, as shown in FIG. 69, the radial projection 1105 will again traverse the curved section 1090*a* and then engage the generally straight section 1090*b* of the adjacent corner portion 1090. Further clockwise rotation of the cam lock member 1052 is hindered because the straight sections 1090*b* extend generally outwardly to the curved side surfaces 1089 of the base portion 1080 of the cam lock member 1052 that are adjacent toward an inner surface of the yoke side walls 1107. A space or clearance 1109 with the yoke side wall that is too small for the abutments 1104 to fit in for sliding on the curved side surfaces of the cam lock member. Even before this would occur, rotation of the cam lock member 1052 is limited by the section 1090*b* pushing the abutment 1104 radially outward into compression with the side wall or post inner surface 1033 such that the collar abutments 1104 and cam lock member 1052 would be wedged within the yoke member 1006 stopping further rotation of the cam lock member 1052.

In this embodiment, the collar 1050 is hindered from rotation as a result of frictional holding forces provided by the resilient flex arm portions 1031*a* and 1031*b* tightly engaged in the collar seat 1064. Frictional forces between the flex arm flanges 1042 and the seat 1064 of the collar 1050 keeps the collar 1050 substantially stationary relative to the yoke member 1006 against rotation when the cam lock member is turned. In this manner, the cam lock member 1052 may be rotated relative to the collar 1050 and the collar abutments 1104 remain in a generally fixed position, as can be seen in FIGS. 68 and 69.

Referring to FIGS. 70-73, a support device 2000 is illustrated in the form of a gimbal retainer, and may be used with any of the embodiments of the spinal fixation systems described herein. The support device 2000 is inserted within the internal space, such as internal space 1028, formed by the various yoke members described herein and cooperates with the anchor member and anvil subassembly to secure the anchor member and anvil in the yoke member, to minimize play between the yoke member and the anchor member, and to keep the yoke member substantially upright or elevated relative to the anchor member prior to the surgeon locking the rod within the yoke member.

Without the support device 2000, the yoke member may tend to shift downward along the axis of the anchor during installation or the anchor member may tend to move axially into the yoke member internal space, which render it more difficult for the surgeon to insert the rod and locking device. Instead, the support device 2000 is operable to keep the head of the screw anchor in the lower portion of the yoke internal space where the seating surface for the anchor head is formed with the yoke extending upwardly from the anchor head albeit at various angles relative to the anchor axis due to the polyaxial nature of the positioning available for the separate yoke and anchor members.

In one form, the support device 2000 includes an annular ring body 2002 having a diameter D sized to be received within the interior space formed by the yoke member. On opposite sides of the ring 2002, about 180 degrees apart, the support device 2000 includes retention tabs or flanges 2004 in the form of narrow, outward projections from the ring body 2002. As best illustrated in the side views of FIGS. 71 and 72, the ring 2002 also includes spinal rod cup portions or downwardly curved portions 2008 on opposite sides of the ring 2002 that are spaced about 90 degrees from the flanges 2004. The curved portions 2008 permit the support device 2000 to conform to the U-shape slots of the yoke member and allow the device 2000 to sit in the bottom of the yokes without interfering with the rods received therein. The support device 2000 also includes a central aperture 2003 that provides access for the drive tool to interface with the anchor member and for the anvil to access the spinal rod.

Preferably, the support device 2000 is manufactured from a biocompatible material such as titanium or titanium alloy, nitinol, stainless steel, or polymers. With such materials, the support device 2000 may experience elastic or plastic deformation under extreme angles of the polyaxial screw head, especially when the cam locking member is locked. It is also preferred that the support device 2000 be machined, stamped, or pressed during manufacture.

Figure 73:
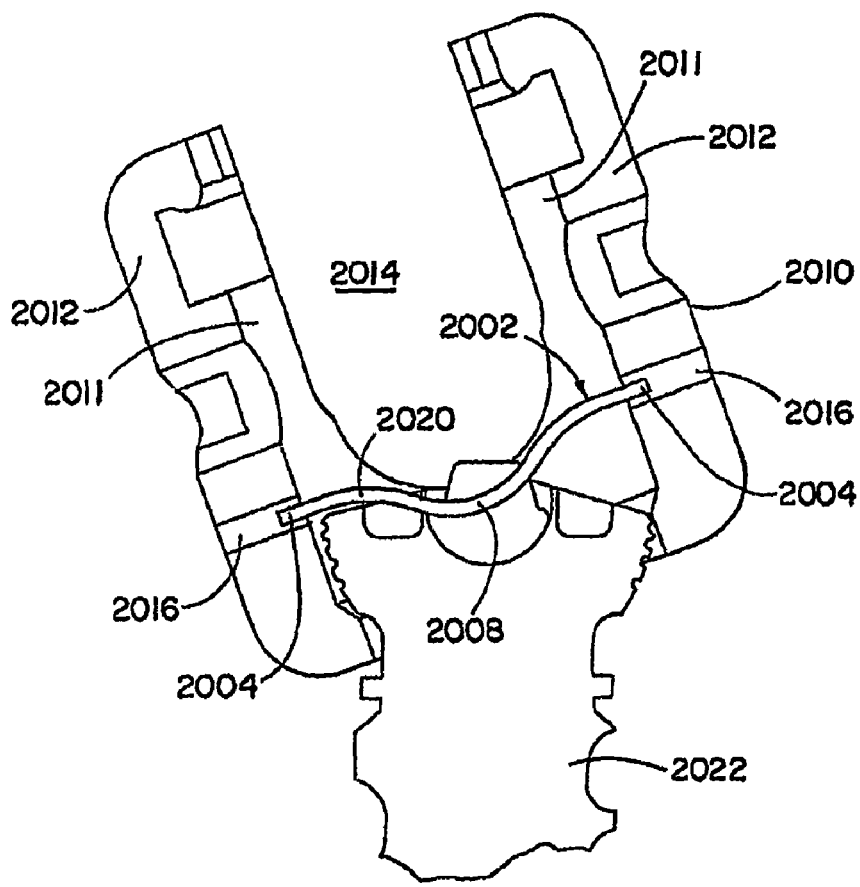
FIG. 73 is a cross-sectional view of the support device shown in an exemplary coupling device.

Referring to FIG. 73, the ring 2002 is shown received within an exemplary yoke member 2010. Similar to the yokes described above, the yoke member 2010 includes spaced side wall portions 2012 that define opposite, generally U-shaped slots 2014 therebetween for receipt of a rod or other elongate member (not shown for clarity). In this embodiment, the yoke member 2010 also includes retention structure or circumferential slots 2016 that may partially extend about the inner circumference of the yoke side walls 2012 in an arc-like manner. The slots 2016 are sized to receive the radially outwardly extending ring flanges 2004 therein and support the ring 2002 within the yoke member 2010. As shown, the slots 2016 may extend through the side walls 2012 or may only partially extend into the side walls from an inner surface 2011 thereof.

Assembly of the support device 2000 may involve elastically compressing the device until the flanges 2004 are able to pass down the inner surface 2011 of each yoke wall portions 2012 until just above the pre-inserted anchor member and anvil. At this point, the support device 2000 is allowed to decompress and the flanges 2004 are directed into the slots 2016.

The ring 2002 includes at least one supporting portion 2020 that cooperates with the anchor member 2022 to position the yoke member in a substantially upright, elevated position as illustrated in FIG. 73. As illustrated, the support portion 2020 may be side portions of the ring downwardly curved portions 2008 adjacent the ring flanges 2004 and adapted to engage along the upper surface of the head of the screw anchor, but may also be other portions of the ring 2002. The support portion 2020 keeps the anchor member 2022 from shifting generally upwardly in the yoke space so that the yoke member 2010 is positioned in a substantially upright position relative to the anchor member. As a result, the surgeon can more easily insert the rod and desired lock device without the yoke member shifting around or dropping down along the axis of the anchor.

Figure 78:
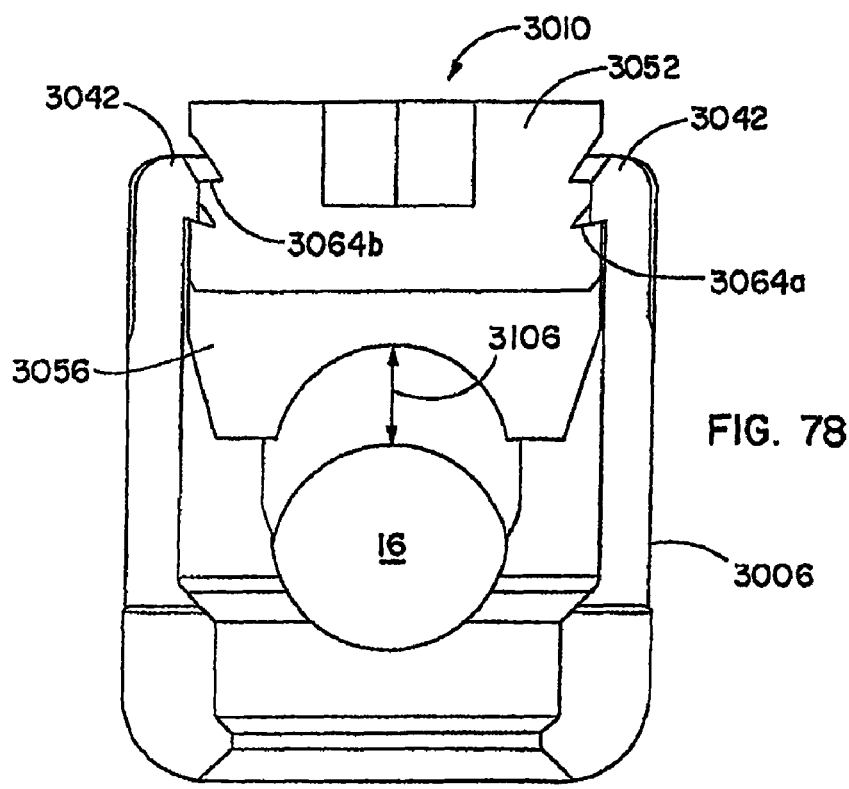
FIG. 78 is a cross-sectional view of the lock device in a first lock-position in the yoke coupling member providing a large gap between the lock device and spinal rod.
Figure 79:
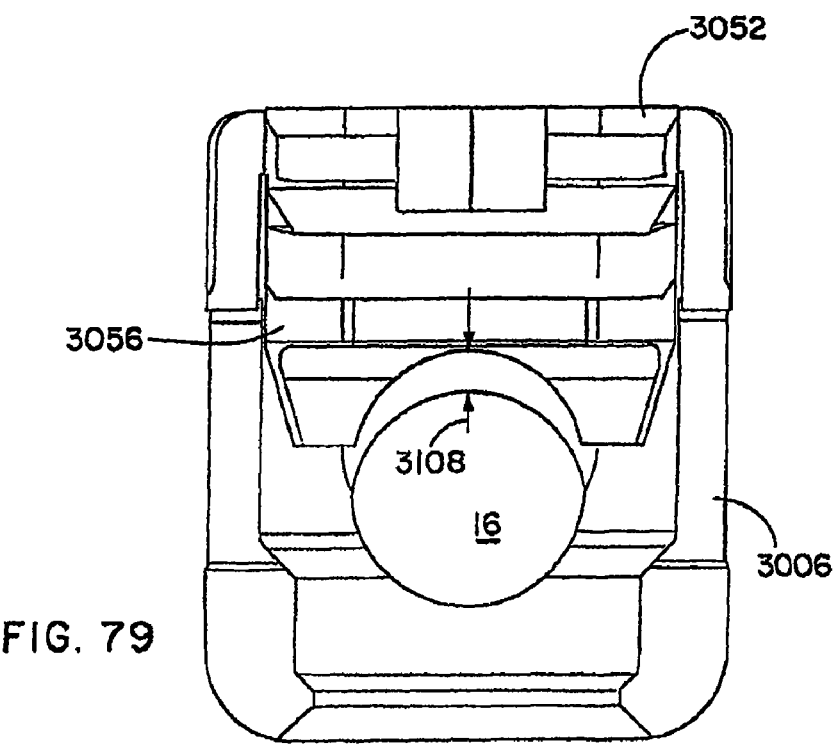
FIG. 79 is a cross-sectional view of the lock device in a second-lock position providing a small gap between the lock device and spinal rod.
Figure 80:
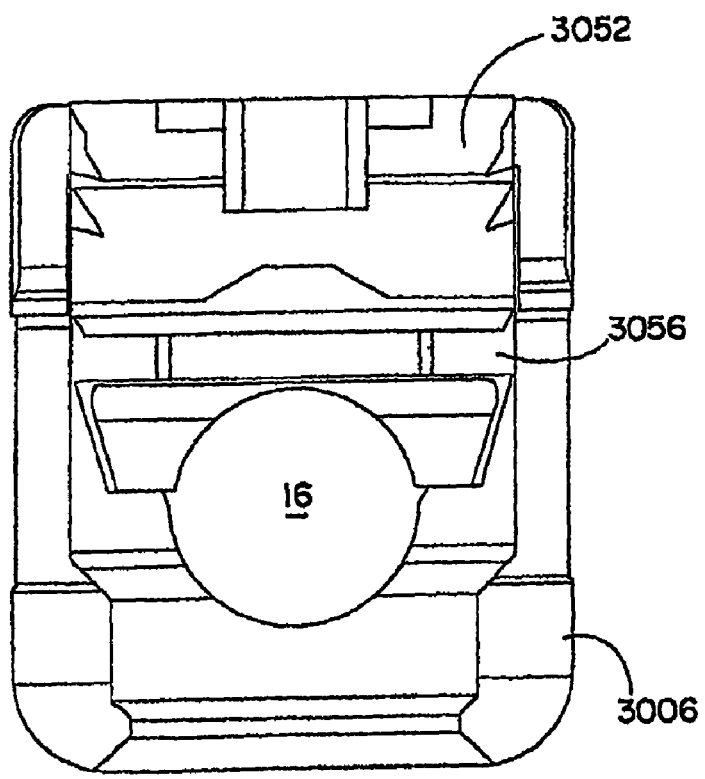
FIG. 80 is a cross-sectional view of the lock device in a third-lock position with a lower surface of the saddle flush against the spinal rod to fix the spinal rod relative to the yoke coupling member.
Figure 81:
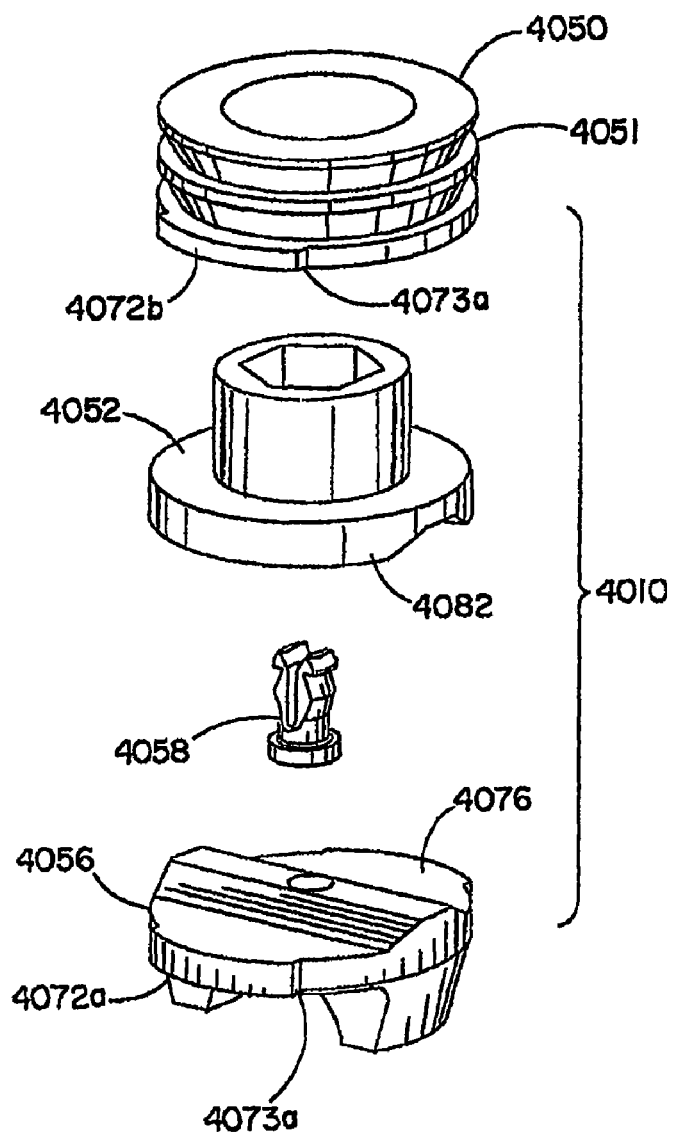
FIG. 81 is a exploded view of an alternative lock device for use in the yoke coupling member shown in FIG. 45 or FIG. 74.
Figure 82:
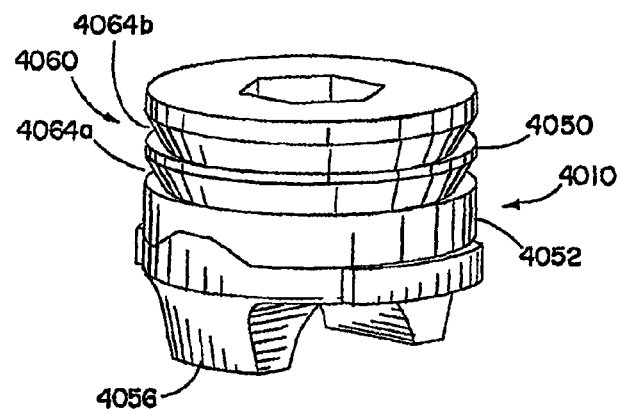
FIG. 82 is a perspective view of the alternative lock device of FIG. 81 shown in an axially compact configuration thereof.

Referring to FIGS. 74-80, a spinal fixation system 3000 for securing the spinal rod 16 relative to the bone screw 12 in accordance with another embodiment is illustrated. Similar to the spinal fixation system 1000, this embodiment includes a yoke member 3006 and a lock or compression device in the form of a cap assembly 3010 that may be inserted into an internal space 3028 of the yoke member 3006 along a yoke axis 21 to a plurality of different cap-lock positions, such as a maximum clearance cap-lock position where the cap assembly 3010 forms a relatively large gap 3106 with the spinal rod 16 (FIG. 78); a minimum clearance cap-lock position where the cap assembly 3010 forms a second, smaller gap 3108 with the spinal rod 16 (FIG. 79); and a rod-lock position where the cap assembly 3010 locks the spinal rod 16 relative to the yoke member 3006 (FIG. 80). The system 3000 is similar to the spinal fixation system 1000; accordingly, the following discussion will focus on the principal differences therefrom.

Figure 74:
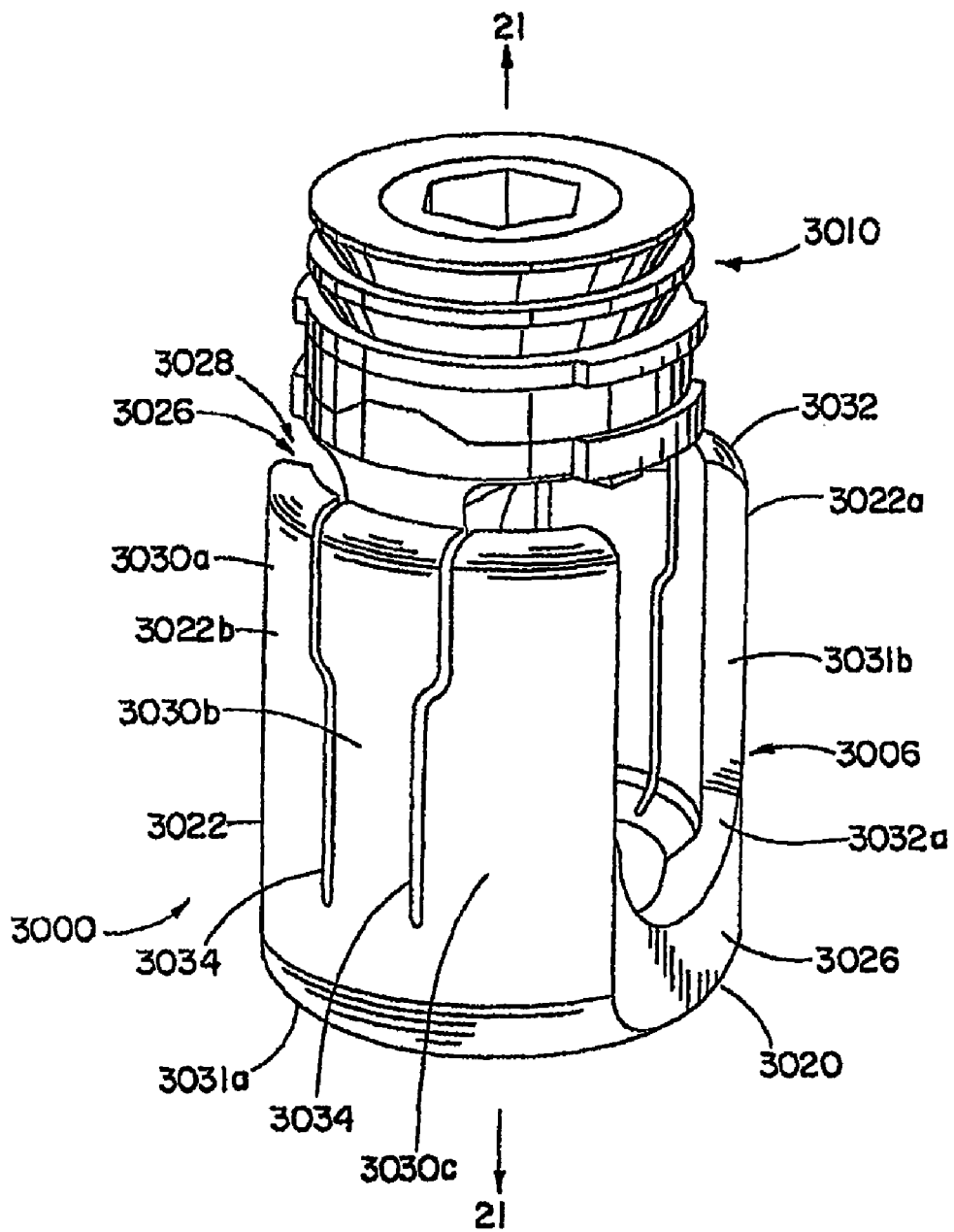
FIG. 74 is a perspective view of another form of the spinal fixation system in accordance with the present invention showing a yoke coupling member and a lock device, the yoke coupling member having slits in side walls thereof to form resiliently flexible portions thereof.

Referring to FIG. 74, the yoke member 3006 is preferably a generally cylindrical structure having a disk-shaped base portion 3020 and an arcuate side wall 3022 that extends upwardly from the base portion 3020. The side wall 3022 has a generally annular configuration that is split into two facing arcuate portions 3022a and 3022b with a pair of opposite, U-shaped upwardly opening slots 3026 between the two arcuate portions 3022a and 3022b. The yoke member 3006 includes at least one resilient portion 3030, and preferably, a pair of resilient portions that resiliently deflect or bend to permit axial receipt of the cap assembly 3010 into the yoke coupling member 3006 along the yoke axis 21.

Resilient arm portions 3031a and 3031b are formed by elongate slits 3034 that generally extend along the length of each side wall portion 3022a and 3022b. In this embodiment, rather than the hour-glass shape of the resilient arm portions 1031a and 1031b, the resilient arm portions 3031a and 3031b each include a wider upper or holding portion 3030a having a generally rectangular shape, and a narrower lower or base portion 3030b with an elongate, generally rectangular shape. In between, a transition portion 3030c tapers inwardly from the wider, upper portion 3022a to the narrower, lower portion 3022b.

The wider upper holding portion 3030a has a radial thickness and width extending in the circumferential direction selected to provide sufficient strength and stiffness to the side wall 3022 at these portions in order to carry any forces or loads applied to the received and locked cap assembly 3010 over the lifespan of the spinal fixation system 3000. The narrower lower portion 3030b has a radial thickness and circumferential width selected to preferably permit primarily elastic rather than plastic bending of the resilient portion 3030 during insertion of the cap assembly 3010 in order to minimize deformation of the yoke member 3006. In this regard, the narrow portion 3030b acts as a hinge section with the upper portion 3030a pivoting relative to the lower portion thereabout during the various states of cap insertion into the yoke member. The radial thickness of the resilient portions 3030 can be similar to that previously specified for resilient portions 1030. The circumferential widths of the upper holding portion 3030a and the lower base portion 3030b can be similar to that specified for the upper holding portion 1030a and the intermediate neck portion 1030b, respectively.

Figure 75:
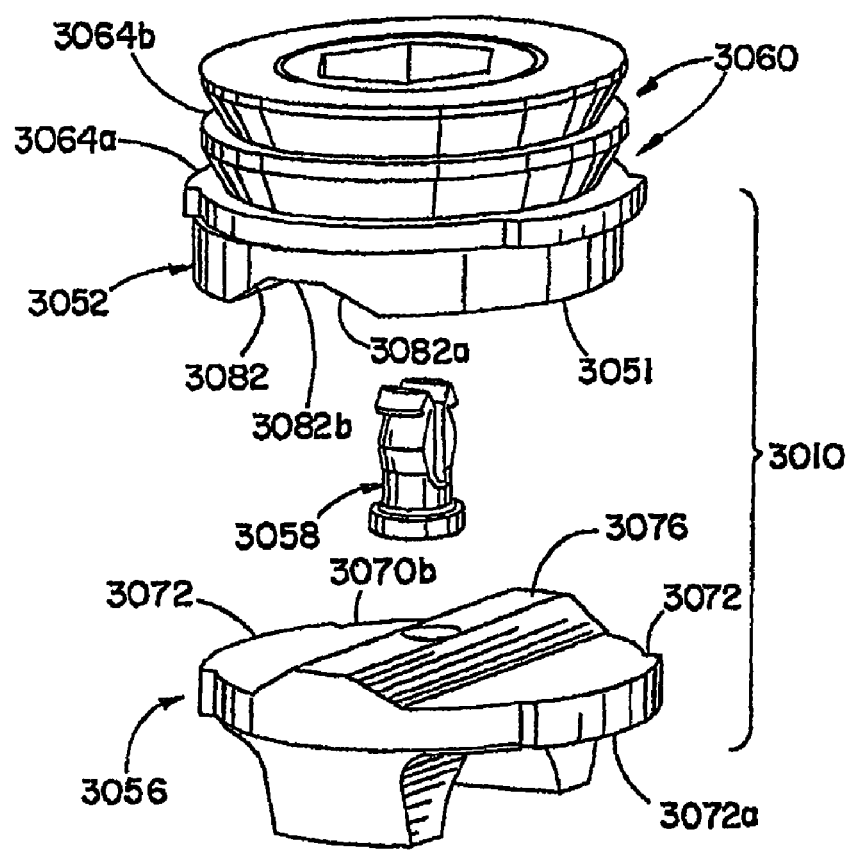
FIG. 75 is a exploded view of the lock device of FIG. 74 showing a lock member, a spring clip, and a saddle.
Figure 76:
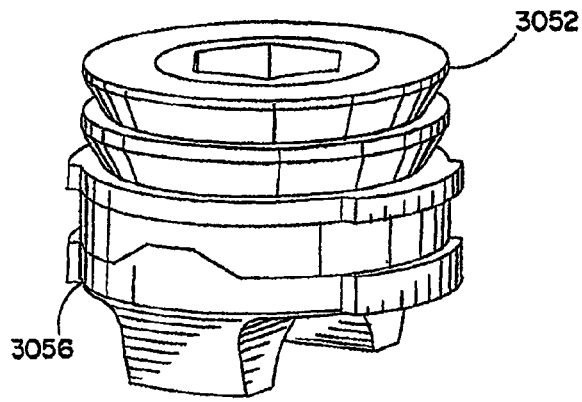
FIG. 76 is a perspective view of the lock device of FIG. 75 shown in an axially compact configuration thereof.
Figure 77:
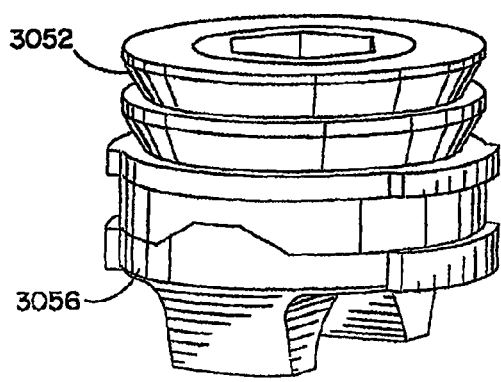
FIG. 77 is a perspective view of the lock device of FIG. 75 shown in an axially extended configuration thereof.

Referring to FIG. 75, the cap assembly 3010 is illustrated in more detail. In this alternative form, the cap assembly 3010 includes a lock member 3052 and a saddle 3056 that is rotatably coupled to the lock member 3052 by a connector 3058 (e.g., the spring clip 519). Upon rotation of the lock member 3052, the saddle 3056 moves axially without rotation thereof, along the yoke axis 21 in order to bear against the spinal rod 16 to lock it relative to the yoke member 3006. Similar to the previous embodiment, a lower surface 3082 of the lock member 3052 has a configuration that preferably conforms to the configuration on the saddle upper surface 3070b. That is, the cam lock member lower surface 3082 includes ramped or inclined surface portions 3082a that extend upwardly and radially inwardly toward each other and an upper surface portion 3082b that extends between the side inclined portions 3082a to cam the saddle 3056 from the axially compact configuration (FIG. 76) to the axially expanded configuration (FIG. 77) upon rotation of the lock member 3052.

Rotation of the saddle 3056 is limited or minimized through opposing extensions 3072 on opposite sides of the saddle 3056. The extensions 3072 are sized and configured to be received within the slots 3026 in the yoke member 3006 when the cap assembly 3010 is received within the yoke internal space 3028. The extensions 3072 permit the saddle 3056 to translate axially along the yoke axis 21, but hinder the rotation of the saddle 3056 relative to the yoke member 3006. Such axial movement of the saddle 3056 with minimal rotation is achieved because side edges 3072a of the saddle are spaced to provide slight clearance with the spacing between side edges 3032a extending along the slot openings 1026. Therefore, the saddle 3056 moves along axis 21 with the extensions 3072 sliding within the yoke slot openings 1026 as the lock member 3052 is rotated, but the saddle 3056 generally does not rotate relative to the yoke member 3006 because the close fitting relationship between the extensions 3072 and the slot openings 1026 provides no space for any significant rotation therebetween.

In order for the cap assembly 3010 to be held in position in the plurality of cap-lock positions, the alternative cap assembly 3010 also includes a plurality of engagement or seat surfaces 3060 that cooperate with yoke flanges 3042 on the resilient arm portions 3031a and 3031b. In this embodiment, the engagement surfaces 3060 are each disposed on the single lock member 3052 rather than different components of the previously described cap assembly 1010. For example, the seat surfaces 3060 of the lock member 3052 can be in the form of a pair of annular grooves 3064a and 3064b that are axially spaced along an annular body 3051 of the lock member 3052.

During axial insertion of the cap assembly 3010, depending on the groove 3064a or 3064b in which the yoke flanges 3042 are received, the cap assembly 3010 will be in either the maximum clearance or minimum clearance cap-lock position. For example, when the lock member 3052 is axially inserted into the yoke member 3006 a first axial distance so that the yoke flanges 3042 are received in the axially upper groove 3064a, the cap assembly 3010 is held in the maximum clearance cap-lock position forming a relatively large gap 1106 between the saddle 3056 and the rod 16 (FIG. 78). When the lock member is advanced axially further into the yoke member 3006 so that the yoke flanges 3042 are received in the axially lower groove 3064b, the cap assembly 3010 is held in the minimum clearance cap-lock position to form a relatively smaller gap 3108 between the saddle 3056 and the rod 16 (FIG. 79). Similar to the cap assembly 1010, the receipt of the cap assembly 3010 in either pre-rod lock or preliminary cap-lock position is preferably achieved through resilient flexing of the resilient portions 3031a and 3031b and also indicated by an audible or tactile signal to the surgeon.

Referring to FIG. 80, the rod-lock position of the system 3000 is illustrated in more detail. To achieve this lock position, after the cap assembly 3010 is positioned in the minimum clearance position (FIG. 79), the lock member 3052 is rotated relative to the yoke member 3006 such that the lock member lower surface 3082 cams against the profile on the saddle upper surface 3076 to axially shift the saddle 3056 downwardly along the yoke axis 21 to bear tightly against the rod 16. As a result, the saddle 3056 locks the spinal rod 16 relative to the yoke member 3006.

Referring to FIGS. 81-86, there is illustrated another alternative lock device or cap assembly 4010 for locking the rod 16 relative to the anchor member 12. Like the other cap assemblies 1010 and 3010, the cap assembly 4010 preferably includes multiple components configured so that it can be top loaded along the yoke axis 21 into either the yoke member 1006 or 3006 to position the cap assembly 4010 in a plurality of different cap-lock positions including those pre-rod lock positions requiring only linear translation of the lock device and a final rod lock position where relative rotation between components of the lock device is operable to axially shift one of the components into locking engagement with the spinal rod. The cap assembly 4010 is similar to the cap assembly 1010; as a result, the following discussion will focus on the principal differences therefrom. Furthermore, for simplicity, the cap assembly 4010 will be discussed with respect to the yoke member 1006, but it will also function in a similar manner in the yoke member 3006.

Figure 83:
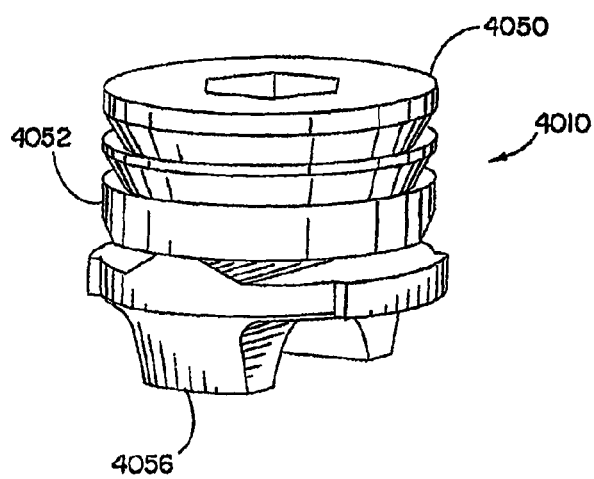
FIG. 83 is a perspective view of the alternative lock device of FIG. 81 shown in an axially extended configuration thereof.

In this alternative form, the cap assembly 4010 preferably includes an upper retainer in the form of a collar 4050, a lock member 4052 rotatably joined to the collar 4050, and a saddle 4056 that is coupled to the lock member 4058 through a connector 1058 (e.g., the spring clip 519). Similar to the other embodiments, the saddle 4056 is configured to translate axially along the yoke axis 21 upon rotation of the lock member 4052 to shift the cap assembly 4010 from an axially compact configuration (FIG. 82) to an axially expanded configuration (FIG. 83). Also similar to the other embodiments, the axial translation of the saddle 4056 is preferably without rotation thereof and is through a camming interaction of a lower or bottom cam surface 4082 on the lock member 4052 and an upper or top cam surface 4076 on the saddle 4056.

Figure 84:
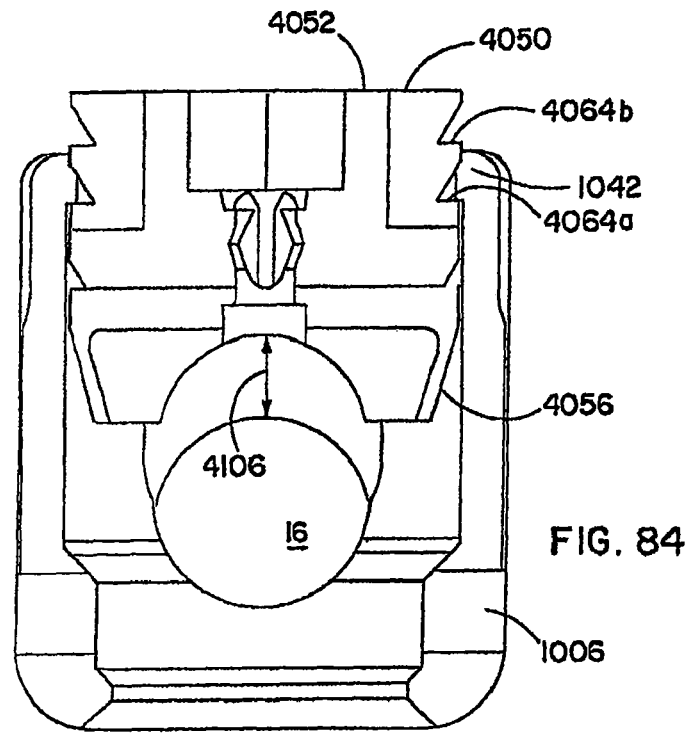
FIG. 84 is a cross-sectional view of the alternative lock device in a first lock-position in the yoke coupling member of FIG. 45 providing a large gap between the lock device and a spinal rod.
Figure 85:
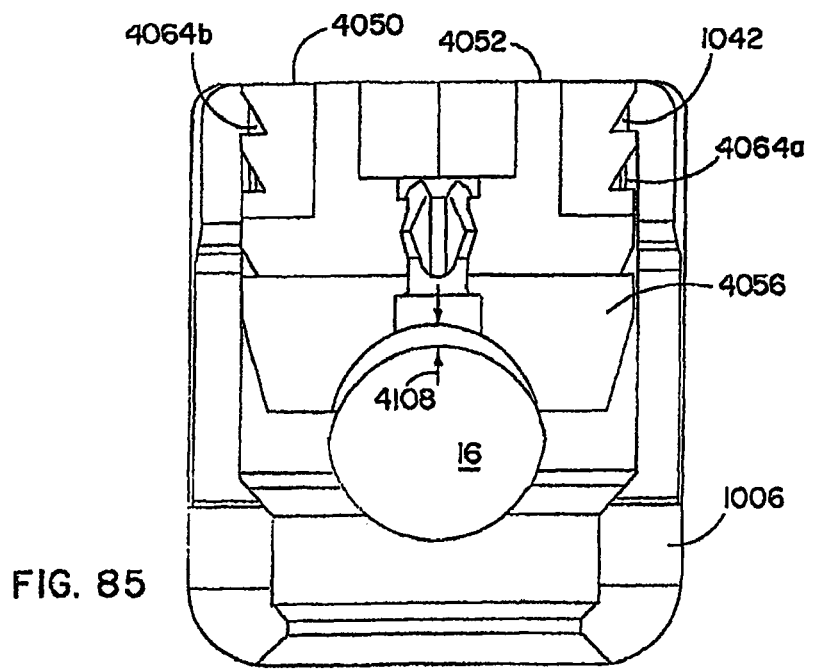
FIG. 85 is a cross-sectional view of the alternative lock device in a second-lock position in the yoke coupling member of FIG. 45 providing a small gap between the lock device and spinal rod.

In this embodiment, the retainer 4050 includes a plurality of engagement or seating surfaces 4060 that cooperate with the yoke flanges 1042 in order to hold the cap assembly 4010 in position in the cap-lock position. In particular, the retainer 4050 has an annular body 4051 including a pair of annular grooves 1064a and 1064b that are axially spaced therealong. Therefore, when the yoke flanges 1042 are received within the lower annular groove 4064a, the cap assembly 4010 is positioned in the maximum clearance cap-lock position to provide a relatively large space 4106 between the saddle 4056 and the rod 16 (FIG. 84). Alternatively, when the cap assembly 4010 is pushed further into the yoke member 1006 such that yoke flanges 1042 are received within the upper annular groove 4064b, the cap assembly 4010 is positioned in the minimum clearance cap-lock position to provide a relatively small space 4108 between the saddle 4056 and the rod 16 (FIG. 85). As with the other embodiments, the proper receipt of the cap assembly 4010 in either of the cap-lock positions is provided by audible and tactile feedback to the surgeon.

Figure 86:
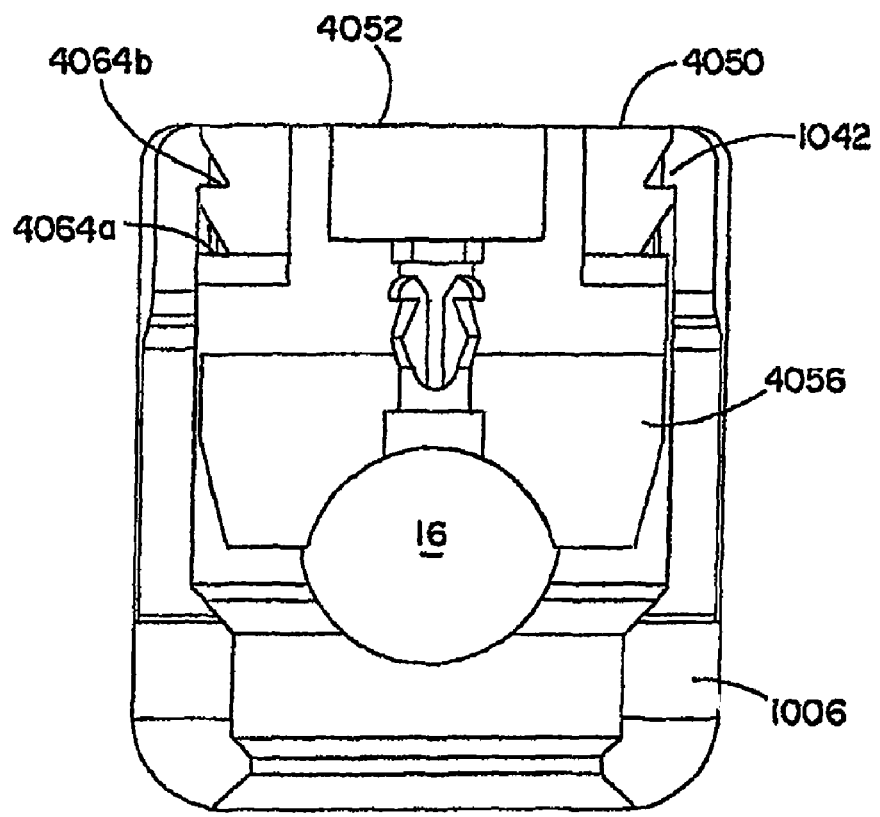
FIG. 86 is a cross-sectional view of the alternative lock device in a third-lock position in the yoke coupling member of FIG. 45 with a lower surface of the saddle flush against the spinal rod to fix the spinal rod relative to the yoke coupling member.

In FIG. 86, the cap assembly 4010 is shown in the rod-lock position within the yoke member 1006 where the saddle 4056 bears against the rod 16. Similar to the previous embodiments, to achieve this rod-locking position with the cap assembly 4010 in the minimum clearance position (FIG. 85), the lock member 4056 is rotated relative to the yoke member 1006 such that the cam surfaces 4082 and 4076 cooperate to cam the saddle 4056 axially along the yoke axis 21 until the saddle 4056 bears against the rod 16 to lock it relative to the yoke member 1006.

Neither the collar 4050 nor the saddle 4056 rotate relative to the yoke member 1006. In this regard, both the collar 4050 and the saddle 4056 may include radial extensions 4072a and 4072b, respectively, at diametrically opposite sides thereof that block rotation relative to the yoke member 1006. The extensions 4072 are sized and configured to be snugly received in the yoke slots 1026 when the cap assembly 4010 is axially advanced into the yoke internal space 1028. Nominal rotation of the collar 4050 and saddle 4056 may occur due to frictional engagement as the lock member 4056 is turned; however, this is due to the slight clearance provided between side edges 4073a, 4073b of the saddle 4056 and collar 4050, respectively, and the side edges 1032a extending along the slot openings 1026 so that the respective collar and saddle tab extensions 4072a and 4072b can be fit within the slot openings 4026. However, once the facing collar or saddle and yoke slot edges engage, relative rotation between the collar and the yoke, and the saddle and the yoke is blocked.

Figure 87:
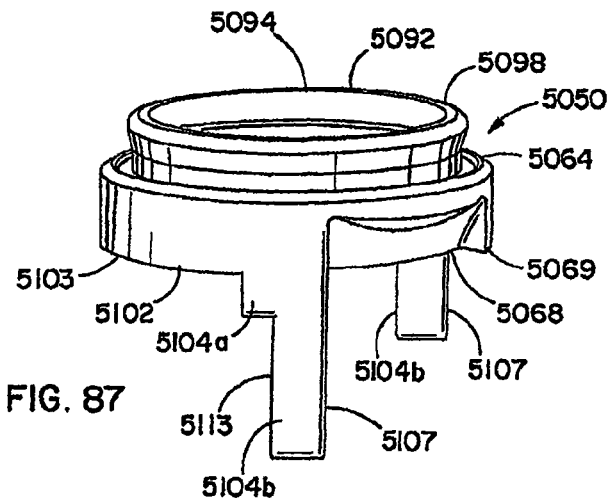
FIG. 87 is a perspective view of an alternative collar member for use in the lock device of FIG. 51 showing a pair of depending posts.
Figure 88:
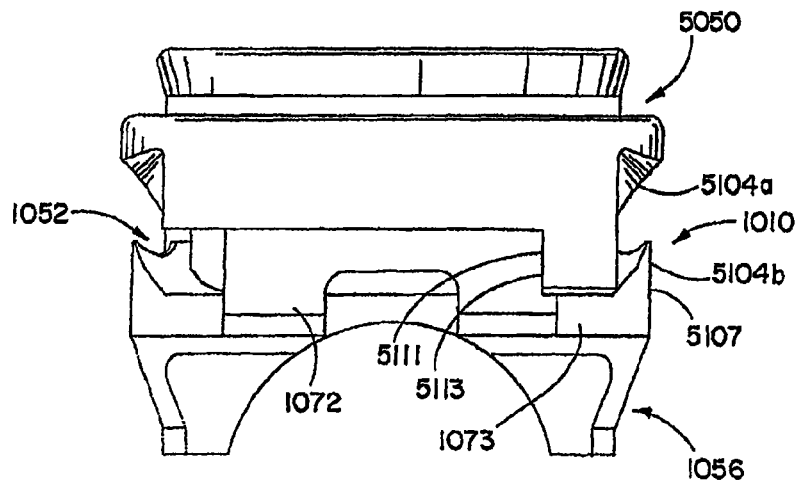
FIG. 88 is an elevational view of the lock device of FIG. 51 including the alternative collar member of FIG. 87 shown in an axially compact configuration with the depending posts of the alternative collar member engaging portions of the saddle member to prevent rotation of the collar member.
Figure 89:
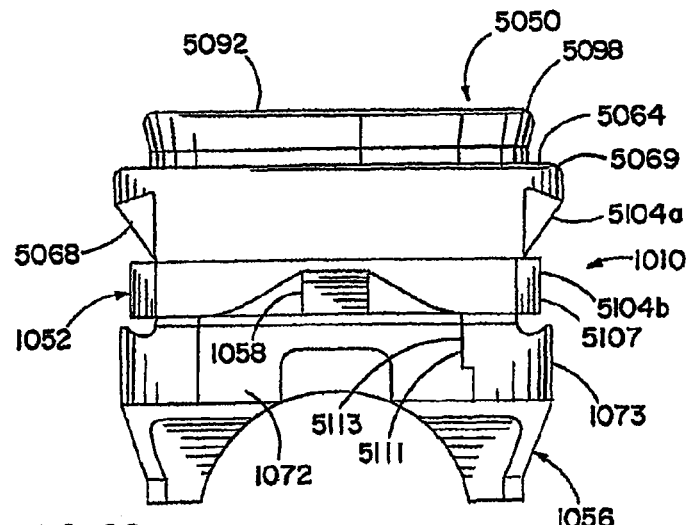
FIG. 89 is an elevational view of the of the lock device of FIG. 88 shown in an axially extended configuration with the depending posts of the alternative collar member still engaging portions of the saddle member.

Referring to FIGS. 87-89, an alternative collar member 5050 is illustrated that includes posts 5107 that extend downwardly from diametrically opposed sides of the collar 5050. The collar member 5050 is similar to the previously described collar member 1050; therefore, only the differences therefrom will be described in detail below. The collar member 5050 may replace the collar member 1050 in the previously described cap assembly 1010 to minimize, and preferably prevent, rotation of the collar 5050 relative to the yoke member 1006 during the final locking of the spinal rod 16 when the cam lock member 1052 is rotated to axially move the saddle 1056 into the locking relationship with the rod 16.

In this form, the collar 5050 includes an annular body portion 5092 defining a central through opening 5094 having an inner diameter sized to receive at least a portion of the cylindrical body 1078 of the cam lock member 1052 therein. The collar 5050 also includes the previously described second seating or engagement surface 1060, preferably in the form of an outer annular groove 5064, extending around the collar 5050. Similar to the collar 1050, the annular groove 5064 receives the resilient portion flanges 1042 when the cap assembly 1010 is inserted to the second cap-lock position.

The collar 5050 also includes ramp surfaces 5068 on opposite sides of the collar annular body 5092. These surfaces 5068 taper inwardly from an axially intermediate rim 5069 of the collar 5050 toward the central opening 5094. The rim 5069 is adjacent the groove 5064 and axially below the upper rim 5098. The lower rim 5069 projects out radially farther than the upper rim 5098, as best seen in FIGS. 88 and 89. The ramp surfaces 5068 on the collar engage the ramp surfaces of the flanges 1042 to push the resilient portions 1030 outwardly away from the yoke axis 21 during axial insertion of the cap assembly 1010 from the first cap-lock position to the second cap-lock position.

Depending below a lower surface 5102 of the collar 5050 are posts 5107. Preferably, the collar 5050 includes a pair of spaced posts 5107 that are in diametrically opposing relation across the annular body portion 5092 of the collar 5050 (see, e.g., FIG. 90). The posts 5107 include a stop or abutment portion 5104a that cooperates with the truncated corner portions 1090 of the cam lock member 1052 to avoid over rotation thereof similar to the abutments 1104 on the collar 1050. The illustrated posts 5107 have an inverted L-shape configuration with the abutment portion 5104a being the base. Accordingly, the posts 5107 also each include an elongate portion 5104b that project downwardly from the stop or abutment portions 5104a and that have an axial length to engage the saddle member 1056, and more particularly, to engage the saddle member side extensions 1072, as shown in FIGS. 88 and 89.

Preferably, each elongate post portion 5104b has a sufficient axial length such that the post portion 5104b engages along at least an upper portion 5111 of a side edge 1073 of the saddle member extensions 1072 when the cap assembly 1010 is both in the axially compact configuration (FIG. 88) as well as the axially extended configuration (FIG. 89). In the axially compact configuration of FIG. 88, a larger portion 5111 of the post 5104b engages the saddle 1056, and in the axially extended configuration of FIG. 89, a smaller portion 5111 of the post 5104b engages the saddle 1056. In either situation, a predetermined axial length of the post 5104b engages the saddle edge 1073. As a result, this engaging portion 5111 of the post 5104b restrains the collar 5050 from rotating relative to the yoke member 1006 because of the interference with the saddle 1056 and specifically the radial extensions 1072 thereof. As previously discussed, the saddle moves substantially axially along the yoke axis 21 and does not rotate due to the receipt of the extensions 1072 within the yoke member U-shaped slots 1026. Therefore, because the saddle 1056 is blocked from rotating, the engagement of the collar posts 5107 with the rotatively fixed saddle 1056 also restrains the collar 5050 from rotating as well when the cam lock member 4052 is being turned for locking the spinal rod 16 in the yoke member 1006.

Figure 90:
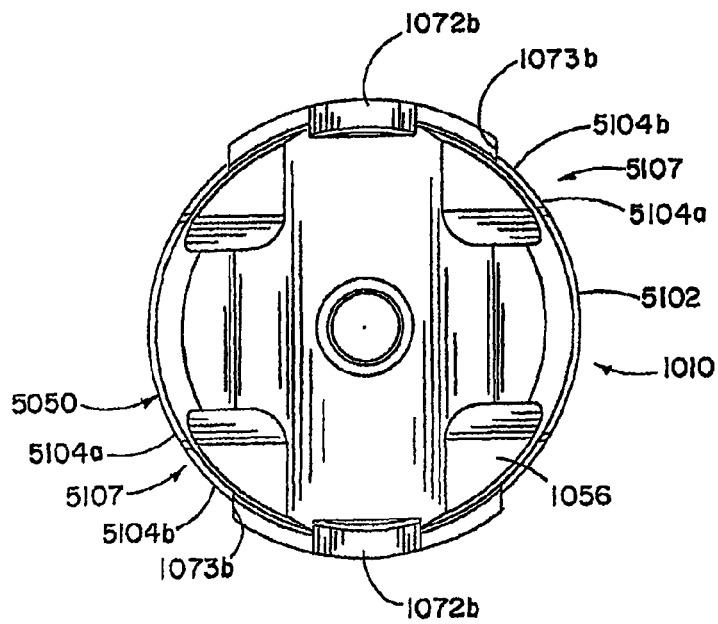
FIG. 90 is a bottom plan view of the lock device of FIG. 51 including the alternative collar member of FIG. 87 showing the depending posts in diametrically opposed portions of the collar body to prevent rotation of the collar member.
Figure 94:
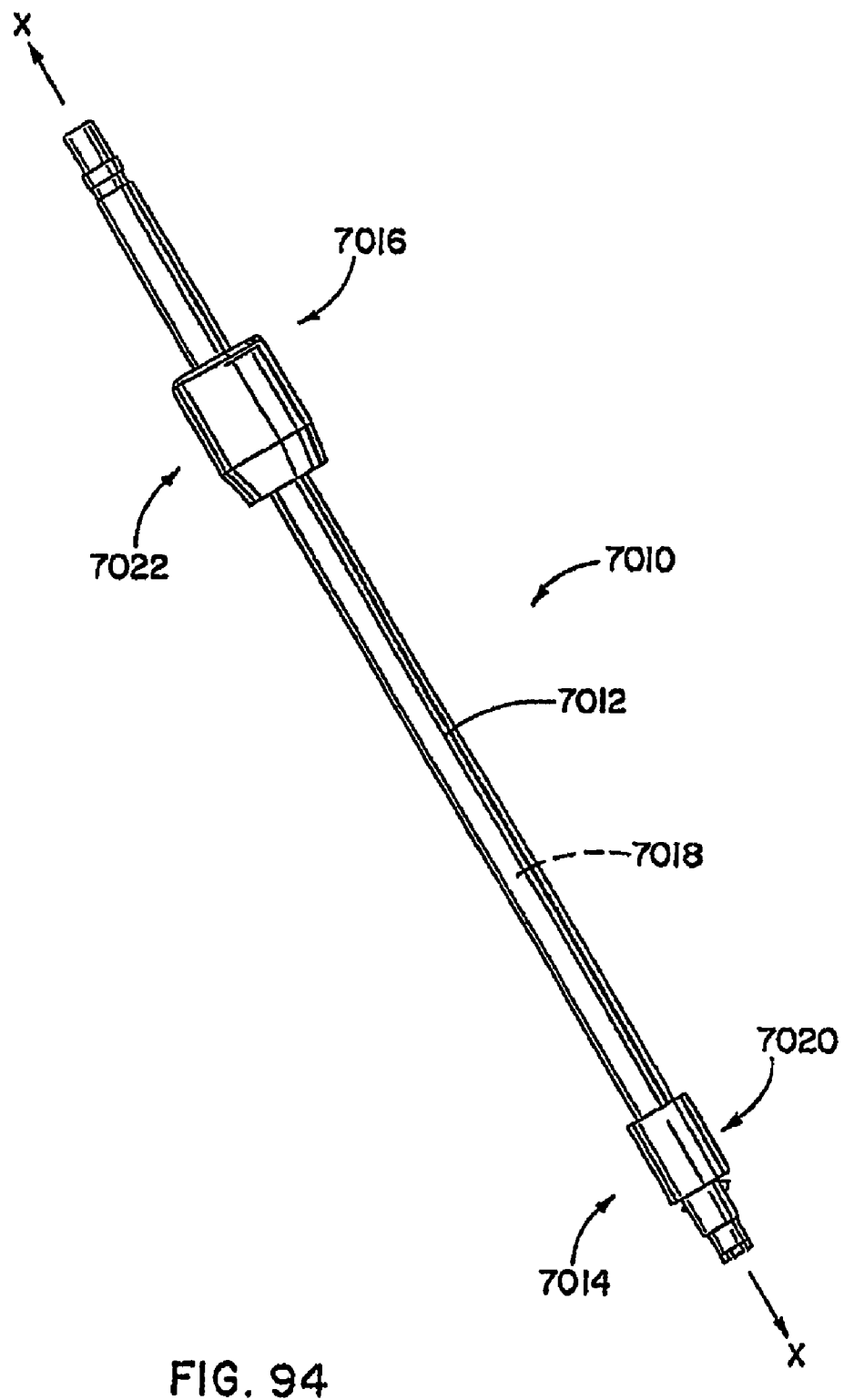
FIG. 94 is a perspective view of an exemplary instrument for installing the spinal fixation systems disclosed herein.

FIG. 90 is a bottom plan view of the cap assembly 1010 with the alternative collar 5050 illustrated showing the relationship between the saddle extensions 1072 and the posts 5107. Preferably, the diametrically opposed posts 5107 engage different sides 1073 of two opposed saddle extensions 1072a and 1072b as shown. For example, reference FIG. 90, the post 5107 at the top right-hand section of the collar 5050 engages the right-hand side 1073a of the saddle extension 1072a while the post 5107 at the bottom left-hand section of the collar 5050 engages the left-hand side 1073b of the saddle extension 1072b. In this manner, the collar 5050 is restrained from turning in either a clockwise or a counter-clockwise direction because one of the posts 5104b blocks rotation in one direction and the other post 5104b blocks rotation in the opposite direction.

Turning to FIGS. 91-93, there is illustrated another alternative lock device for locking the rod 16 relative to the anchor member 12. In contrast to the other cap assemblies 1010, 3010, 4010, and 5010, the lock device 6010 preferably is a single or unitary component configured to be top loaded along the yoke axis 21 into either the yoke member 1006 or 3006. As with the other cap assemblies, the unitary or one-piece cap member 6010 may be positioned in a plurality of different cap-lock positions including those pre-rod lock positions requiring only linear translation of the lock device and a final rod-lock position where rotation of the cap member 6010 is operable to axially shift the cap member 6010 into locking engagement with the spinal rod 16. The cap member 6010 is similar to the cap member 1010 and the cam lock member 18, particularly with respect to its operation for being shifted to the rod-lock position; as a result, the following discussion will focus on the principal differences therefrom. Furthermore, for simplicity, the cap member 6010 will be discussed with respect to the yoke member 1006, but it will also function in a similar manner in the yoke member 3006.

In this embodiment, the cap member 6010 includes a unitary, generally annular body 6052 that may be inserted into the internal space 1028 of the yoke member 1006 along the yoke axis 21 to the plurality of different cap-lock positions, such as the maximum clearance cap-lock position where the cap member 6010 forms the relatively large gap with the spinal rod 16; the minimum clearance cap-lock position where the cap member 6010 forms the second, smaller gap with the spinal rod 16; and the rod-lock position where the cap member 6010 locks the spinal rod 16 relative to the yoke member 1006. In this regard, the cap member 6010 is configured to be inserted axially along the yoke axis 21 to achieve the maximum clearance and minimum clearance rod-lock positions, and also be rotated to achieve the rod-lock position. With the cap member 6010 being formed of the unitary, annular body 6052, the cap member 6010 can have a more compact or low profile configuration that provides the advantage that the yoke member 1006 may also be configured to have a more compact or low profile.

Referring to FIGS. 91 and 92, in order for the annular body 6052 to be held in either the maximum clearance or minimum clearance cap-lock position, the annular body 6052 has an annular side wall 6051 that includes a plurality of engagement or seat surfaces 6060 that cooperate with the yoke flanges 1042 on the resilient arm portions 1031a and 1031b. The seat surfaces 6060 can be in the form of a pair of annular grooves 6064a and 6064b that are axially spaced along the side wall 6051 of the annular body 6052.

During axial insertion of the cap member 6010, depending on the groove 6064a or 6064b in which the yoke flanges 1042 are received, the annular body 6052 will be in either the maximum clearance or minimum clearance cap-lock position. For example, similar to the other embodiments, when the cap member 6010 is initially axially inserted into the yoke member 1006 a predetermined axial distance such that the yoke flanges 1042 are received in the axially lower groove 6064a, the cap member 6010 is releasably held in the maximum clearance cap-lock position forming a relatively large gap between a lower surface 6082 of the annular body 6052 and the rod 16. When the cap member 6010 is advanced axially further into the yoke member 1006 a sufficient axial distance so that the yoke flanges 1042 are received in the axially upper groove 6064b, the cap member 6010 is held in the minimum clearance cap-lock position to form a relatively smaller gap between the lower surface 6082 and the rod 16. Inserting the cap member 6010 into the yoke internal space 1028 is accomplished similar to the other cap assemblies.

The third or final rod-lock position of the cap member 6010 is achieved by rotating the cap member 6010 relative to the yoke member 1006 after the cap member 6010 is positioned in the minimum-clearance position. The rotation of the cap member 6010 causes the lower profiled surface 6082 thereof to cam against the rod 16 in order to lock the rod 16 relative to the anchor member 12 and yoke member 1006. To this end, the bottom or lower surface 6082 of the annular body 6052 includes ramped or inclined surface portions 6082a that extend upwardly and radially inwardly toward each other and an upper surface portion 6082b that extends between the side inclined portions 6082a, as best illustrated in FIG. 93.

In this embodiment, the lower surface 6082 of the annular body 6052 also includes a lower holding portion 6082c and tapered transition portions 6082d, as shown in FIG. 93. The lower holding portion 6082c extends radially outward from lower edges of the inclined portions 6082a to an outer edge of the annular body 6052. The holding portions 6082c are configured for locking against an upper surface of the rod 16 after rotation of the lock device 6052 to the final rod-lock position. The tapered transition portions 6082d are positioned along the outer edge of the annular body 6051 and provide an incline between the annular body outer edge and the ramped surfaces 6082a. The transition portions 6082d permit ease of rotation of the cap member 6010 because they facilitate the sliding of an upper curved surface portion of the rod 16 between the inclined surface 6082a to the holding portion 6082c. Because the corner portions of the ramped surfaces 6082a are truncated providing clearance to rotate the cap member 6010 relative to the rod 12.

As best shown in FIGS. 92 and 93, to avoid over rotation of the annular body 6052 beyond the rod-lock position, the holding portion 6082c includes at least one nub or stop protrusion 6084 that extends axially below the holding portion 6082c. The stop protrusion 6084 acts as a stop which is located and sized so that it will be in interference and engagement with the rod 16 so that rotation of the annular body 6052 beyond the rod-lock position is not permitted.

Referring now to FIGS. 94-122, a variety of instruments are illustrated for the installation and/or removal of the spinal fixation systems disclosed herein. The instruments are adapted and configured to retain and install the anchor members and coupling assemblies previously described. In addition, the instruments are configured to grasp, install, or remove the various cap assemblies for locking the rods relative to the yoke members and anchor members.

Turning to FIGS. 94-98, a first instrument 7010 is illustrated that is adapted and configured to implant any of the spinal fixation systems discussed herein. Preferably, the instrument 7010 is adapted to permit installation of the spinal fixation system 1000, which includes the yoke member 1006 having the resilient portions 1030 on the yoke sides wall 1022. Therefore, while the instrument 7010 may be used with other spinal fixation systems and anchor members, it will be described and illustrated in conjunction with the spinal fixation system 1000.

In general, the instrument 7010 includes an elongate tubular shaft 7012 with an operative end portion 7014 and an actuator end portion 7016. The tubular shaft 7012 includes a longitudinal axis X and defines a passage 7018 extending therethrough. The operative end portion 7014 includes a holding mechanism 7020 configured to retain the yoke member 1006 and the anchor member 12. On an opposite end, the actuator portion 7016 includes an actuator 7022 operative to manipulate the holding mechanism 7020 into a holding position (FIG. 97) for retaining the yoke member 1006 and into a releasing position (FIG. 96) where the yoke member 1006 is released from the holding mechanism 7020. Coupling the actuator 7022 to the holding mechanism 7020 is an elongate control shaft 7024 that extends through the passage 7018 and is configured to slide along the longitudinal axis X in response to the actuator 7022.

The holding mechanism 7020 cooperates with a distal end 7026 of the control shaft 7024 to shift from the releasing position (FIG. 96) to the holding position (FIG. 97) and vise versa. More specifically, the holding mechanism 7020 includes a driver tip 7028 fixed to the operative end 7014 of the tubular shaft 7012 and a pair of actuator dogs 7030a and 7030b, which are both coupled to the distal end 7026 of the control shaft 7024 via a pivot pin 7032 and also coupled to the driver tip 7028 via a cam shaft pin 7033. In this manner, the actuator dogs 7030a and 7030b are configured to pivot via the pivot pin 7032 about a pivot axis P1 from the releasing position (FIG. 96) to the holding position (FIG. 97). In the holding position, hooks 7034a and 7034b on respective ends of the actuator dogs 7030a and 7030b are positioned to engage the yoke arm flanges 1042 on the yoke member 1006 in order to retain and hold the yoke member 1006 within the holding mechanism 7020.

Figure 95:
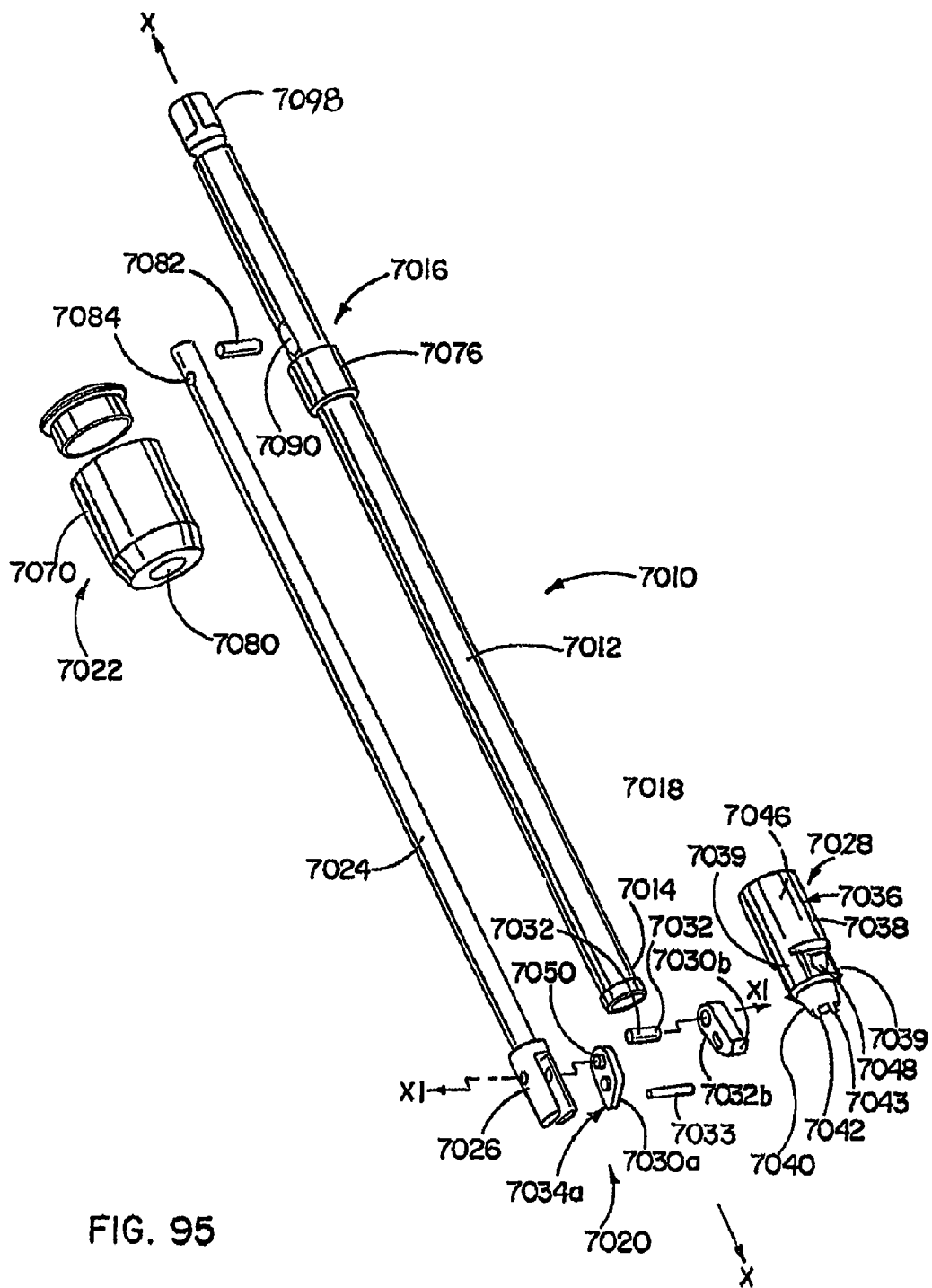
FIG. 95 is an exploded view of the instrument of FIG. 94 showing a holding mechanism at one end of a tubular shaft, an actuator at an opposite end of the tubular shaft, and a control shaft operatively connected therebetween.
Figure 96:
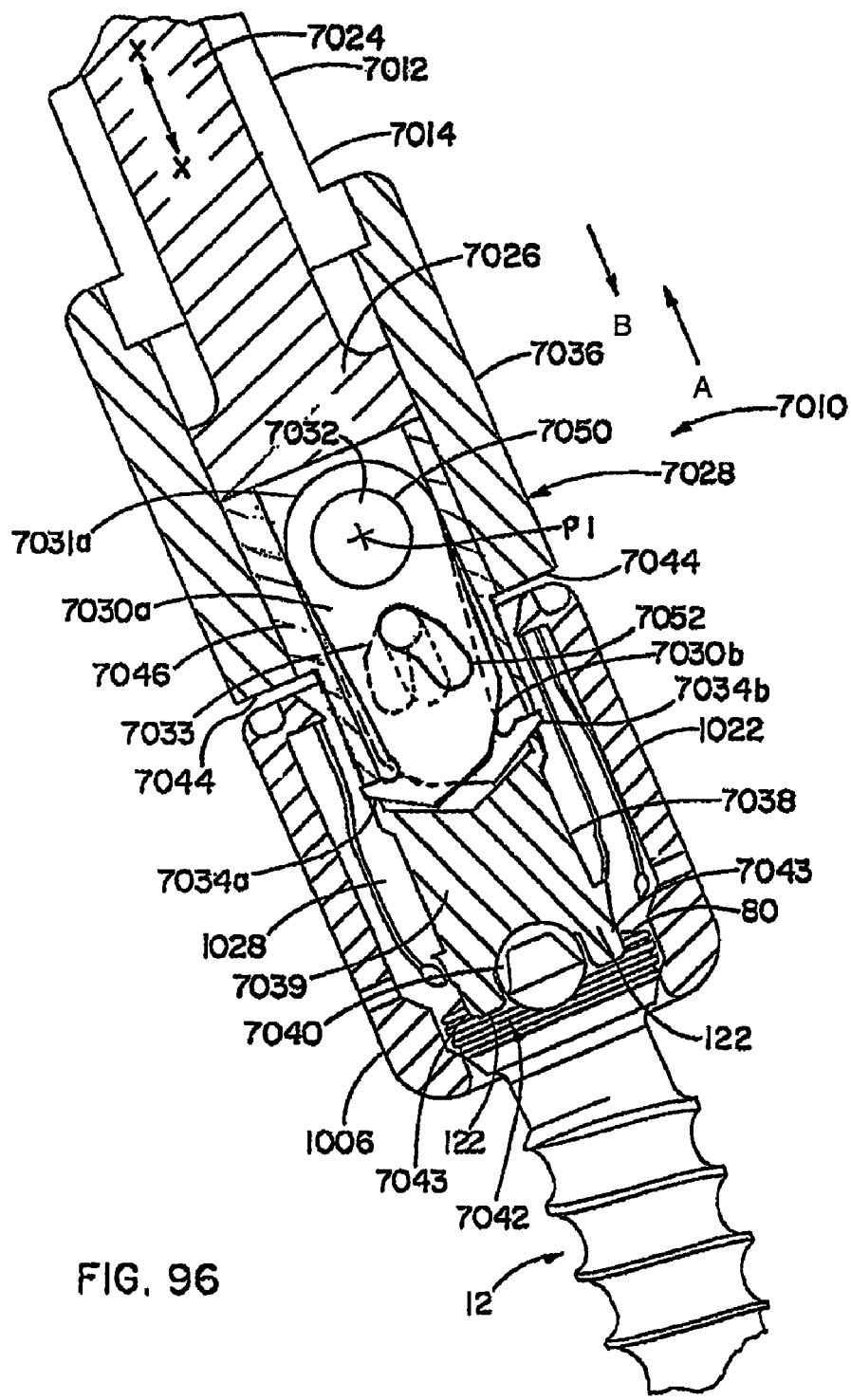
FIG. 96 is a cross-sectional view of the holding mechanism shown in a releasing position.
Figure 97:
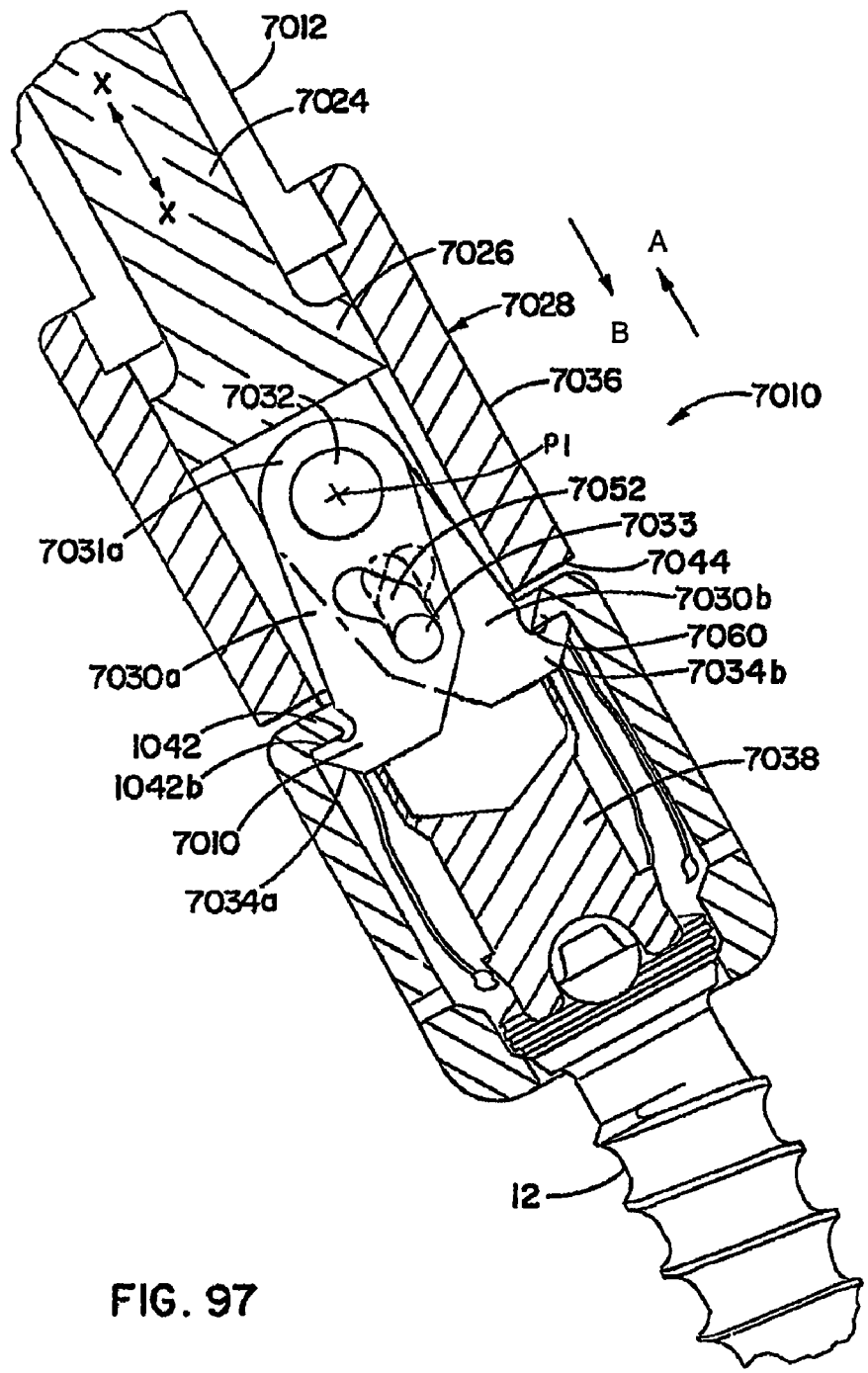
FIG. 97 is a cross-sectional view of the holding mechanism shown in a holding position.

Referring to FIGS. 95-97, the driver tip 7028 is a generally annular member having an enlarged, upper cylindrical portion 7036 and a narrowed, lower protruding portion 7038. The lower portion 7038 includes spaced walls 1039 that taper inwardly toward each other at a distal end 7040 thereof, and is sized and configured to be received within the internal space 1028 formed between the yoke side walls 1022. In order to couple with the anchor member 12, the lower portion distal end 7040 defines a mating surface 7042 in the form of a plurality of protrusions 7043 that are arranged and configured to mate with the peripheral driving surfaces 120 and recessed notches 122 formed in the top surface 80 of the anchor member 12. (FIGS. 15 and 96-97).

The upper cylindrical portion 7036 includes lower compression surfaces 7044 that extend radially outward from the lower portion 7038. The compression surfaces 7044 are designed to engage the upper edge 1036 of the yoke arm portions 1030 and hold the yoke member 1006 in a tight arrangement when the hook portions 1034a,b or the actuator dogs 1030a,b engage the yoke flanges 1042 in the holding position.

The driver tip 7028 defines an internal cavity 7046 extending through both the upper portion 7036 and the lower portion 7038 that communicates with the tubular shaft passage 7018. Within the internal cavity 7046, the distal end 7026 of the control shaft 7024 and the actuator dogs 7030a and 7030b are received. The spaced side walls 1039 of the driver tip lower portion 7038 include windows or openings 7048, which are positioned so that the hook portions 7034a,b of the actuator dogs 7030a,b can protrude through when pivoted to the holding position in order to engage the yoke flanges 1042.

In order to pivot from the releasing position to the holding position, the actuator dog 7030a includes a pivot opening 7050 sized to receive the pivot pin 7032 therethrough and a cam slot 7052 that cooperates with the cam pin 7033 extending through the cam slot 7052. As a result, sliding the control shaft 7024 in the passage 7018 about the longitudinal axis X in a first or holding direction (arrow A) is operative to cam or pivot the actuator dog hook portion 7034a about the pivot axis X1 from the releasing position (FIG. 96) to the holding position (FIG. 97). This pivoting motion is achieved because the actuator dog 7030b is pivotably coupled to the end 7026 of the control shaft 1024 via the pivot pin 7032, but the cam pin 7033 is fixed to the driver tip 7028 and slidably received through the actuator dog cam slot 7052. Therefore, movement of the control shaft 7024 in the holding direction (arrow A) causes a pivot end 7031a of the actuator dog 7030a in move in a similar direction. Movement of the actuator dog 7030a causes the cam slot 1052 to engage the fixed cam pin 7033, and cams or pivot the hook portion 7034a outwardly to the holding position of FIG. 97. Actuator dog 7030b includes similar features in order to cam between the two positions.

Referring to FIG. 97, the holding mechanism 7020 is shown in the holding position. In this position, undercut grooves 7060 formed by the actuator dog hook portions 7034a,b engage the yoke flanges 1042. Preferably, the undercut grooves 7060 engage the lower surfaces 1042b of the flanges and pull the yoke member 1006 along the longitudinal axis X toward the compression surfaces 7044. In this manner, the yoke flanges 1042 are compressed between the compression surfaces 7044 of the driver tip upper portion 7036 and the undercut grooves 7060 of the actuator dogs 7030a,b so that the yoke member 1006 is securely held to the instrument 7010.

Figure 98:
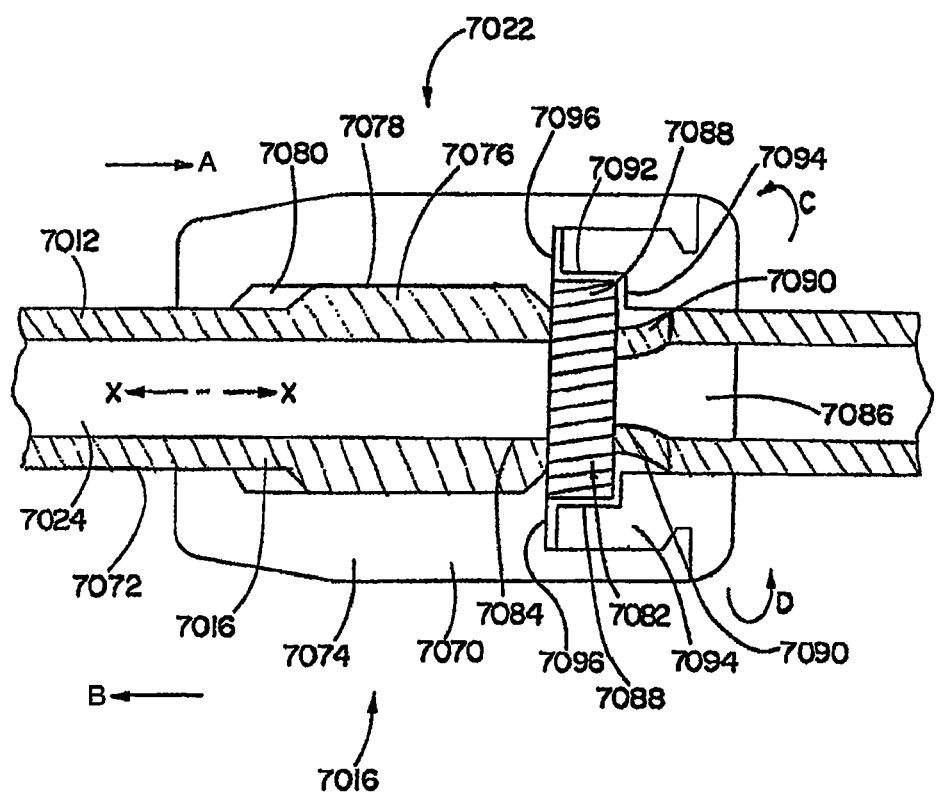
FIG. 98 is a cross-sectional view of the actuator showing a handle and a control pin coupled to the tubular shaft and control shaft.

Turning to FIG. 98, the actuator portion 7022 is illustrated in more detail. As previously mentioned, the actuator portion 7022 is coupled to the actuator end 7016 of the tubular shaft 7012 and is operative to move the holding member 7020, and in particular the actuator dogs 7030a and 7030b, from the releasing position of FIG. 96 to the holding position of FIG. 97.

More specifically, the actuator portion 7022 is operative to move the control shaft 7024 in the holding direction (arrow A) to pivot the actuator dogs 7030a and 7030b as described above, and in the opposite, releasing direction (arrow B) to pivot the dogs 7030a and 7030b to the releasing position. To this end, the actuator portion 7022 includes a handle 7070 that is threadably mated to an outer surface 7072 of the tubular shaft 7012 via mating threads 7074, which includes external threads 7076 on the outer surface 7072 of the sleeve 7012 and internal threads 7078 on an internal surface of a bore 7080 that extends through the handle 7070. In this manner, the handle 7070 can be rotated relative to the sleeve 7012 about the longitudinal axis X to slide the control shaft 7024 along the longitudinal axis.

To accomplish such control shaft movement, the handle 7070 is operatively connected to the control shaft 7024 via a control pin 7082 such that rotation of the handle 7070 in a first direction slides the control shaft 7024 in the holding direction (arrow A) and rotation of the handle 7070 in a second, opposite direction slides the control shaft 7024 in the releasing direction.

The control pin 7082 is coupled to the control shaft 7024 by extending through an aperture 7084 in a proximate end portion 7086 of the control shaft. Opposite ends 7088 of the control pin 7082 extend through slots 7090 defined in opposing sides of the tubular shaft 7012 such that the control pin ends 7088 protrude through the slots 7090. The control pin 7082 is configured to slide within the slots 7090 in response to rotation of the handle 7070. Such motion is achieved because the exposed control pin ends 7088 are captured within a pocket 7092 formed in the handle 7070.

Upon rotation of the handle 7070 in one direction (arrow C), an upper interference surface 7094 of the handle pocket 7092 contacts the control pin 7082 to push the control pin 7082 along the longitudinal axis X such that is slides within the slot 7090 in the holding direction (arrow A). Because the control pin 7082 is coupled to the control shaft 7024 as it extends through the control shaft aperture 7084, movement of the control pin 7082 in the holding direction within the slot 7090 via threaded rotation of the handle 7070 also moves the control shaft 7024 in the same direction. To pivot the actuator dogs 7030a and 7030b back to the releasing position, the handle 7070 is rotated in an opposite direction (arrow D), and a lower interference surface 7096 of the handle 7070 contacts the control pin 7082 to slide the control pin 7082 in the releasing direction (arrow B). Because the control pin 7082 is coupled to the control shaft 7024, such movement of the control pin 7082 by the handle 7070 also slides the control shaft 7024 in the same direction along the longitudinal axis X.

To implant or screw a locked anchor member 12 into the bone, the tubular shaft 7012 preferably includes a profiled end cap 7098 on the actuator end 7016 thereof. The profiled end cap 7098 is adapted to receive any suitable driving tool or other instrument to screw, impact, or drive the anchor member 12 held within the holding mechanism 7020 into bone.

Turning to FIGS. 99-122, a variety of additional instruments are illustrated that are adapted and configured to manipulate any of the spinal fixation systems discussed herein. Preferably, these instruments are configured to cooperate with a housing assembly 8010 adapted to hold the spinal fixation system 1000, which includes the yoke member 1006 having the resilient arm portions 1030 on the yoke sides wall 1022. Therefore, while the instruments and housing assembly 8010 may be used with other spinal fixation systems and anchor members, it will be described and illustrated in conjunction with the spinal fixation system 1000.

Referring now to FIGS. 99-108A, 108B, the housing assembly 8010 will first be described in more detail. The housing assembly 8010 includes an elongate tubular housing 8012 defining a passage 8014 therethrough with a longitudinal axis X1 extending along the passage 8014. The tubular housing 8012 includes an operative portion 8016 configured to hold and retain the yoke member 1006 and an actuator portion 8018 configured to control the operative portion 8016.

Figure 101:
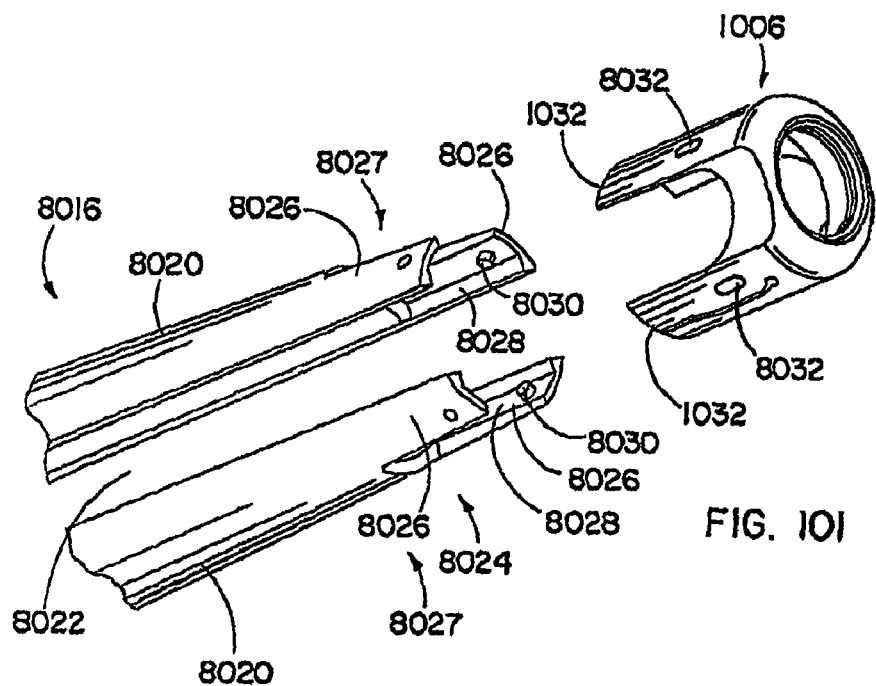
FIG. 101 is a perspective view of the instrument of FIG. 99 showing inwardly extending protrusions configured to mate in elongate slots defined in the yoke member.

The operative portion 8016 of the tubular housing 8012 includes facing arcuate side walls 8020 that define a U-shaped slot 8022 therebetween. At a distal end 8024 of the operative portion 8016, each side wall 8020 is further split into a pair of spaced arcuate fingers 8026 that define an elongate receiving slot 2027 therebetween. The spaced fingers 8026 are sized and configured to be received around the outside of the yoke member 1006 and retain the yoke member 1006 therein. To this end, inner surfaces 8028 of each finger 8026 include a locking cleat or protrusion 8030, which are positioned to be received within spaced slot apertures 8032 can be provided within the side wall post portions 1032 of the yoke member 1006 as can be seen in FIG. 101.

Figure 100:
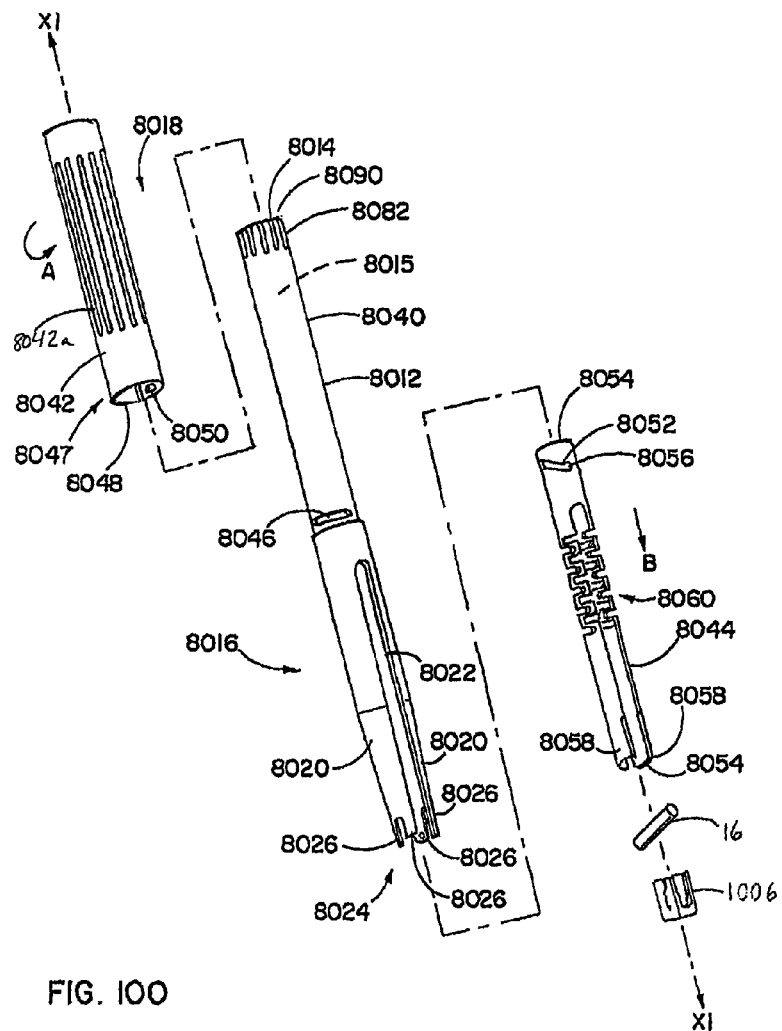
FIG. 100 is an exploded view of the instrument of FIG. 99 showing a housing, lock sleeve and handle.
Figure 104:
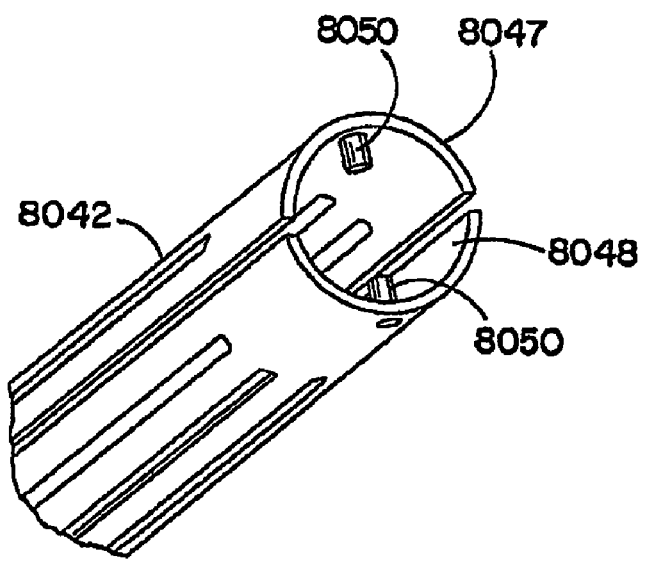
FIG. 104 is a perspective view of the handle of FIG. 100 showing guide pins therein.
Figure 105:
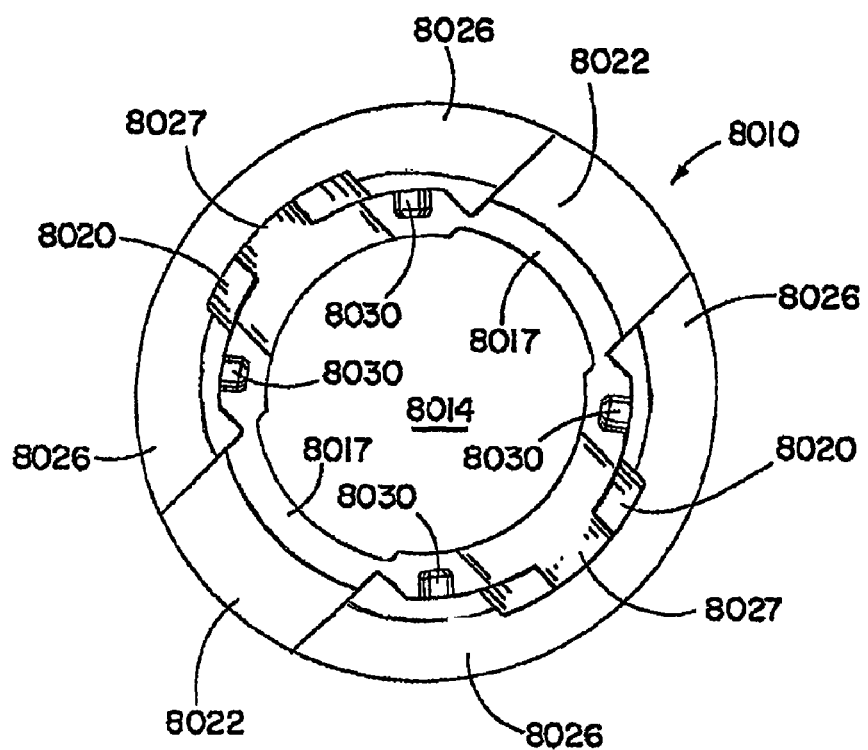
FIG. 105 is a plan view of the housing of FIG. 100 showing the inwardly extending protrusions thereof.

The actuator portion 8018 of the housing 8012 includes a cylindrical side wall 8040 surrounding the passage 8014 and a handle 8042 that is configured to rotate about the side wall 8040. Coupling the handle 8042 of the actuator portion 8018 to the housing operative portion 8016 is an elongate lock sleeve 8044 that extends through and slides within the passage 8014. This coupling is achieved through a pair of guide pins 8050 that are approximately 180° apart on an inner surface 8048 of the handle 8042 (FIG. 104). The guide pins 8050 extend through facing annular slots 8046 that are preferably defined on opposite sides of the housing side wall 8040 and that extend generally transverse to the longitudinal axis X1. Preferably, the slots 8046 are located intermediate the housing 8012 so that they are positioned adjacent a distal end 8047 of the handle 8042. Each guide pin 8050 is positioned to extend through one of the annular slots 8046 and also be received in one of a pair of facing angled cam slots 8052 that are defined in a proximate end 8054 of the lock sleeve 8044 (FIG. 100).

Figure 106A:
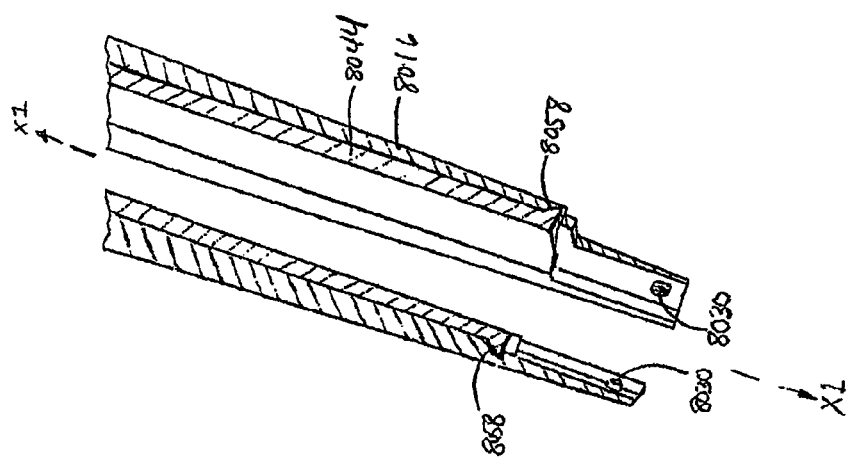
FIGS. 106A,B-108A,B are cross-sectional views of the instrument of FIG. 99 shown in various stages during an exemplary locking operation to the yoke member.
Figure 106B:
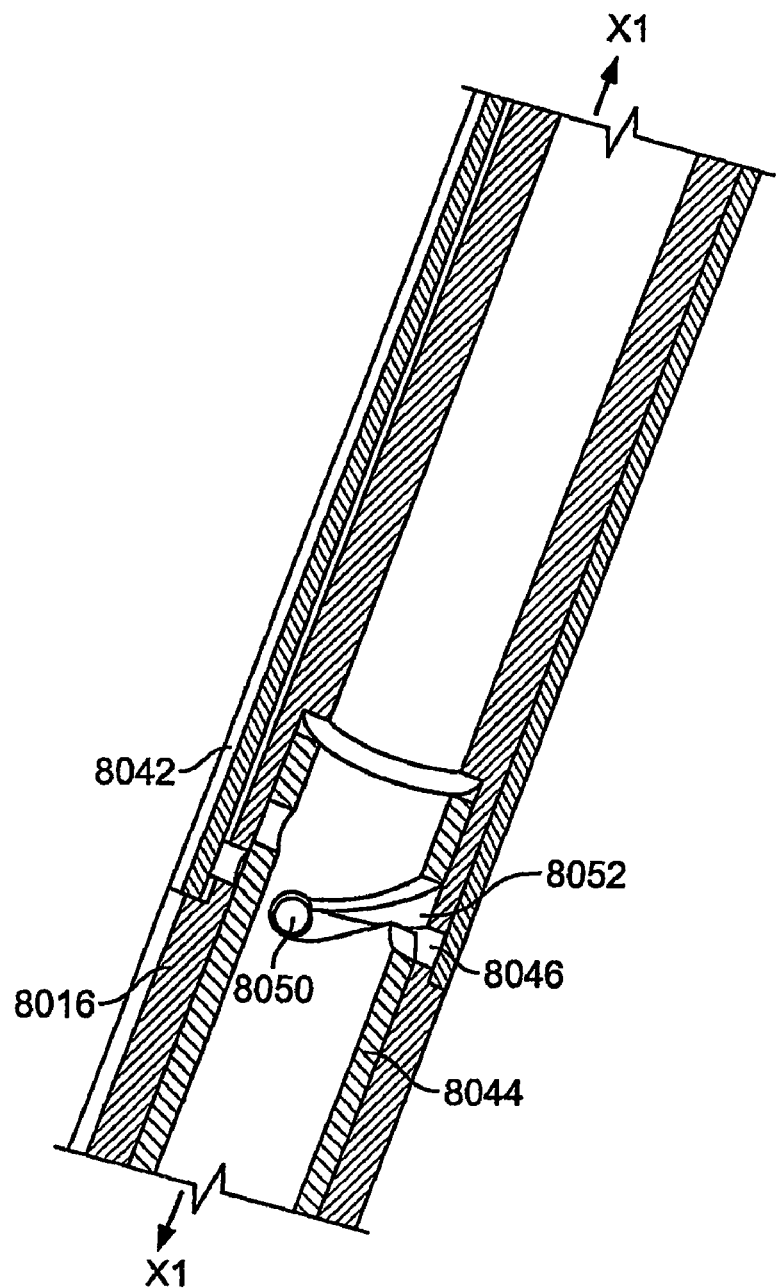
Figure 107A:
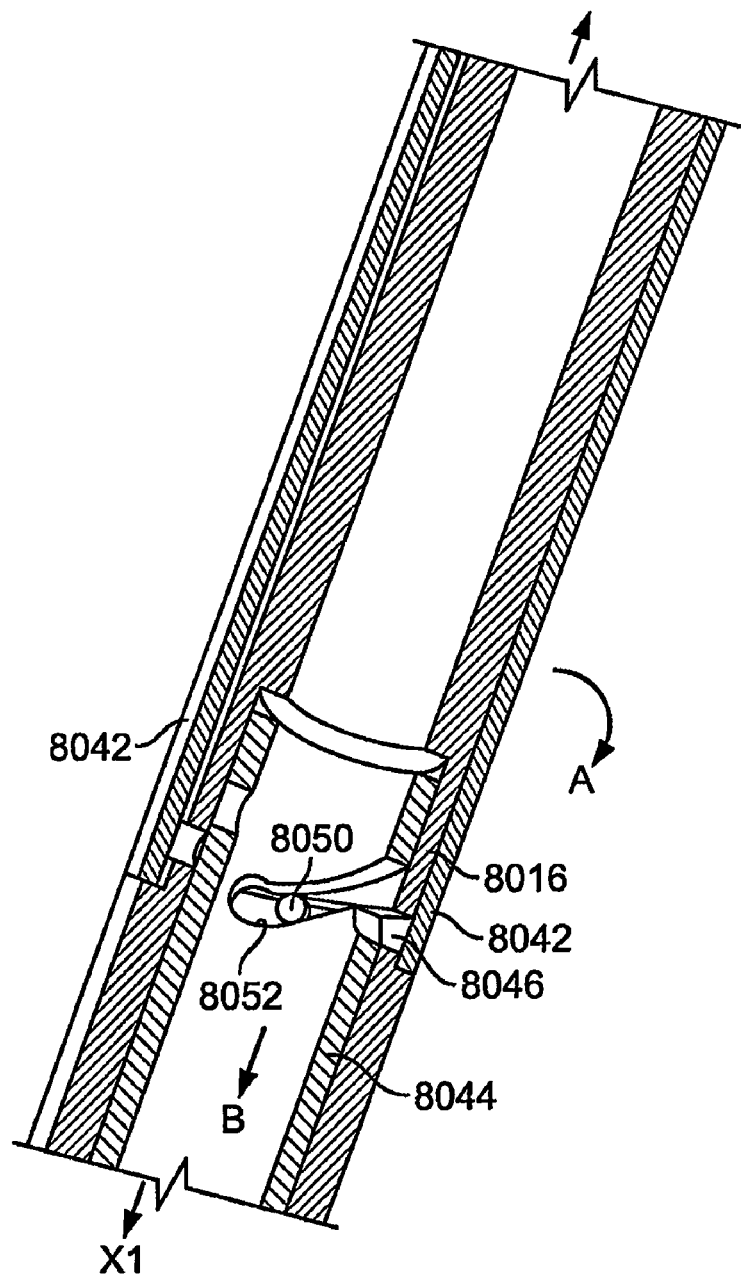
Figure 107B:
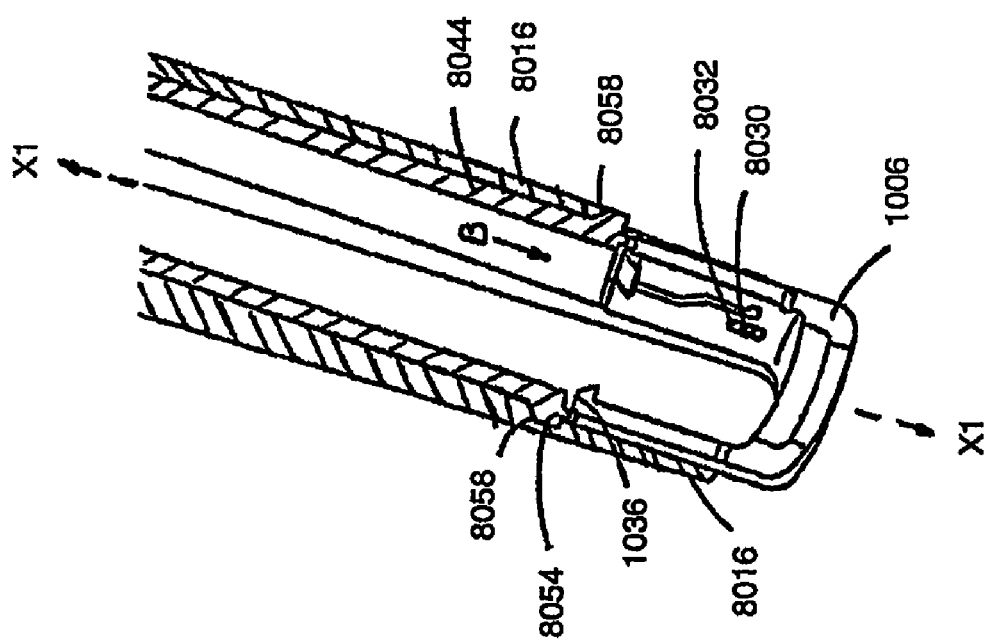
Figure 108A:
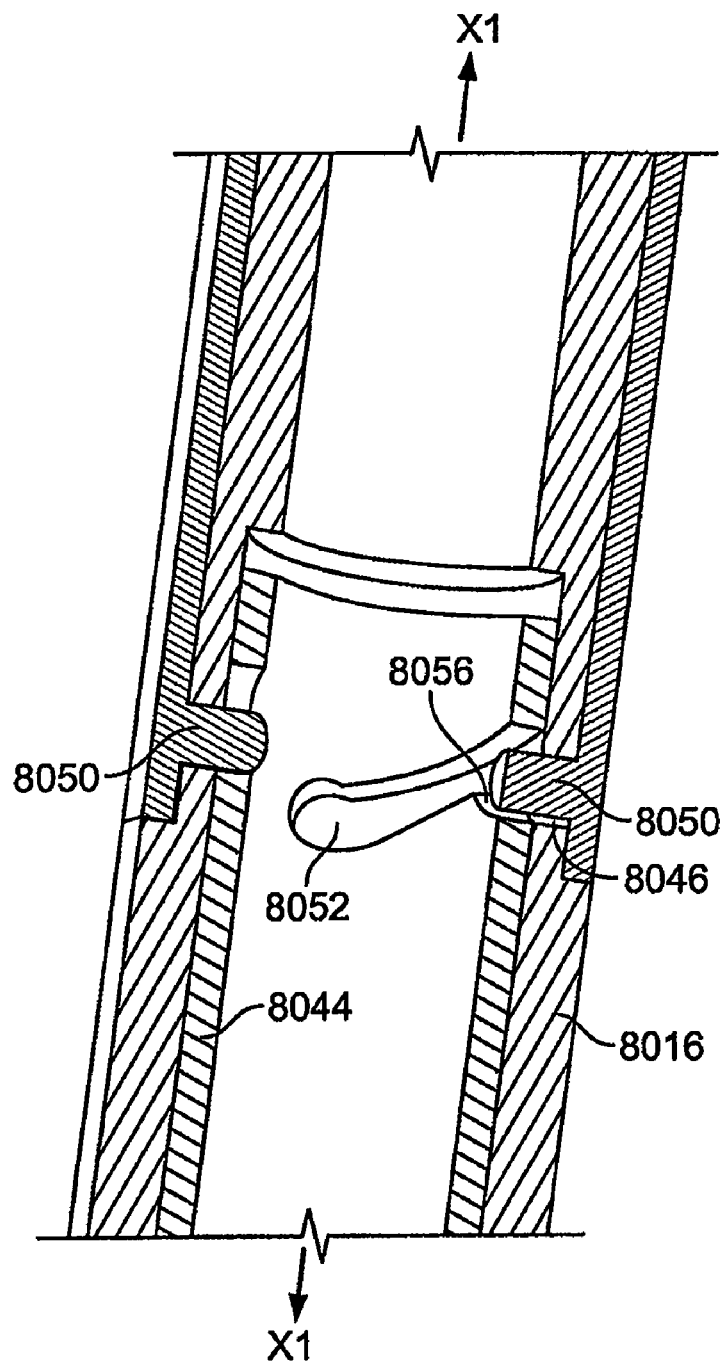
Figure 108B:
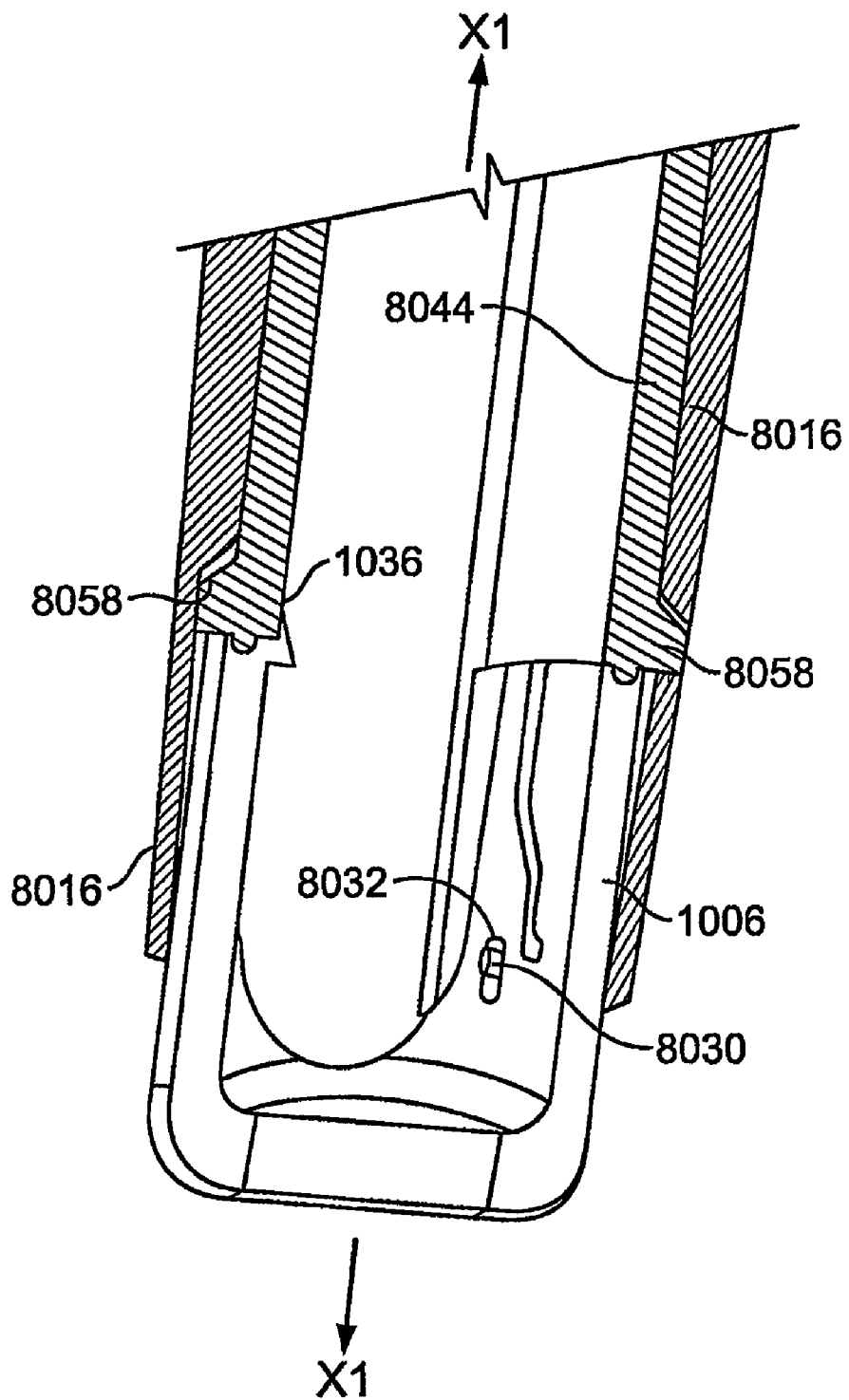
Figure 109:
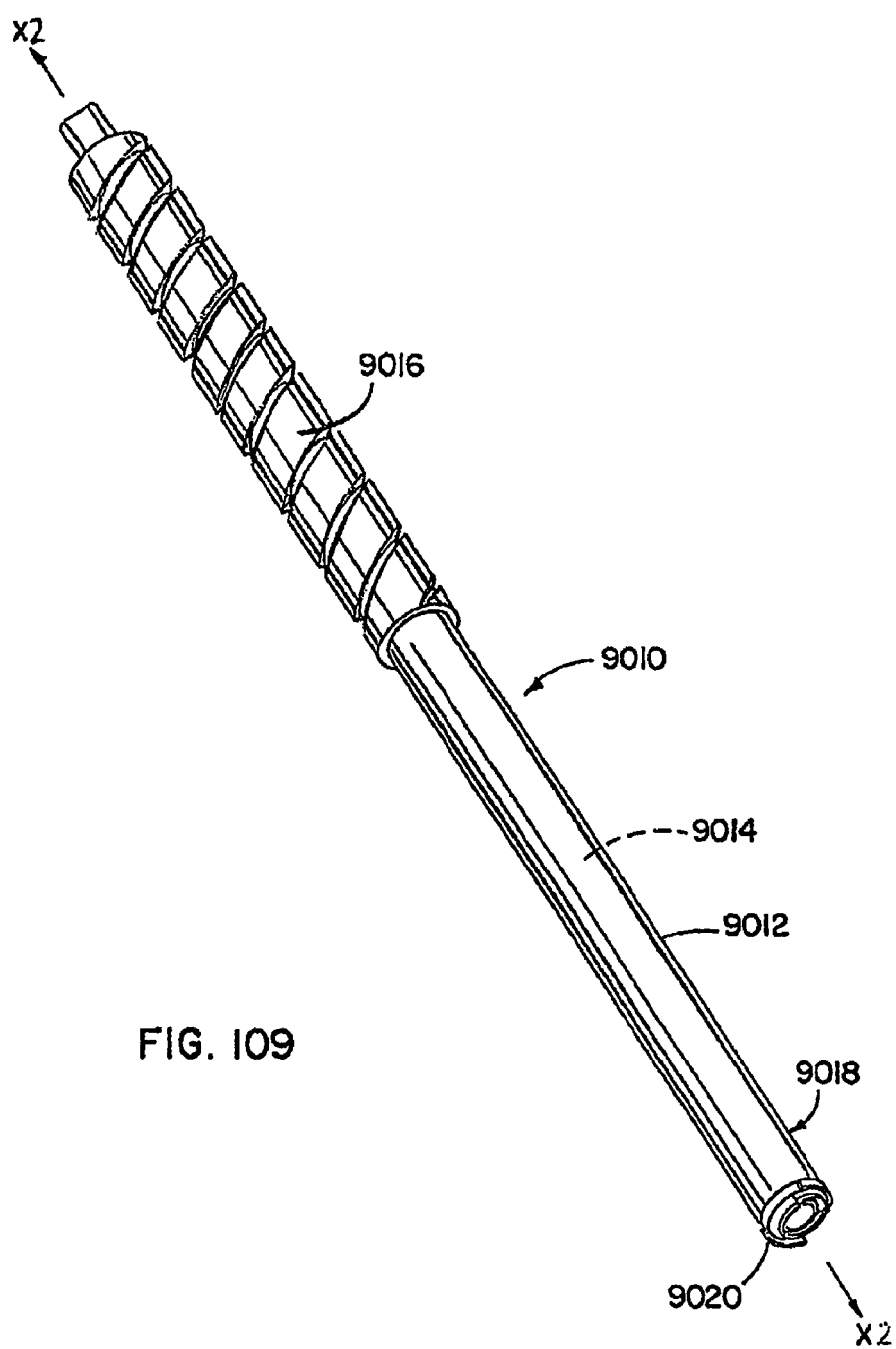
FIG. 109 is a perspective view of another instrument configured to be received within a passage defined in the instrument of FIG. 99.
Figure 110:
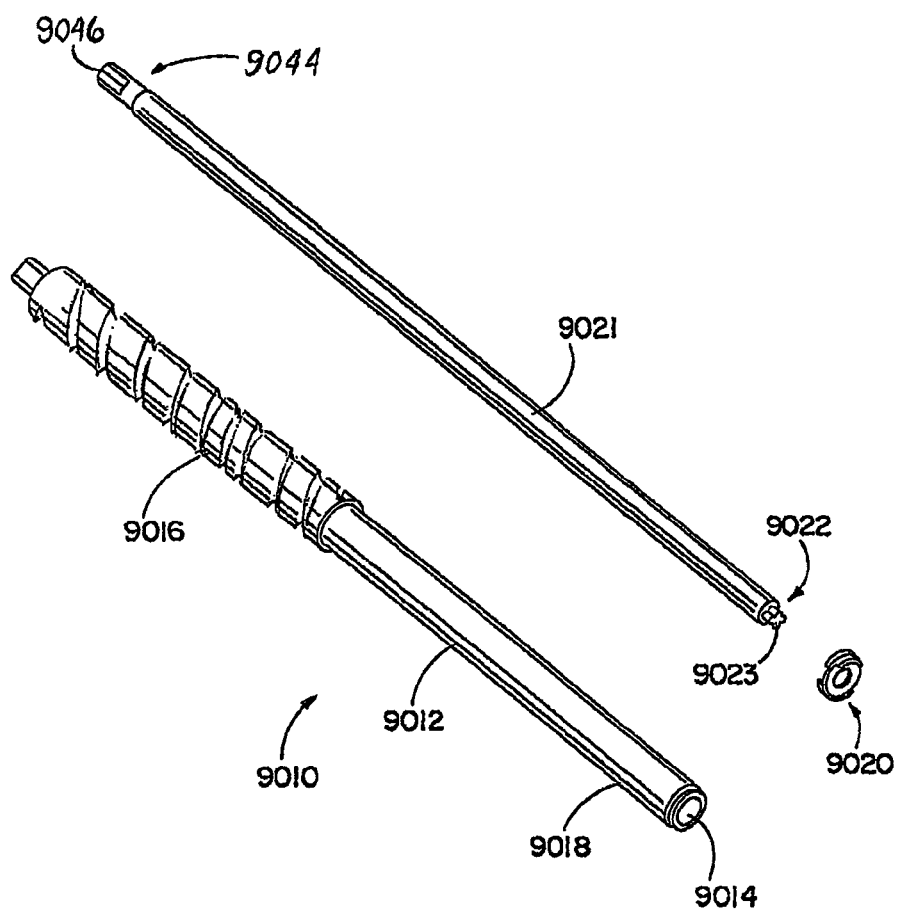
FIG. 110 is an exploded view of the instrument of FIG. 109 showing an elongate shaft, a locking shaft, and a bearing member.

With the above described coupling between the handle 8042 and lock sleeve 8044, rotation of the handle 8042 about the housing side wall 8040 is operative to slide the lock sleeve 8044 along the longitudinal axis X1 within the housing passage 8014 as illustrated in FIGS. 106A,B-108A,B. For example, rotation of the handle 8042 in one direction (arrow A) causes the guide pins 8050 to slide transverse to the axis X1 within the annular slots 8046 and also within the angled cam slots 8052 in order to provide a camming force on the lock sleeve 8044. This camming force is operative to slide the lock sleeve 8044 in a first or locking direction (arrow B) along the longitudinal axis X1. Upon sufficient translation of the lock sleeve 8044 along the axis X1 (i.e., about 2 mm of travel), a distal end 8054 of the lock sleeve 8044 will engage the upper edge 1036 of the yoke member 1006, which has previously been received in the housing operative end 8016 as described above, such that the yoke member 1006 is compressed between the lock sleeve distal end 8054 and the cleats 8030 within the yoke slot apertures 8032. After about 2 mm of axial travel of the lock sleeve 8044, the guide pin 8050 will be received in a pocket 8056 that provides a positive locking of the lock sleeve 8044 in this locked configuration. As shown in FIG. 100, the handle 8042 includes one or more slits 8042a that allow deformation of the handle upon over rotation thereof to prevent guide pins 8050 from being forced out of the slots 8046 and 8052 or from being damaged.

To substantially ensure axial translation of the lock sleeve along the axis X1 (rather than rotation thereabout), outwardly extending flanges 8058 are provided on the distal end 8054 of the lock sleeve 8044. The flanges 8058 are received within the housing elongate slots 8027 formed between the spaced housing fingers 8026 on the distal end 8024 of the housing operative portion 8016. The flanges 8058 are sized and configured to slide within the elongate slots 8027 so that upon the guide pins 8050 providing the camming force in the cam slots 8052, the lock sleeve 8044 will translate axially along the axis X1 rather than rotate thereabout because the flanges slide in the elongate slots 8027 to substantially hinder such rotation.

Figure 103:
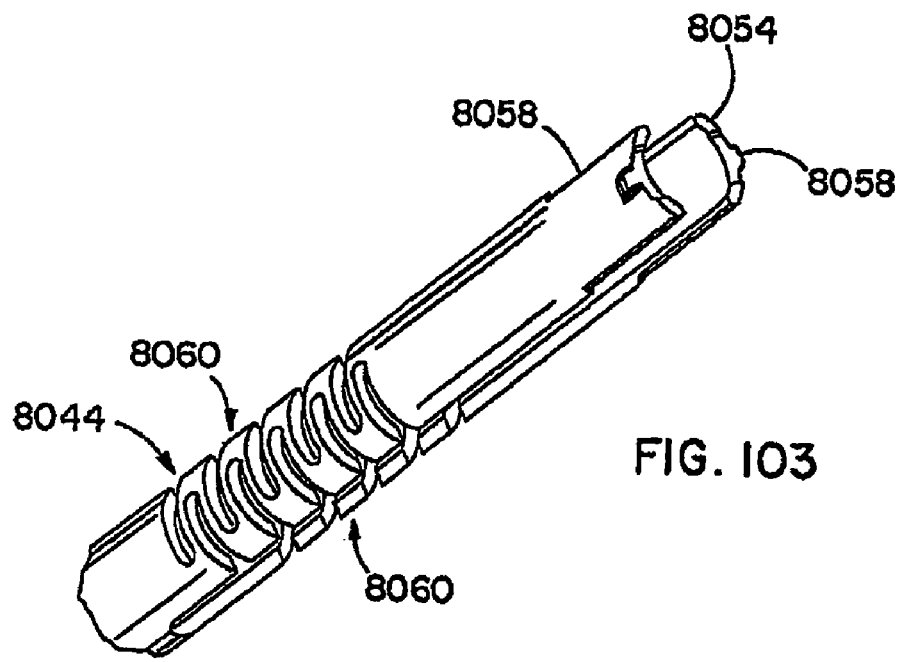
FIG. 103 is a perspective view of the lock sleeve of FIG. 100 showing a resilient portion thereof.

The lock sleeve 8044 preferably includes a resilient or compressible portion 8060 configured to compress and distribute the strain on the lock sleeve 8044 when in a locked position. As shown in FIGS. 100 and 103, the resilient portion 8060 is in the form of a plurality of bias members 8062 that are configured to permit the lock sleeve to resiliently compress along the longitudinal axis X1 when the guide pins 8050 are positively seated in the pockets 8056 when the assembly 8010 is in the locked configuration. When in a non-locked configuration, the resilient portion 8060 flexes back to its original configuration.

Figure 102:
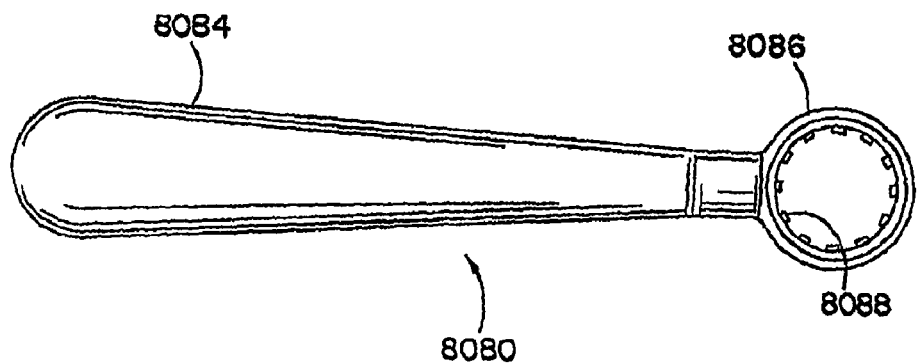
FIG. 102 is a plan view of an optional anti-torque wrench configured to be mated with the instrument of FIG. 99.

Referring to FIG. 102, there is illustrated an optional anti-torque handle 8080 adapted and configured to be received on a proximate end 8082 of the elongate housing 8012. The anti-torque handle 8080 hinders the rotation of the housing assembly 8010 during use of the other instruments to be described below. To this end, the handle 8080 includes a holding portion 8084 and a ring portion 8086. The ring portion 8086 defines internal spaced ribs 8088 that extend along the ring portion 8086, which are sized and configured to mate with corresponding slots 8090 in the proximate end 8082 of the housing 8012. When coupled, there is preferably no rotation between the handle 8080 and the assembly 8010.

Figure 99:
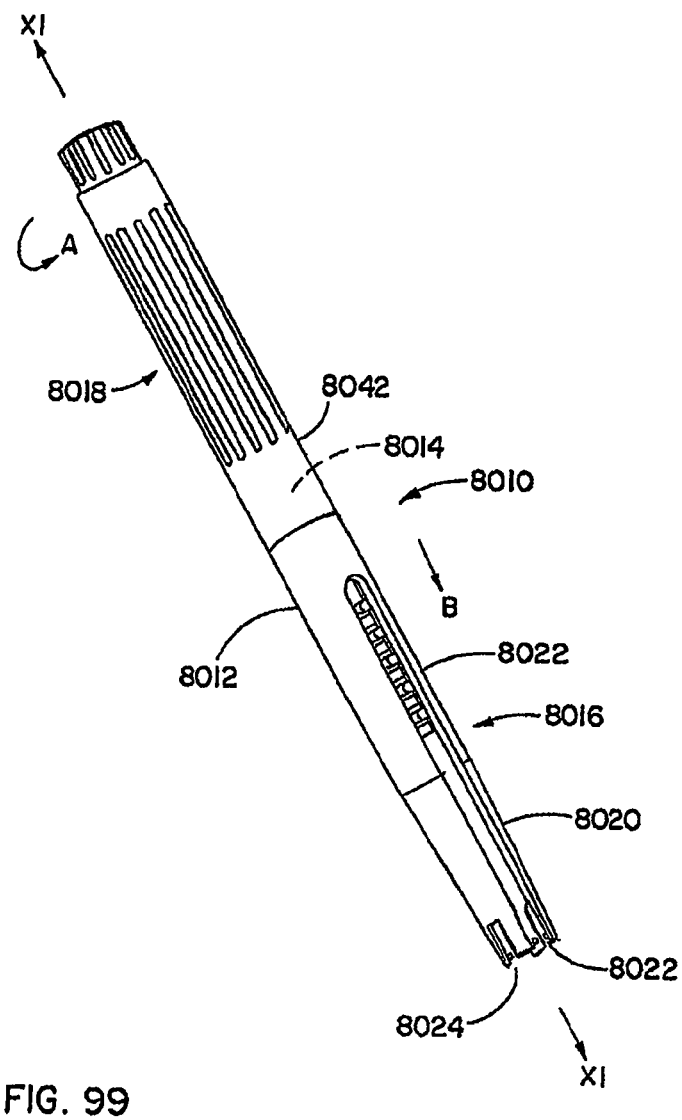
FIG. 99 is a perspective view of a second instrument for installing the spinal fixation systems disclosed herein.

Turning to FIGS. 109-114, a first instrument 9010 is provided that is adapted and configured to be received within the housing passage 8014 of the housing assembly 8010 (FIGS. 99-100). Instrument 9010 is for installing the cap assembly 1010 into the plurality of cap-lock positions. That is, the instrument 9010 is adapted and configured to install the cap assembly 1010 into the first or maximum clearance cap-lock position, the second or minimum clearance cap-lock position, and the third or rod-lock position. To this end, the instrument 9010 is capable of inserting the cap assembly 1010 axially along the yoke axis 21 to position the cap assembly 1010 into either the first or second locks position and also to rotate the cap assembly 1010 so as to position the cap assembly 1010 into the rod-lock position.

Turning to the details, the instrument 9010 includes an elongate persuader shaft 9012 defining a passage 9014 extending therethrough having a longitudinal axis X2. The persuader shaft 9012 has an outside diameter such that is can be inserted into the passage 8014 of the housing assembly 8010. Preferably, the persuader shaft 9012 has a threaded outer portion 9016 that threadably mates with a threaded inner portion 8015 of the housing assembly passage 8014 (FIG. 100). In this manner, the shaft 9012 may be threadably rotated within the passage 8014 in order to translate along the housing axis X1. On a distal end 9018 of the shaft 9012, a bearing member 9020 is received. The bearing member 9020 is adapted and configured to receive the cap assembly 1010 in an interference or press-fit arrangement. Extending through the persuader shaft passage 9014, there extends a locking shaft 9021 having a distal end 9022 with a profile end 9023 arranged and configured to mate the lobed profile 36 on the top of the cap assembly actuating member 1052.

Figure 112:
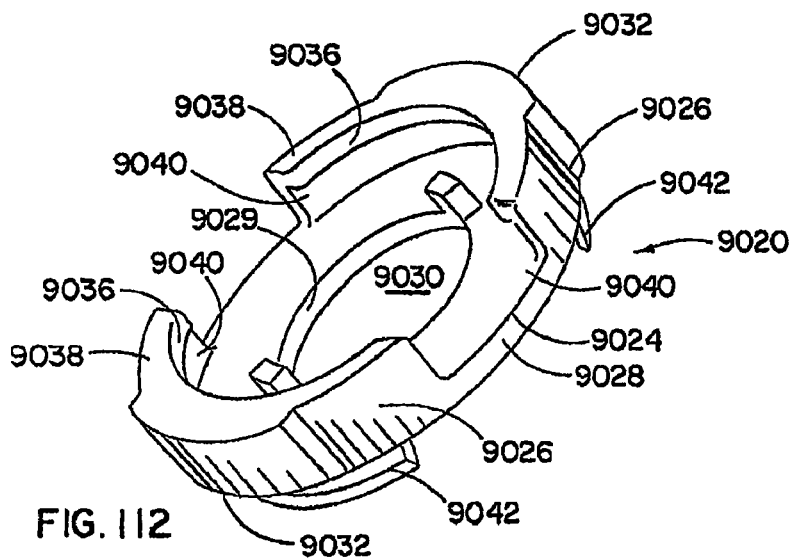
FIG. 112 is a perspective view of the bearing member of FIG. 110.

Turning for a moment to FIG. 112, the bearing member 9020 is preferably a disk-shaped base member 9024 with a pair of facing, arcuate upstanding side walls 9026 that extend axially upward from an outer edge 9028 of the base member 9024. An internal edge 9029 of the base member 9024 defines a central opening 9030 sized to permit the locking shaft, and in particular the profiled end 9023, to extend therethrough. The bearing member 9020 has an outer diameter permitting receipt within the housing passage 8014.

The bearing member 9020 is preferably configured to permit the persuader shaft 9012 to threadably rotate as it translates down the housing axis X1, but also permit the cap assembly 1010 to be axially inserted along the yoke axis 21 without substantial rotation thereof into the maximum-clearance and minimum clearance cap-lock positions. To this end, the bearing member 9020 includes radially outward extending bosses or flanges 9032 that are sized to be received within facing axial slots 8017 that extend the length of the housing passage 8014 (see, e.g., FIG. 105). The flanges 9032 permit the bearing member 9020 to slide within the passage 8014, but substantially hinder the rotation of the bearing member 9020. Once the cap assembly 1010 has been positioned into the second or minimum cap lock position, the flanges 9032 are free of the axial slots 8017 so that the instrument 9010 is now free to rotate the cap assembly 1010 into the final or rod lock position. To this end, the plurality of fingers 8026 at the distal end 8024 of the housing operative portion 8016 have a wider inner diameter than the other portions of the passage 8014 in order to permit the bearing member 9020 to rotate within the passage 8014 (FIG. 105) after clearing the axial slots 8017.

Figure 111:
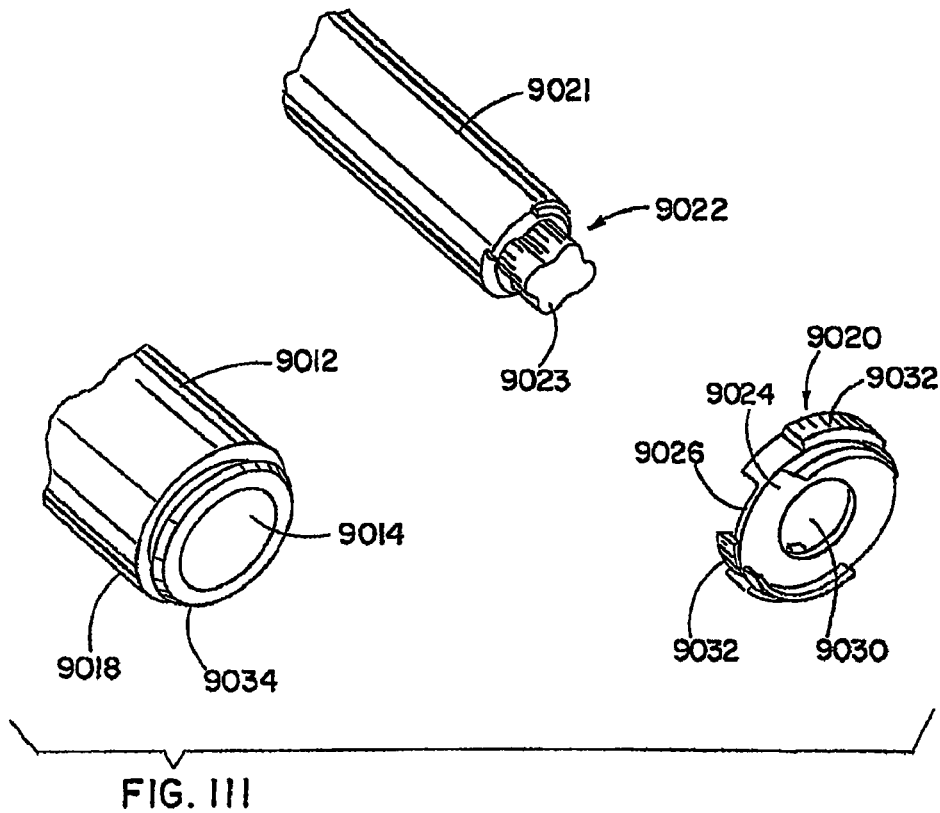
FIG. 111 is a perspective view of the distal ends of the elongate shaft, the locking shaft, and bearing member of FIG. 110.

The bearing member 9020 is preferably snap-fit onto the distal end 9018 of the persuader shaft 9012. Specifically, as best shown in FIGS. 111 and 112, the persuader shaft 9012 defines an annular snap ring 9034 that projects radially outward, and the bearing member 9020 includes radially inwardly projecting lips 9036 on opposite sides thereof that extend radially inward from upper edges 9038 of the bearing member side walls 9026. The projecting lips 9036 define an annular, undercut groove 9040 that receives the snap ring 9034 in a snap-fit arrangement so that the persuader shaft can rotate about the axis X2 when the bearing member 9020 is received in the housing passage 8014. In order to receive the snap ring 9034, the bearing member side walls 9026 preferably resiliently flex outwardly and then snap back into their original configuration after the snap ring 9034 has been received within the under cut groove 9040.

Figure 113:
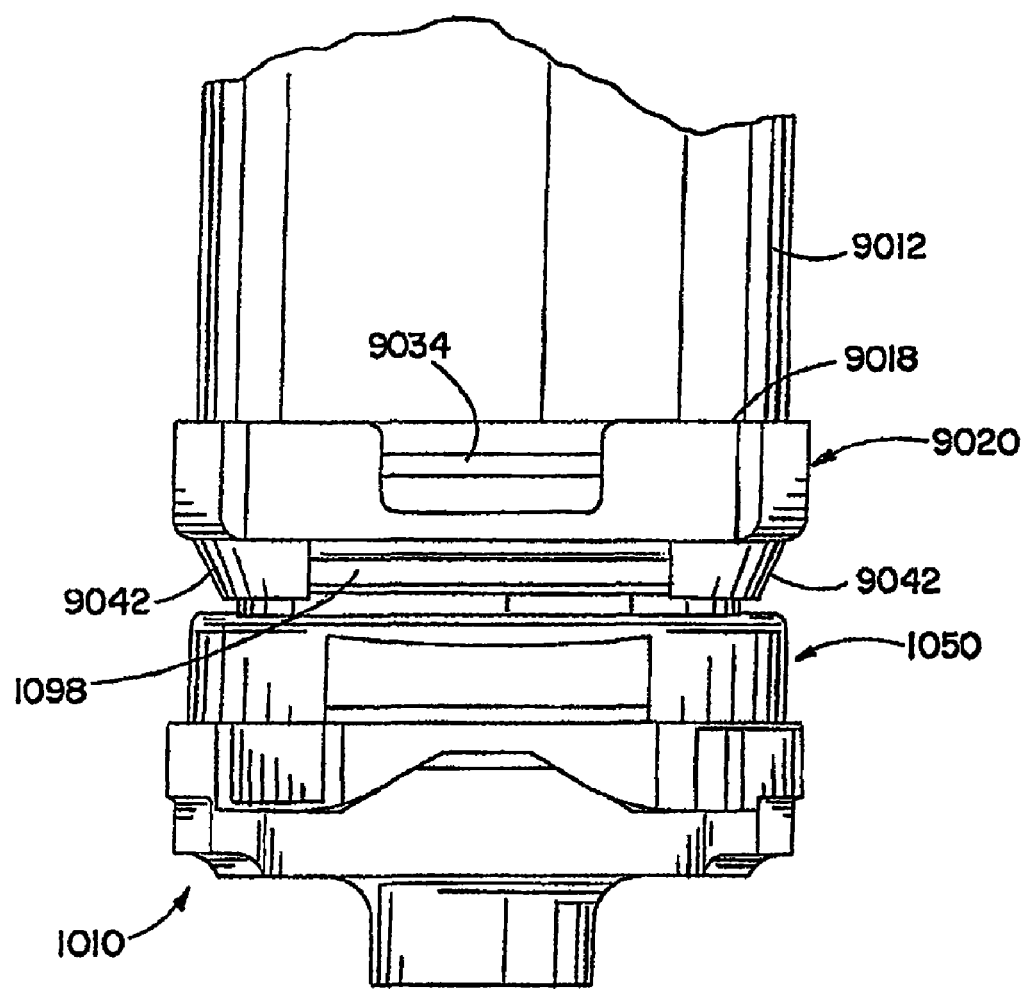
FIG. 113 is an elevational view of the instrument of FIG. 109 shown coupled to the cap assembly of FIGS. 51-64.

Referring now to FIGS. 112 and 113, the bearing member is configured to hold the cap assembly 1010 in an interference or friction fit. In this manner, the instrument 9010, and in particular the persuader shaft 9012, is configured to retain the cap assembly 1010 thereon while being inserted into the passage 8014 in housing assembly 8010 for insertion into the yoke member 1006, but the persuader shaft 9012 may be easily removed from the cap assembly 1010 after it has been locked into the yoke member 1010 by simply translating the persuader shaft 9012 in a reverse direction along the axis X1. The press or friction fit of the cap assembly 1010 to the bearing member 9020 will be separated upon the reverse translation of the shaft 9012 within the housing assembly 8010.

More specifically, the bearing member 9020 preferably includes arcuate, lock fingers 9042 that extend axially downward from opposite sides of the base member outer edge 9028. Preferably, the lock fingers 9042 are inclined or tapered radially inward towards the central opening 9030. In this manner, as best shown in FIG. 113, the lock fingers 9042 are configured to receive the upstanding annular rim 1098 of the cap assembly collar 1050 (FIG. 63) because the inward taper of the lock fingers 9042 preferably matches the outward taper of the upstanding annular rim 1098.

Figure 114:
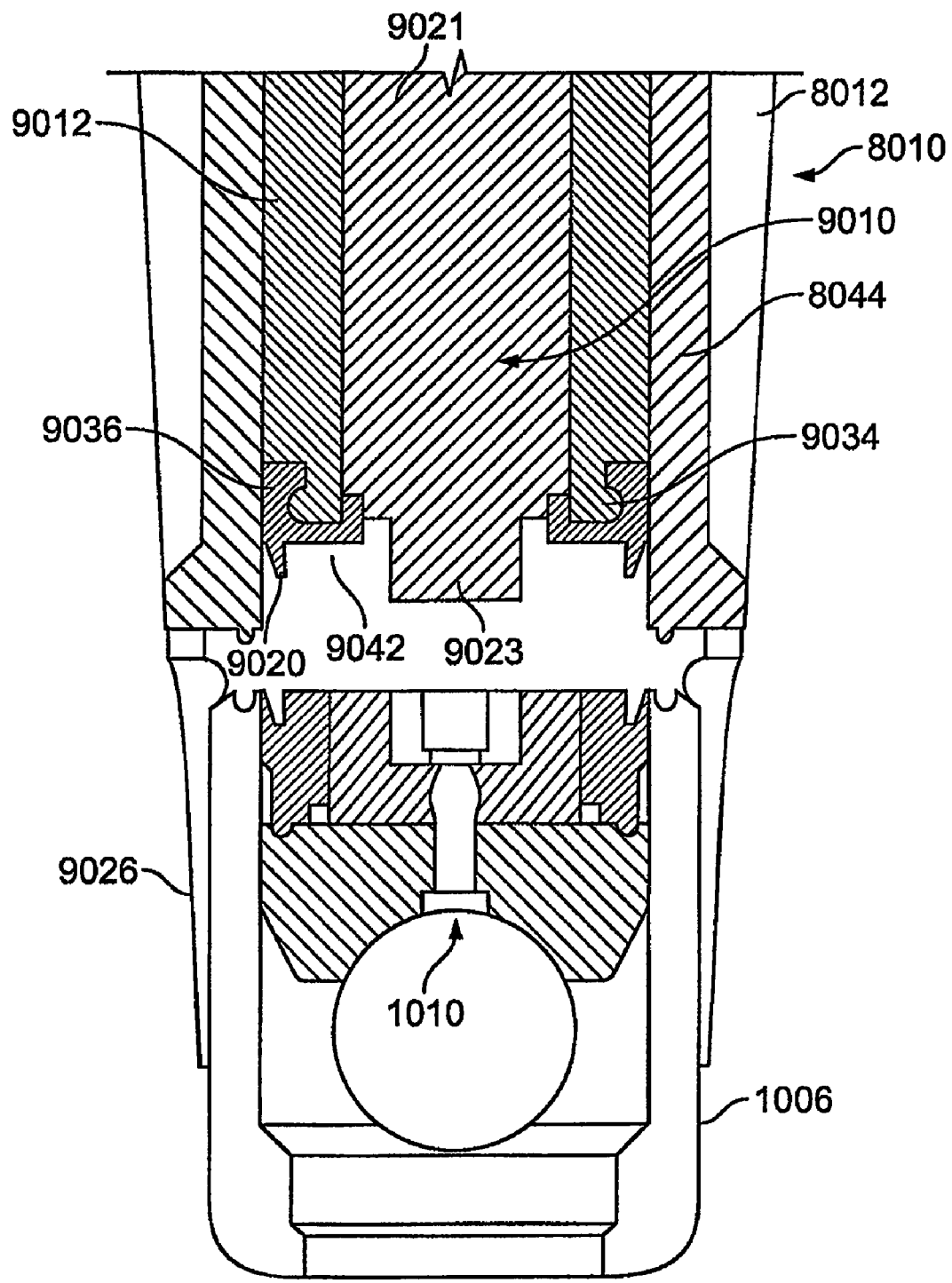
FIG. 114 is a cross-sectional view of the instrument of FIG. 109 shown coupled to the case assembly and yoke member.
Figure 115:
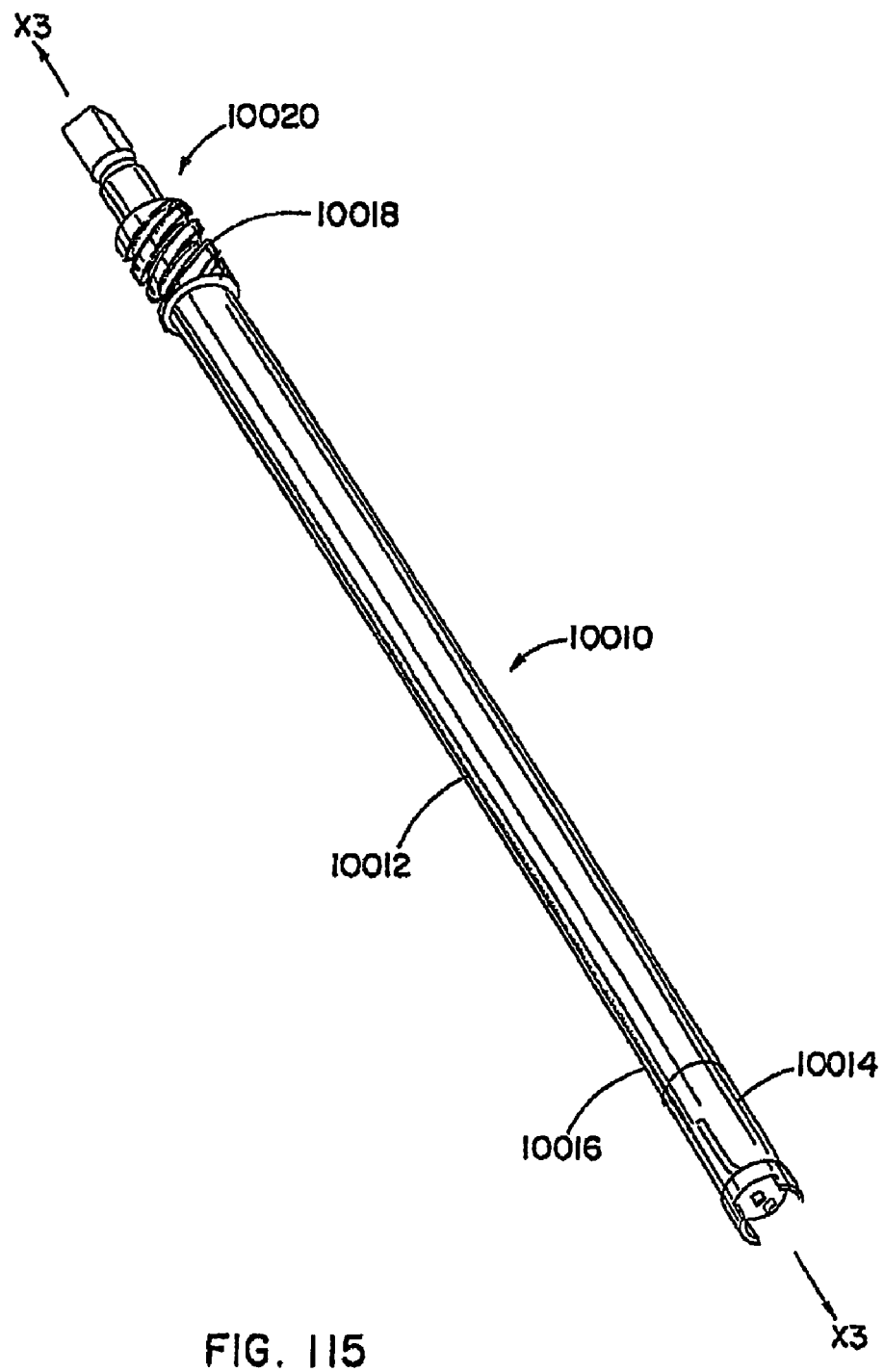
FIG. 115 is a perspective view of another instrument configured to be received within the passage defined in the instrument of FIG. 99.

Once the persuader shaft 9012 has installed the cap assembly 1010 into the minimum clearance cap lock position, the locking shaft 9021 is rotated so that the cap-assembly is rotated into the third or final cap-lock position. To this end, a proximate end 9044 of the locking shaft 9021 preferably defines a profiled end 9046, such as a hexagonal shape, that permits receipt of a rotating instrument thereon (not shown). Referring to FIG. 114, the cap assembly 1010 is shown in the rod-lock position (the rod shown removed for clarity) and the persuader shaft 9012 and lock shaft 9021 shown removed from the cap assembly 1010.

Referring now to FIGS. 115-118, a second instrument 10010 is illustrated for removing a previously installed cap assembly 1010. The instrument 10010 is also sized and configured for insertion into the housing assembly passage 8014 in order to interface with a yoke member 1006 locked onto the distal end 8024 of the housing assembly 8010. In this embodiment, as discussed further below, the housing assembly 8010 is preferably modified in order to resiliently flex the yoke arm portions 1030 outwardly in order to remove the cap assembly from the yoke member 1006.

The instrument 10010 includes an elongate cap removal shaft 10012 and a cap puller tip 10014 located on a distal end 10016 of the cap removal shaft 10012. The shaft 10012 and tip 10014 are sized for receipt in the housing assembly passage 8014, and in particular, for sliding along the longitudinal axis X1. To this end, the shaft 10012 also includes outer threads 10018 on a proximate end 10020 of the shaft 10012 for threadably mating with the internal threads 8015 within the housing assembly passage 8014. In this regard, the shaft 10012 may be threaded into the passage 8014 and turned in order to translate the tip 10014 along the housing longitudinal axis X1.

Figure 116:
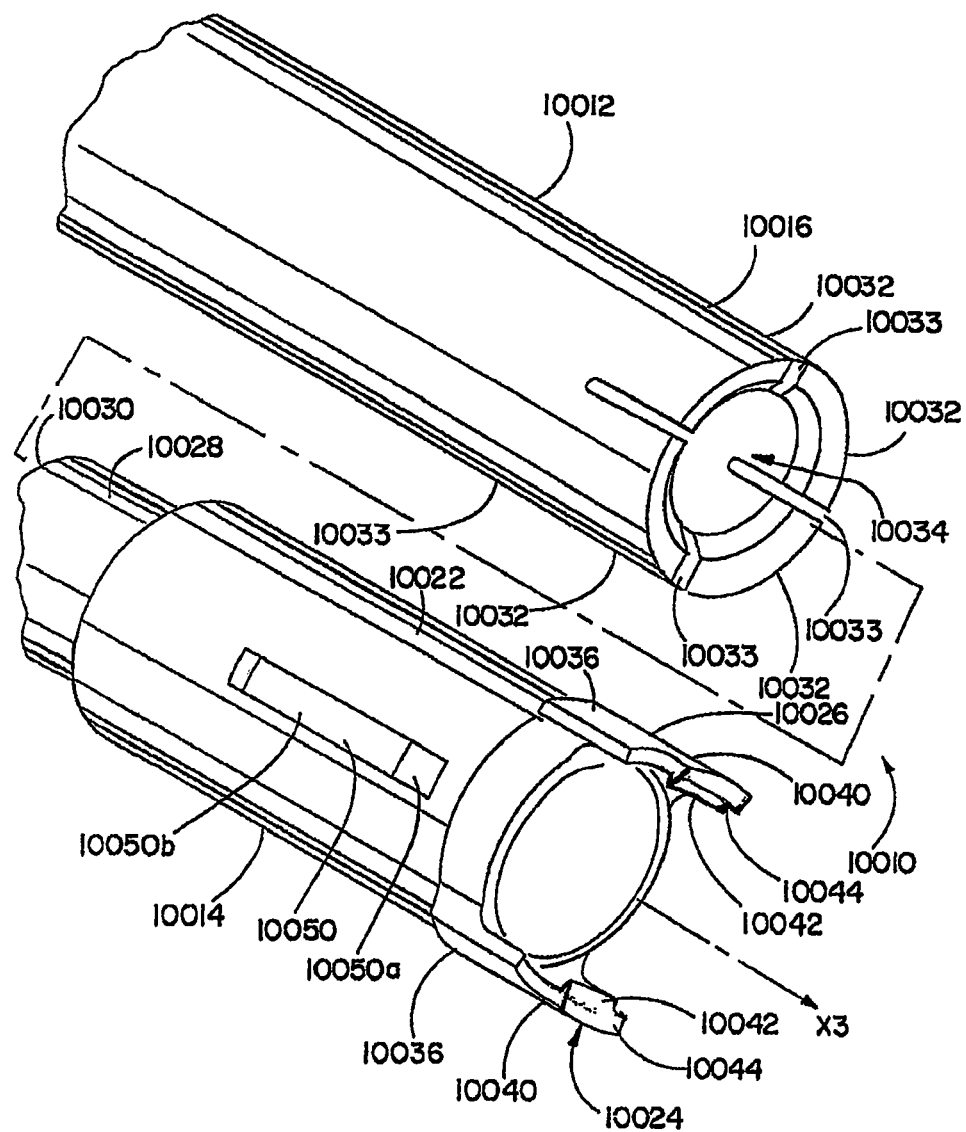
FIG. 116 is an exploded view of the instrument of FIG. 115 showing an elongate shaft and a driver tip.

Referring to FIG. 116, the cap puller tip 10014 is a generally elongate cylindrical body 10022 having a grasping assembly 10024 on a distal end 10026 and a protrusion 10028 on a proximate end 10030. The grasping assembly 10024 is for grasping and holding the previously installed cap assembly. To receive the cap puller tip 10014, the shaft distal end 10016 includes a plurality of resilient flanges 10032 having elongate slots 10033 therebetween that define a receiving aperture 10034 in the distal end 10016 of the shaft 10012. The aperture 10034 and resilient flanges 10032 are configured to receive the tip protrusion 10028 in a friction-fit or a snap-fit arrangement. This arrangement between the shaft 10012 and the tip 10014 permits rotation of the shaft 10012 while it is threadably inserted into the housing passage 8014, but due to radial flanges 10036 that extend outwardly from the body 10022 of the tip 10014 that are received in the axial slots 8017 in the housing assembly passage 8014 (FIG. 105), the cap puller tip 10014 is substantially prevented from rotating.

Figure 117:
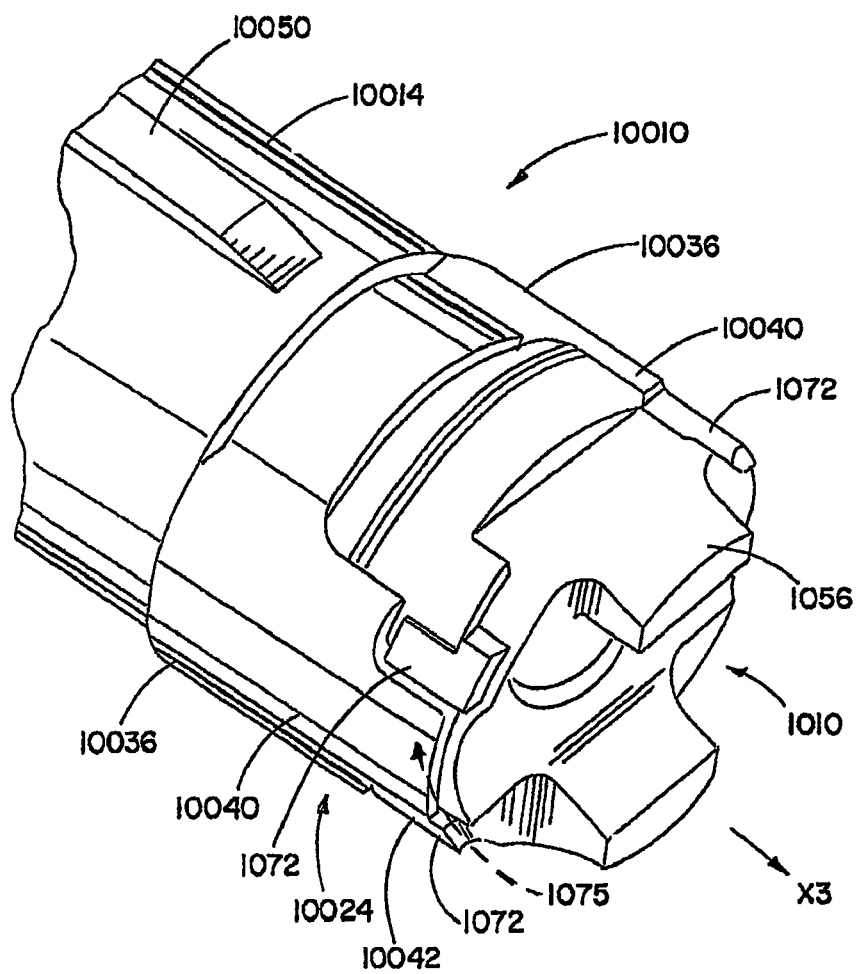
FIG. 117 is a perspective view of the instrument of FIG. 115 shown coupled to the cap assembly of FIGS. 51-64.

Referring to FIGS. 116 and 117, the grasping assembly 10024 is shown in more detail. Preferably, the grasping assembly includes a pair of facing resilient fingers 10040 that project outwardly from the body 10022 of the cap puller tip 10014. Each resilient finger 10040 includes a radially inward extending flange or barb 10042 at a distal end 10044 of each finger 10040. The barb 10042 is for holding the cap assembly 1010 within the grasping assembly 10024.

Figure 56:
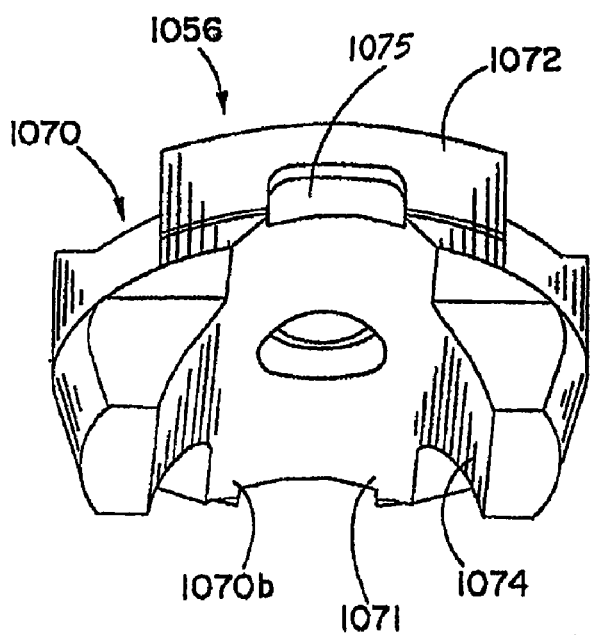
FIG. 56 is a perspective view of the saddle member showing a lower surface thereof curved to match the configuration of the spinal rod.
Figure 57:
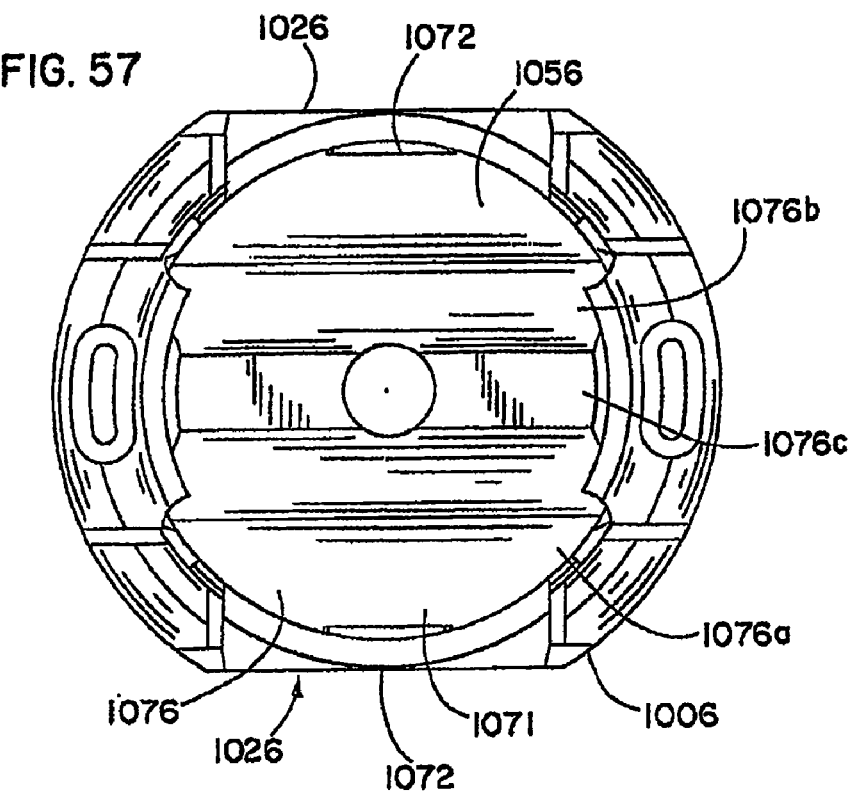
FIG. 57 is a plan view of the saddle member in the yoke member with the collar member and the cam lock member removed.

For instance, as best shown in FIGS. 56 and 117, the barb 10042 is adapted to be received within slots 1075 defined in the upward extensions 1072 of the cap assembly saddle 1056 in order to retain and hold the cap assembly 1010 within the grasping assembly 10024. To this end, for the barbs 10042 to be received within the saddle slots 1075, the fingers 10040 resiliently flex outward from a longitudinal axis X3 extending through the cap puller tip when an inclined cam surface 10044 on a lower edge of the barbs 10042 engages the upper edge of the saddle upward extensions 1072. When the barb 10042 is received within the saddle slots 1075, the fingers 10040 resiliently snap back to their original configuration to grasp a hold of the cap assembly. As a result, as the elongate shaft is reversibly threaded within the housing passage 8014, the cap assembly 1010 can be removed from the yoke member 1006 along the housing assembly longitudinal axis X1 because the resilient arm portions 1030 of the yoke 1006 are flexed outward, as described below.

Figure 118:
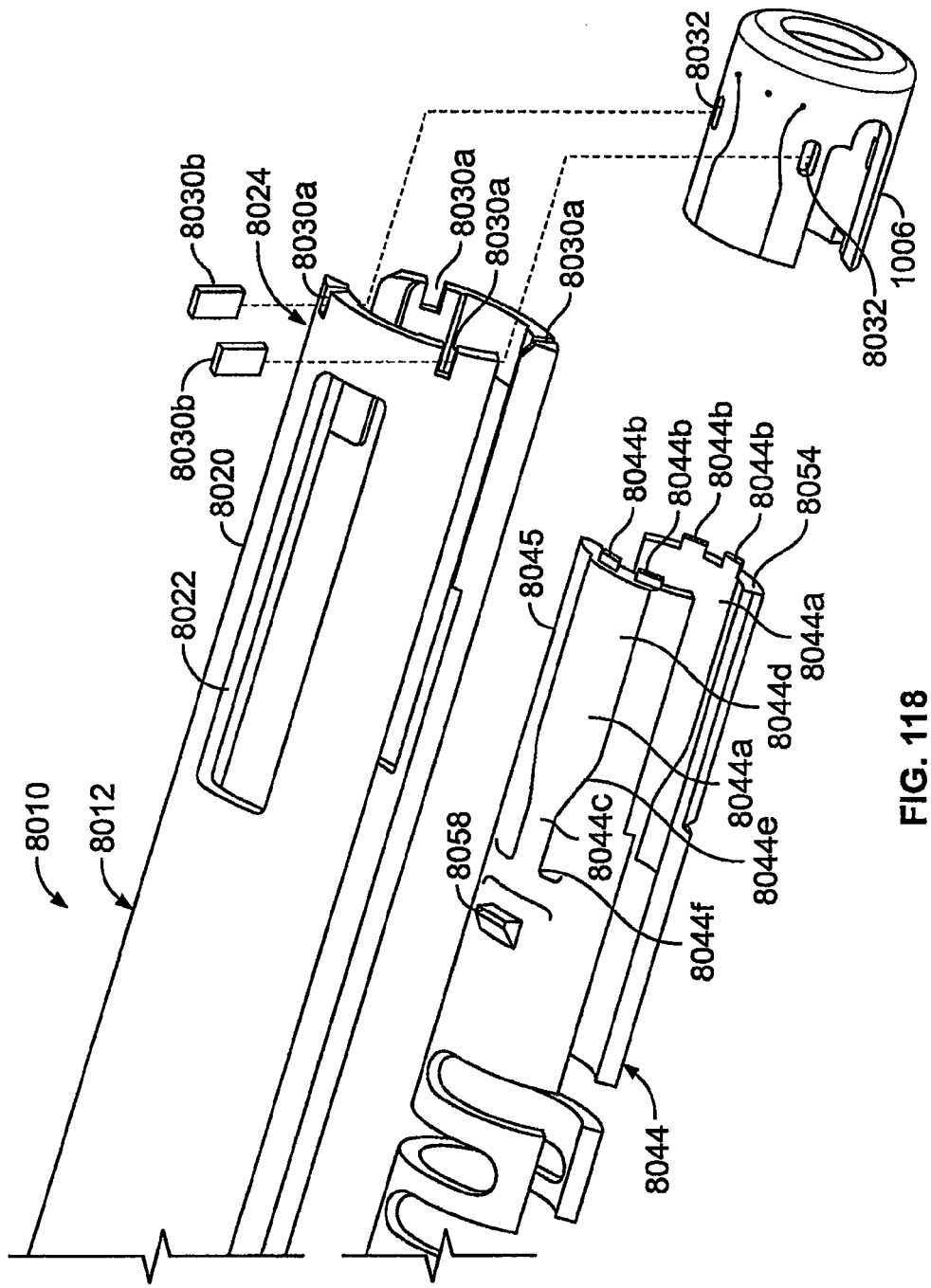
FIG. 118 is an exploded view of an alternative configuration of the instrument of FIG. 99 adapted for use with the instrument of FIG. 115.
Figure 119:
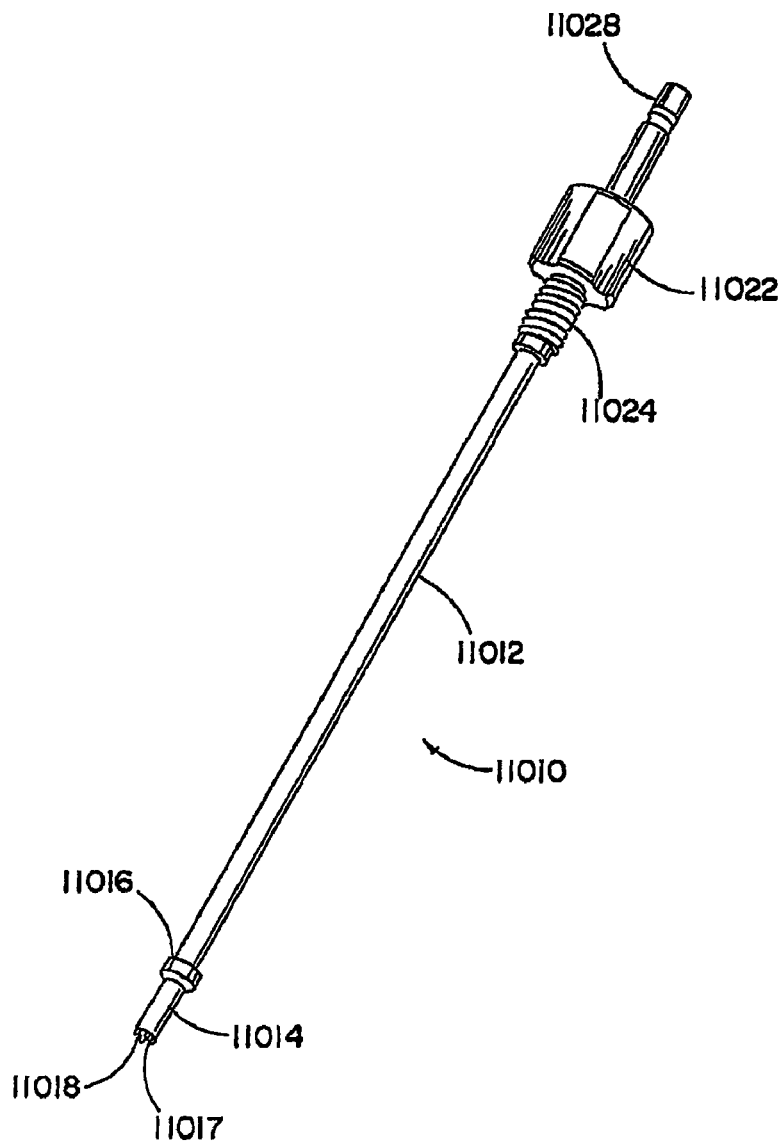
FIG. 119 is a perspective view of another instrument configured to be received within the passage defined in the instrument of FIG. 99.
Figure 122:
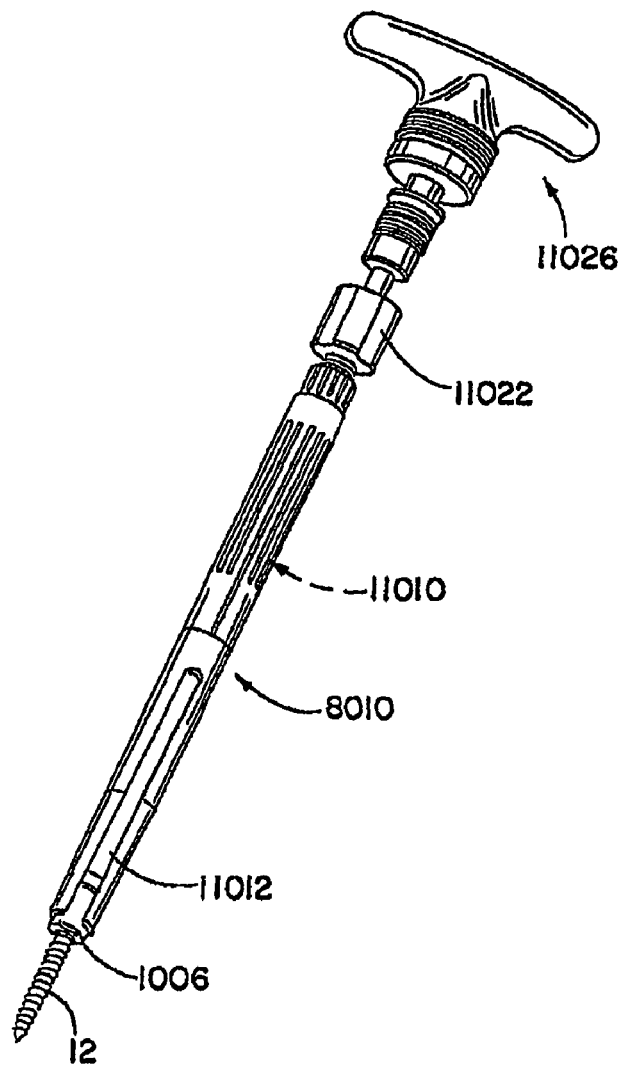
FIG. 122 is a perspective view of the instrument of FIG. 119 shown inserted into the instrument of FIG. 99 and coupled to a T-handle driver tip.

Turning to FIG. 118, the housing assembly 8010 is preferably modified for use with the cap removal instrument 10010. For example, the fingers 8020 preferably include a plurality of spaced slots 8030a, each spaced slot 8030a receive a peg 8030b that is also received in a slot aperture 8032 to secure yoke member 1006 to the housing assembly 8010 at the distal end 8024 that receive a plurality of pegs 8030b instead of the cleats 8030. In addition, the locking sleeve 8044 is modified to include resilient arms 8044a in a distal end portion 8045 that flex outwardly in response to a camming action from cam ribs 10050 (FIG. 116, 117) positioned on opposite sides of the cap puller tip 10014. The lock sleeve arms 8044a include axial flanges 8044b on the distal end 8054 thereof that are received on inner surfaces of the yoke member flanges 1042 when the lock sleeve 8044 is locked against the yoke member as previously described with reference to FIGS. 99 through 108B. Therefore, upon the cap puller tip 10014 engaging the cap assembly 1010, the cam ribs 10050 engage the lock sleeve resilient arms 8044a and cam them outwardly from the housing longitudinal axis X. Because of the lock sleeve flanges 8044b being received on an inside edge of the yoke member flanges 1042, the outward motion of the lock sleeve arms 8044a causes the yoke member arms 1030 to flex or bend outwardly so that the cap assembly 1010 can be removed therefrom.

In order to resilient flex, the lock sleeve arms 8044a include a more narrow flex portion 8044c and a larger yoke engaging portion 8044d. These lock sleeve arm portions are defined in the side walls of the lock sleeve by a narrow slit 8044e that also defines a curved portion 8044f adjacent the narrow, flexing portion 8044c in order to prevent stress risers. To cam the arms 8044a outwardly, the cam rib 10050 includes an inclined cam surface 10050a and a flat holding surface 10050b.

In this modified form of the lock sleeve, rather than the radial flanges 8058 being located at the distal end of the sleeve, the flanges 8058 are positioned prior to the flex arms 8044a. The flanges 8058 are configured to slide within the slot 8022 defined within the fingers 8020 so that the lock sleeve is substantially prevented from rotating during the locking operation previously described.

Referring now to FIGS. 119-122, a third instrument or driver 11010 is illustrated for implanting the anchor member 12 within a bone material. The instrument 11010 is also configured to be received within the housing assembly passage 8014 in order to interface with a yoke member 1006 and bone screw 12 that have been locked within the housing assembly 8010 as previously described.

The instrument 11010 includes an elongate shaft 11012 having a driving tip 11014 on a distal end 11016 thereof. In order to couple with the anchor member 12, the distal end 11017 of the driving tip 11016 defines a mating surface 11018 in the form of a plurality of protrusions 11020 that are arranged and configured to mate with the peripheral driving surfaces 120 and recessed notches 122 formed in the top surface 80 of the anchor member 12. (FIGS. 15 and 121).

Opposite the driving tip 11014, the instrument 11010 includes handle 11022 having an outer threaded portion 11024 that is configured to threadably mate with the internal threads 8015 within the housing assembly passage 8014 so that the housing assembly 8010 can securely receive the driver instrument 11010 therein. The elongate shaft 11012 is designed to rotate relative to the handle 11022, preferably with a T-handle 11026 (FIG. 122) coupled to a profiled driver end 11028 (FIG. 119) of the elongate shaft 11012. In this manner, the rotation of the T-handle 11026 rotates the elongate shaft 11012 relative to the handle 11022 and also relative to the housing assembly 8010 in order to drive an anchor member 12 into a bone material.

Figure 123:
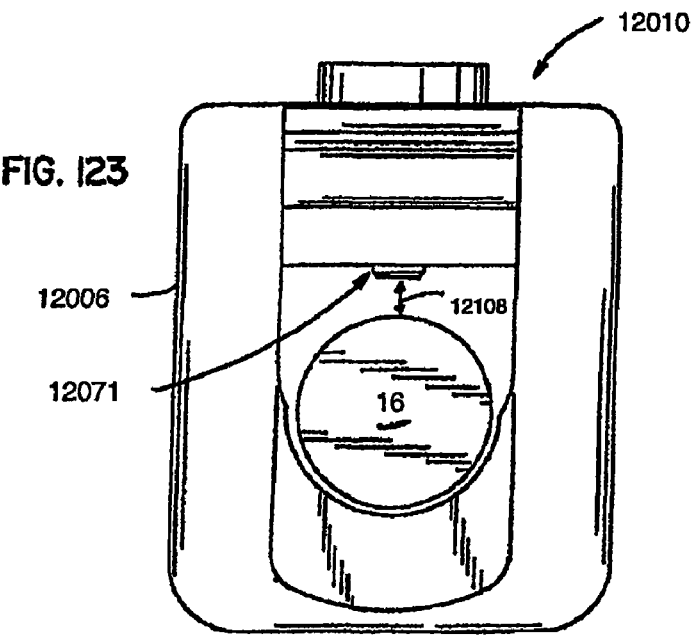
FIG. 123 is an elevational view of another form of the spinal fixation system in accordance with the present invention showing a yoke coupling member, spinal rod, and a lock device in the minimum clearance cap-lock position.
Figure 124:
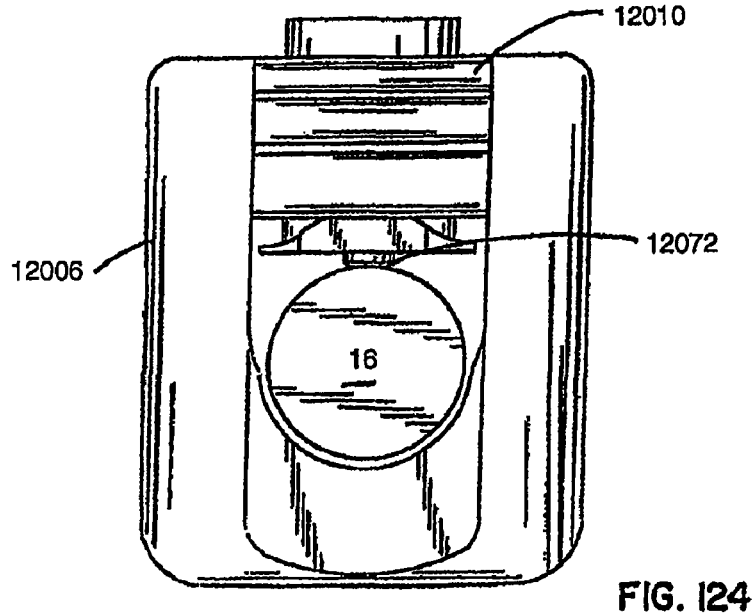
FIG. 124 is an elevational view of the spinal fixation system of FIG. 123 showing the lock device in the rod-lock position.

Turning to FIGS. 123-130 there is illustrated another form of the spinal fixation system that includes a yoke coupling member 12006 and a lock device 12010 to lock the spinal rod relative to a coupling member. Similar to the other embodiments, the lock device may be received within the yoke member in a plurality of cap-lock positions. For example, as illustrated in FIG. 123, the lock device is in a minimum clearance cap-lock position where a relatively small gap 12108 is formed between the bottom of the lock device 12071 and the rod 16. While not shown, the lock device may also be inserted in a maximum clearance cap-lock position where a relatively large gap exists between the rod 16 and lock device 12071. In FIG. 124, the lock device 12010 is in the rod-lock position where the bottom thereof, and in particular, a locking protrusion 12072 is compressed against the rod 16.

Figure 125:
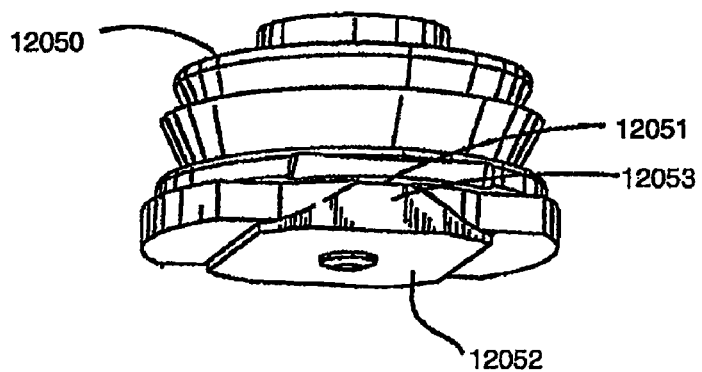
FIG. 125 is a perspective view of the lock device of FIG. 123 showing respective engaging surfaces of a collar and a lock member in mating relation to position the collar and lock member in an axially compact configuration.
Figure 126:
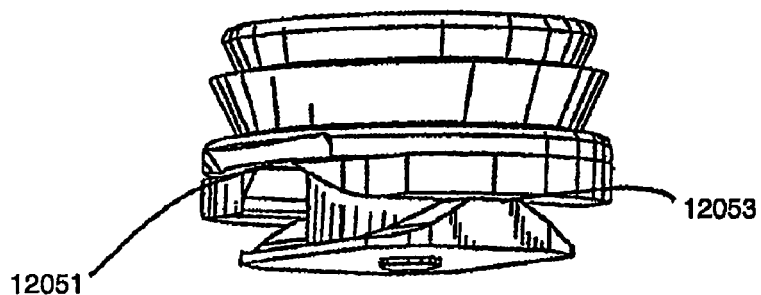
FIG. 126 is a perspective view of the collar and lock member of FIG. 125 showing the respective engaging surfaces rotated relative to each other to shift the collar and the lock member into an axially extended configuration.

FIG. 125 illustrates the lock device including a collar 12050 and lock member 12052. In the maximum and minimum clearance cap lock position, the lock device includes respective engaging surfaces 12051 and 12053 of the collar and the lock member in a mating relation to position the collar and lock member in an axially compact configuration. In the rod-lock position, as shown in FIG. 126, the respective engaging surfaces may be rotated relative to each other to shift the collar and the lock member into an axially extended configuration. That is, the lock device is rotated relative to the collar.

Figure 127:
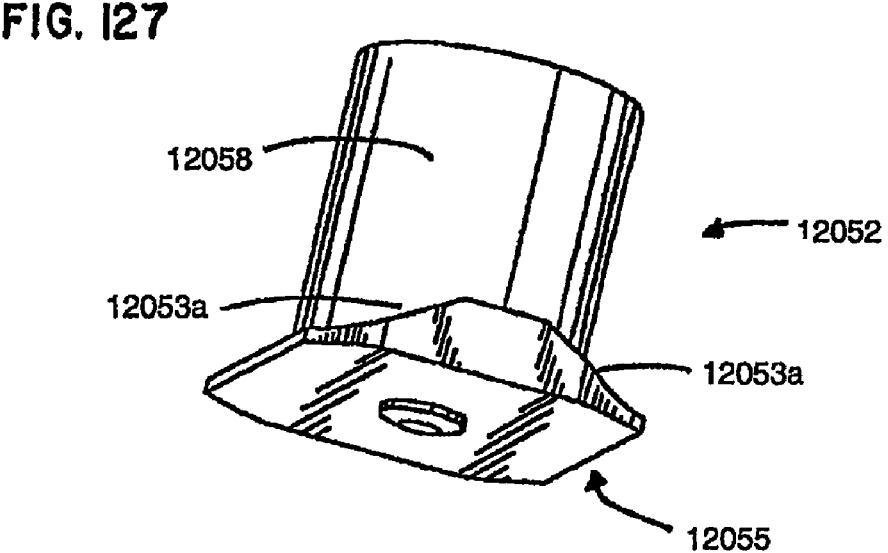
FIG. 127 is a perspective view of the lock member of FIG. 125 showing a base member having ramped cam surfaces on an upper surface thereof and a central cylindrical body member configured to be coupled to the collar.
Figure 128:
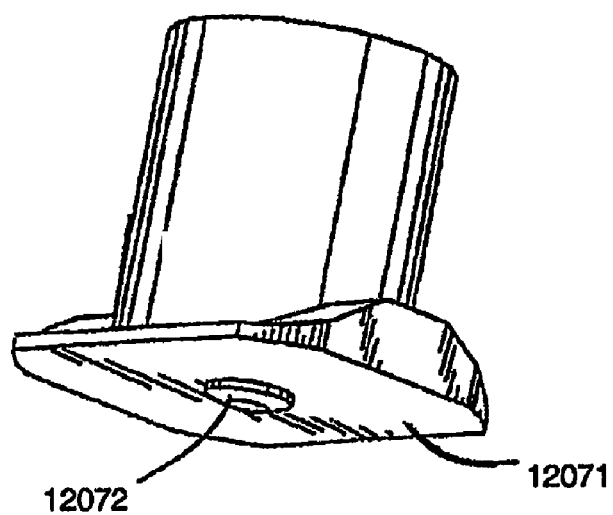
FIG. 128 is a perspective view of the lock member of FIG. 125 showing a lower surface of the base member including a locking protrusion configured to engage the spinal rod in the rod-lock cap lock position.

FIG. 127 illustrates the lock member in more detail. For example, the lock member includes a base member 12055 having ramped cam surfaces 12053a on an upper surface thereof and a central cylindrical body member 12058 configured to be coupled to the collar. FIG. 128 shows a lower surface 12071 of the base member including the locking protrusion 12072 configured to engage the spinal rod in the rod-lock cap position.

Figure 129:
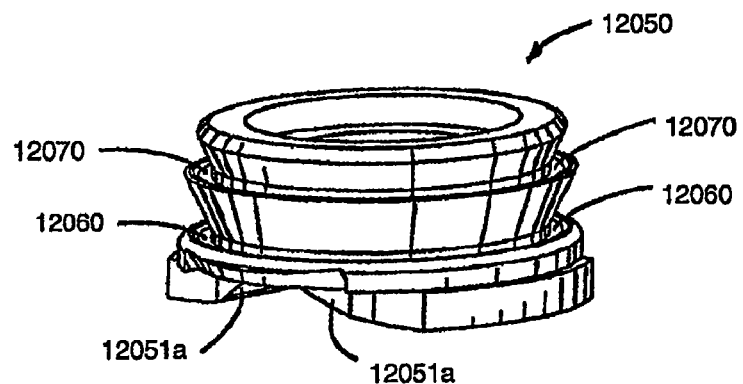
Figure 130:
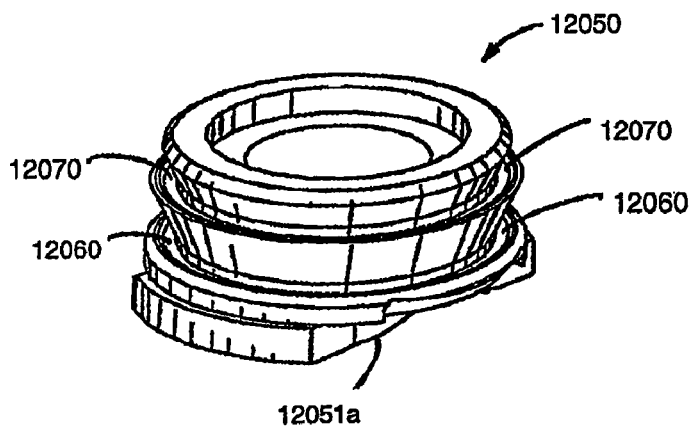

FIG. 129 illustrates the collar in more detail. It illustrates a pair of annular seating grooves 12060 and 12070 on a sidewall thereof. Depending on which seating groove receives the yoke flanges, the lock device will either be in the maximum clearance or minimum clearance cap lock position. FIG. 130 shows the lower surface of the collar, and in particular, ramped cam surfaces on a lower surfaced thereof and a central passage configured to receive the cylindrical body member of the lock member.

Figure 131:
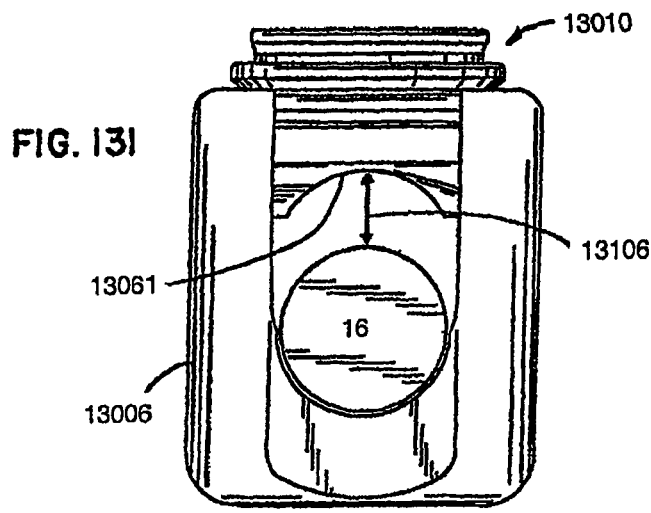
Figure 132:
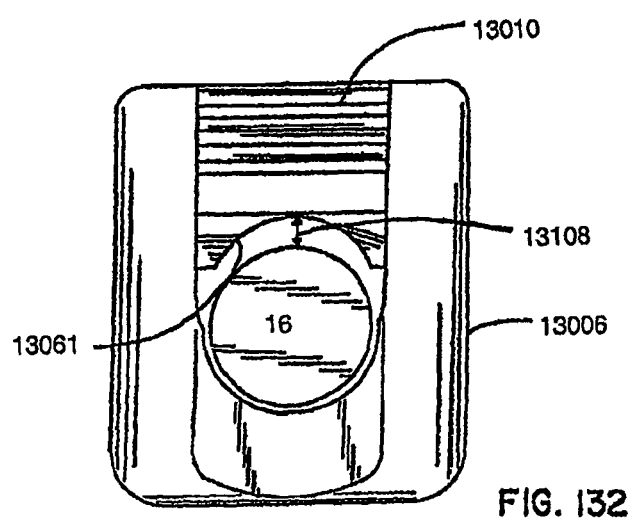
Figure 133:
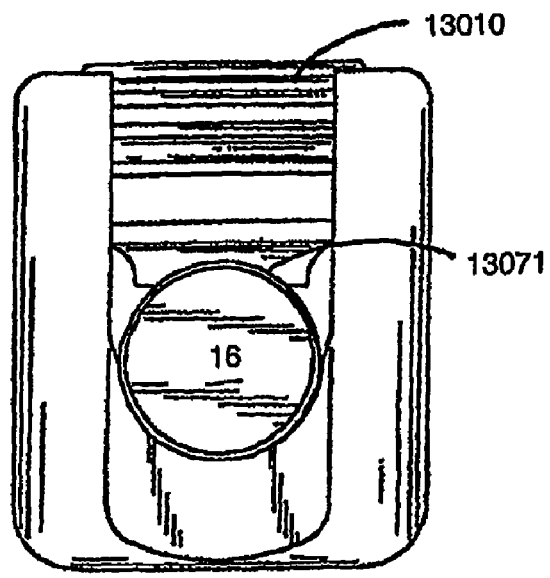

Turning to FIGS. 131-137, there is illustrated another form of the spinal fixation system that includes a yoke coupling member 13006 and a lock device 13010 to lock the spinal rod 16 relative to a coupling member. In this embodiment, the lock device is a unitary, one-piece member. The lock device of this embodiment may also be received with the yoke coupling member within a plurality of cap-lock positions. For example, FIG. 131 shows a yoke coupling member and a lock device received in the maximum clearance cap-lock position with a relatively large gap 13106 between the lock device and a rod received within an internal space of the yoke coupling member. FIG. 132 shows the lock member translated along the yoke axis and positioned in the minimum clearance cap-lock position with a smaller gap 13108 between the lock device and the rod. FIG. 133 shows the lock member 13010 in the rod lock cap-lock position where a curved lower surface 13071 presses against the rod to lock it relative to the coupling member.

Figure 134:
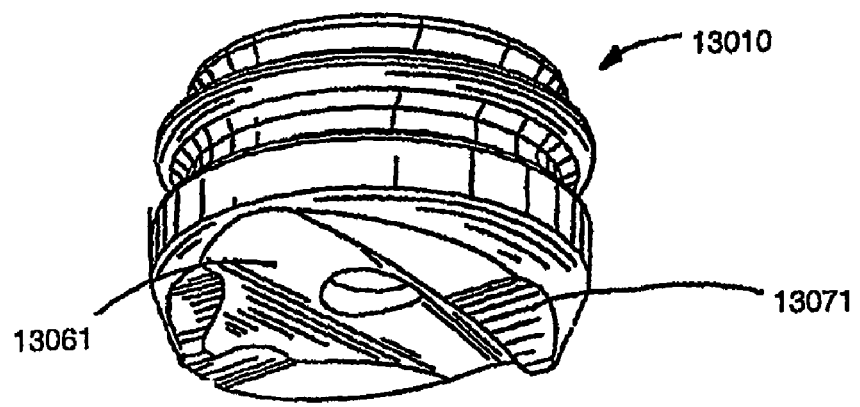
Figure 135:
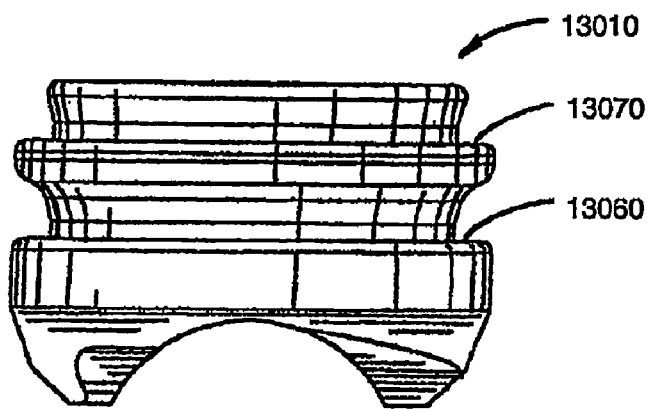
Figure 136:
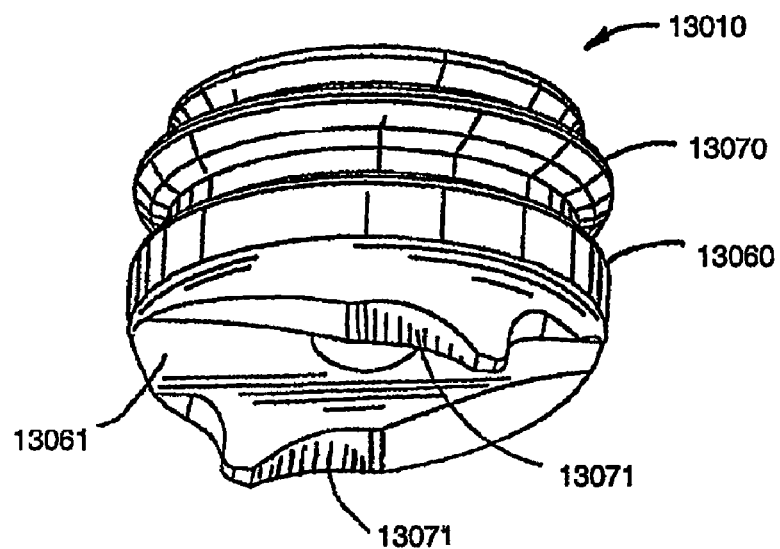
Figure 137:
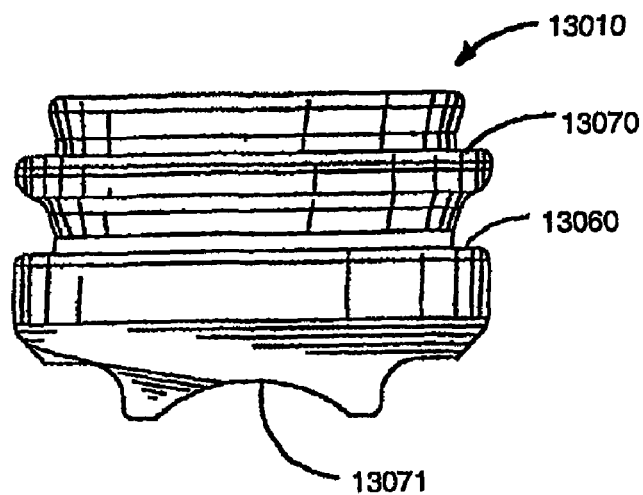

FIGS. 134-137 illustrate the lock device 13010 in more detail. In particular, FIGS. 134 and 136 shows curved cam surfaces 13061 and 13071 on a lower surface thereof. FIGS. 135 and 137 show a curved portion of the lower surface thereof and annular seating grooves 13060 and 13070 on a side wall thereof. Depending on which seating groove the yoke flange is received in, the lock device will either be in the maximum or minimum clearance cap-lock position.

Figure 139:
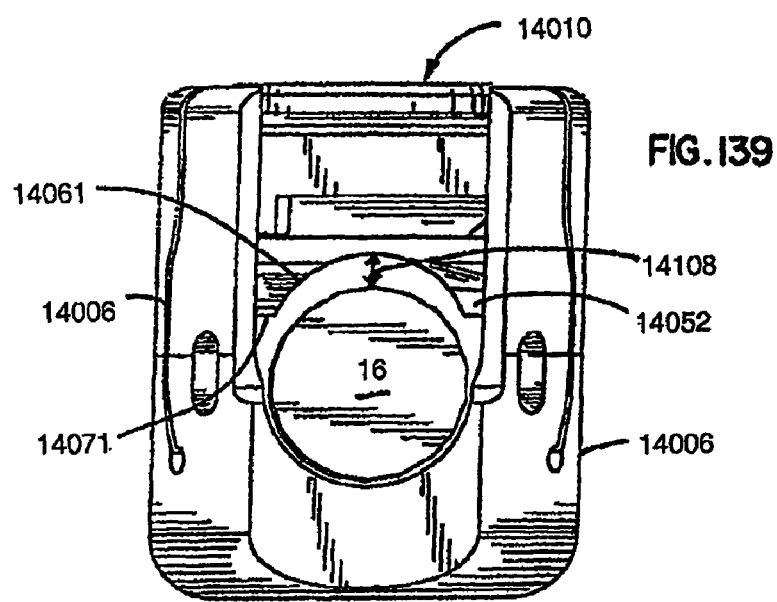
Figure 140:
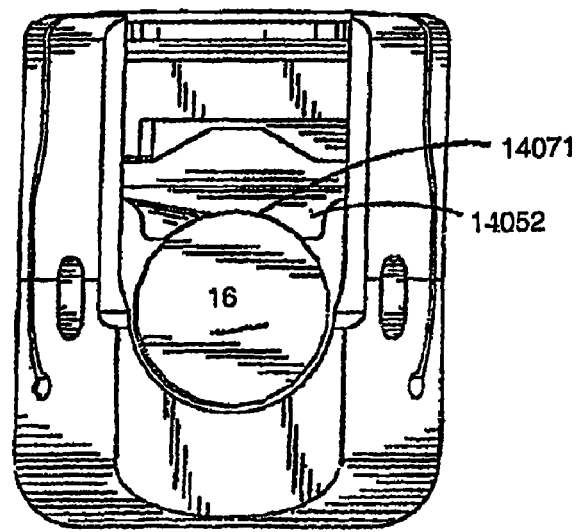

Turning to FIGS. 138-148 there is illustrated another form of the spinal fixation system that includes a yoke coupling member 14006 and a lock device 14010 to lock the spinal rod 16 relative to a coupling member. The lock device is configured to be received along a yoke axis into a plurality of lock positions. For example, FIG. 138 is shows a yoke coupling member and a lock device in the maximum clearance cap-lock position where a relatively large gap 14106 exists between the spinal rod and lock member. FIG. 139 shows the lock device in a minimum clearance cap-lock position where a relatively small gap 14108 exists between the spinal rod and the lock member. FIG. 140 shows the lock device in the rod lock cap-lock position where a curved lower surface 14071 of the lock member locks the rod relative to the coupling member.

FIGS. 141-144 show the lock device in more detail the lock device 14010 is generally a combination of the one piece locking device of FIG. 134 together with the collar similar to that of FIG. 64. For example, FIGS. 141-142 illustrate respective engaging surfaces of a collar and a lock member in mating relation such that the collar and lock member are in an unlocked configuration. FIG. 143-144 show the respective engaging surfaces rotated relative to each other to shift the collar and the lock member into an locked configuration. That is, the lock member is rotated relative to the collar. Herein, while collar 14050 remains substantially fixed relative to the yoke, the lock member 14052 can be rotated so that the contoured surfaces 14061 and 14071 on the bottom of the lock member 14052 engage the rod 16 and lock it relative to the yoke. As shown in FIGS. 139, 141, and 142 the curved surface 14061 is aligned with the rod 16 providing a clearance 14108 between the lock member and rod. As shown in FIGS. 140, 143, and 144, the curved surface 14071 is aligned with the Rod 16 to lock it relative to the yoke.

FIGS. 145-146 show the lock member in more detail. For instance, FIG. 145 shows a base member having ramped surfaces 14076 on an upper surface thereof and a main cylindrical body 14078 having a lobed recess 14081 therein. FIG. 146 illustrates a lower surface of the base member including curved cam surfaces thereof 14061 and 14071. Post 14513 on the collar 14050 limits over rotation of the lock member 14052 by interfering with ramp surface 14076 on the lock member 14052.

FIGS. 147-148 show the collar in more detail. For example, FIG. 147 illustrates inclined ramp surfaces on an annular sidewall 14011 thereof and depending lock arms 14107. FIG. 148 shows an annular seating surface thereof.

Turning to FIGS. 149-158, there is illustrated another form of the spinal fixation system that includes a yoke coupling member 15006 and a lock device 15010 to lock the spinal rod relative to a coupling member. The lock device is configured to be received along a yoke axis into a plurality of lock positions. For example, FIG. 149 shows a yoke coupling member and a lock device in a minimum clearance cap-lock position where a relatively small gap 15108 exists between the spinal rod and lock member. While not shown, similar to the other embodiment, the lock device is also configured to be received in the maximum clearance cap lock position. FIG. 150 shows the lock device 15010 in the rod lock cap-lock position where the lock device locks the rod 16 relative to the coupling member 15006.

FIG. 151-154 illustrates the lock device in more detail. For example, FIGS. 151 and 153 show respective engaging surfaces (15051 and 15053) of a lock member 15052 and a saddle member 15056 in mating relation to position the lock member and saddle member in an axially compact configuration. FIGS. 152 and 154 show the respective engaging surfaces 15051 and 15053 rotated relative to each other to shift the lock member and the saddle member into an axially extended configuration. That is, the lock member is rotated and the saddle member is translated axially without substantial rotation thereof to form the axially extended configuration.

FIGS. 155-156 show the saddle member in more detail. For example, FIG. 155 illustrates a disk-shaped base member 15056*a* and extensions 15056*b* extending upwardly from outer edges thereof; seating surfaces 15056*d* on the extensions; and ramp surfaces 15053*a* on an upper surface thereof. The seating surfaces are configured for receiving the lock device in the maximum cap-lock position. FIG. 156 shows a saddle surface 15056*c* on a lower surface of the base member.

FIGS. 157-158 show the lock member in more detail. For example, FIG. 157 shows the lock member including an annular body having upwardly inclined ramp surfaces 15068 on a lower surface thereof. The ramp surfaces for camming the resilient arms in the yoke member side walls. FIG. 158 shows an annular seating surface on a side wall thereof. The annular seating surface receives the lock device in the minimum clearance cap lock position.

While there have been illustrated and described particular embodiments of the present invention, it will be appreciated that numerous changes and modifications will occur to those skilled in the art, and it is intended in the appended claims to cover all those changes and modifications which fall within the true spirit and scope of the present invention.

What is claimed is:

1. A spinal fixation system for fixing an elongate member in a desired position relative to a patient's spine, the spinal fixation system comprising:
   an anchor member for being secured to a vertebral bone of the spine;
   a coupling member having an internal space for securing the elongate member relative to the anchor member in the internal space, an upper opening leading to the internal space, and a central axis extending through the internal space and the upper opening;
   opposing side wall portions of the coupling member each extending axially upward toward top ends thereof and including slot openings therebetween with the elongate member extending through the slot openings and out from either side of the coupling member;
   a locking device for being received axially through the upper opening and in the internal space to be operable to fix the elongate member in the coupling member;
   at least one of the side wall portions including a resilient portion that cooperates with the locking device for being inserted into the internal space of the coupling member via resilient flexing of the resilient portion;
   substantially rigid portions on either side of the resilient portion of the at least one sidewall portion that guide the locking device for receipt in the coupling member;
   a pair of narrow slits extending along each side of the resilient portion and opening to the top end of the sidewall, the slits extending substantially vertically between the rigid portions and the resilient portion; and
   linear camming portions of the locking device and the resilient portion arranged and configured so that linear advancement of the locking device along the coupling member axis without rotation of the locking device causes camming engagement of the linear camming portions to resiliently shift the resilient portion for insertion of the locking device through the upper opening and into the internal space of the coupling member.

2. The spinal fixation system of claim 1, wherein the resilient portion comprises a resilient arm portion of each of the side wall portions.

3. The spinal fixation system of claim 1, wherein the linear camming portion of the locking device includes opposite linear camming portions configured to cause resilient flexing of both resilient arm portions as the locking device portion is inserted into the coupling member.

4. The spinal fixation system of claim 1, wherein the slits extend arcuately in the side wall portions to form sections of the resilient portions that are of varying flexibility from each other.

5. The spinal fixation system of claim 1, wherein the coupling member and the locking device include cooperating structure therebetween to define a plurality of distinct positions of the locking device in the coupling member including an adjustment position which allows for shifting of the elongate member in the coupling member and a locked position with the locking device fixing the elongate member in the coupling member.

6. The spinal fixation system of claim 5, wherein the cooperating structure defines two adjustment positions for the locking device in the coupling member including a maximum clearance position that allows for adjustments of the elongate member along an axis thereof and up along the coupling member side wall portions, and a minimum clearance position that primarily only allows for axial adjustments of the elongate member.

7. The spinal fixation system of claim 1, wherein the resilient portion includes an upper holding portion configured to couple with the locking device, an intermediate neck portion configured to resiliently flex, and a base portion configured to minimize stress in the coupling member during resilient flexing of the resilient portion.

8. The spinal fixation system of claim 7, wherein the resilient portion has a generally hour-glass shape such that the upper holding portion and the base portion each have a circumferential width that is larger than the intermediate neck portion.

9. The spinal fixation system of claim 7, wherein the upper holding portion includes the linear camming portion comprising an inclined portion which cammingly engages the linear camming portion of the lock device during insertion thereof into the coupling member for causing the resilient flexing of the resilient portion.

10. The spinal fixation system of claim 1, further comprising a support device received within the coupling member to hold the coupling member substantially upright relative to the anchor member.

11. A spinal fixation system for fixing an elongate member in a desired position relative to a patient's spine, the spinal fixation system comprising:
   an anchor member for being secured to a vertebral bone of the spine;
   a coupling member having an axis and an internal space for receiving the elongate member therethrough extending in a direction transverse to the coupling member axis; and
   a lock device received in the internal space in a plurality of predetermined axial positions along the coupling member axis comprising a maximum clearance position, a minimum clearance position, and a rod lock position;
   wherein the coupling member has an upstanding side wall with the lock device and side wall being configured so that:
   to position the lock device in the maximum clearance position the lock device is linearly inserted along the coupling member axis into the coupling member internal space without rotation thereof substantially fixed against removal from the coupling member with the side wall releasably holding the lock device in a predetermined rotational position thereof at the maximum clearance position for providing a relatively large gap between the elongate member and the lock device when the elongate member is engaged against the anchor member to permit movement of the elongate member both transverse to and along the coupling member axis;
   to position the lock device in the minimum clearance position the lock device is linearly advanced along the coupling member axis in the coupling member internal space without rotation thereof from the maximum clearance position to the minimum clearance position with the side wall releasably holding the lock device at the minimum clearance position and in the same predetermined rotational position as the lock device has in the maximum clearance position providing a relatively small gap between the elongate member and the lock device when the elongate member is engaged against the anchor member to permit movement of elongate member transverse to the coupling member axis with minimal movement along the coupling member axis; and
   to position the lock device in the rod lock position at least a portion of the lock device is configured for rotation so that rotation of the lock device portion shifts the lock device from the minimum clearance position to the rod lock position in the internal space at which the lock device fixes the elongate member relative to the coupling member.

12. The spinal fixation system of claim 11, wherein the lock device comprises a collar, a lock member joined to the collar by a retainer permitting the lock member to rotate about the coupling member axis, and a saddle joined to the lock member by a connector permitting the saddle to translate along the coupling member axis without substantial rotation relative to the coupling member.

13. The spinal fixation system of claim 12, wherein the side wall and the saddle are configured so that the saddle is releasably held by the coupling member side wall in the maximum clearance position.

14. The spinal fixation system of claim 12, wherein the side wall and the collar are configured so that the collar is releasably held by the coupling member side wall in the minimum clearance position.

15. The spinal fixation system of claim 12, wherein the side wall and the collar are configured so that the collar is releasably held by the coupling member side wall and the saddle pushes against the elongate member to fix the elongate member relative to the coupling member in the rod lock position.

16. The spinal fixation system of claim 11, further comprising a support device received within the internal space of the coupling member configured to position the coupling member substantially upright relative to the anchor member.

17. The spinal fixation system of claim 11, wherein the lock device is a unitary member.

* * * * *